United States Patent
Hwang et al.

(10) Patent No.: US 8,057,920 B2
(45) Date of Patent: *Nov. 15, 2011

(54) HETEROCYCLIC COMPOUND AND ORGANIC LIGHT EMITTING DEVICE COMPRISING THE SAME

(75) Inventors: Seok-Hwan Hwang, Suwon-si (KR); Young-Kook Kim, Suwon-si (KR); Yoon-Hyun Kwak, Suwon-si (KR); Hee-Joo Ko, Suwon-si (KR)

(73) Assignee: Samsung Mobile Display Co., Ltd., Giheung-Gu, Yongin, Gyunggi-Do (KR)

( * ) Notice: Subject to any disclaimer, the term of this patent is extended or adjusted under 35 U.S.C. 154(b) by 339 days.

This patent is subject to a terminal disclaimer.

(21) Appl. No.: 12/292,016

(22) Filed: Nov. 10, 2008

(65) Prior Publication Data

US 2009/0146555 A1     Jun. 11, 2009

(30) Foreign Application Priority Data

Nov. 16, 2007  (KR) ........................ 10-2007-0117370

(51) Int. Cl.
*H01J 1/63*      (2006.01)
*C07D 487/04*    (2006.01)

(52) U.S. Cl. ........ 428/690; 428/917; 313/504; 313/506; 548/433

(58) Field of Classification Search ........................ None
See application file for complete search history.

(56) References Cited

U.S. PATENT DOCUMENTS 4,115,397 A   9/1978 Siegl
(Continued)

FOREIGN PATENT DOCUMENTS

EP   0 673 979    9/1995
(Continued)

OTHER PUBLICATIONS

Registration Determination Certificate dated Aug. 30, 2010 issued by the Korean Intellectual Property Office corresponding to to Korean Priority Application No. 10-2007-0117370, together with a Request for Entry.

(Continued)

*Primary Examiner* — Dawn Garrett
(74) *Attorney, Agent, or Firm* — Robert E. Bushnell, Esq.

(57) ABSTRACT

Provided is a heterocyclic compound represented by Formula I:

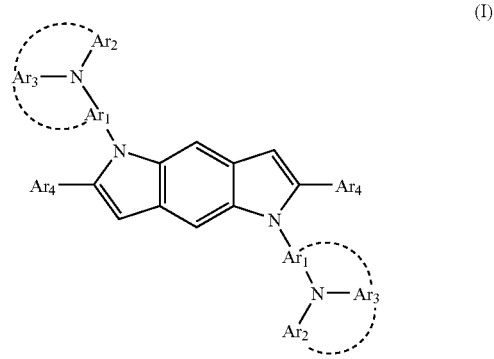

(I)

wherein $Ar_1$ is a linking group and a C6-C16 arylene or heteroarylene group; $Ar_2$ and $Ar_3$ are each independently a C6-C20 aryl group, a C4-C20 heteroaryl group or a C6-C20 fused polycyclic group; $Ar_4$ is a C6-C20 aryl group, a C6-C20 aryloxy group, a C4-C20 heteroaryl group or a C6-C20 fused polycyclic group; and $Ar_1$ and $Ar_3$, or $Ar_2$ and $Ar_3$ may be connected to each other to form a ring. The heterocyclic compound has high electrical stability and excellent charge transporting capability, and thus can be efficiently used as a material for forming at least one of a hole injecting layer, a hole transporting layer and an emitting layer suitable for fluorescent and phosphorescent devices realizing all colors including red, green, blue and white.

20 Claims, 1 Drawing Sheet

U.S. PATENT DOCUMENTS

| | | | |
|---|---|---|---|
| 4,874,756 | A | 10/1989 | Mertens et al. |
| 4,916,711 | A | 4/1990 | Boyer et al. |
| 7,846,559 | B2* | 12/2010 | Hwang et al. ............... 428/690 |
| 2002/0128514 | A1* | 9/2002 | Uemura et al. ............... 564/426 |
| 2006/0115680 | A1* | 6/2006 | Hwang et al. ............... 428/690 |
| 2006/0199882 | A1 | 9/2006 | Heckmann et al. |
| 2008/0107919 | A1* | 5/2008 | Hwang et al. ............... 428/691 |
| 2009/0128013 | A1* | 5/2009 | Hwang et al. ............... 313/504 |

FOREIGN PATENT DOCUMENTS

| | | |
|---|---|---|
| JP | 62-51686 | 3/1987 |
| JP | 2196865 A | 8/1990 |
| JP | 2004231709 A | 8/2004 |
| JP | 2007-88222 | 4/2007 |
| WO | 2006/122630 | 11/2006 |

OTHER PUBLICATIONS

Abstract of EP0216165, which is corresponding to JP62-51686 and cited in the Information Disclosure Statement filed on Apr. 19, 2010 of the related Patent No. 7,846,559.

Korean Registration Determination Certificate dated Feb. 22, 2010, issued in corresponding Korean Patent Application No. 10-2007-0117369, which was cited in the Information Disclosure Statement filed on Apr. 19, 2010 of the related Patent No. 7,846,559.

Kinsley, D.A.; Plant, S. P. G. Journal of the Chemical Society, 1958, pp. 1-7, which was cited in the Office Action (Paper No. 20100226) mailed Mar. 8, 2010 of the related Patent No. 7,846,559.

Sanji, T.; Shiraishi, K.; Kashiwabara, T.; Tanaka, M. Organic Letters, 2008, vol. 10 (13), pp. 2689-2692, which was cited in the Office Action (Paper No. 20100226) mailed Mar. 8, 2010 of the related Patent No. 7,846,559.

Machine English translation of JP2007088222 A. Feb. 26, 2010, which was cited in the Office Action (Paper No. 20100226) mailed Mar. 8, 2010 of the related Patent No. 7,846,559.

European Search report issued by the European Patent Office on Mar. 19, 2009, which was cited in the Information Disclosure Statement filed on Jun. 10, 2009 of the related Patent No. 7,846,559.

The Office Action (Paper No. 20100226) mailed on Mar. 2, 2010 containing the initialed PTO-1449 form of the related Patent No. 7,846,559.

The Notice of Allowance and Allowability (Paper No. 20100813) mailed on Aug. 20, 2010 containing the initialed PTO-1449 form of the related Patent No. 7,846,559.

* cited by examiner

HETEROCYCLIC COMPOUND AND ORGANIC LIGHT EMITTING DEVICE COMPRISING THE SAME

CROSS-REFERENCE TO RELATED PATENT APPLICATION AND CLAIM OF PRIORITY

This application claims the benefit of Korean Patent Application No. 10-2007-0117370 filed on Nov. 16, 2007, in the Korean Intellectual Property Office, the disclosure of which is incorporated herein in its entirety by reference.

BACKGROUND OF THE INVENTION

1. Field of the Invention

The present invention relates to a heterocyclic compound and an organic light emitting device including the same, and more particularly, to a heterocyclic compound having two pyrrole rings fused with a benzene ring.

2. Description of the Related Art

Electroluminescent emitting devices, which are self-emitting devices, have the advantages of having wide viewing angles, excellent contrast and quick response time, and thus have received a lot of public attention. An electroluminescent emitting device can be classified into two types, an inorganic light emitting device which includes an inorganic compound in an emission layer, and an organic light emitting device (OLED) which includes an organic compound in an emission layer. An OLED has higher brightness, lower operating voltage, quicker response time, and can realize more colors compared to an inorganic light emitting device, and thus much research thereon has been carried out.

Typically, an OLED has an anode/organic emission layer/cathode structure. An OLED can also have various other structures such as an anode/hole transport layer/organic emission layer/cathode structure and an anode/hole transport layer/organic emission layer/electron transport layer/cathode structure by interposing a hole injection layer and/or a hole transport layer and electron injection layer between the anode and the emission layer or between the emission layer and the cathode.

A polyphenyl compound or an anthracene derivative is known as a material used to form a hole transport layer (U.S. Pat. Nos. 6,596,415 and 6,465,115). However, characteristics of organic light emitting devices formed of materials that are conventionally used to form a hole injection and/or transport layer such as lifetime, efficiency and power consumption are not satisfactory. Thus, there is a need to improve those characteristics of organic light emitting devices.

SUMMARY OF THE INVENTION

The present invention provides a heterocyclic compound as a material having high electrical stability, excellent charge transporting capability and a high glass transition temperature, and which can be used as a material for an organic layer suitable for fluorescent and phosphorescent devices realizing all colors including red, green, blue and white.

The present invention also provides an organic light emitting device having high efficiency, low driving voltage, high brightness and long lifetime by employing an organic layer including the heterocyclic compound.

According to an aspect of the present invention, there is provided a heterocyclic compound represented by Formula I below:

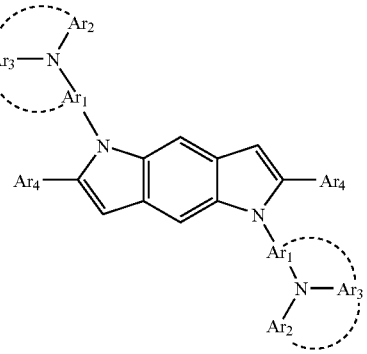

Formula I wherein $Ar_1$ which is a bivalent linking group is a C6-C16 substituted or unsubstituted arylene or heteroarylene group;

$Ar_2$ and $Ar_3$ are each independently selected from the group consisting of a C6-C20 substituted or unsubstituted aryl group, a C4-C20 substituted or unsubstituted heteroaryl group and a C6-C20 substituted or unsubstituted fused polycyclic group;

$Ar_4$ is selected from the group consisting of a C6-C20 substituted or unsubstituted aryl group, a C6-C20 substituted or unsubstituted aryloxy group, a C4-C20 substituted or unsubstituted heteroaryl group and a C6-C20 substituted or unsubstituted fused polycyclic group; and $Ar_1$ and $Ar_3$ or $Ar_2$ and $Ar_3$ may be linked to each other to form a ring.

According to another aspect of the present invention, there is provided an organic light emitting device including: a first electrode; a second electrode; and an organic layer interposed between the first electrode and the second electrode, wherein the organic layer includes the heterocyclic compound.

The organic layer may be a hole injection layer, a hole transport layer, a single layer having hole injecting and transporting functions or an emission layer.

The heterocyclic compound has high electrical stability and excellent charge transporting capability, and thus can be efficiently used as a hole injecting material, a hole transporting material and/or an emitting material suitable for fluorescent and phosphorescent devices realizing all colors such as red, green, blue and white colors. An organic light emitting device having high efficiency, low driving voltage, high brightness and long lifetime can be prepared using the heterocyclic compound.

According to another aspect of the present invention, there is provided a method of preparing a heterocyclic compound represented by Formula I, including: reacting 5-dimethyl-1,4-phenylenediamine and

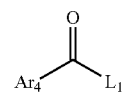

to prepare a compound (b) represented by

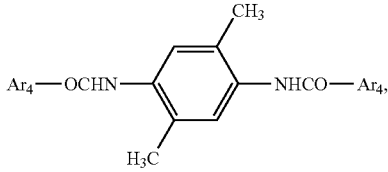

wherein Ar$_4$ is selected from the group consisting of a C6-C20 substituted or unsubstituted aryl group, a C6-C20 substituted or unsubstituted aryloxy group, a C4-C20 substituted or unsubstituted heteroaryl group and a C6-C20 substituted or unsubstituted fused polycyclic group, and L$_1$ is a leaving group;

performing a cyclization reaction of the compound (b) to prepare a compound (c) represented by and reacting the compound (c) and to prepare the heterocyclic compound represented by Formula I.

BRIEF DESCRIPTION OF THE DRAWINGS

The above and other features and advantages of the present invention will become more apparent by describing in detail exemplary embodiments thereof with reference to the attached drawing in which.

DETAILED DESCRIPTION OF THE INVENTION

Figure 1:
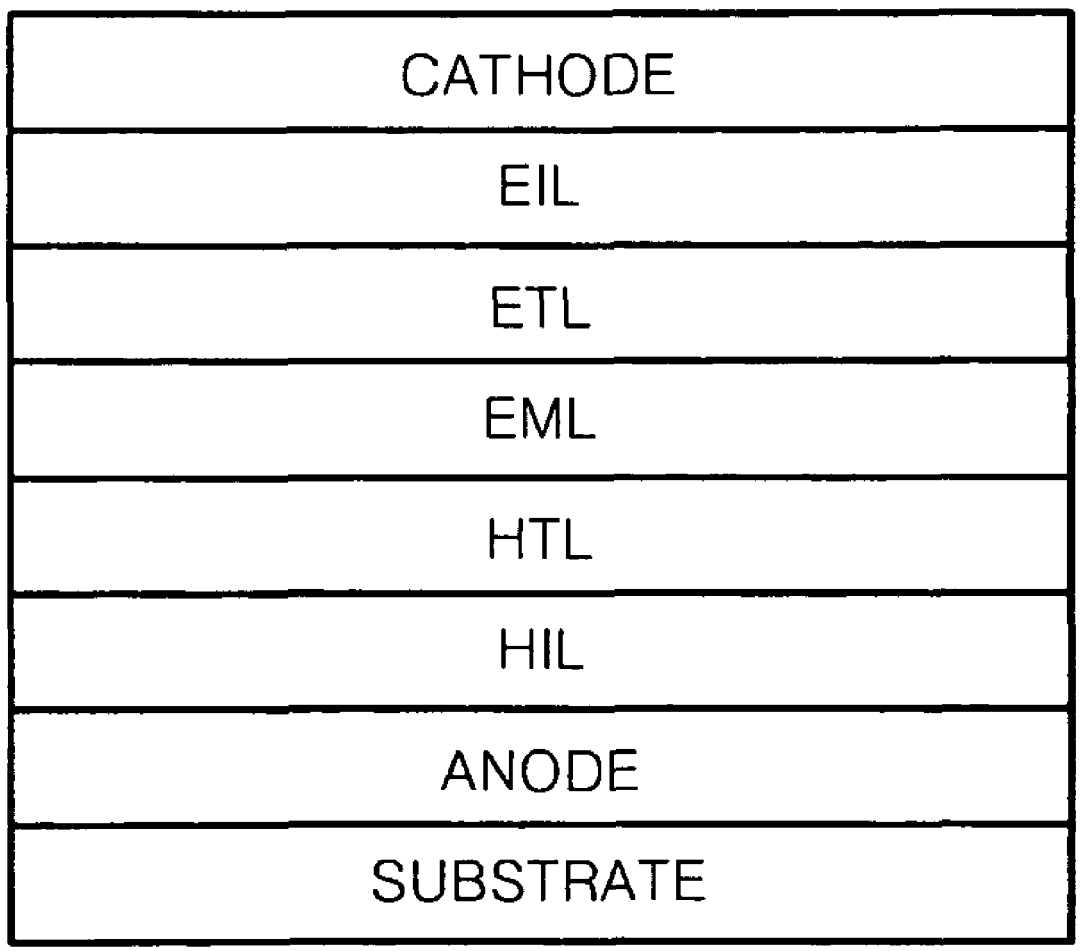
FIG. 1 shows a structure of an organic light emitting device according to an embodiment of the present invention.

The present invention provides a heterocyclic compound represented by Formula I having a novel structure in which two pyrrol groups are fused with a single benzene ring, and an organic light emitting device using the heterocyclic compound as a material used to form an organic layer such as a hole injection layer, a hole transport layer or an emission layer.

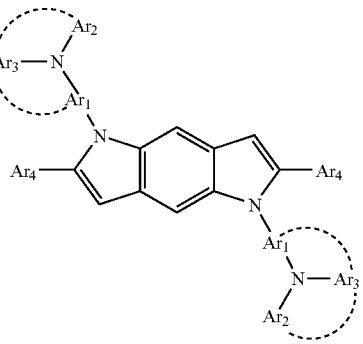

Formula I

Here, Ar$_1$, which is a linking group, is a C6-C16 substituted or unsubstituted arylene or heteroarylene group;

Ar$_2$ and Ar$_3$ are each independently selected from the group consisting of a C6-C20 substituted or unsubstituted aryl group, a C4-C20 substituted or unsubstituted heteroaryl group and a C6-C20 substituted or unsubstituted fused polycyclic group;

Ar$_4$ is selected from the group consisting of a C6-C20 substituted or unsubstituted aryl group, a C6-C20 substituted or unsubstituted aryloxy group, a C4-C20 substituted or unsubstituted heteroaryl group and a C6-C20 substituted or unsubstituted fused polycyclic group; and Ar$_1$ and Ar$_3$, or Ar$_2$ and Ar$_3$ may be linked to each other to form a ring.

The number of carbon atoms forming the Ar$_1$, Ar$_2$, Ar$_3$ and Ar$_4$ in Formula I may be in the range of 4 to 20 in order to be efficiently deposited by having an appropriate molecular weight.

Examples of the unsubstituted arylene or heteroarylene group applied to Ar$_1$ of Formula I are a phenylene group, a biphenylene group, a thiophenylene group, a pyridinylene group, a pyrrolylene group and a fluorenylene group. At least one of the hydrogen atoms of the arylene or heteroarylene group may be substituted with a halogen atom, a cyano group, a C1-C5 alkyl group or a C1-C5 alkoxy group. Preferably, Ar$_1$ may be a phenylene group or a biphenylene group.

An unsubstituted aryl group applied to the compound of Formula I as Ar$_2$, Ar$_3$ and Ar$_4$ may be used alone or in combination. The C6-C20 aryl group indicates an aromatic carbocyclic system having 6-20 carbon atoms and at least one ring, wherein such rings may be bonded together in a pendent manner or may be fused. Examples of the unsubstituted aryl group are a phenyl group, a biphenyl group, a triphenyl group and a pentaphenyl group. At least one of the hydrogen atoms of the aryl group may be substituted with a C1-C5 alkyl group, a C1-C5 alkoxy group, a C6-C14 aryl group, a C6-C20 aryloxy group, a halogen atom, an amino group, a cyano group, or the like. More particular examples of the aryl group applied to the compound of Formula I are a phenyl group, an ethylphenyl group, a biphenyl group, an ethylbiphenyl group, an o-, m- and p-fluorophenyl group, a dichlorophenyl group, a dicyanophenyl group, a trifluoromethoxyphenyl group, an o-, m-, and p-tolyl group, a mesityl group, a phenoxyphenyl group, a mesitylyl group, a (α,α-dimethylbenzene)phenyl group, a (N,N'-dimethyl)aminophenyl group and a (N,N'-diphenyl)aminophenyl group, but are not limited thereto.

Examples of the unsubstituted heteroaryl group applied to the compound of Formula I are a furanyl group, a pyridinyl group, and a thiophenyl group. At least one of the hydrogen atoms of the heteroaryl group may be substituted with a C1-C5 alkyl group, or the like.

Examples of the unsubstituted fused polycyclic group applied to the compound of Formula I are a pentalenyl group, a naphthyl group, an azulenyl group, a heptalenyl group, an acenaphtyl group, an anthryl group, a phenanthryl group, a quinolyl group, an anthraquinolyl group, a fluorenyl group, and a carbazolyl group. At least one of the hydrogen atoms of the fused polycyclic group may be substituted with a C1-C5 alkyl group, a C1-C5 alkoxy group, a C6-C14 aryl group, a C6-C20 aryloxy group, a halogen atom, an amino group or a cyano group. More particular examples of the unsubstituted fused polycyclic group applied to the compound of Formula I are a pentalenyl group, a naphthyl group, a methylnaphthyl group, an anthracenyl group, an azulenyl group, a heptalenyl group, an acenaphthylenyl group, a fluorenyl group, a 9,9-dimethylfluorenyl group, an anthraquinolyl group, a phenanthryl group, a triphenylene group, a carbazolyl group, and a 9-phenylcarbazolyl group, but are not limited thereto.

Examples of the unsubstituted aryloxy group applied to the compound of Formula I are a phenyloxy group, a naphthyloxy group, an anthryloxy group, and a phenanthryloxy group. At least one of the hydrogen atoms of the aryloxy group may be substituted with a C1-C5 alkyl group, a C1-C5 alkoxy group, a C6-C14 aryl group, a C6-C20 aryloxy group, a halogen atom, an amino group or a cyano group.

$Ar_2$ and $Ar_3$ may be a cyclic compound having 1-3 rings selected from the group consisting of a phenyl group, a naphthyl group, a biphenyl group, a fluorenyl group or a carbazolyl group, wherein 1-4 hydrogen atoms of the cyclic compound are optionally substituted with a C1-C4 short-chain alkyl group, a C1-C5 short-chain alkoxy group, a cyano group, an amino group, a phenoxy group, a phenyl group or a halogen atom. Preferably, $Ar_2$ and $Ar_3$ may be selected from the group consisting of a phenyl group, a tolyl group, a fluorophenyl group, a biphenyl group, a (N,N'-diphenyl)aminophenyl group, a naphthyl group, a phenylcarbazolyl group and a dimethylfluorenyl group.

$Ar_4$ may be a cyclic compound having 1-3 rings and a phenoxy group, wherein 1-4 hydrogen atoms of the cyclic compound may be substituted with a C1-C4 short-chain alkyl group, a C1-C5 short-chain alkoxy group, a cyano group, an amino group, a phenoxy group, a phenyl group or a halogen atom. Preferably, $Ar_4$ may be selected from the group consisting of a phenyl group, a tolyl group, a cyanophenyl group, a fluorophenyl group, a biphenyl group, a naphthyl group and a naphthylphenyl group.

When the $Ar_1$ and $Ar_3$ or $Ar_2$ and $Ar_3$ are connected to each other in the compound of Formula I to form a ring, the ring may be a carbazolyl group.

The compound represented by Formula I functions as a hole injecting material, a hole transporting material and/or an emitting material. In addition, since the heterocyclic compound of Formula I according to an embodiment of the present invention includes a rigid 3-ring structure in the center, a glass transition temperature (Tg) or a melting point of the compound is increased. Accordingly, the organic light emitting device has increased thermal resistance against Joule's heat generated in the organic layer, between the organic layers and between the organic layer and a metal electrode and is stable in a hot environment. Thus, the organic light emitting device according to an embodiment of the present invention has high durability during storage and operation.

Examples of the heterocyclic compound represented by Formula I may be the compounds represented by Formulae 1 to 183, and preferably Formulae 1, 13, 25, 37, 49, 61, 73, 85 and 112 shown below, but are not limited thereto.

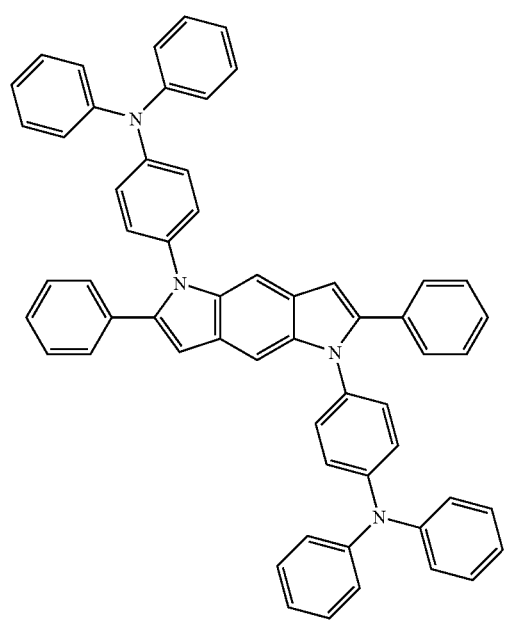

1

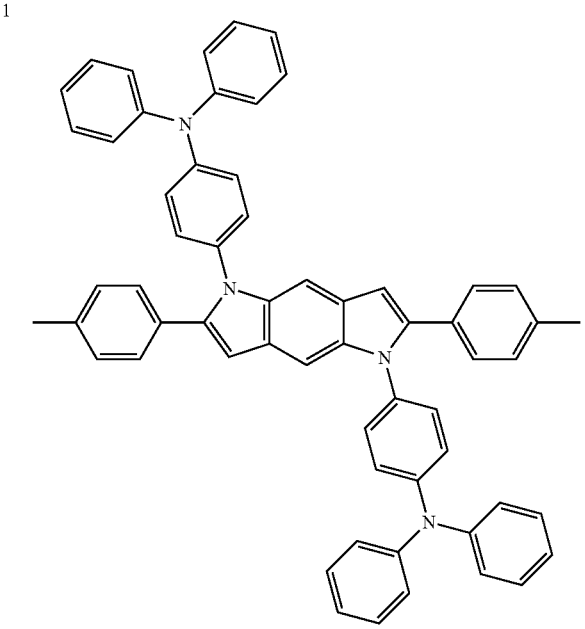

2

-continued
3
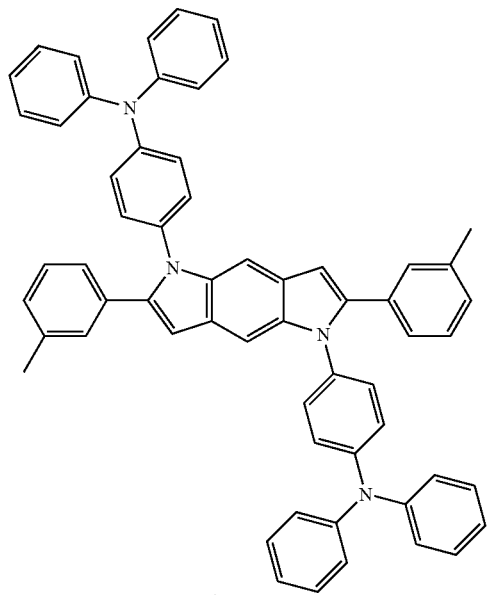
4
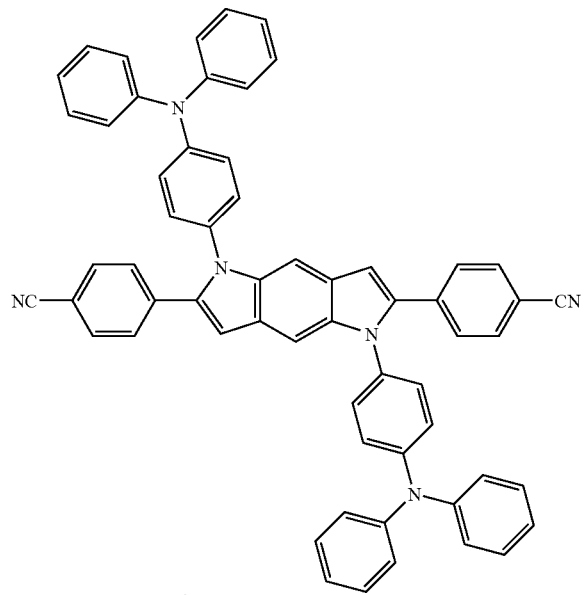
5
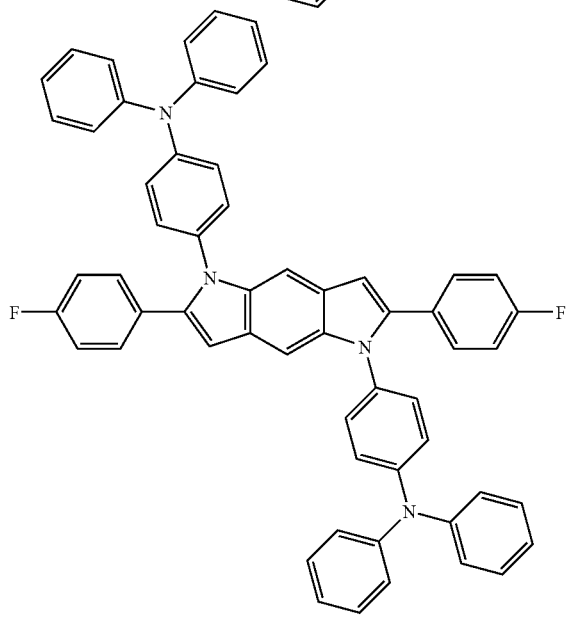
6
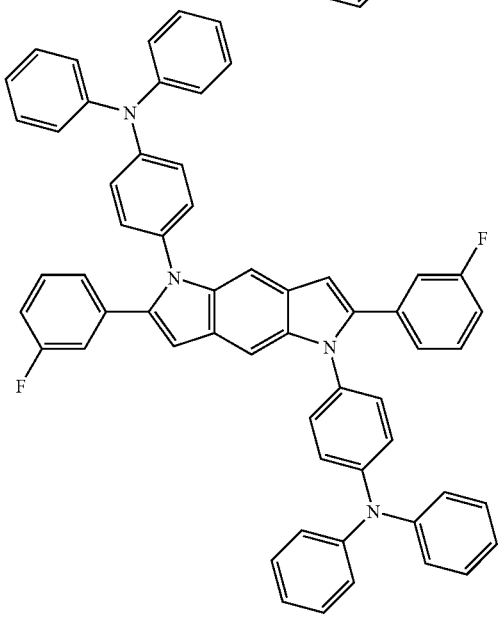
7
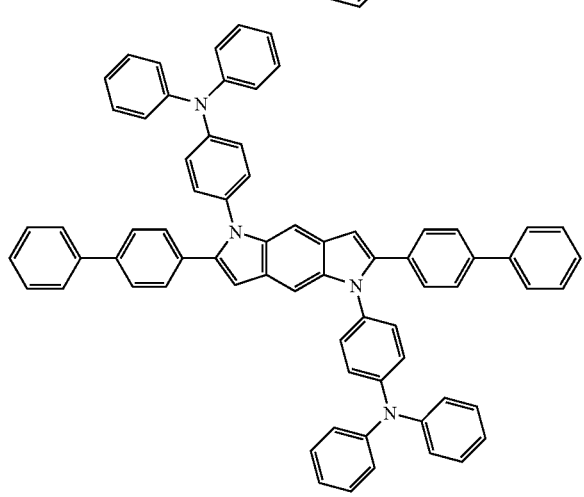
8
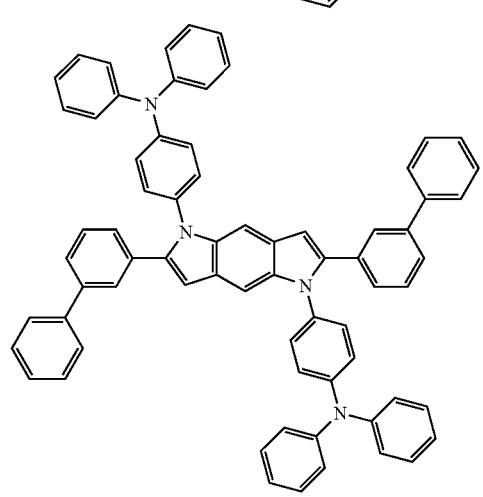

-continued
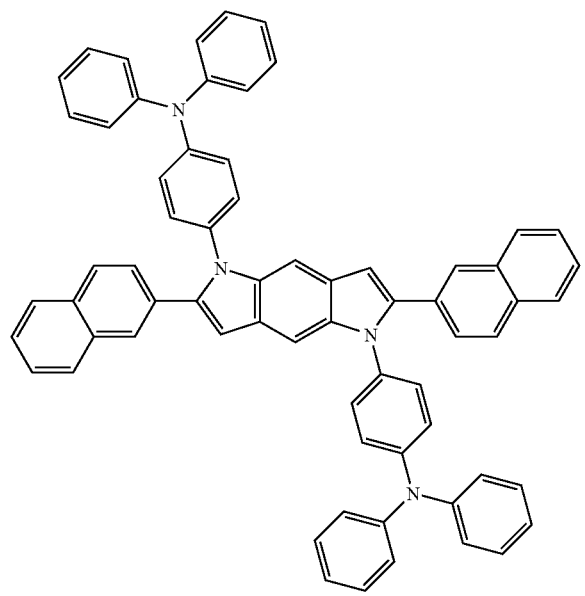
9
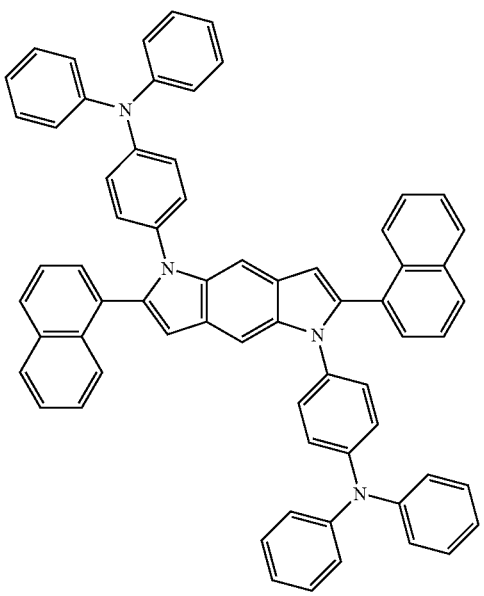
10
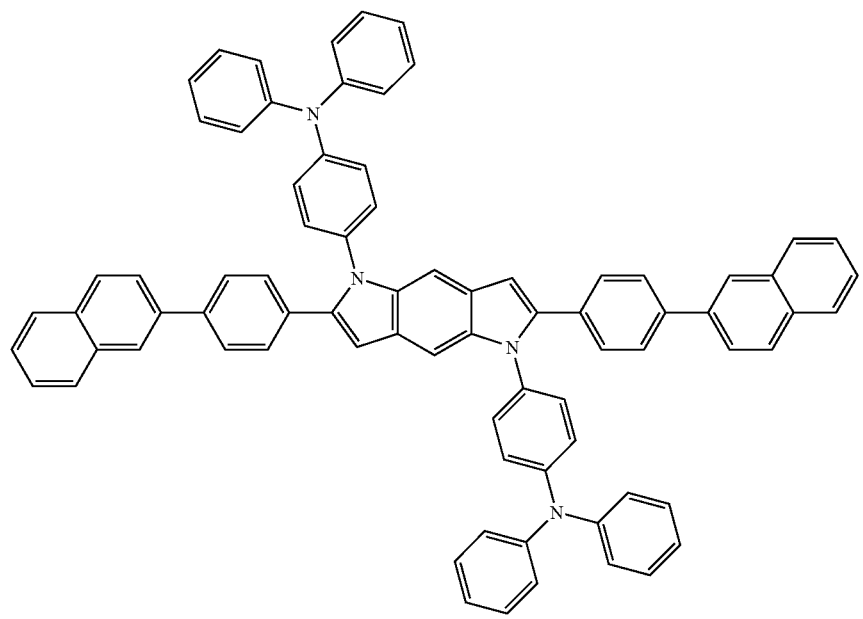
11

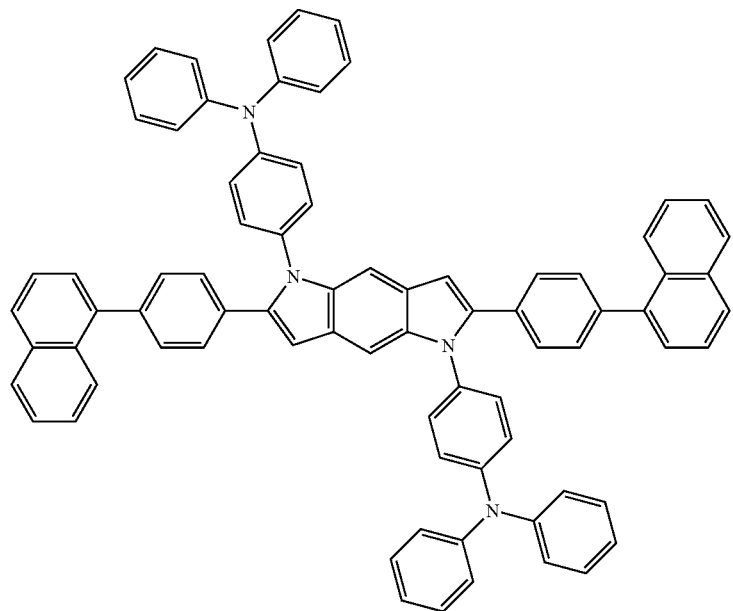
12
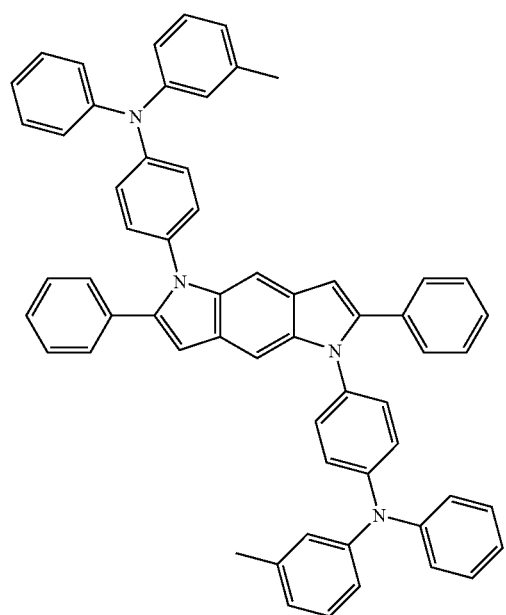
13
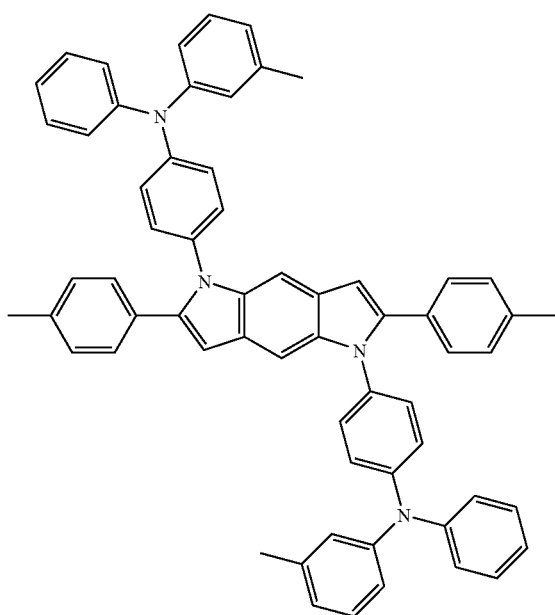
14

-continued
15
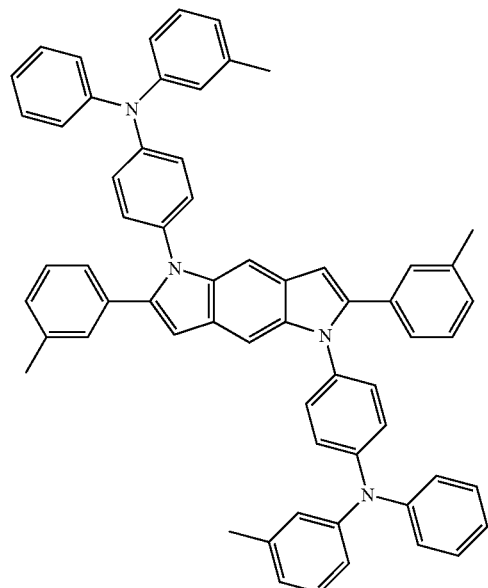
16
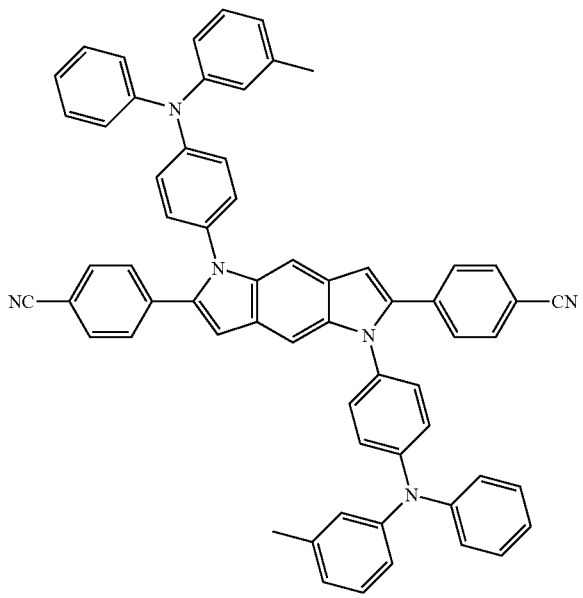
17
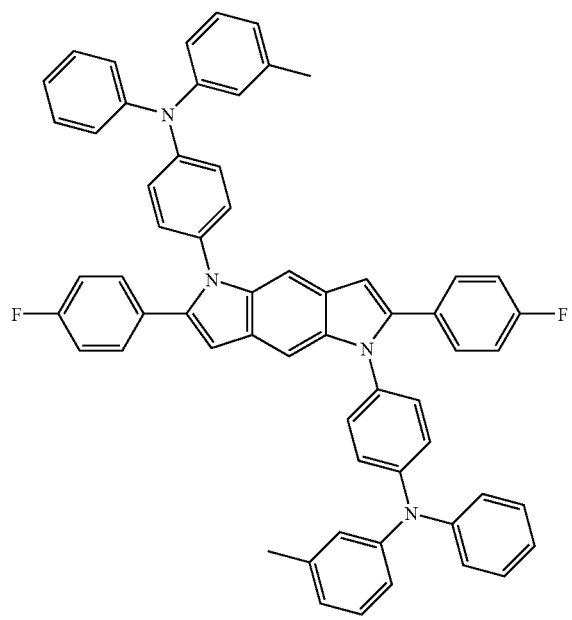
18
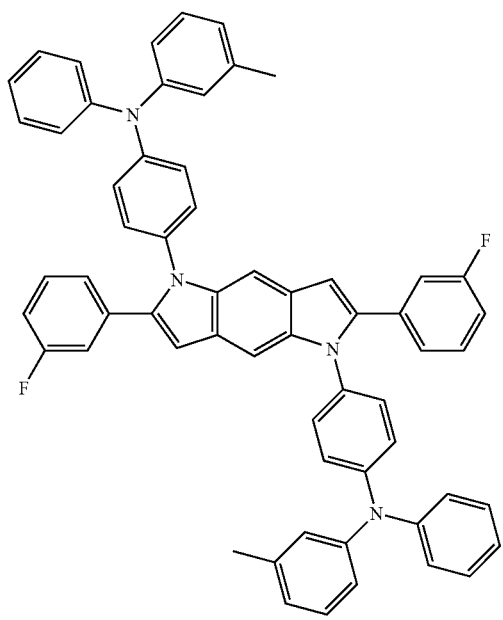

-continued
19
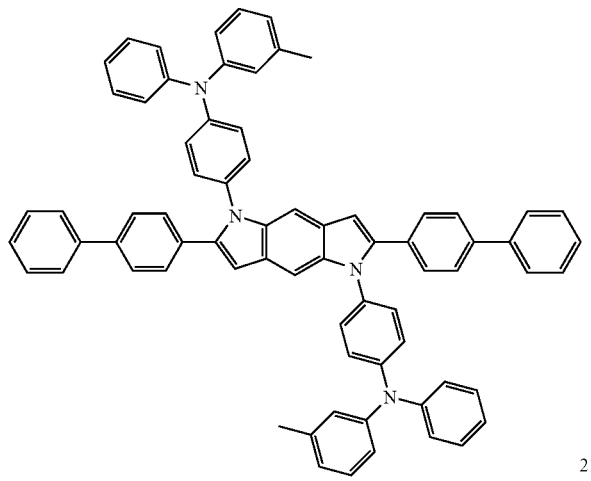
20
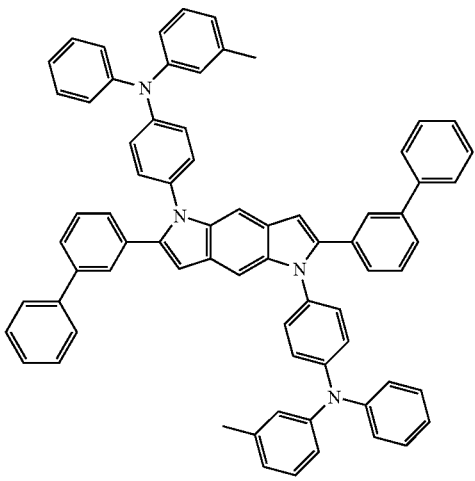
21
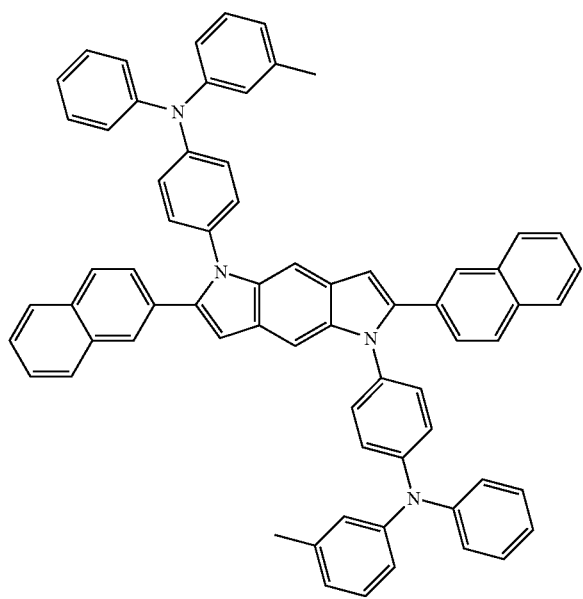
22
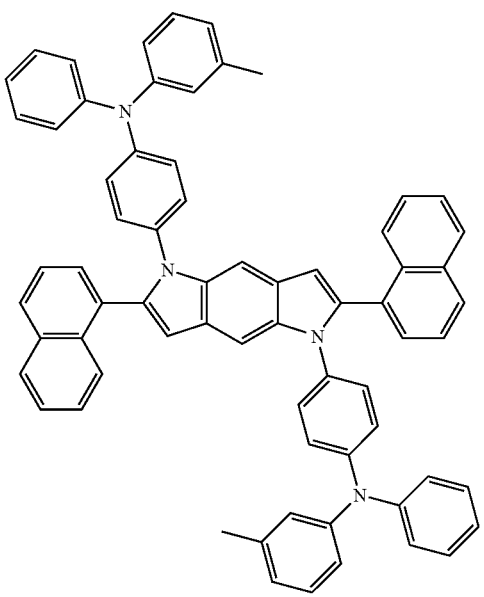
23
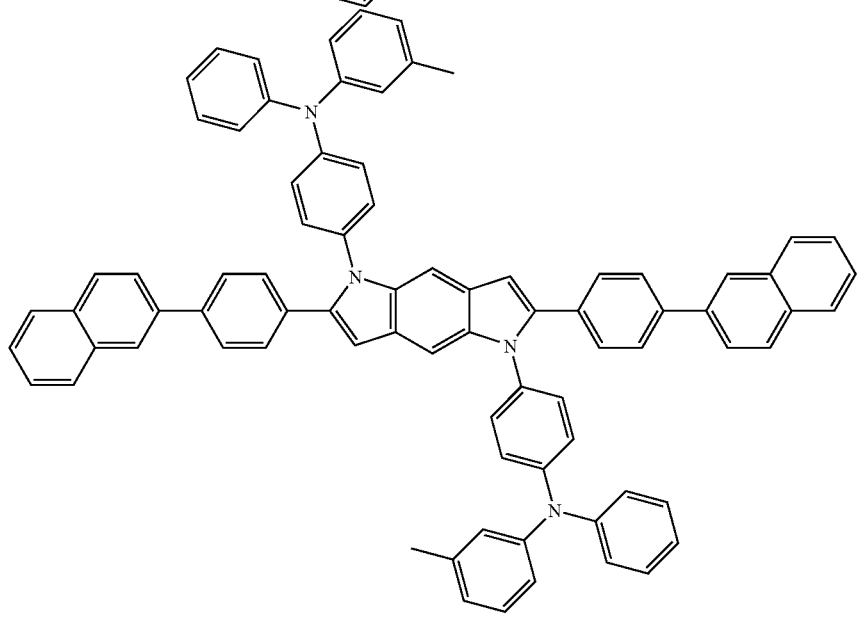

24
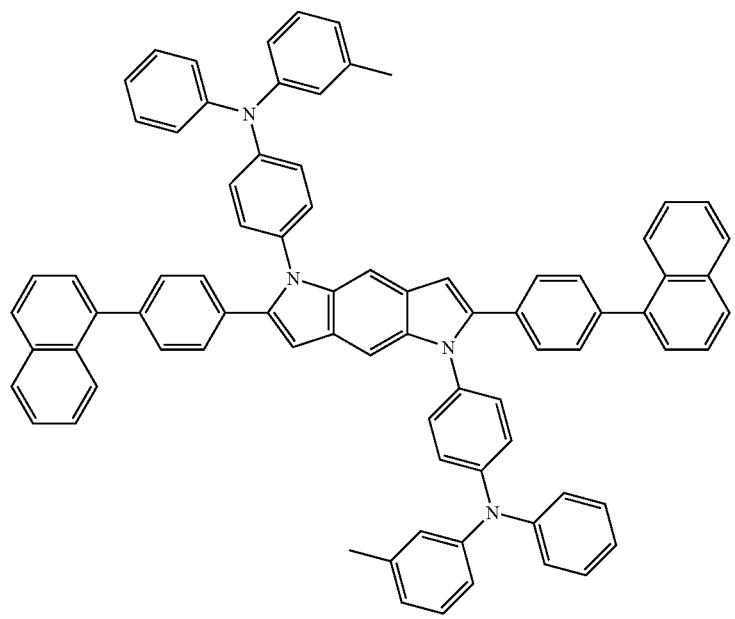
25
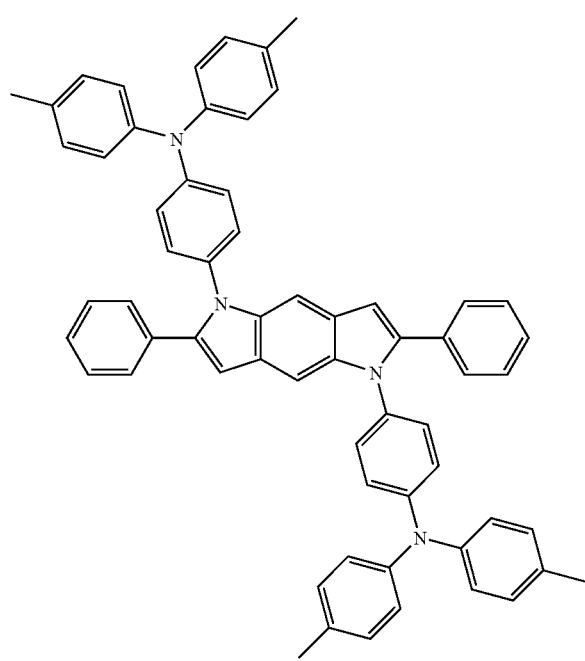
26
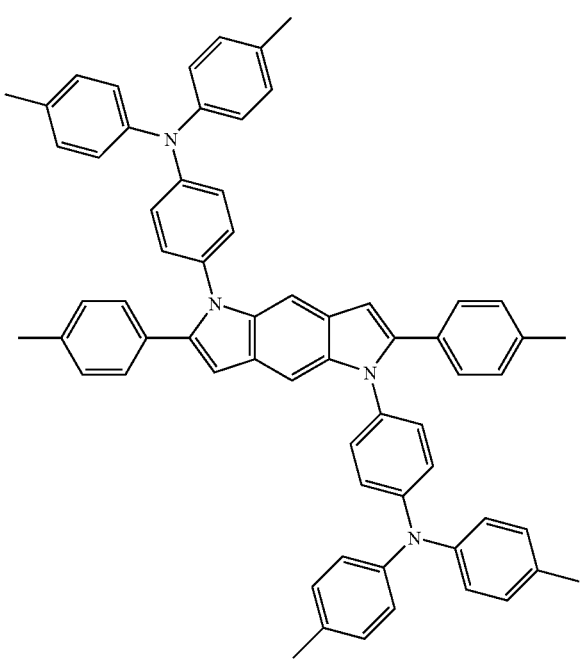

-continued
27
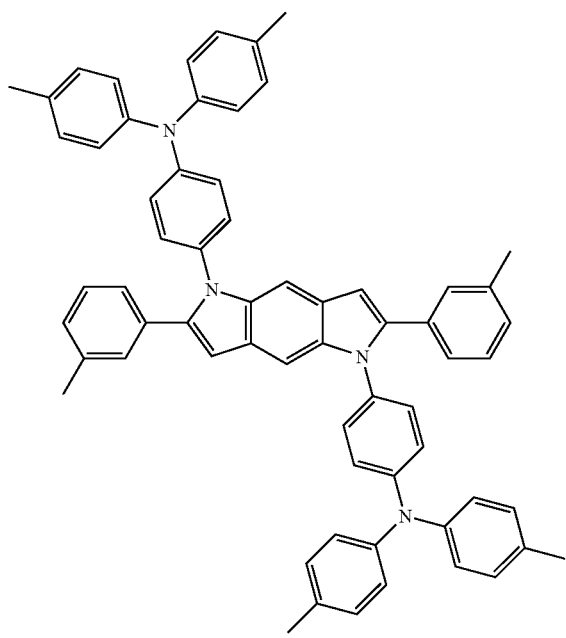
28
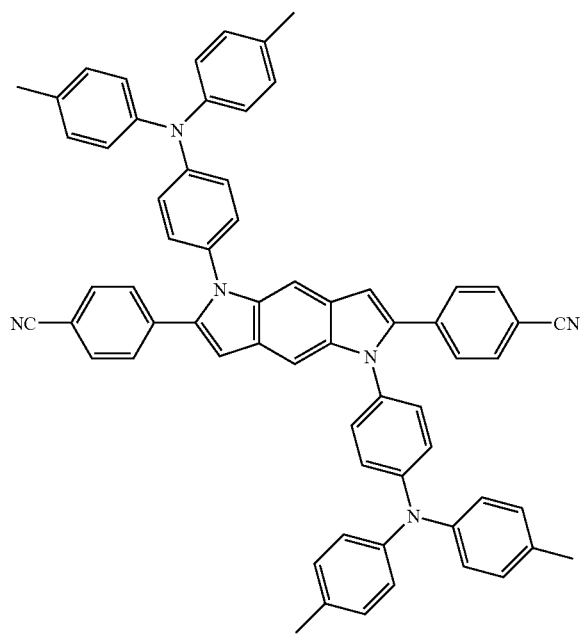
29
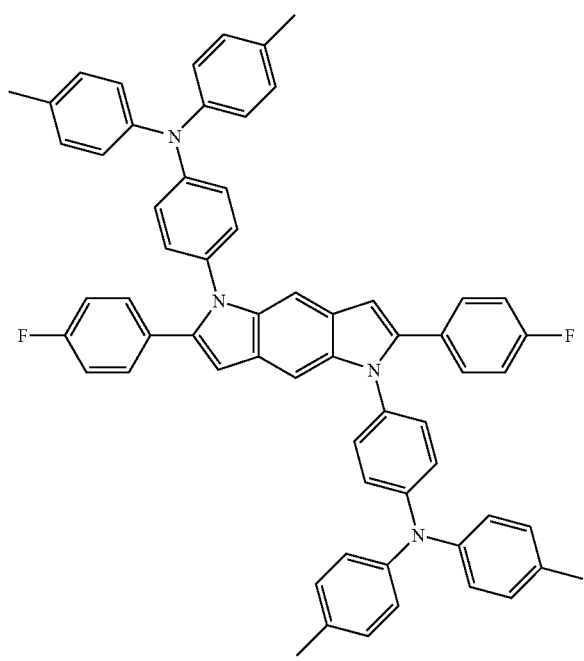
30
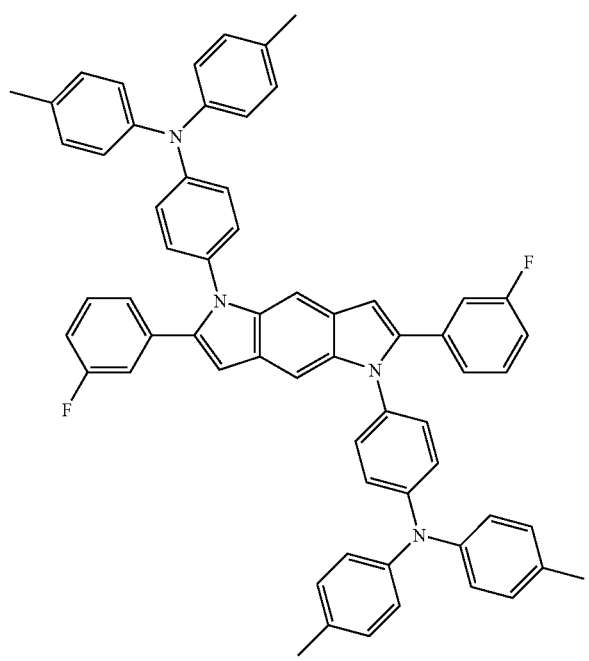

31
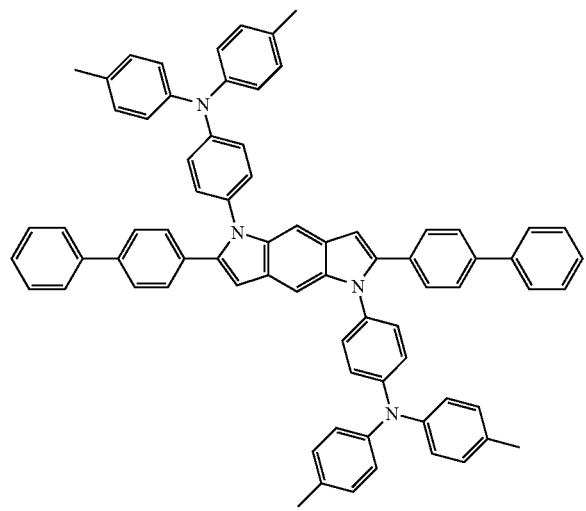
32
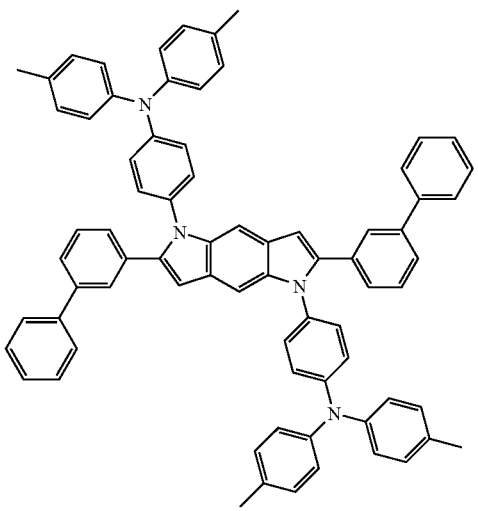
33
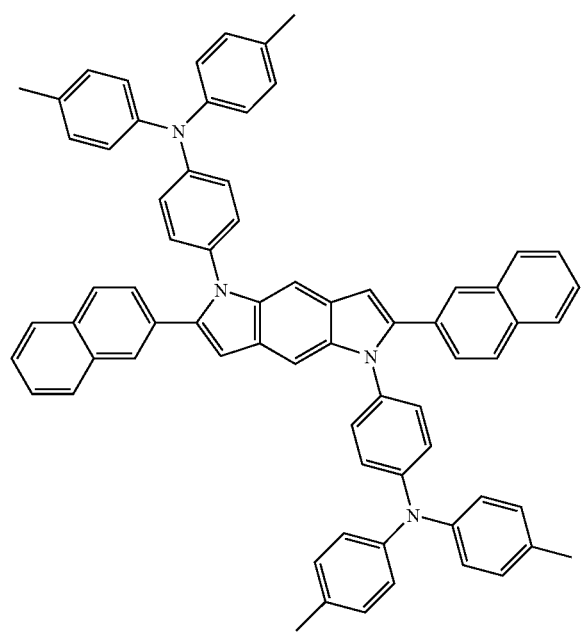
34
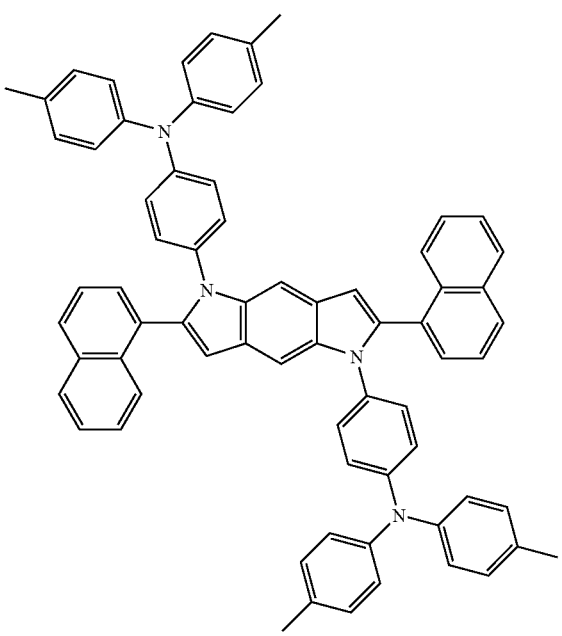

-continued
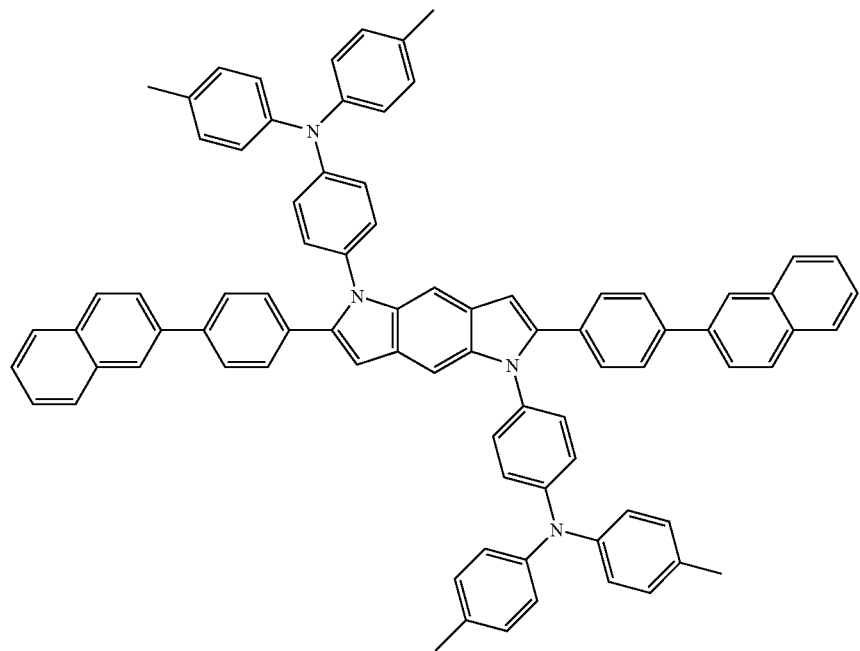
35
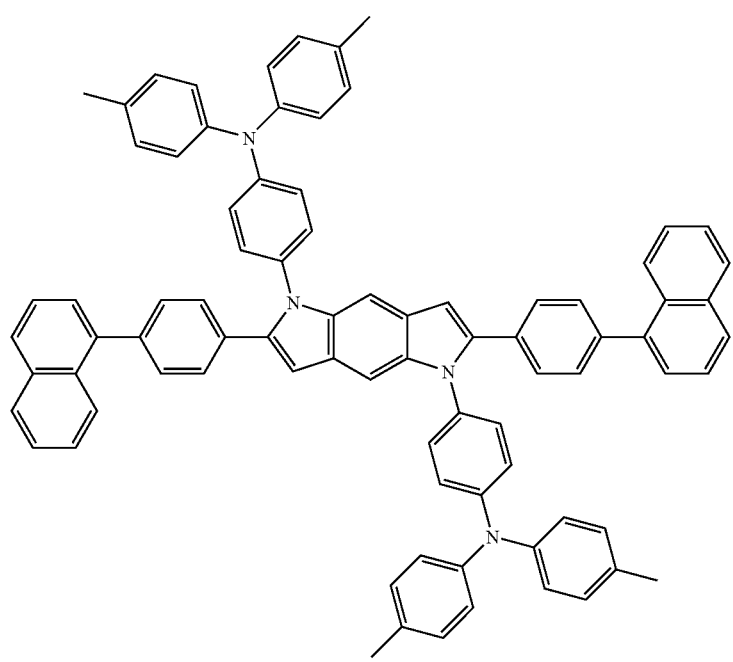
36

-continued
37
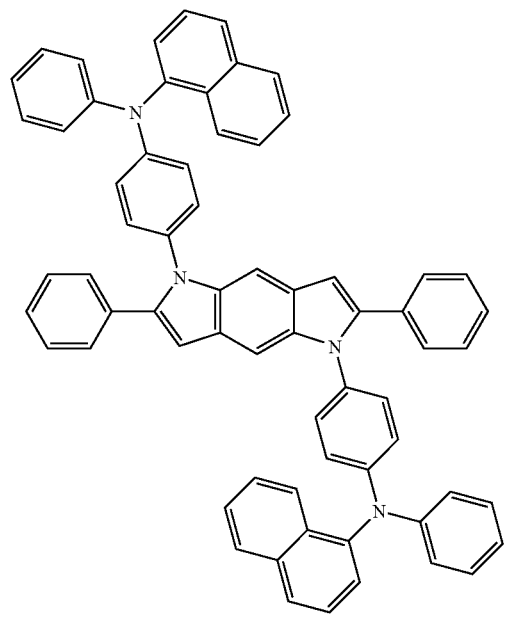
38
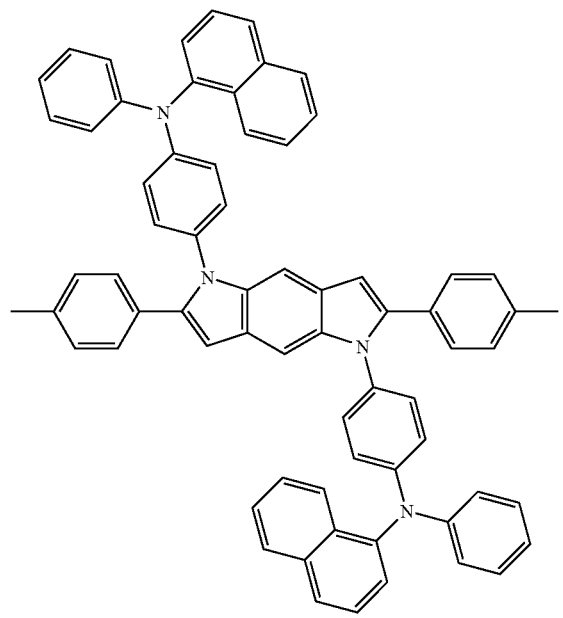
39
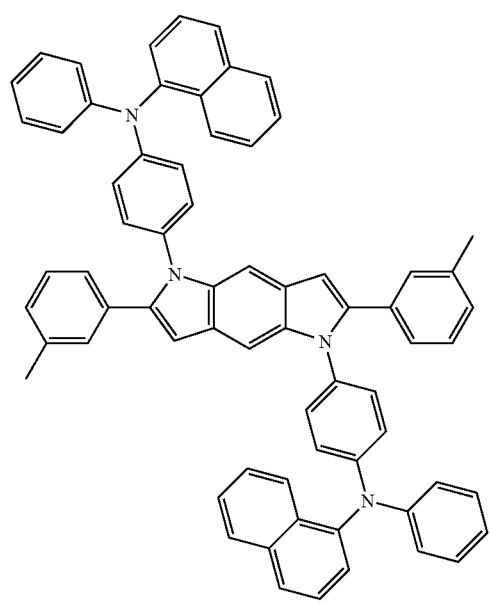
40
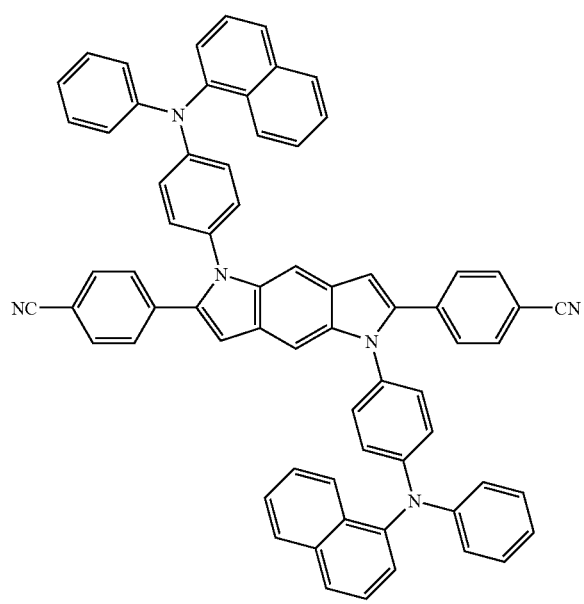

-continued
41
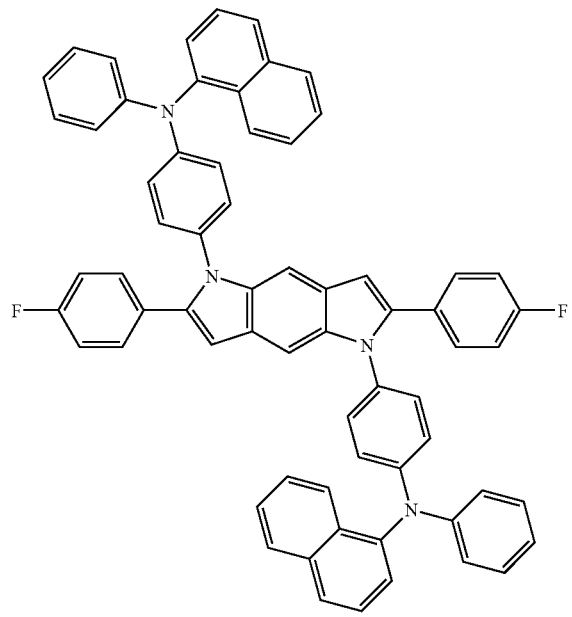
42
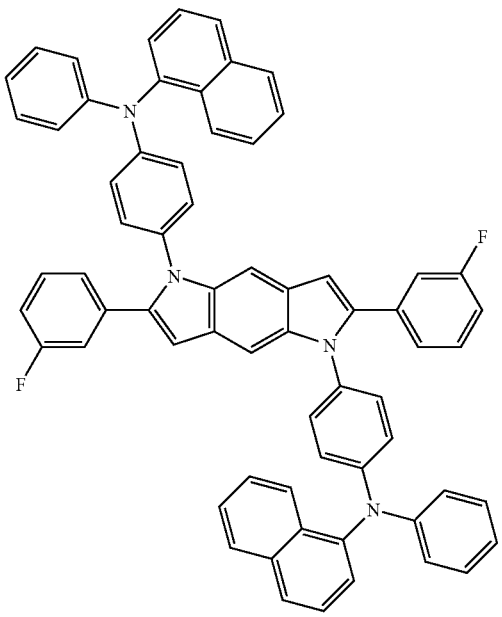
43
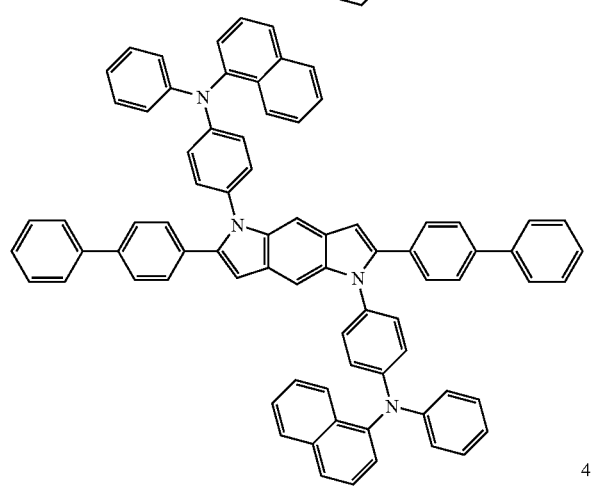
44
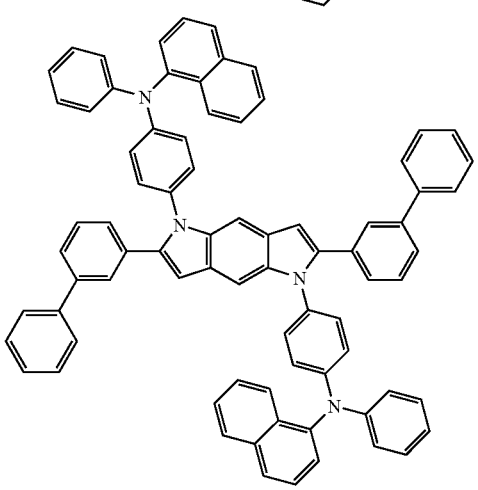
45
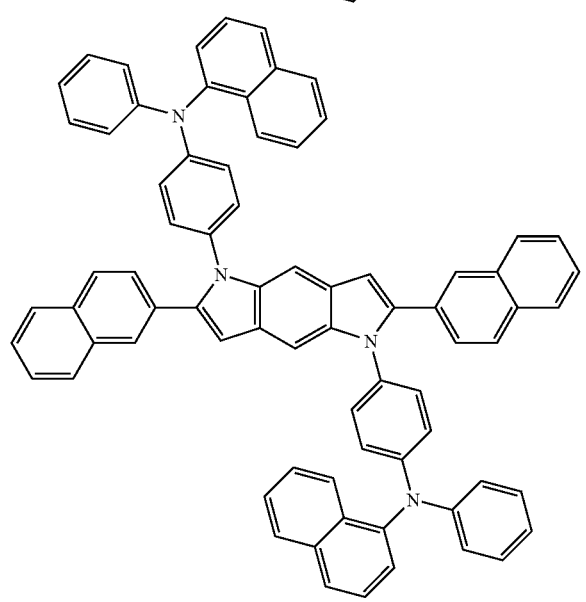
46
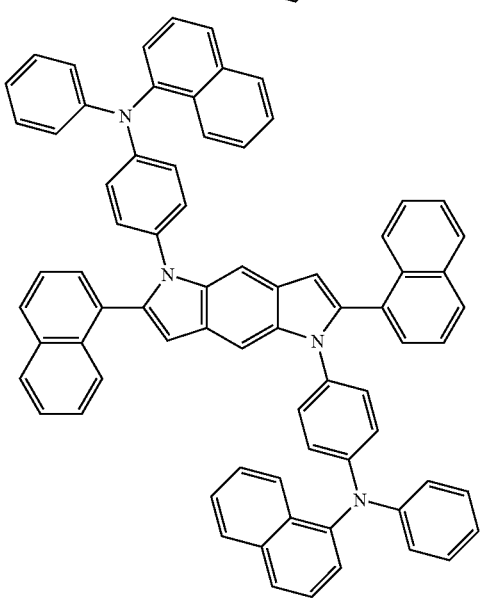

-continued
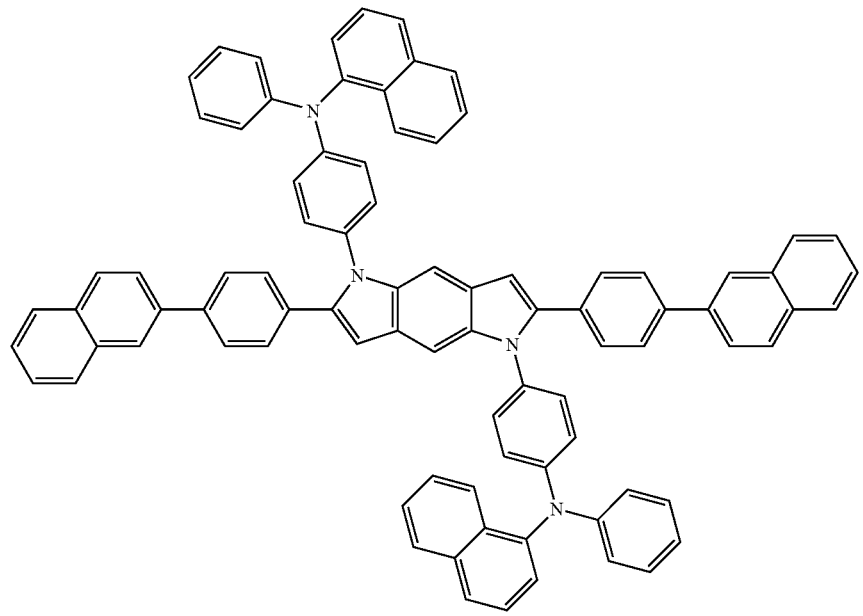
47
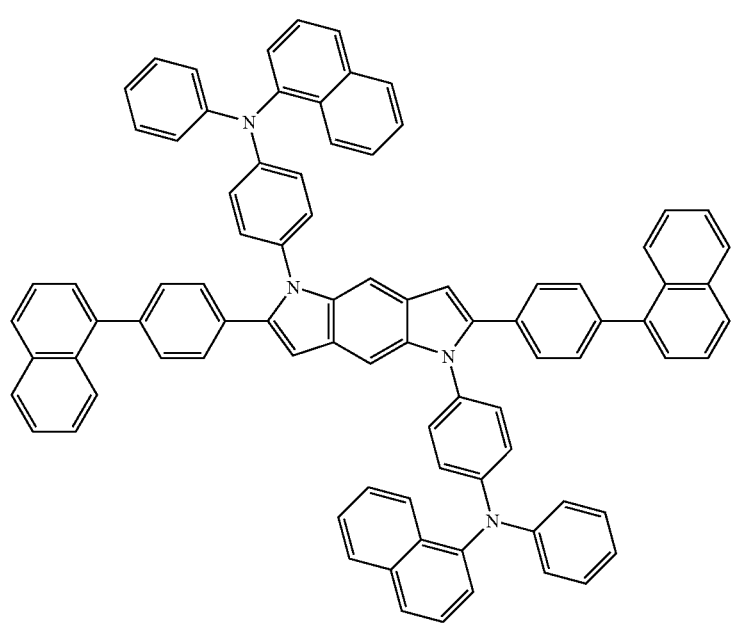
48

-continued
49
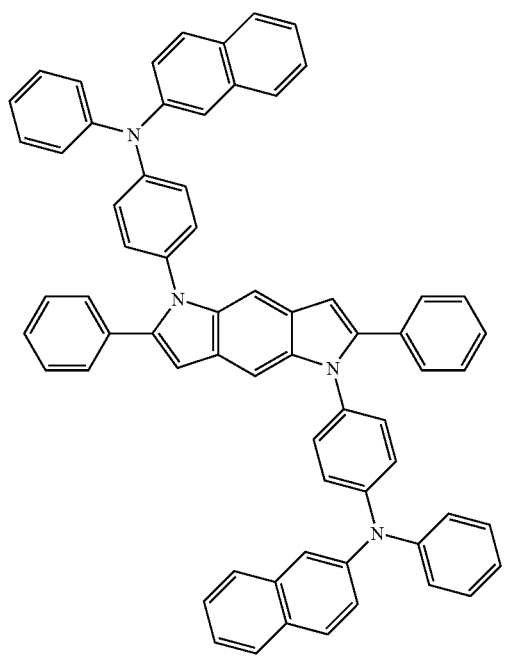
50
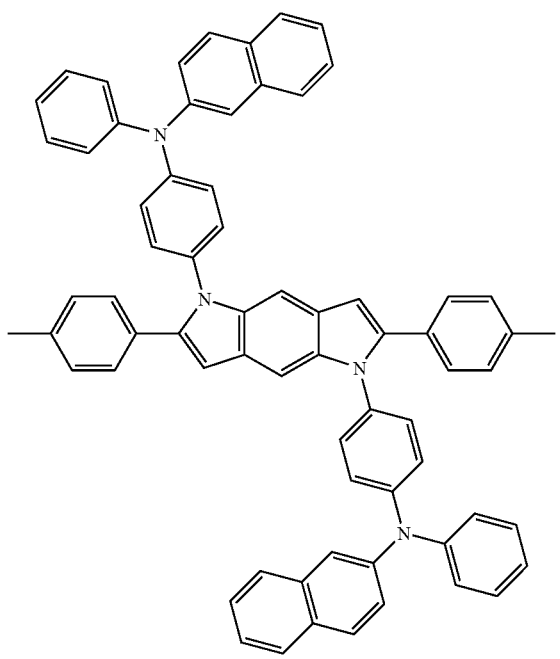
51
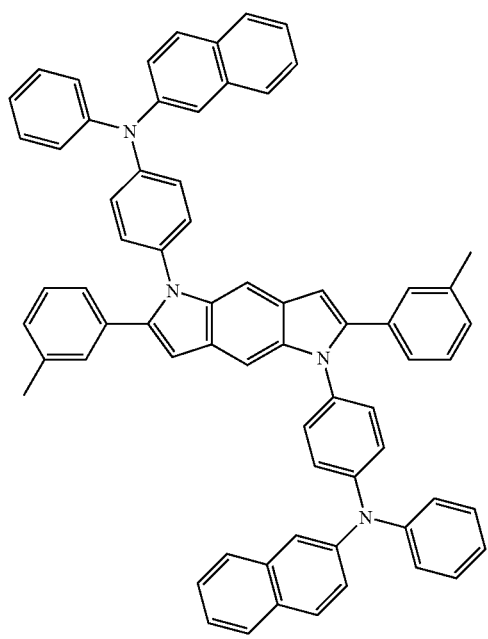
52
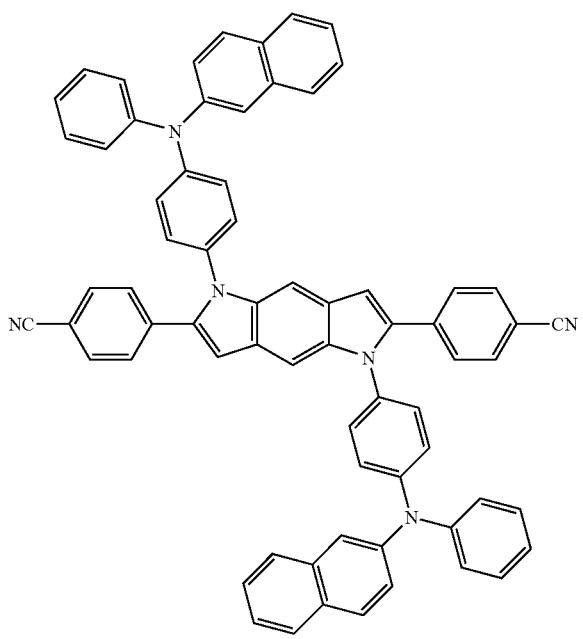

53
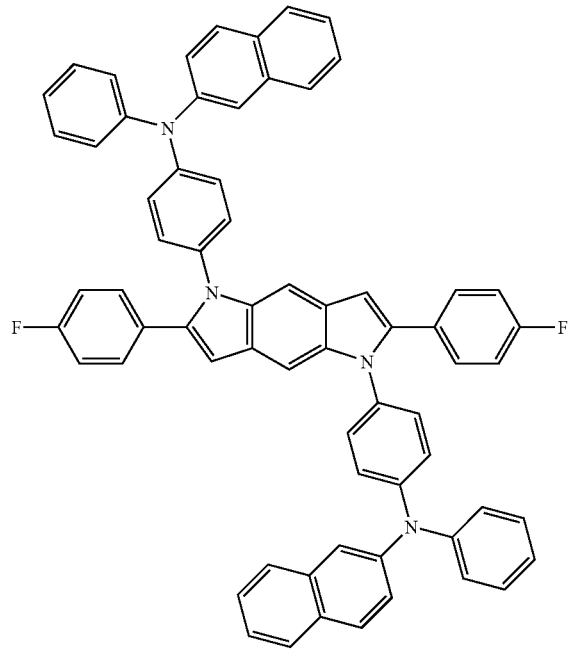
54
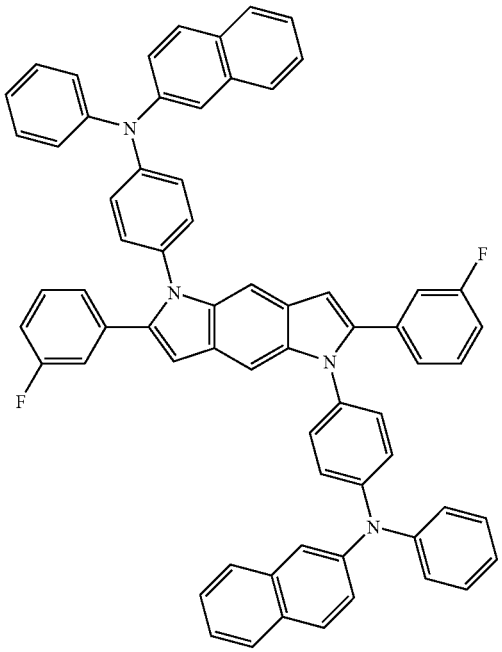
55
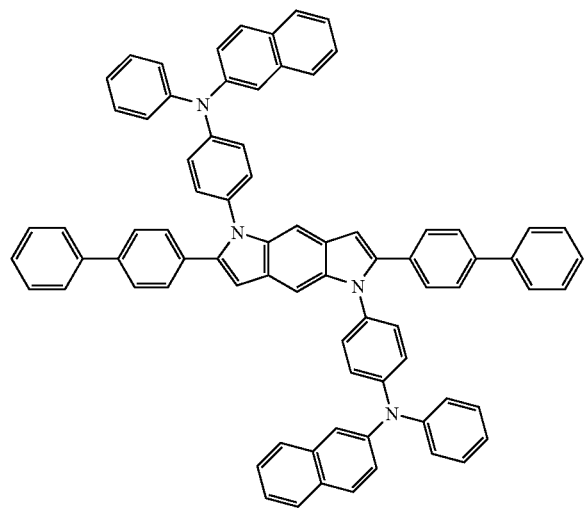
56
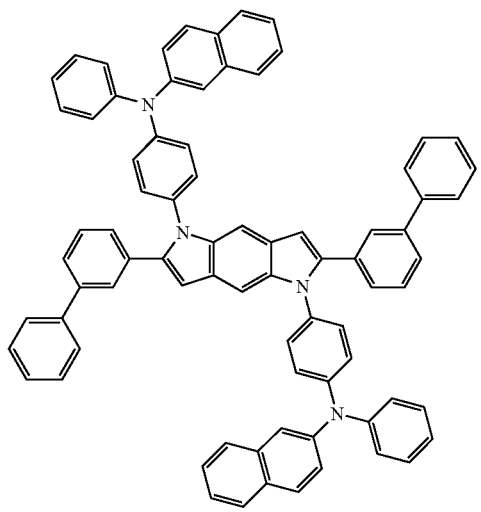

-continued
57
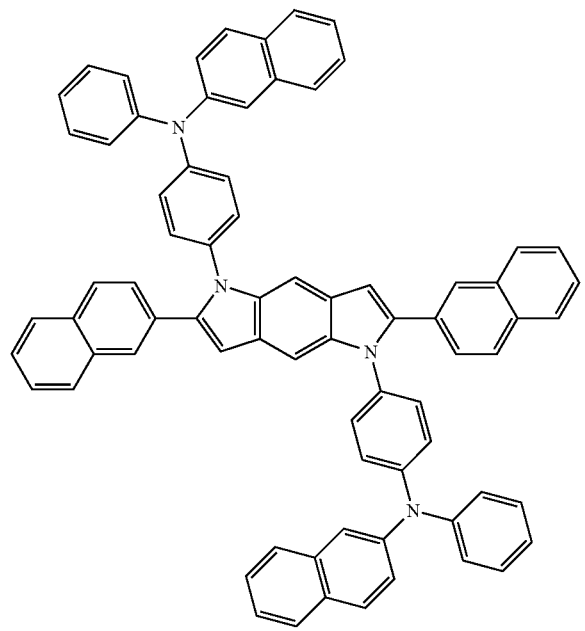
58
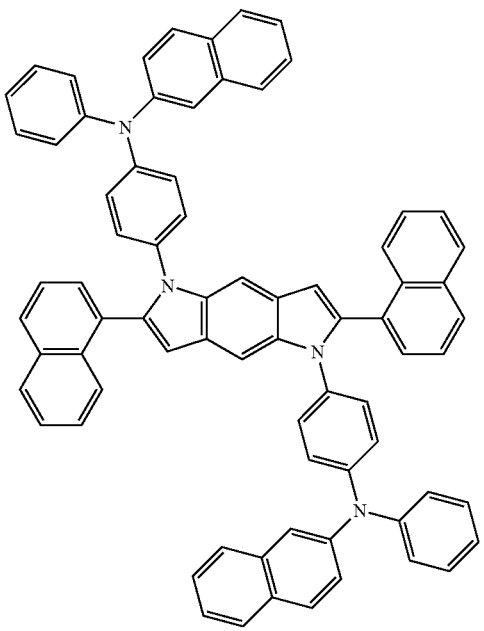
59
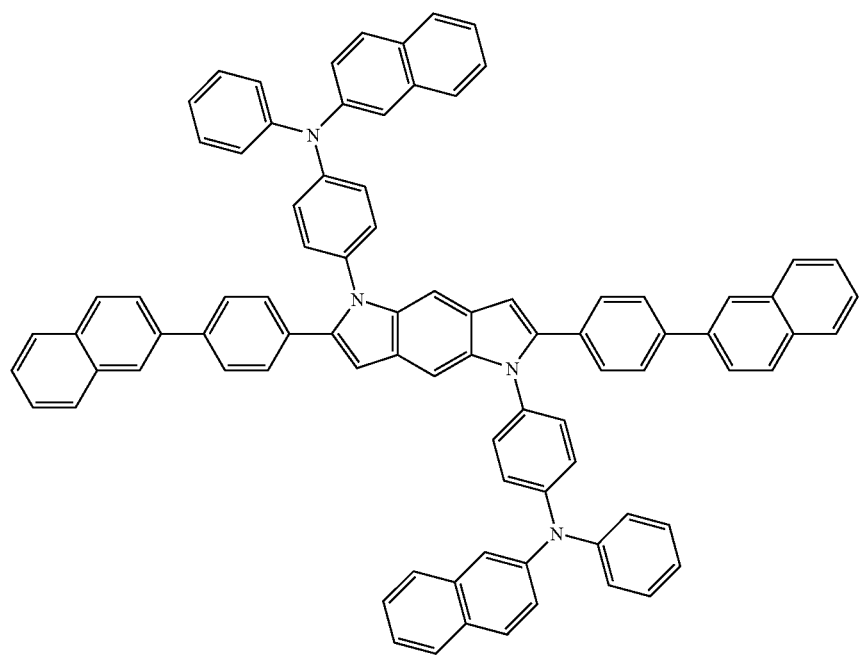

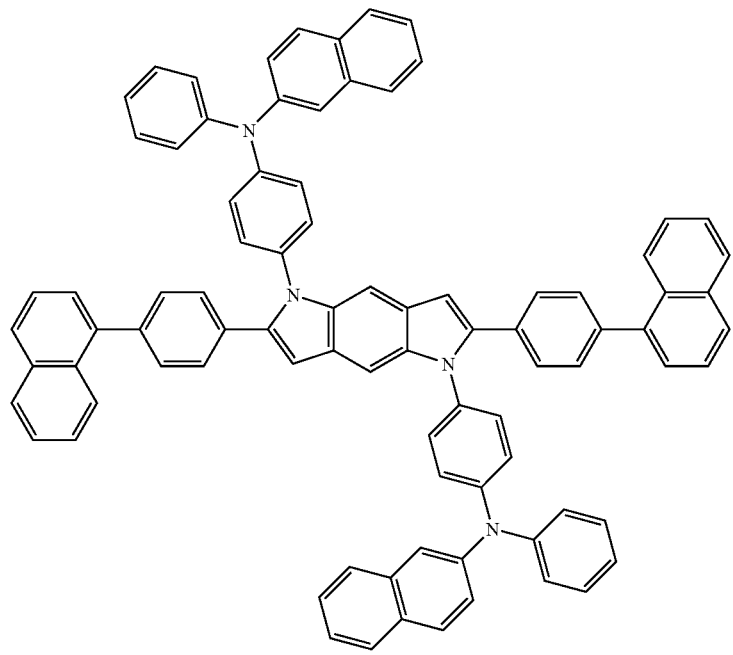
60
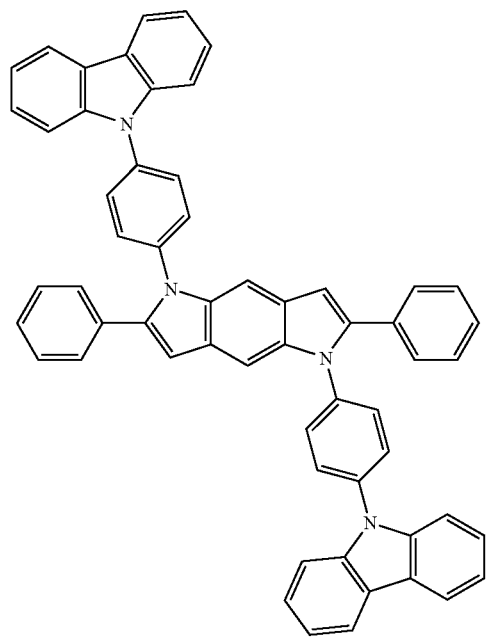
61
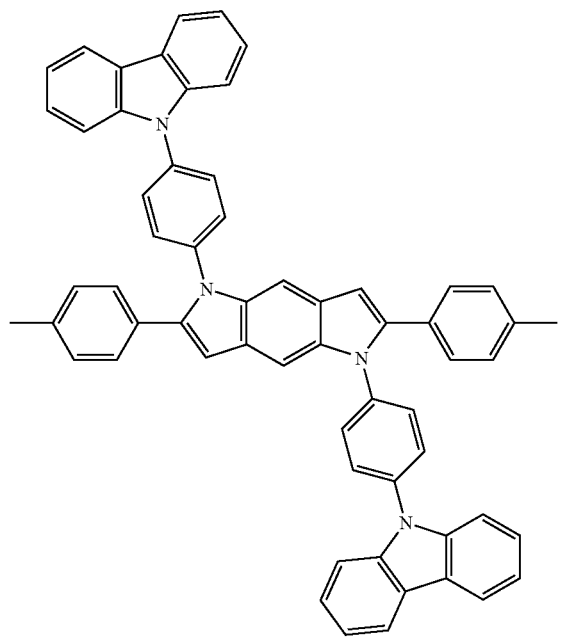
62

-continued
63
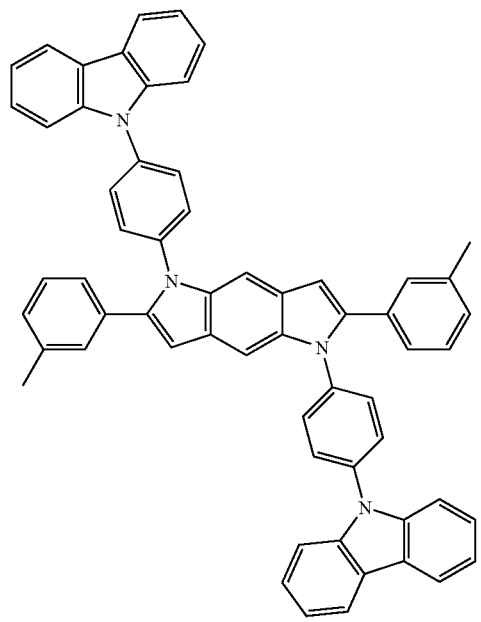
64
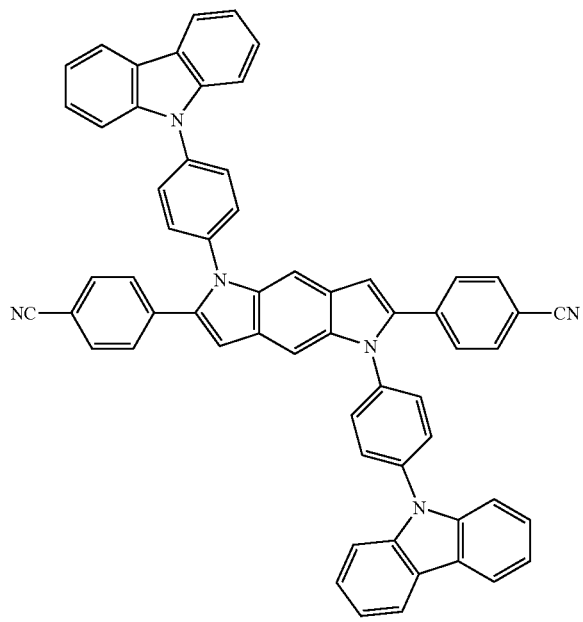
65
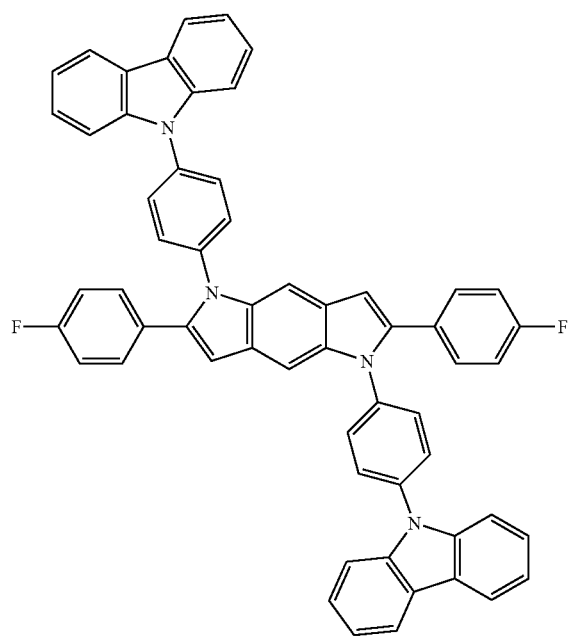
66
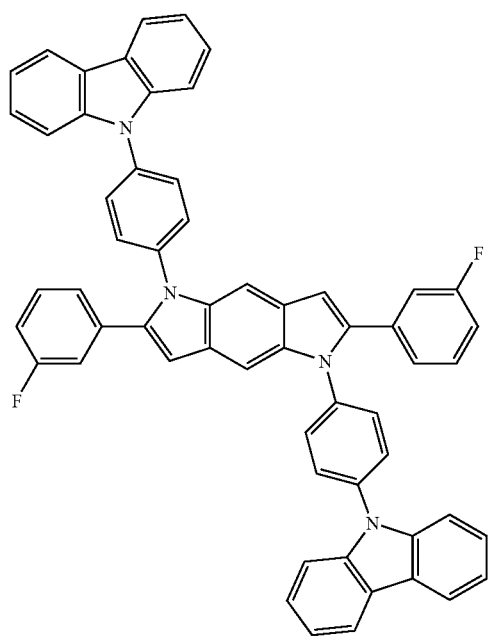

-continued
67
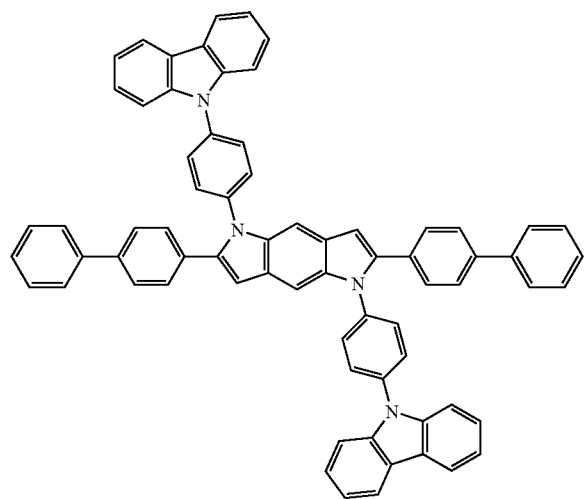
68
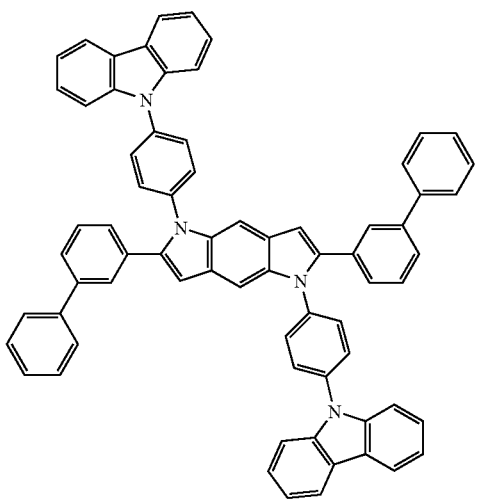
69
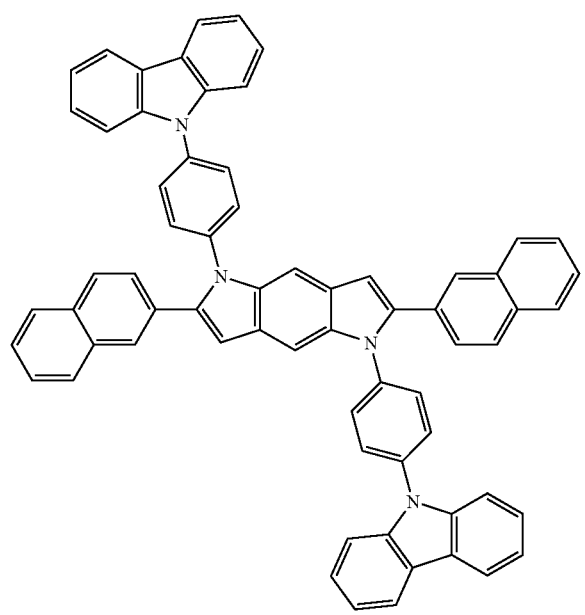
70
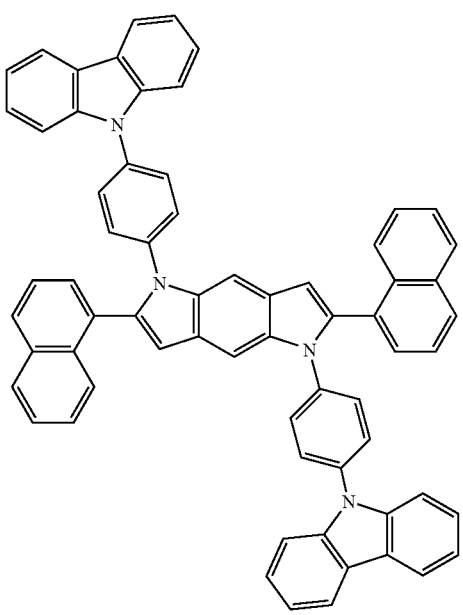

-continued
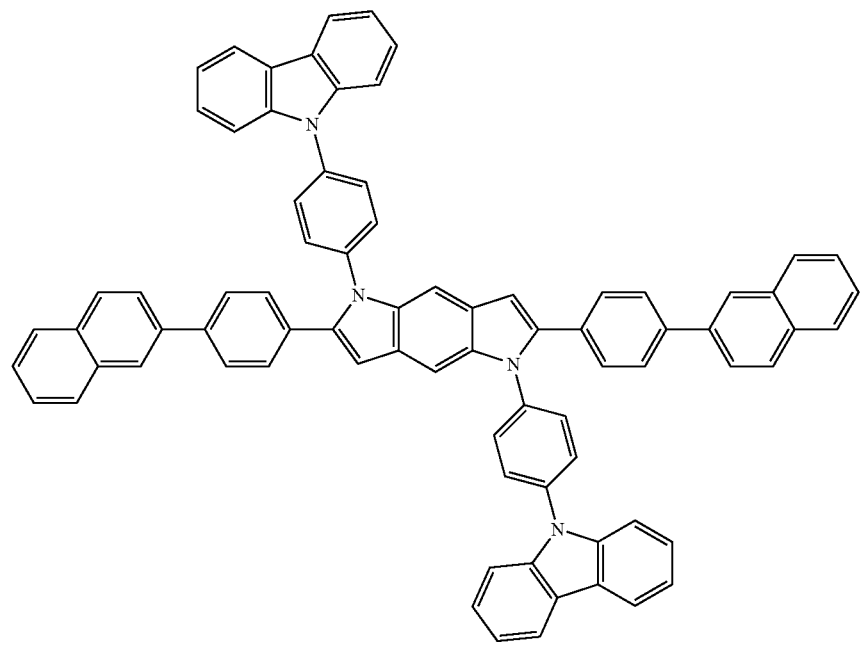
71
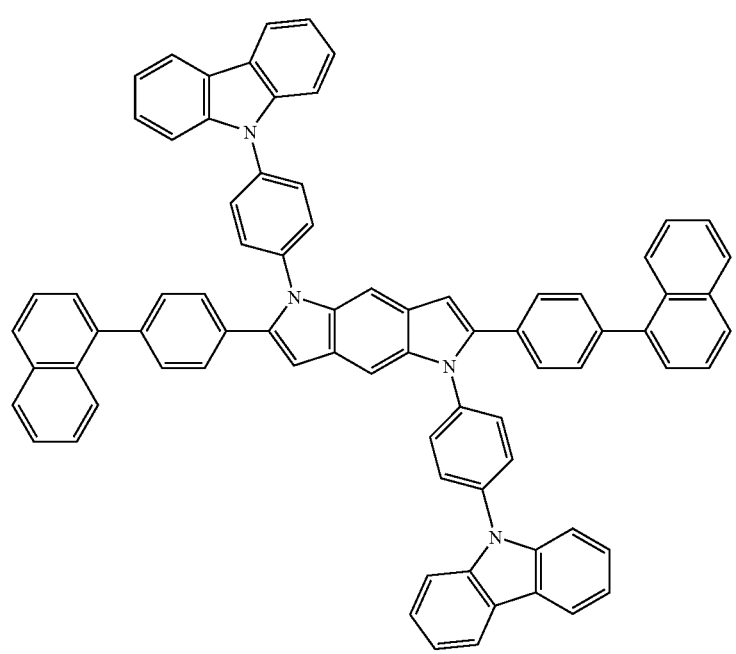
72

73
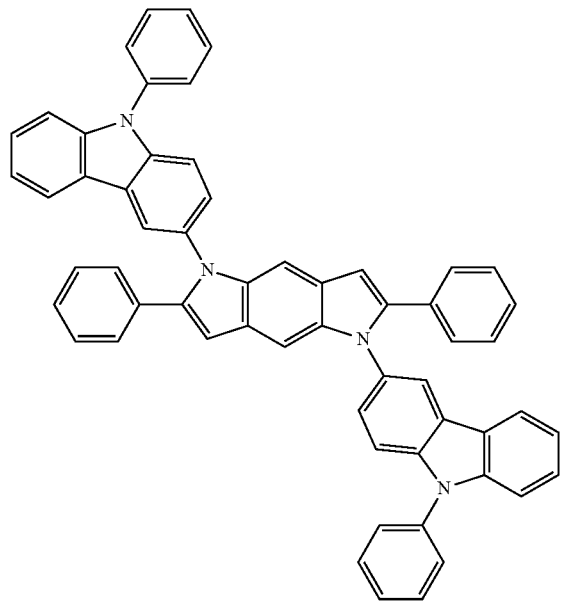
74
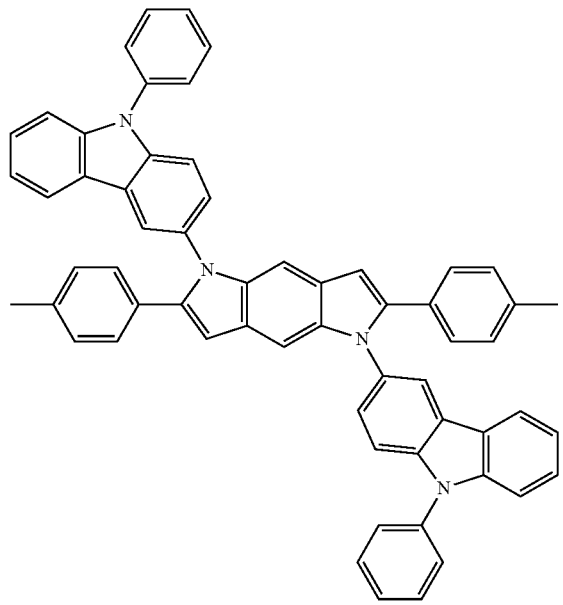
75
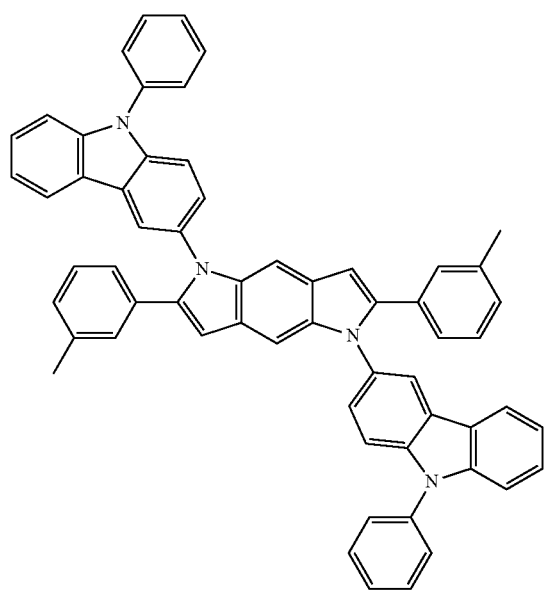
76
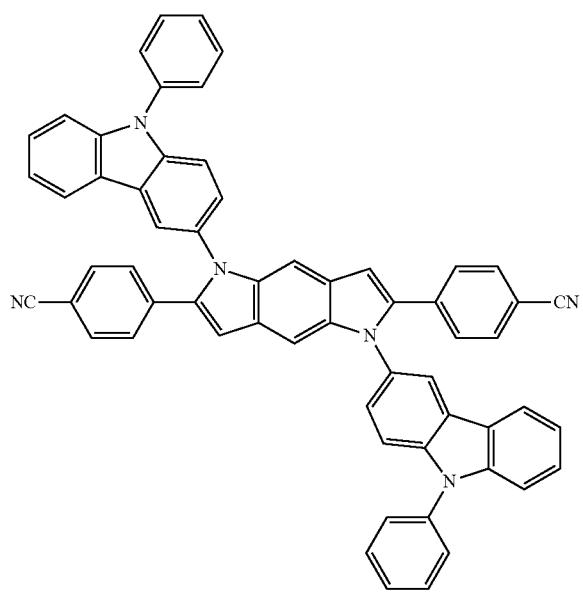

-continued
77
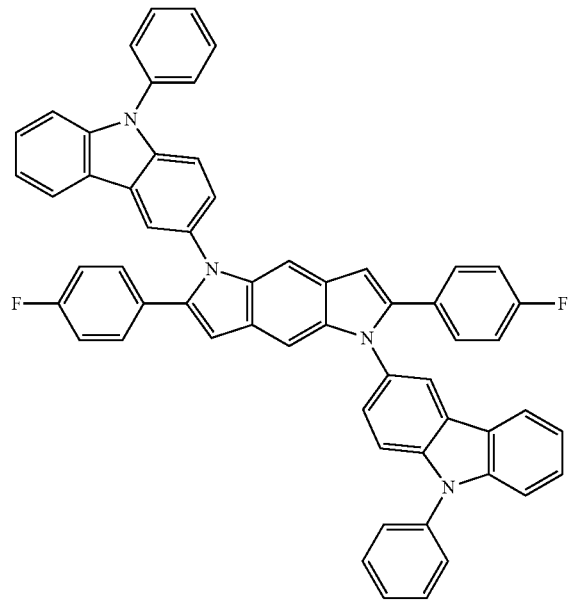
78
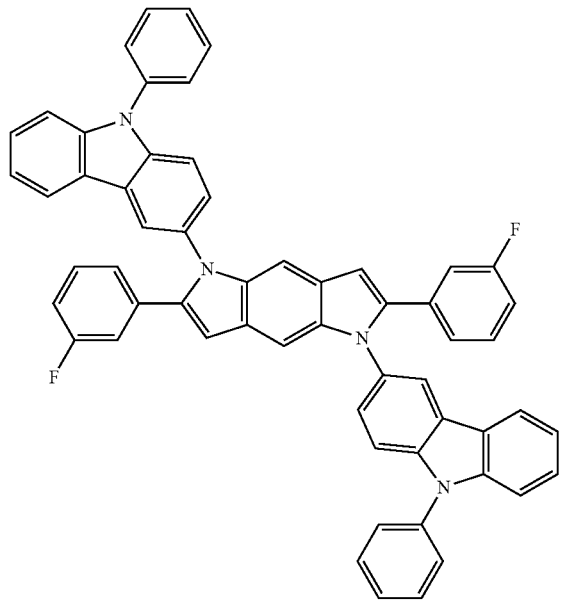
79
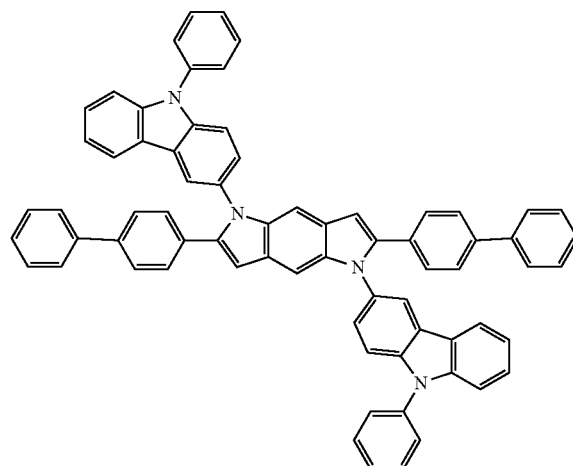
80
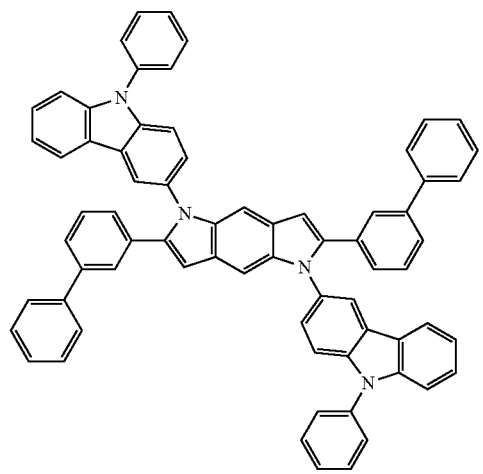
81
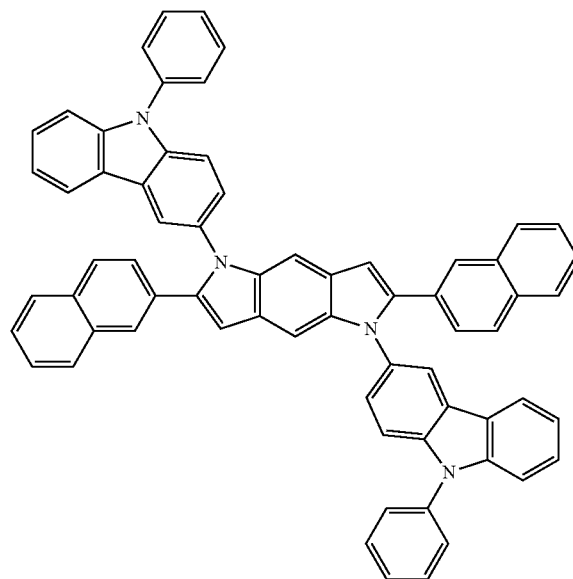
82
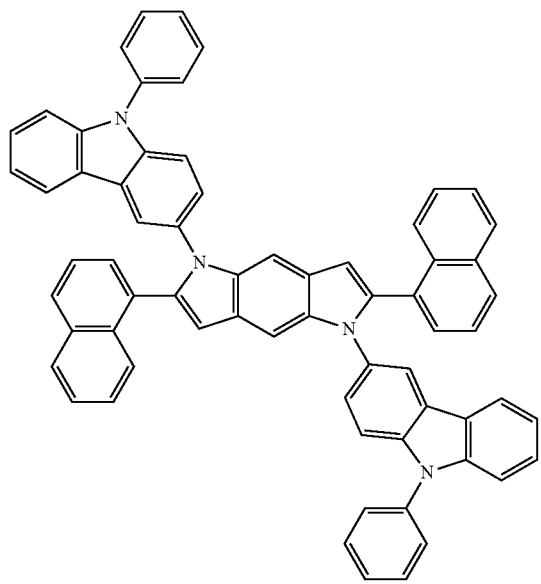

83
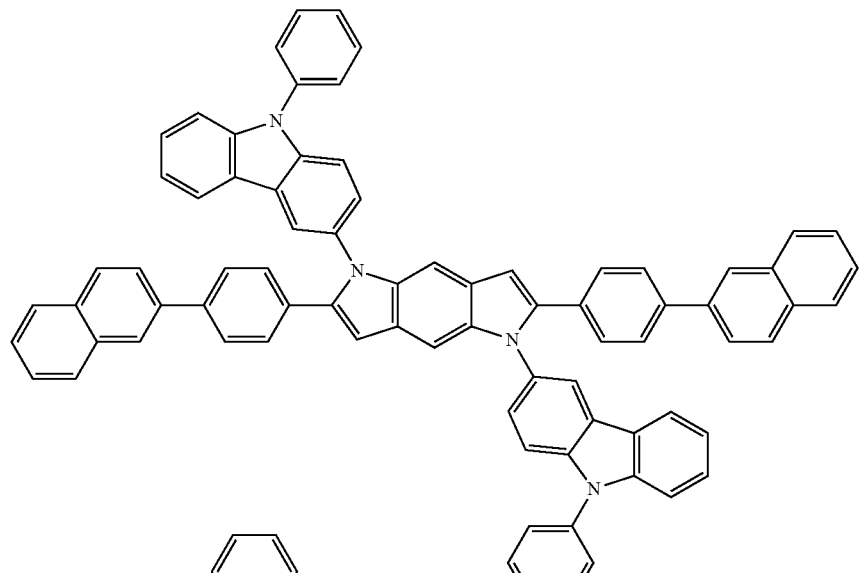
84
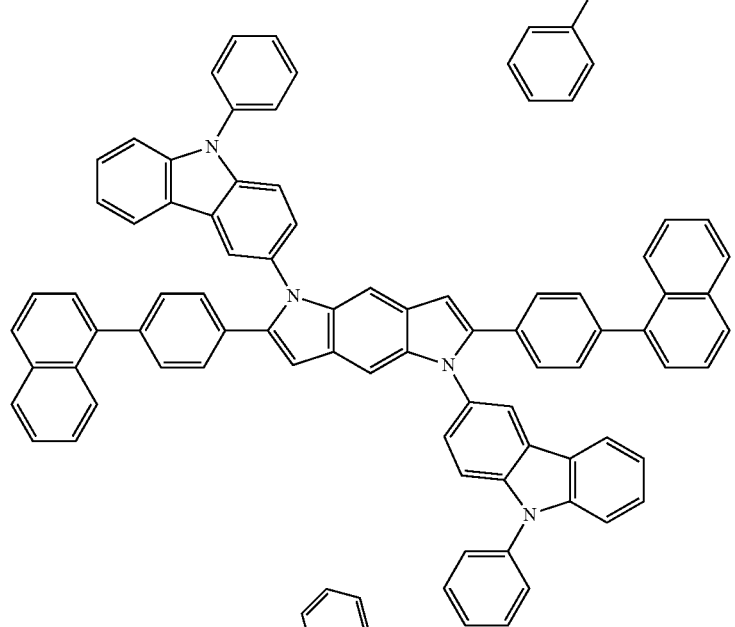
85
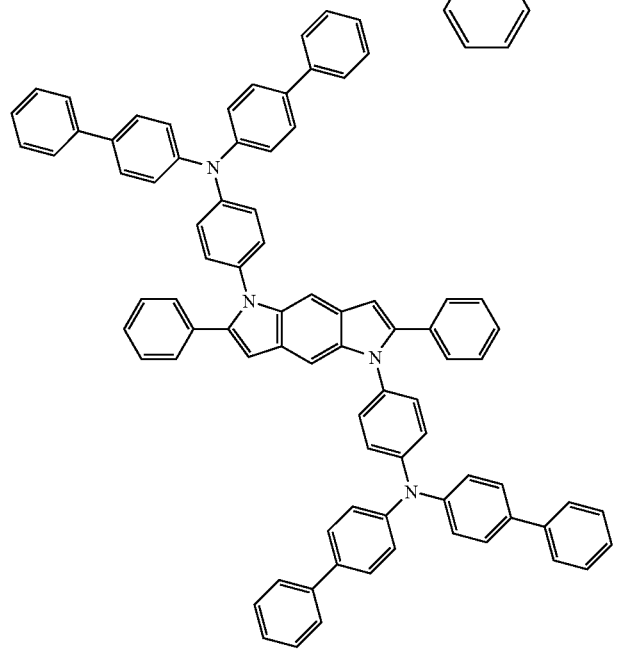

-continued
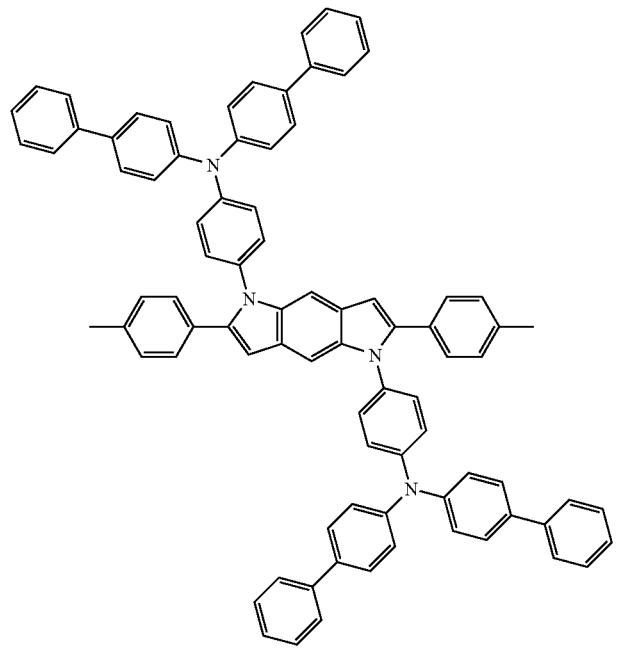
86
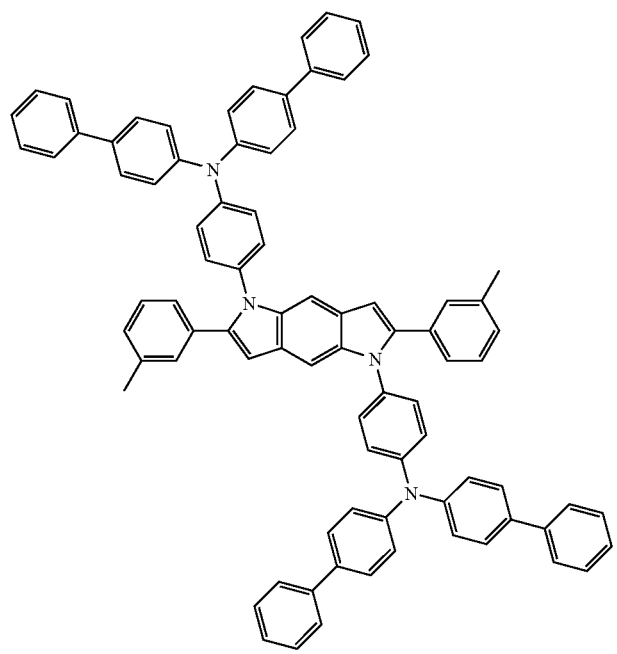
87

-continued
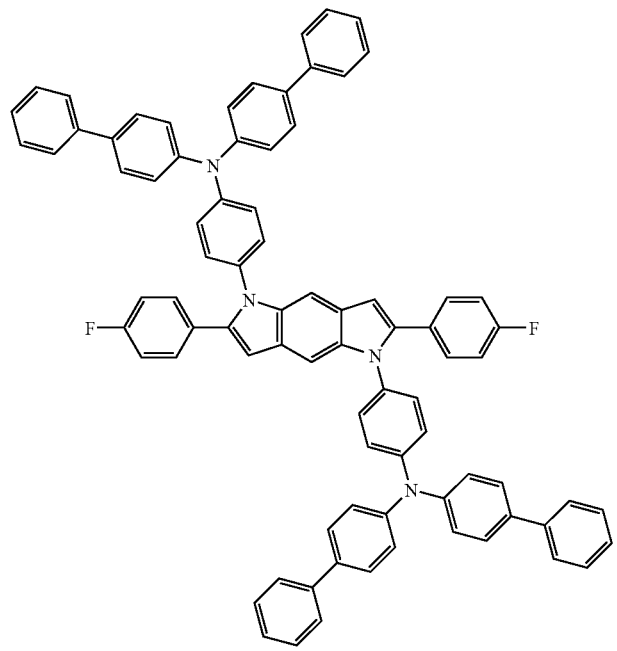
88
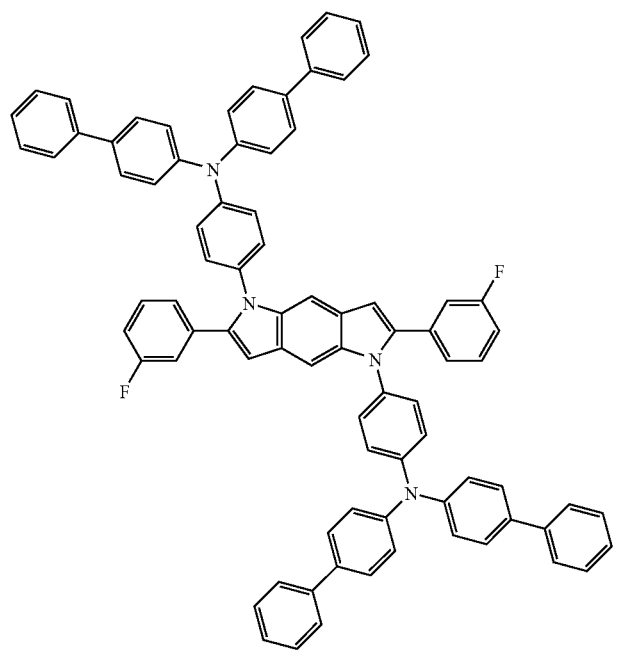
89

-continued
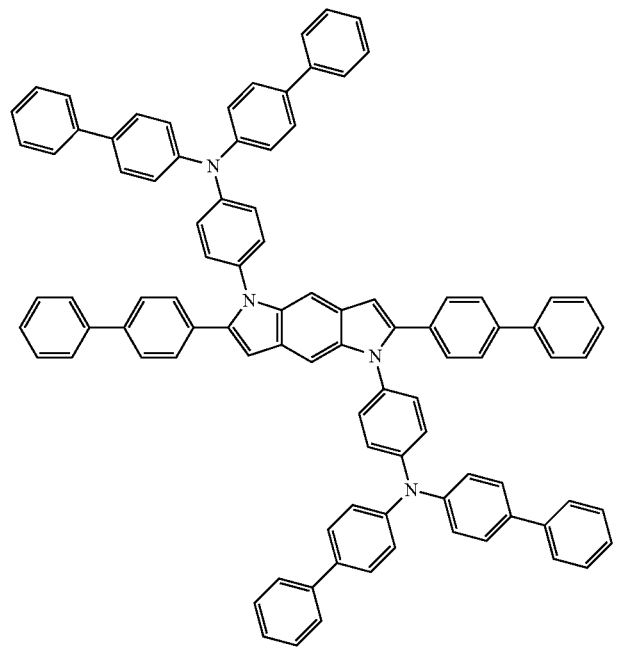
90
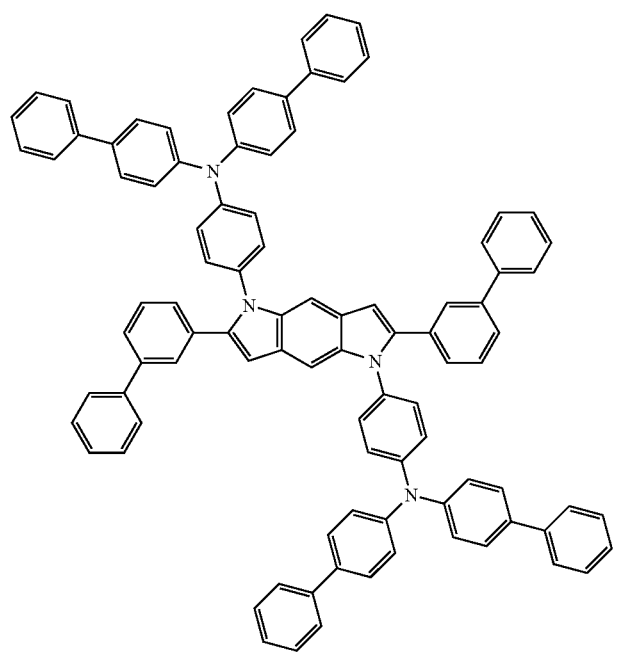
91

-continued
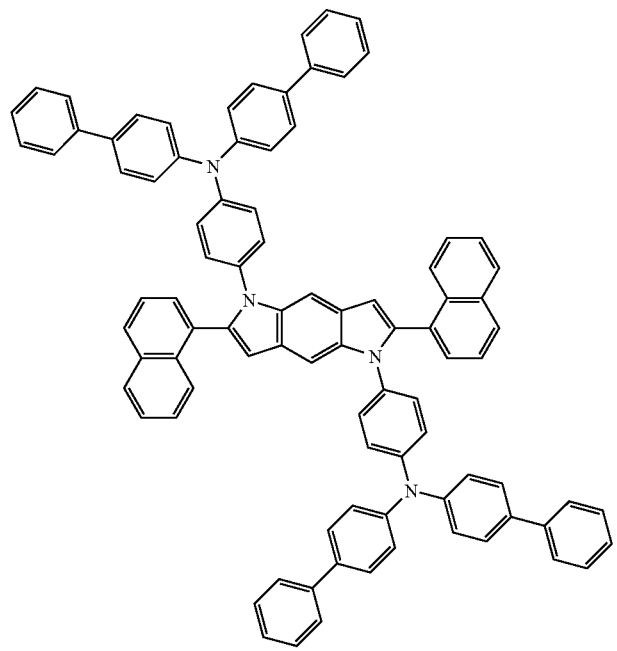
92
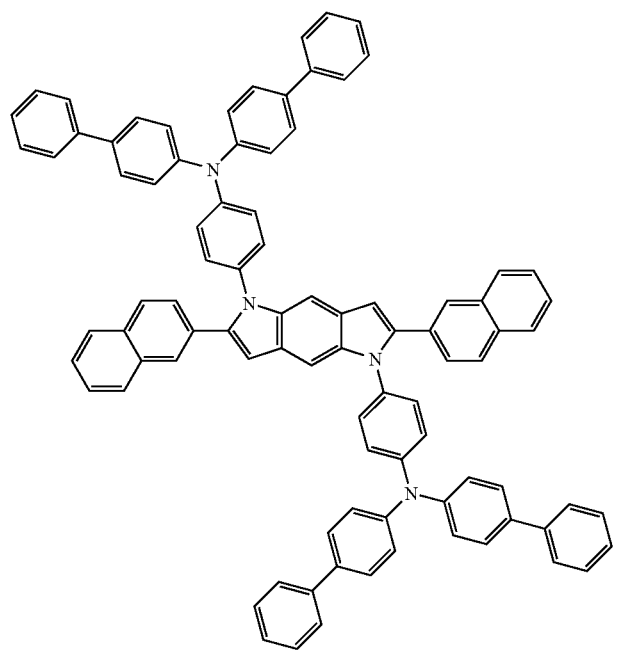
93

-continued
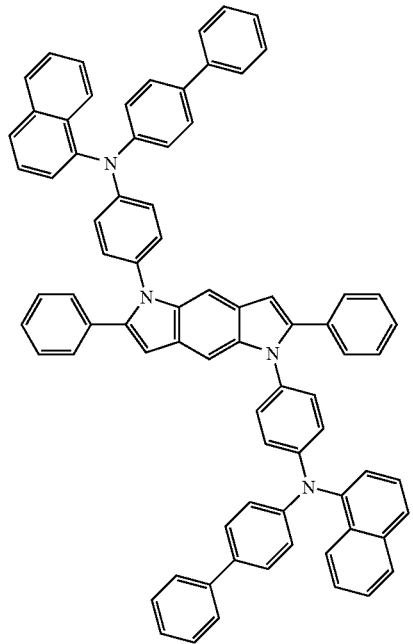
94
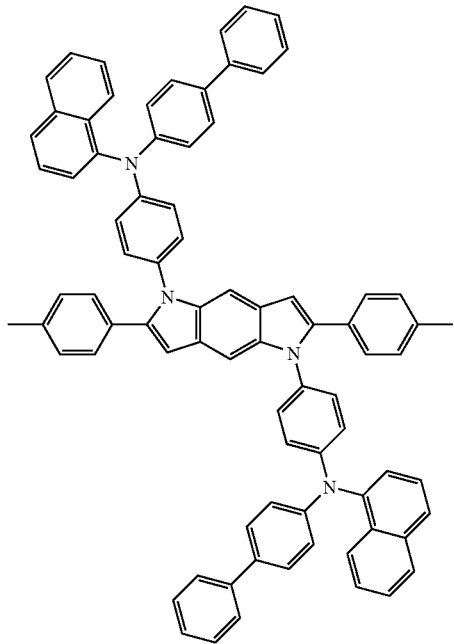
95
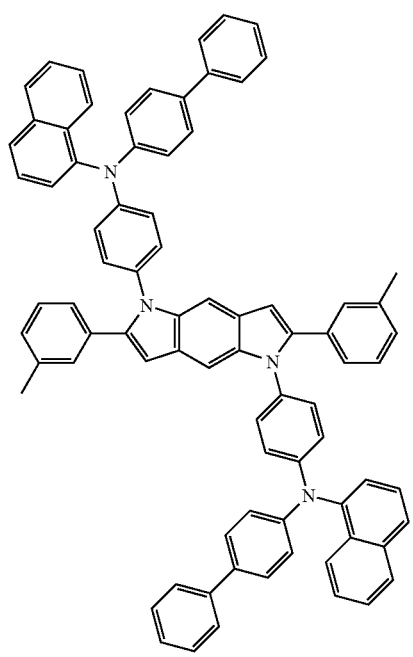
96
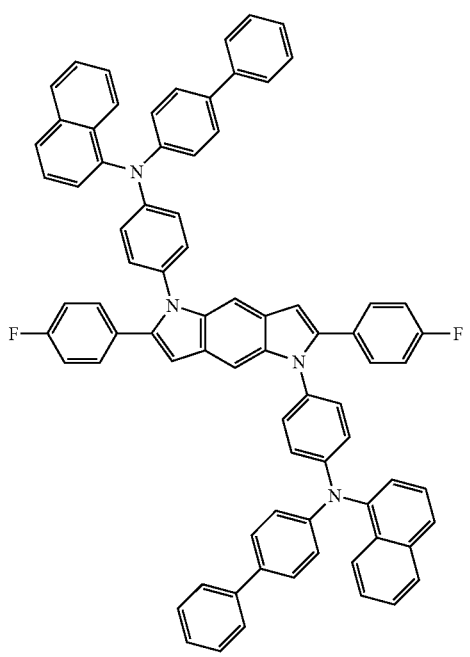
97

-continued
98
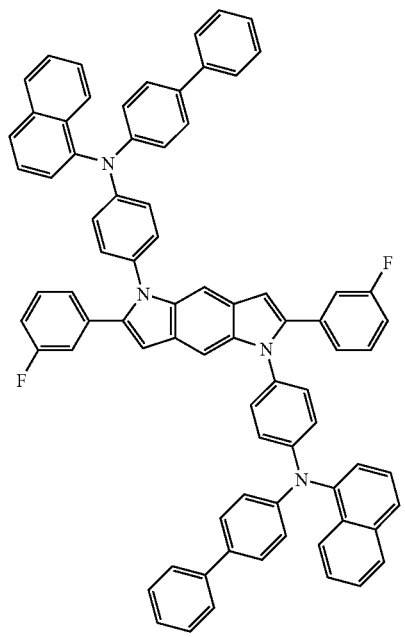
99
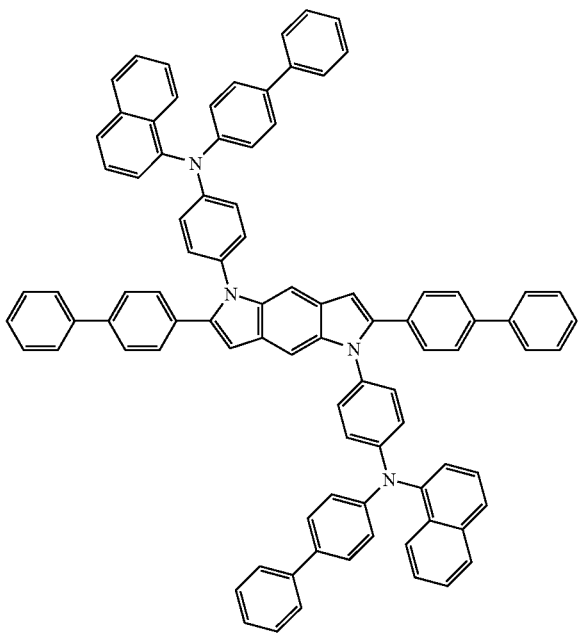
100
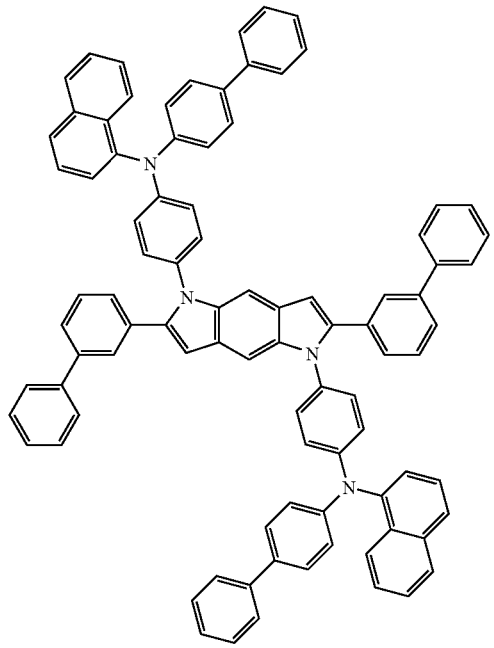
101
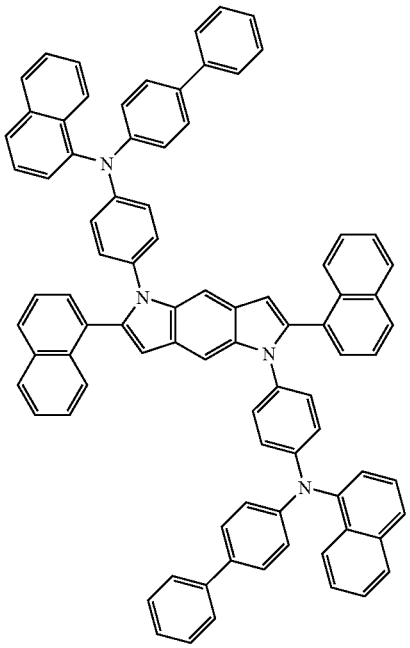

102
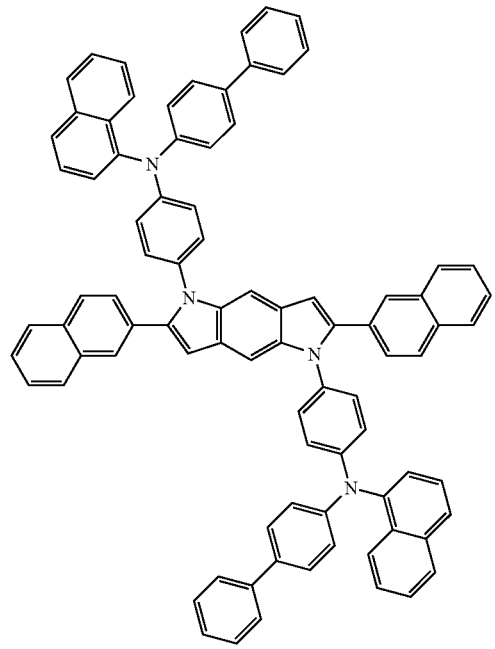
103
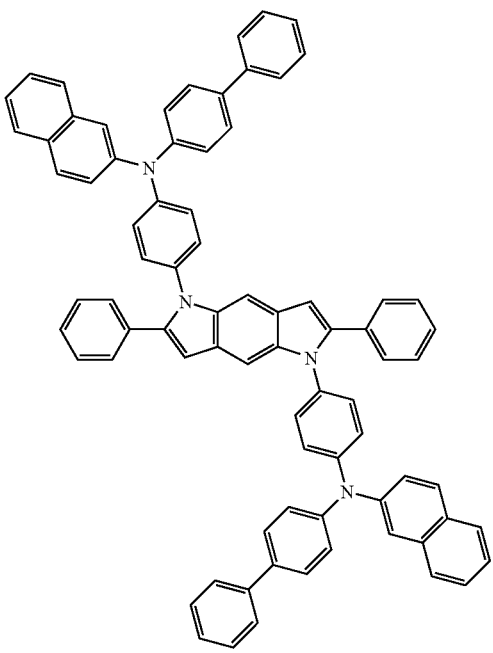
104
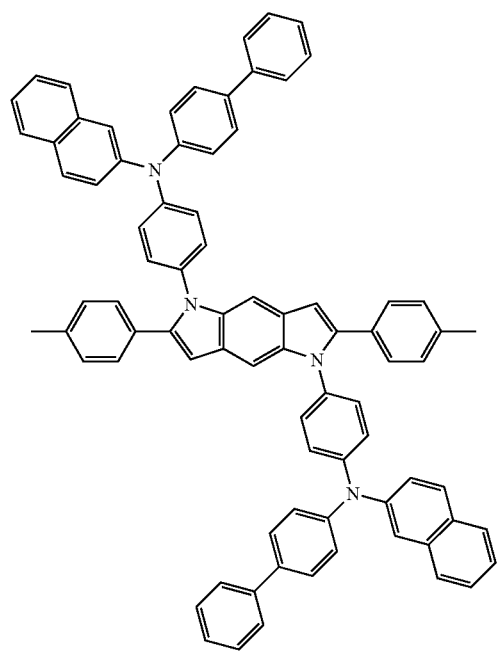
105
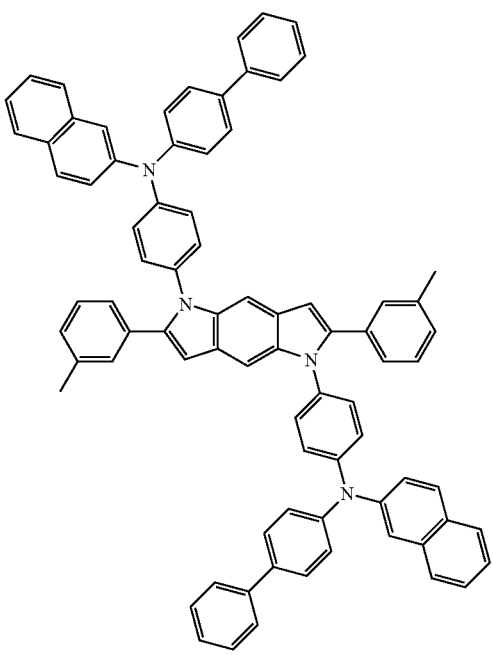

106
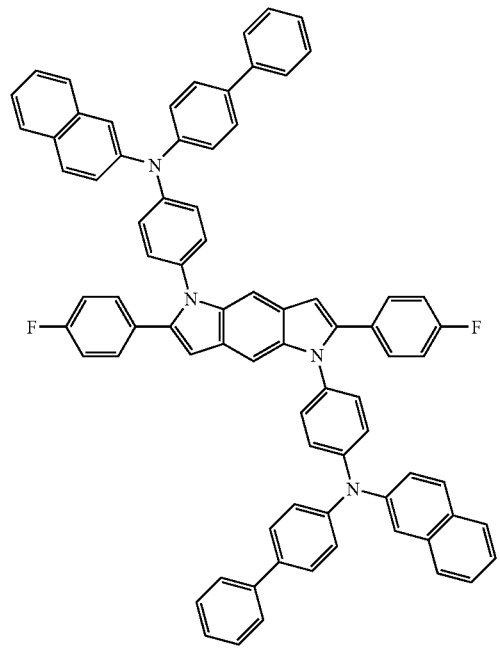
107
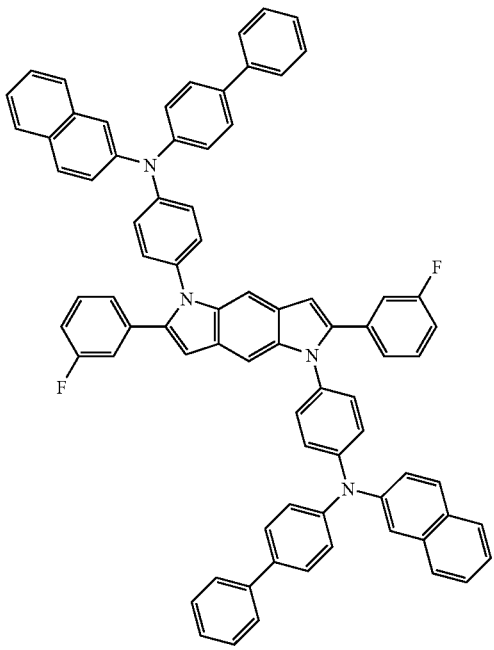
108
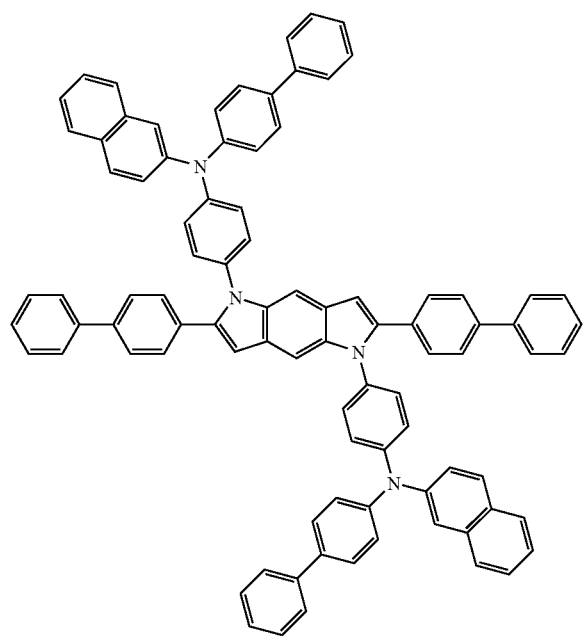
109
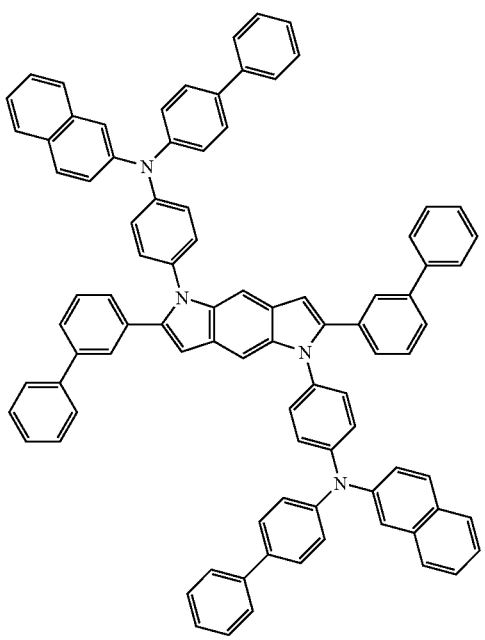

-continued
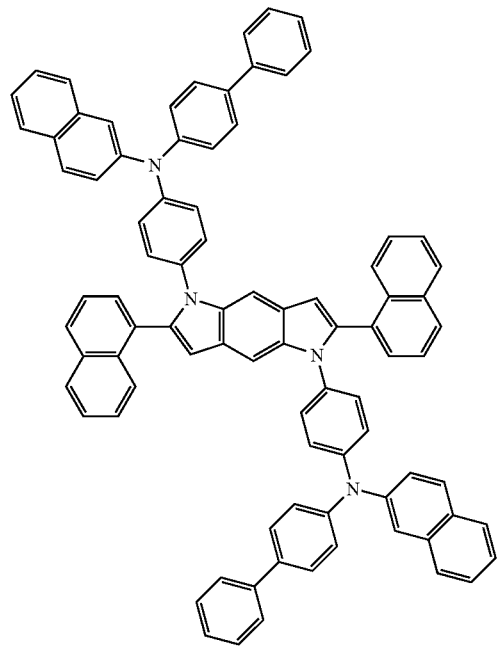
110
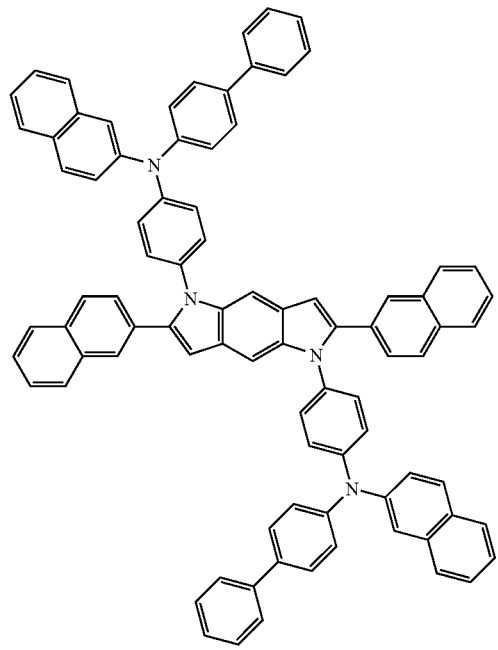
111
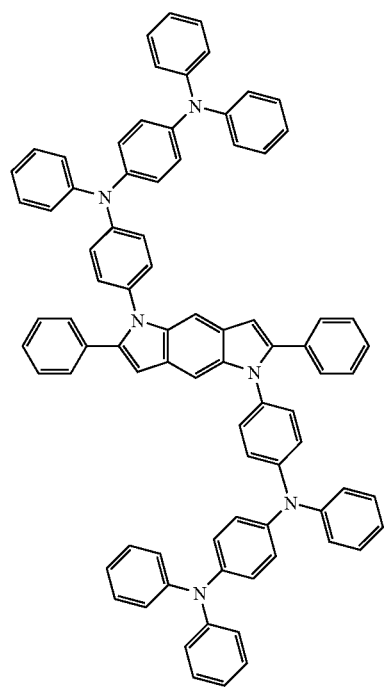
112
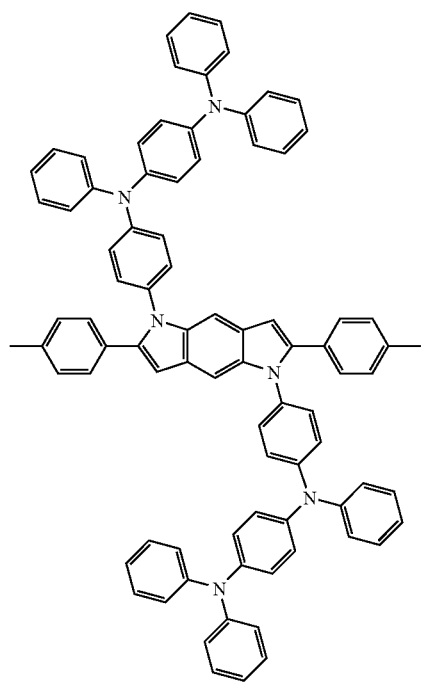
113

114
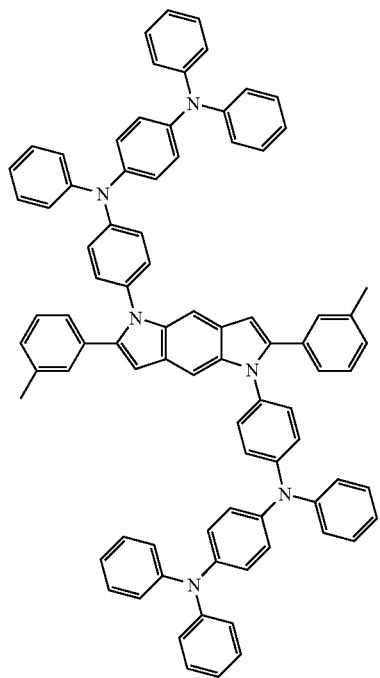
115
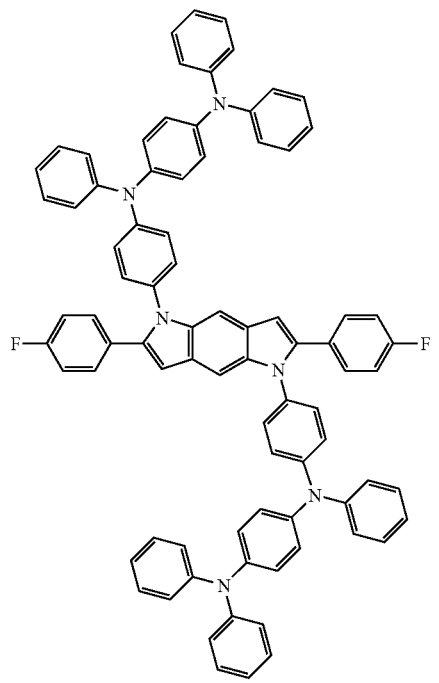
116
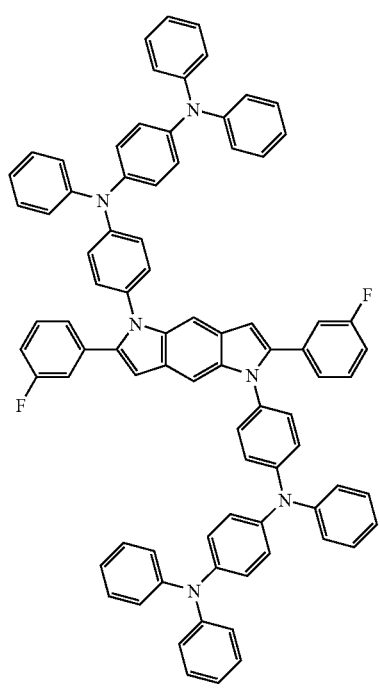
117
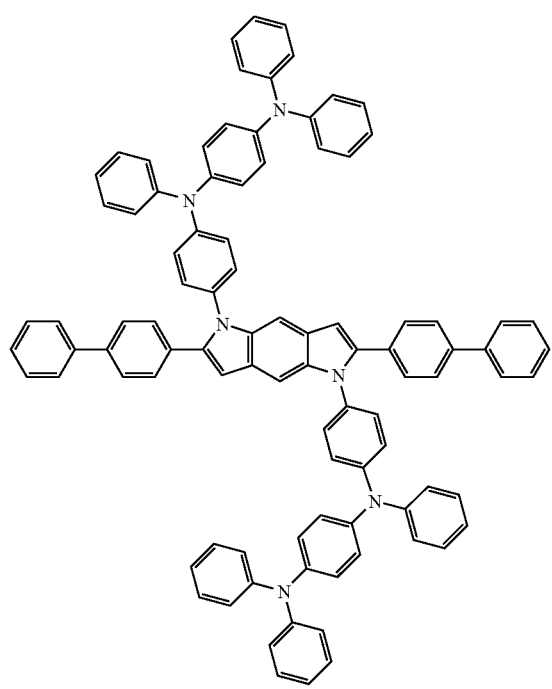

-continued
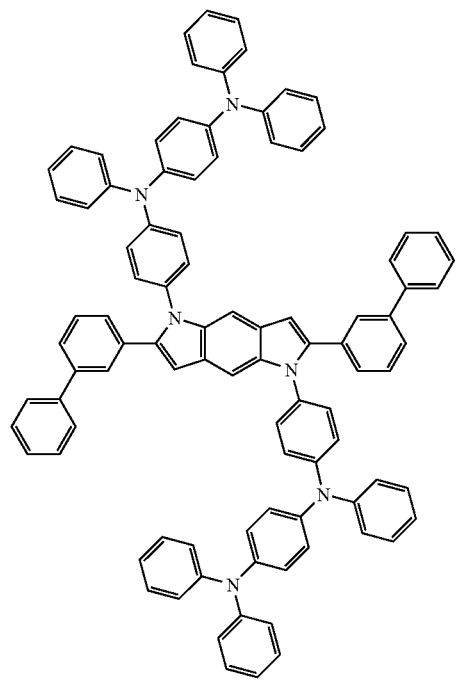
118
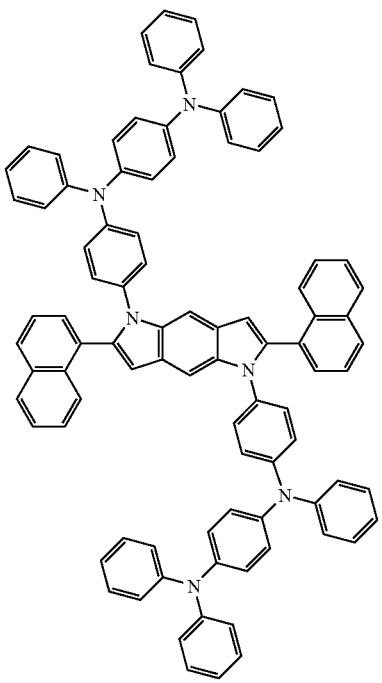
119
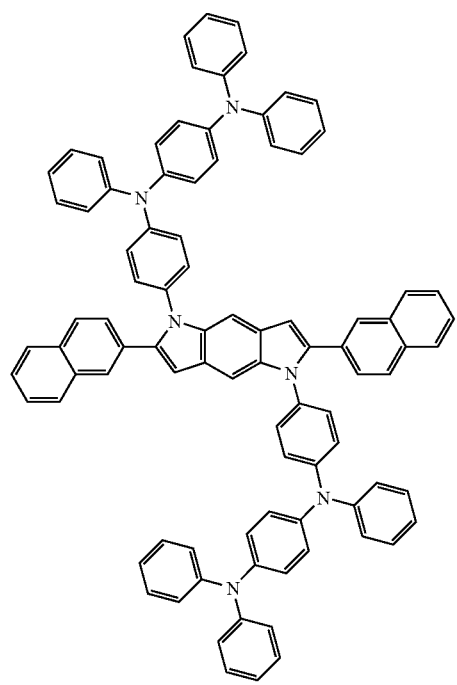
120
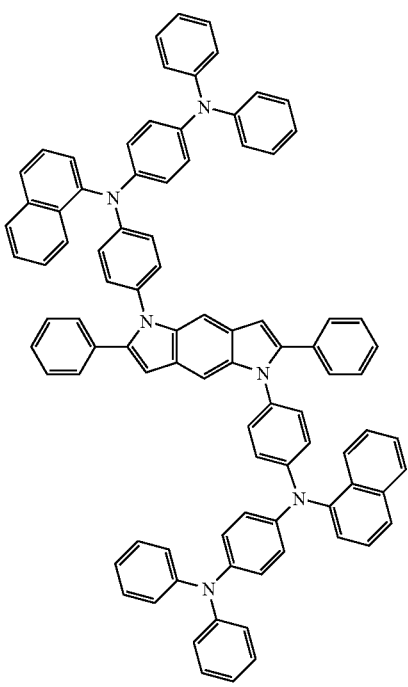
121

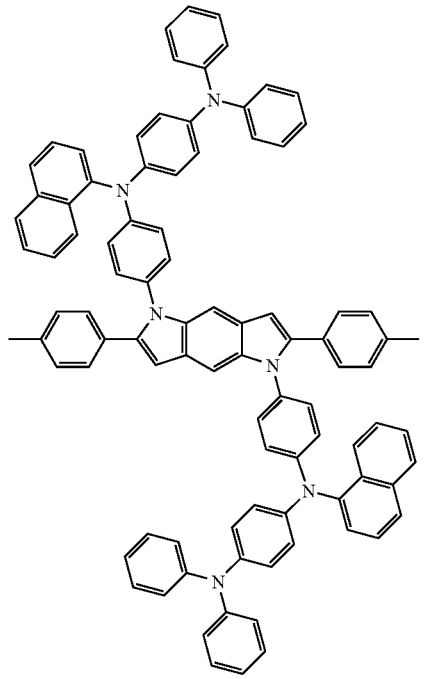
122
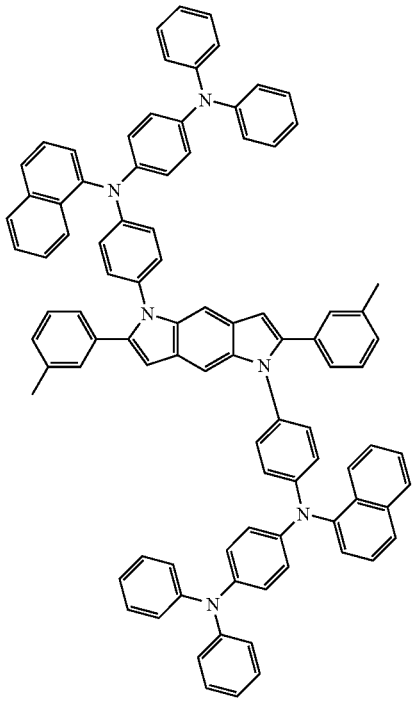
123
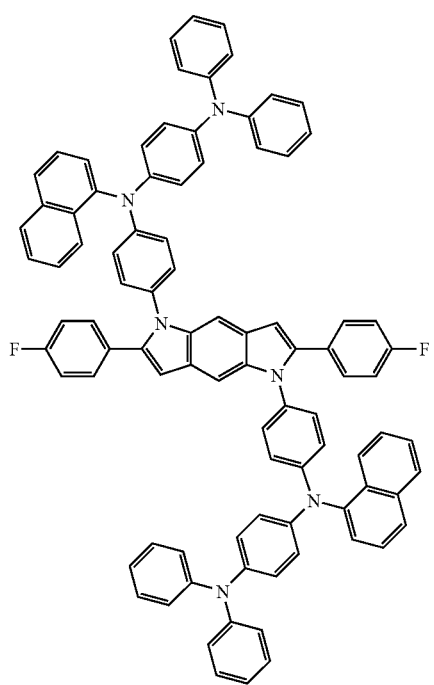
124
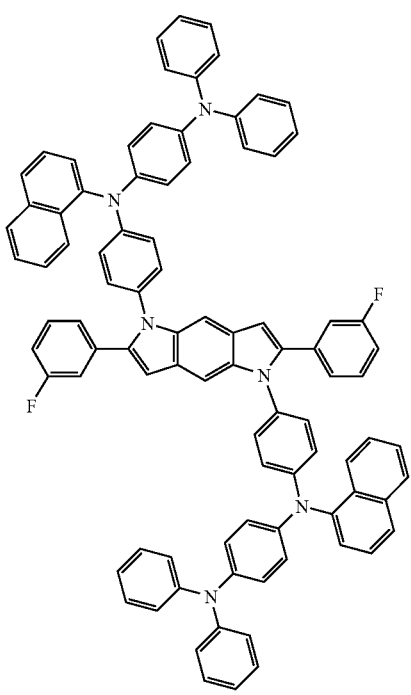
125

126
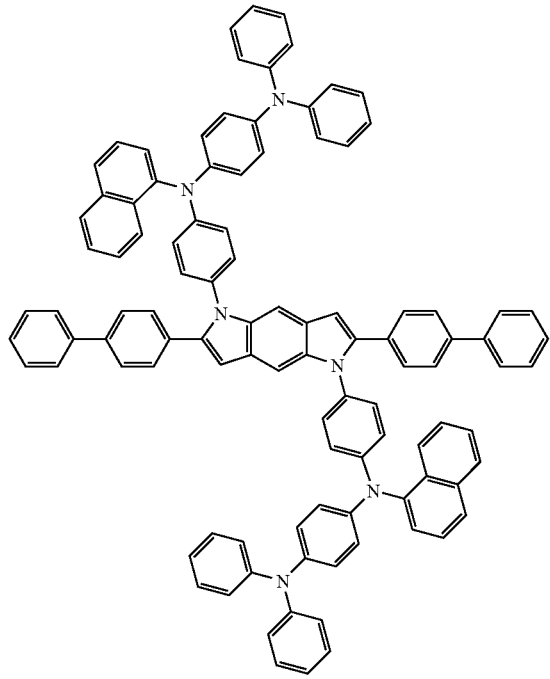
127
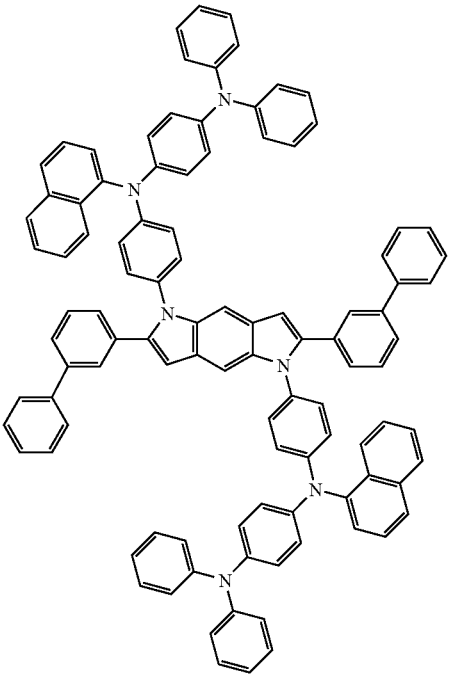
128
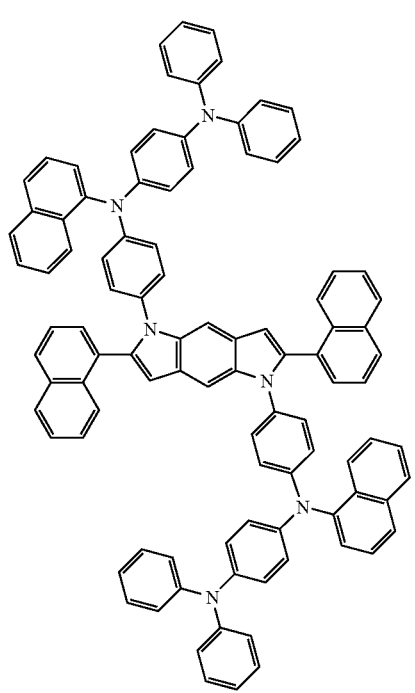
129
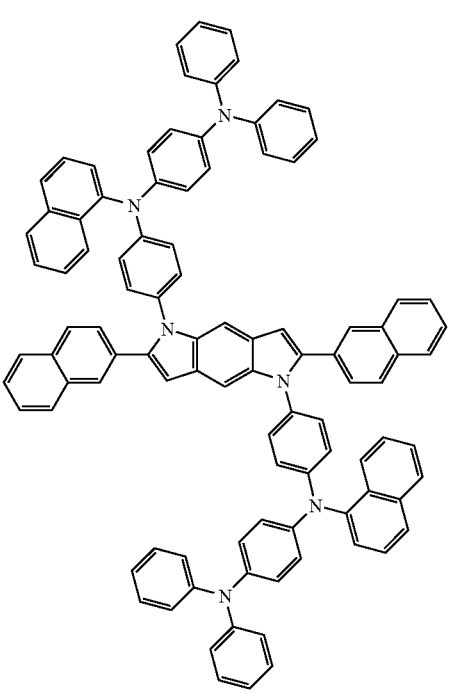

130
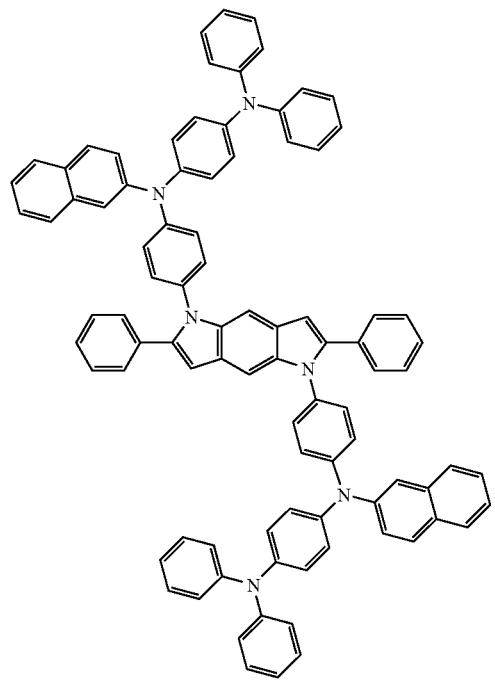
131
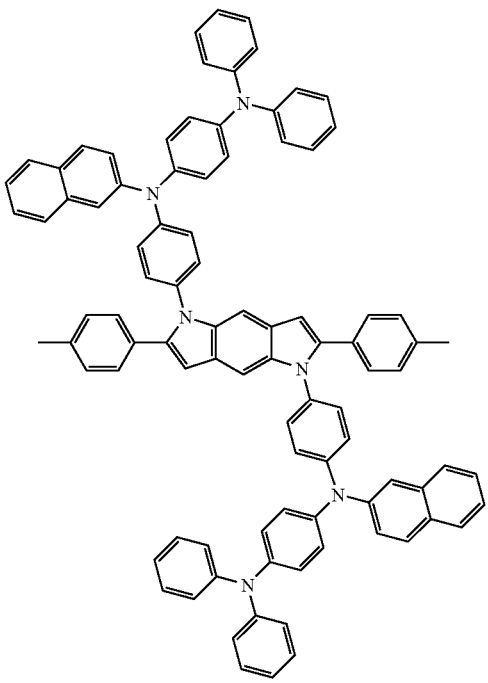
132
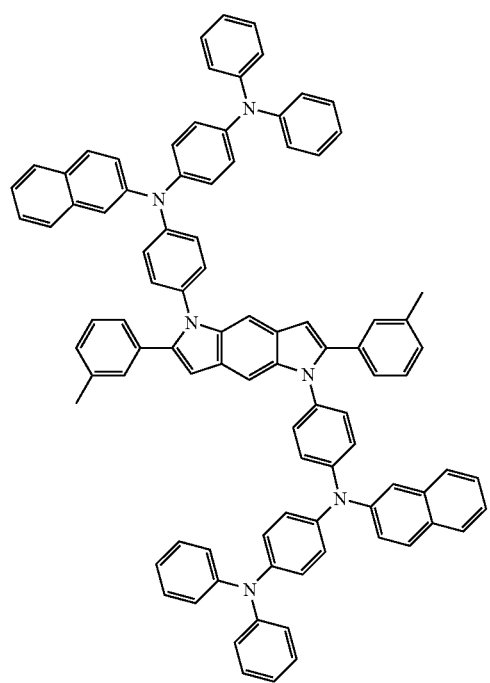
133
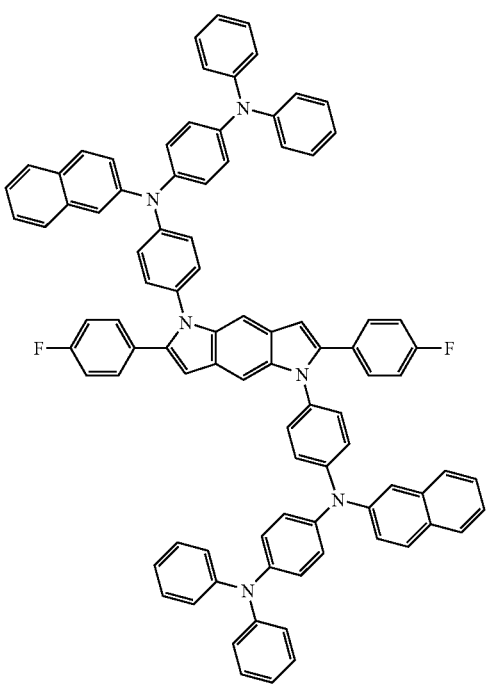

-continued
134
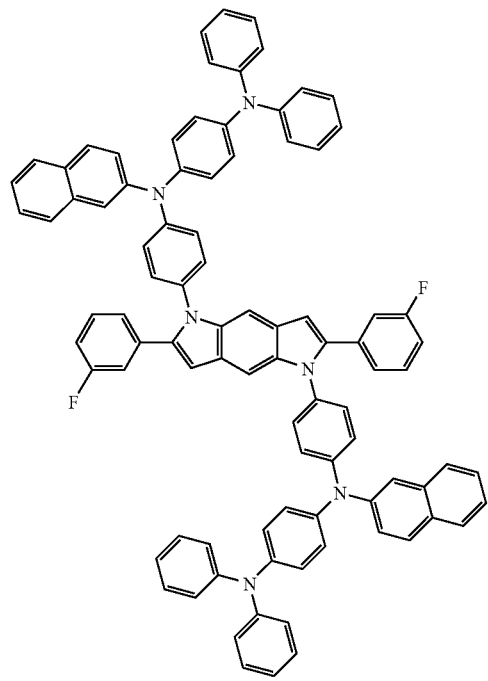
135
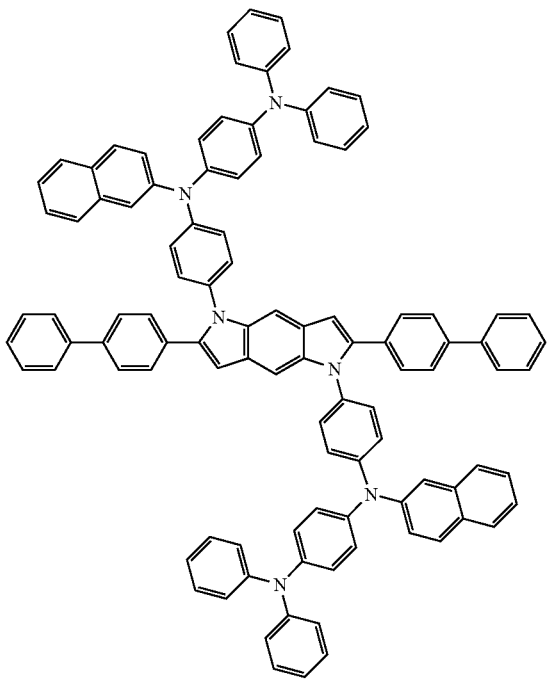
136
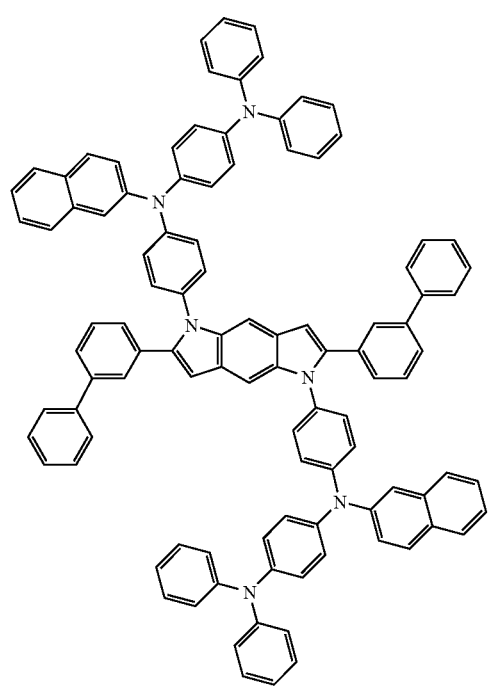
137
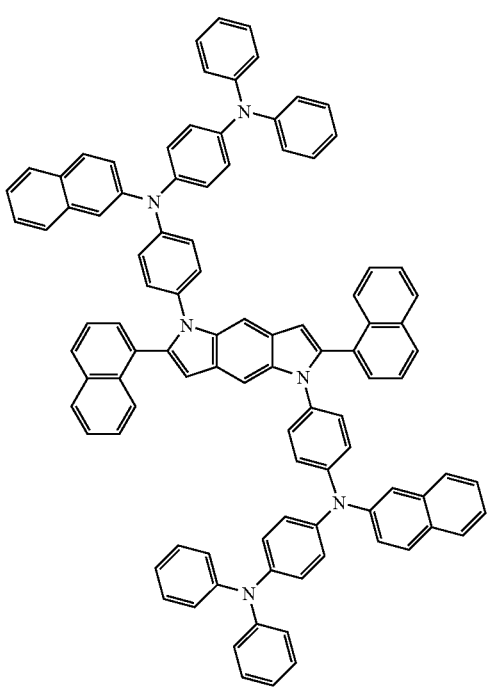

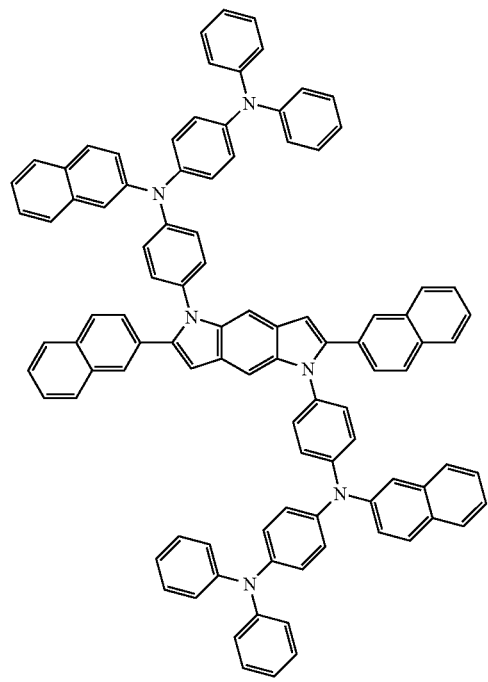
138
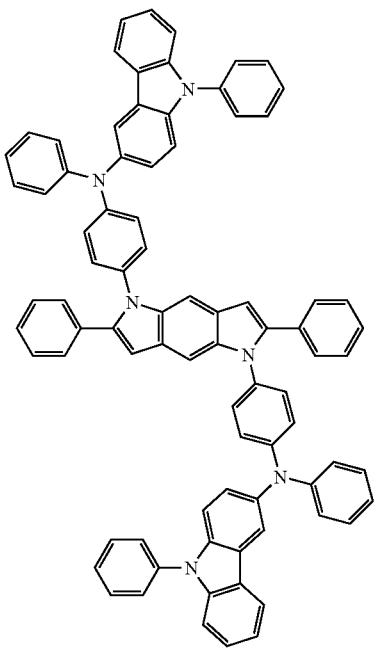
139
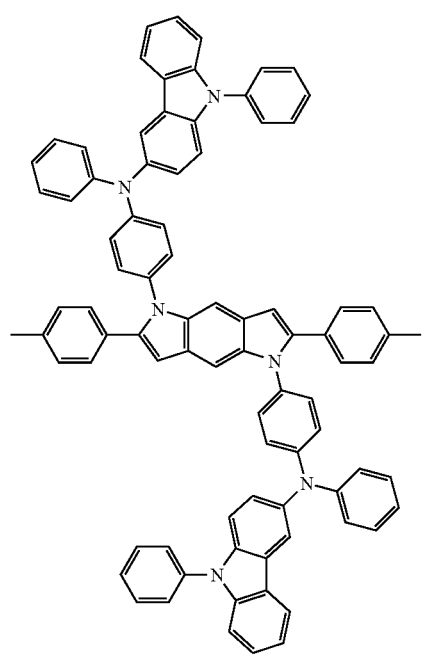
140
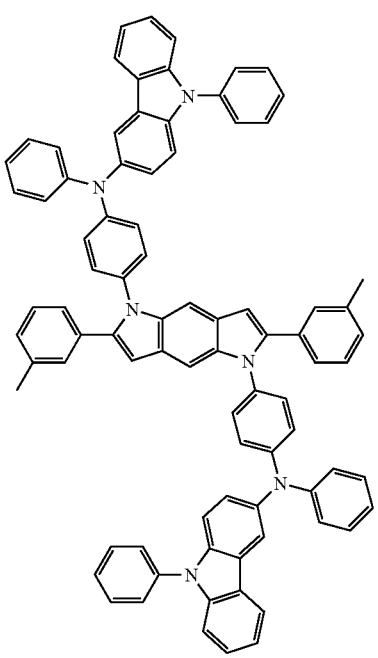
141

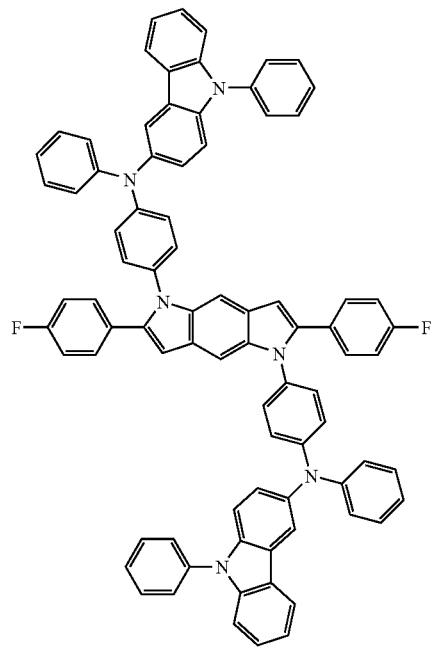
142
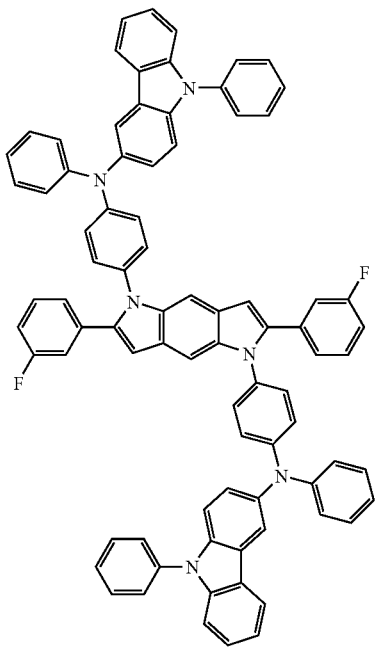
143
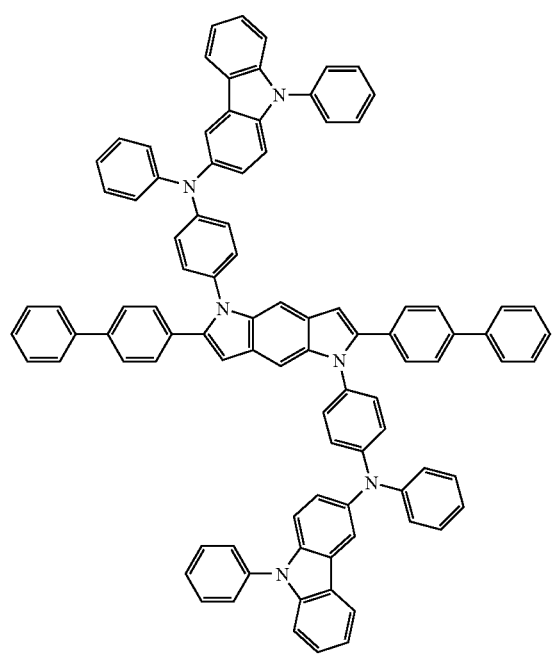
144
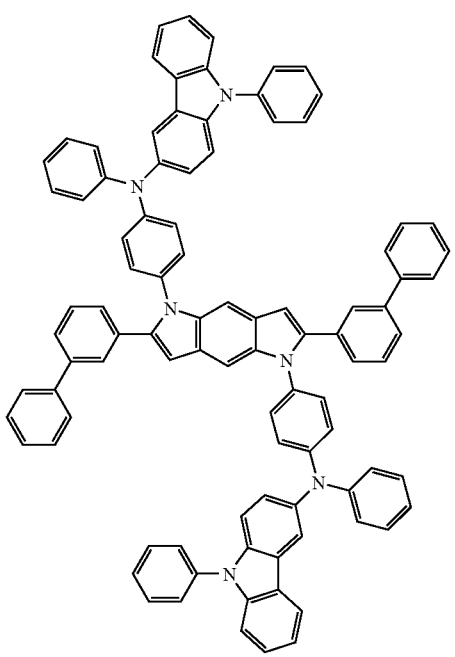
145

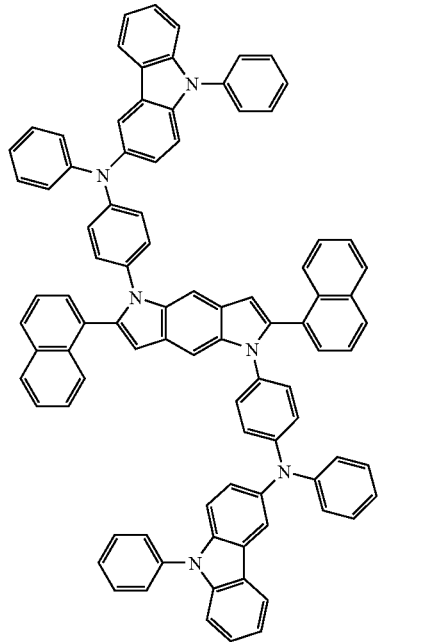
146
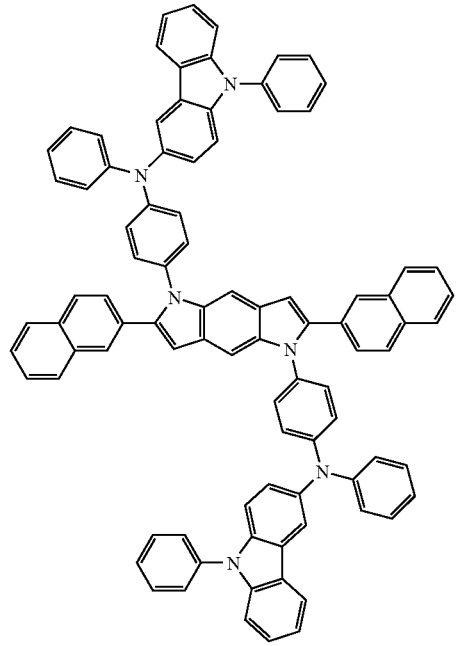
147
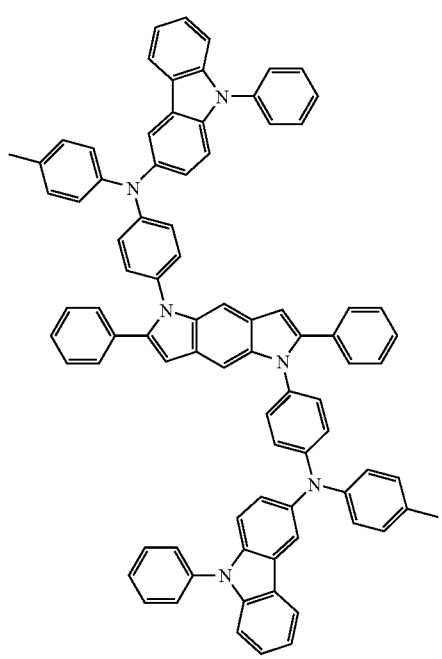
148
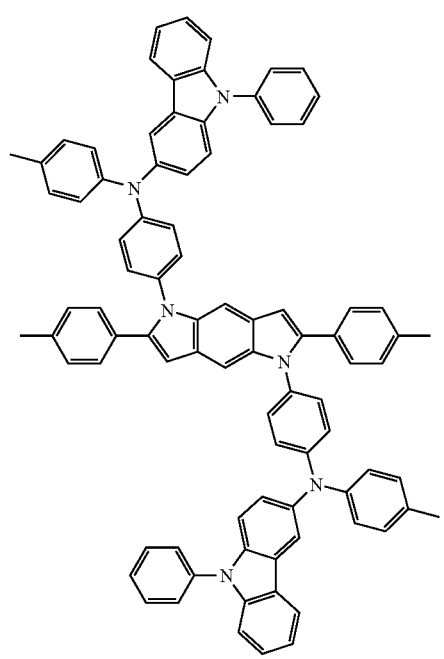
149

150
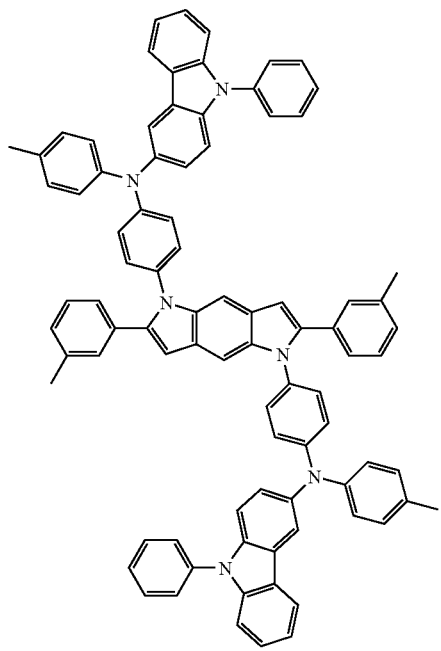
151
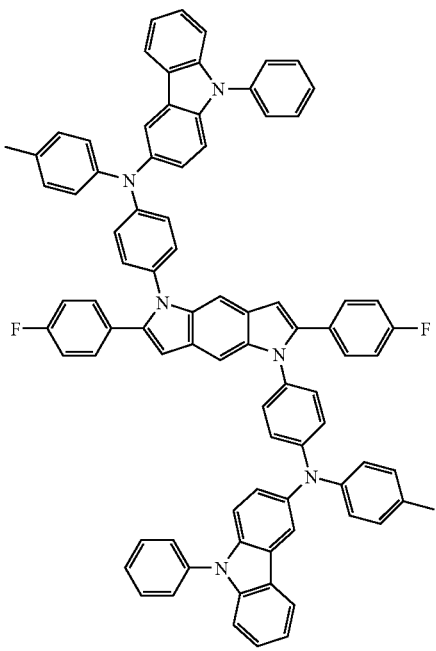
152
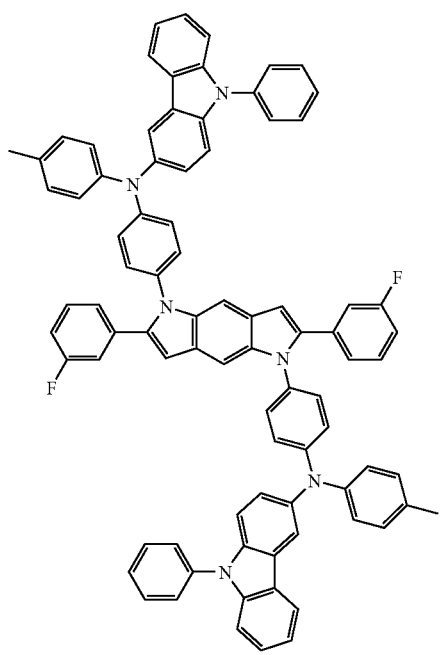
153
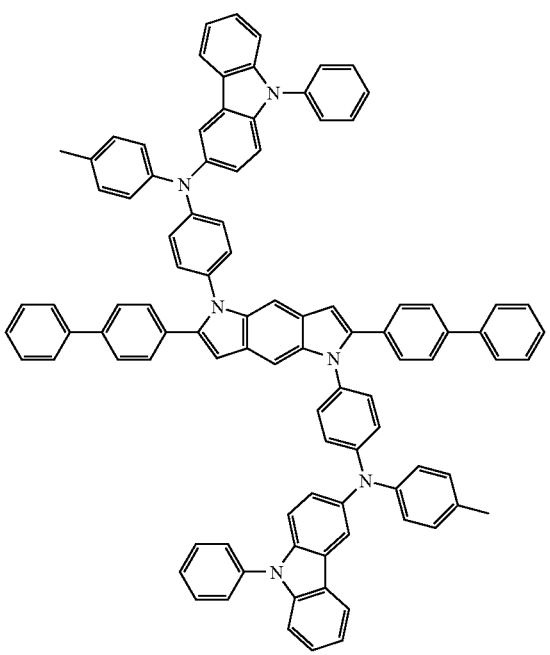

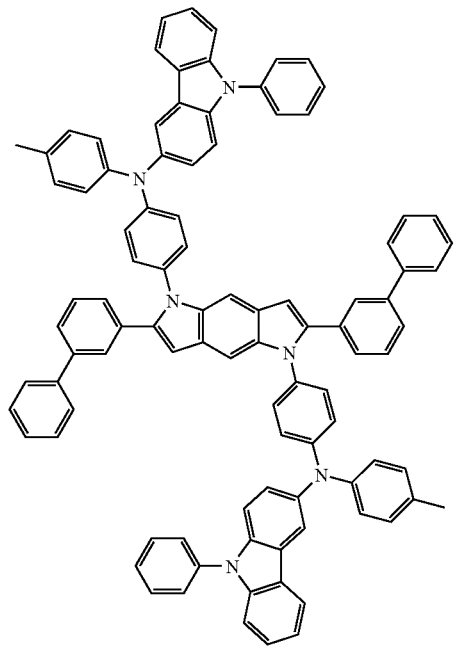
154
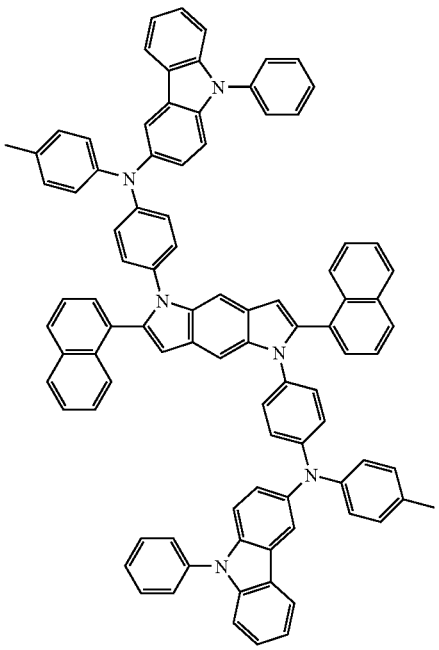
155
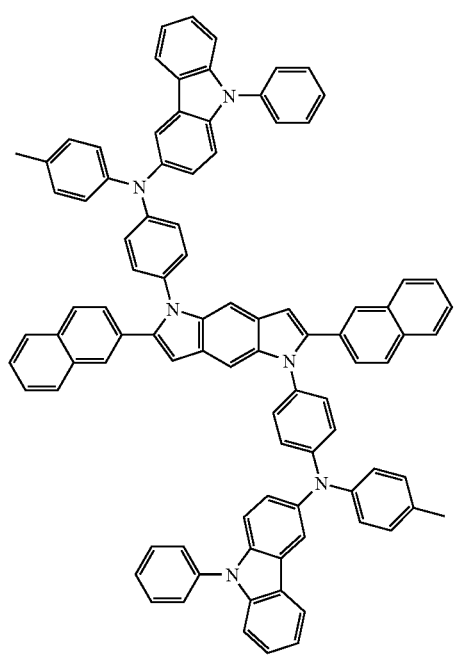
156
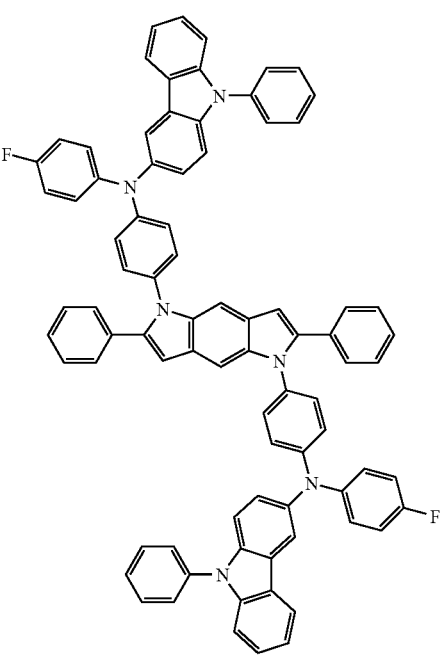
157

158
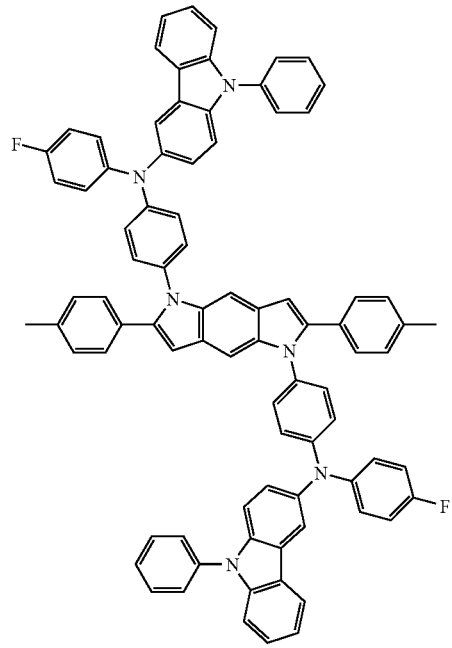
159
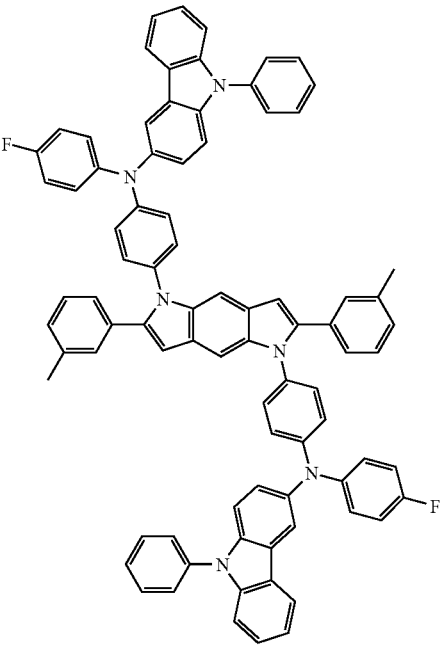
160
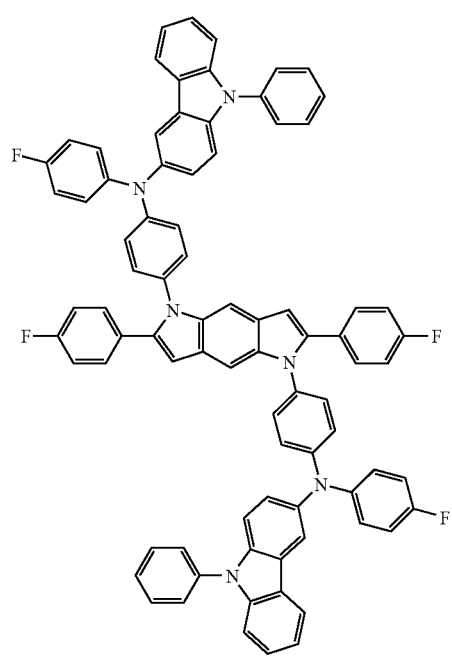
161
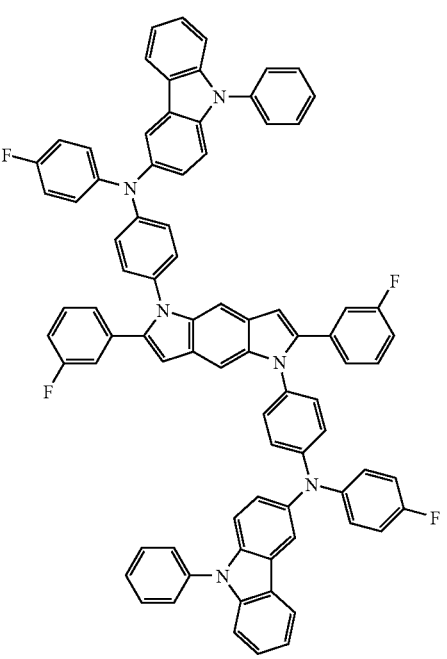

-continued
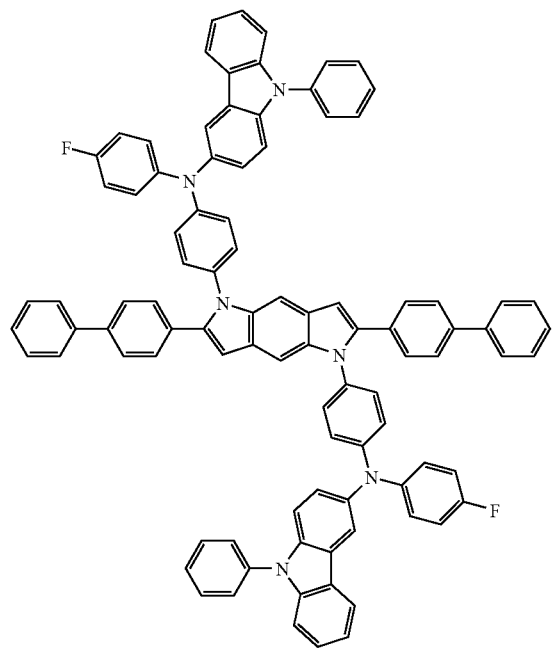 162
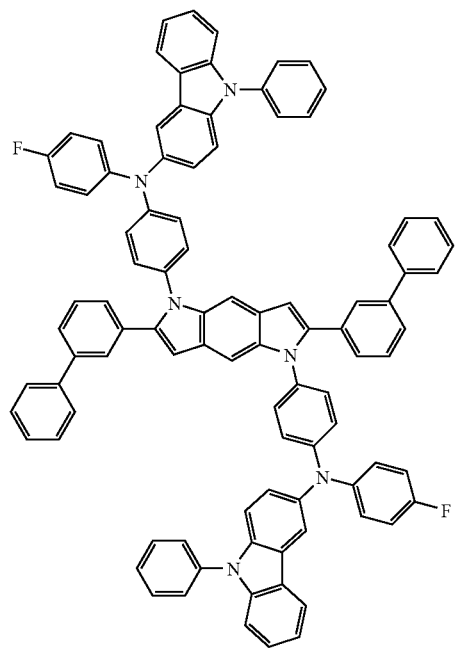 163
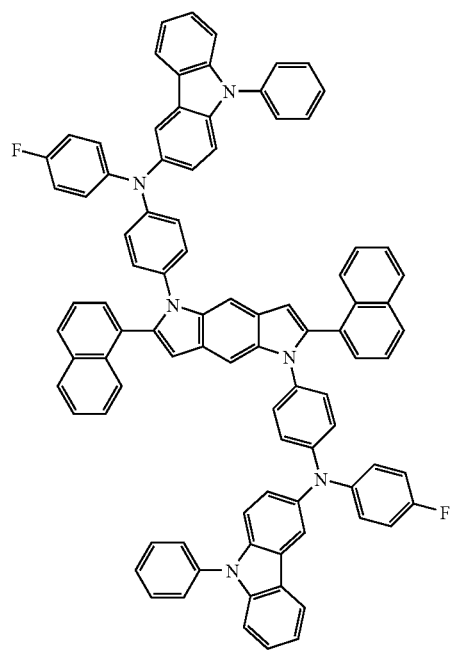 164
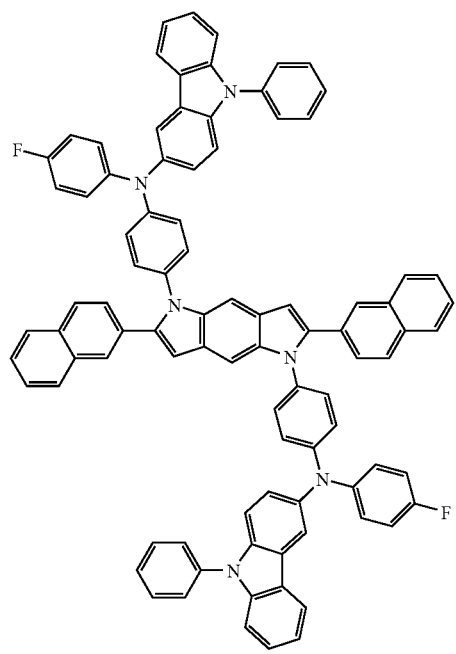 165

-continued
166
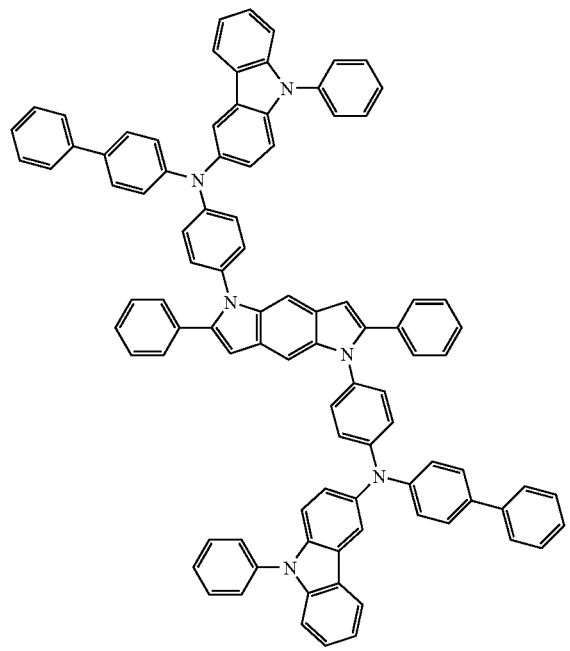
167
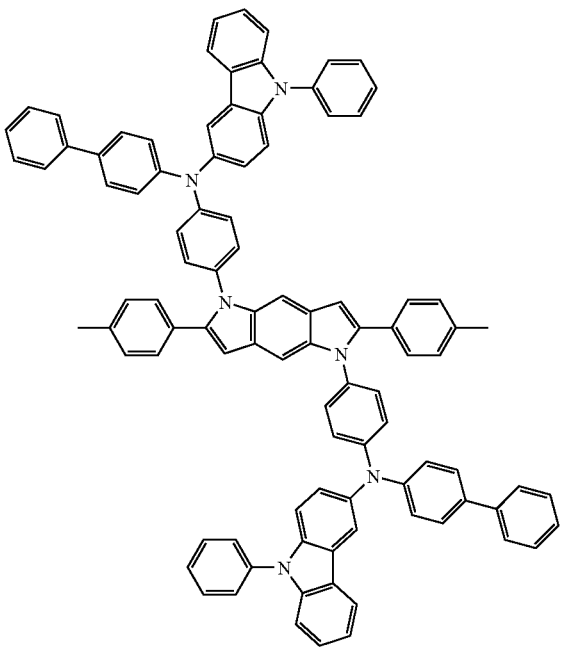
168
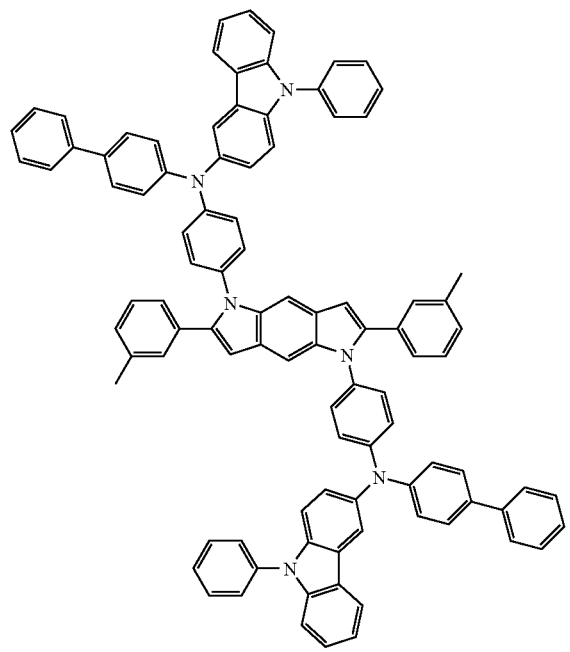
169
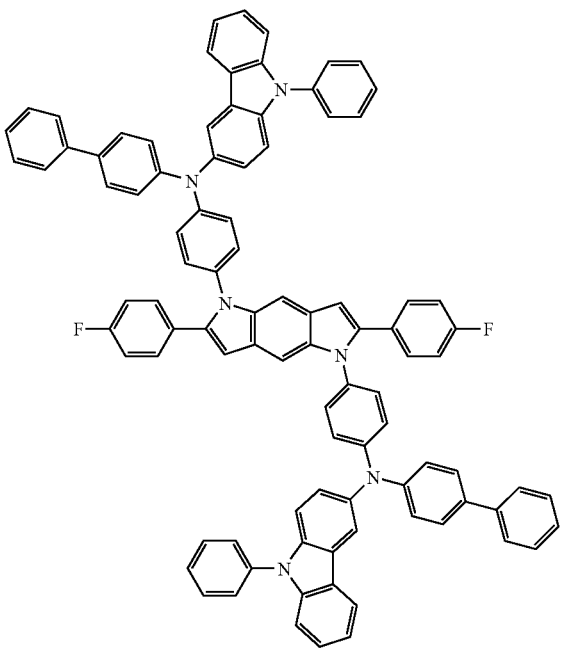

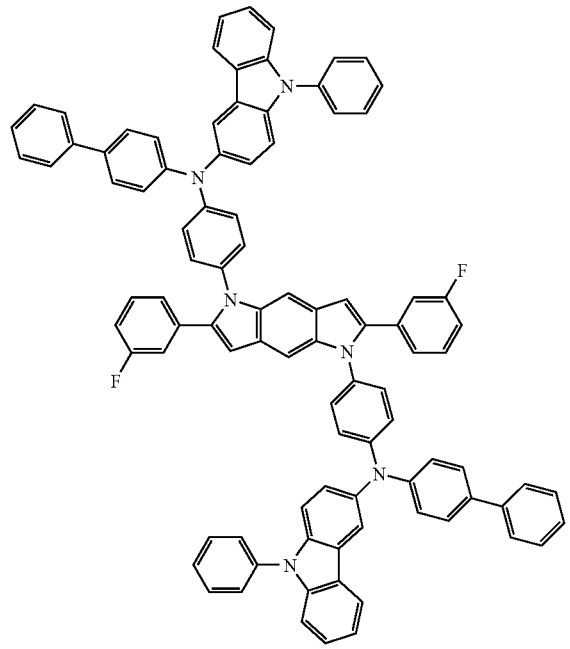
170
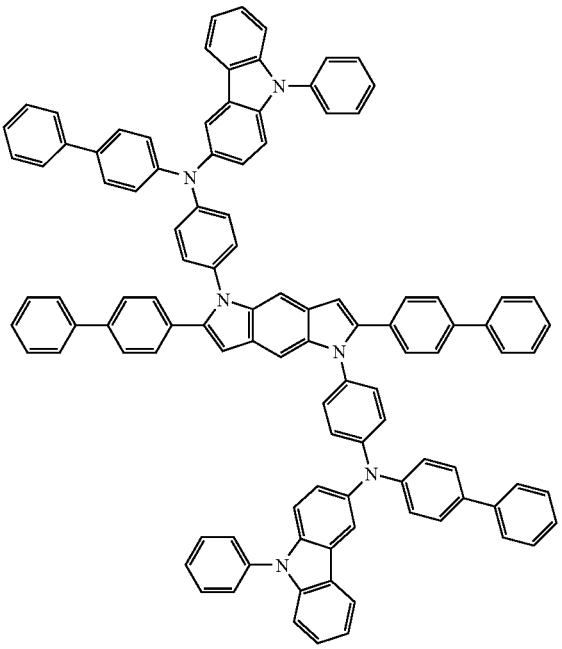
171
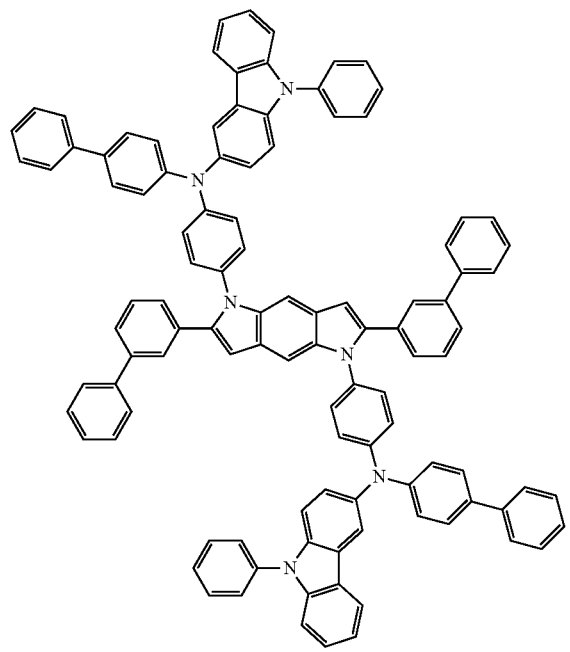
172
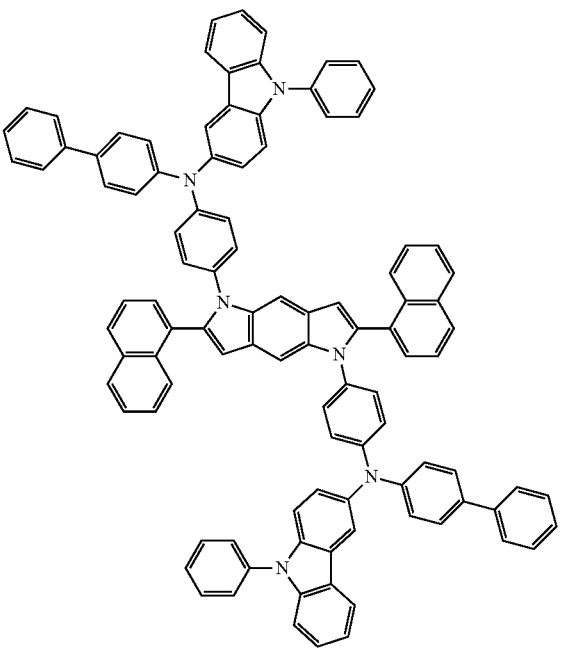
173

174
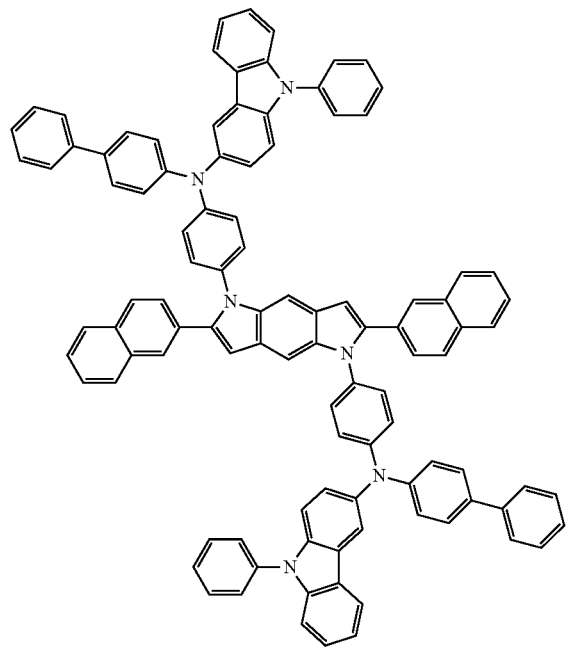
175
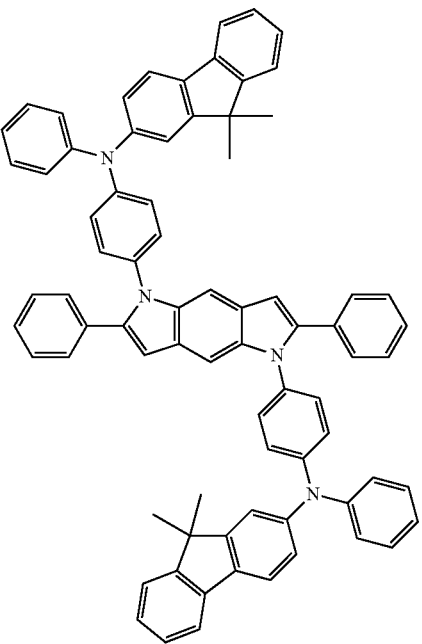
176
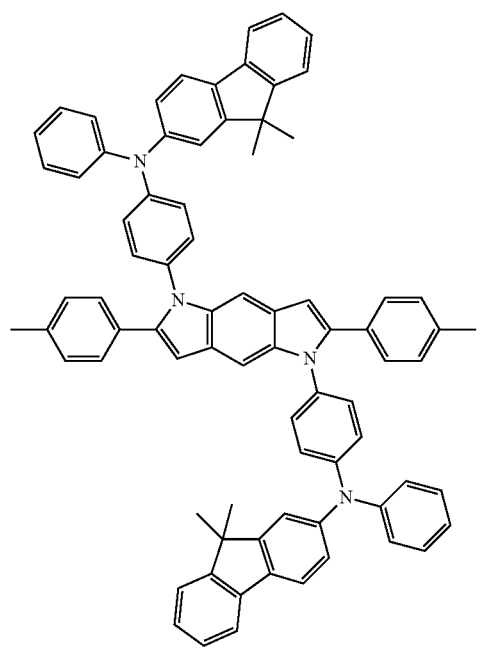
177
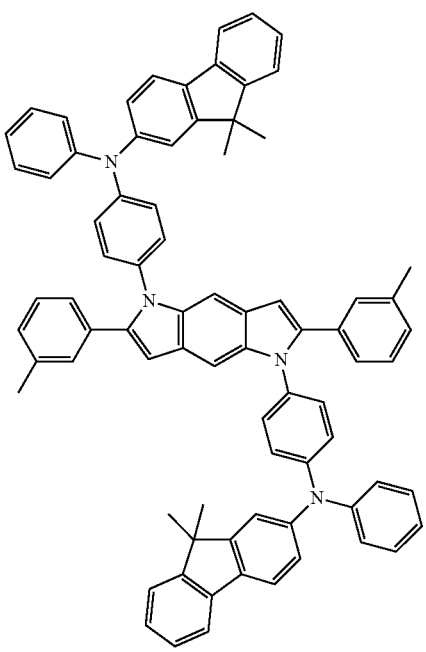

178
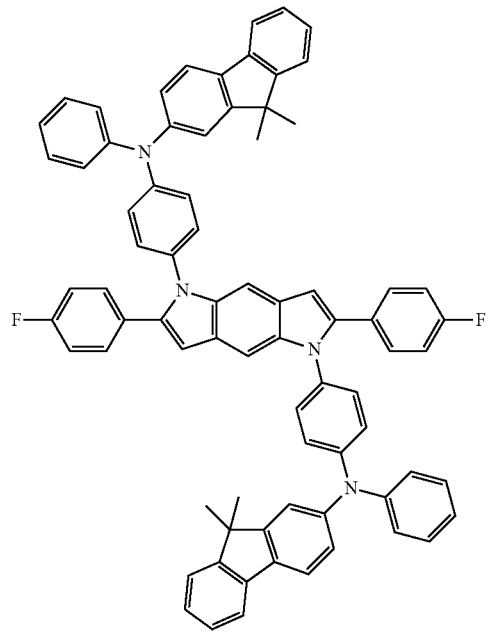
179
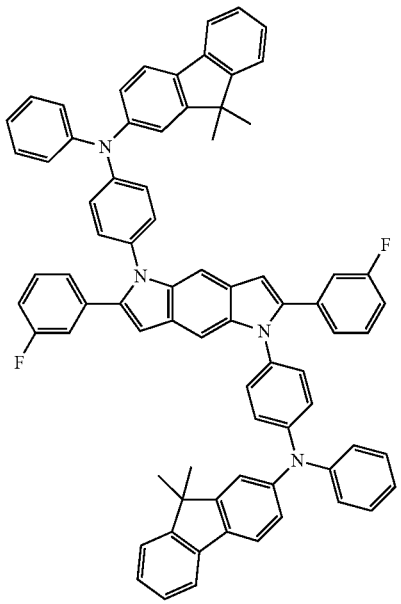
180
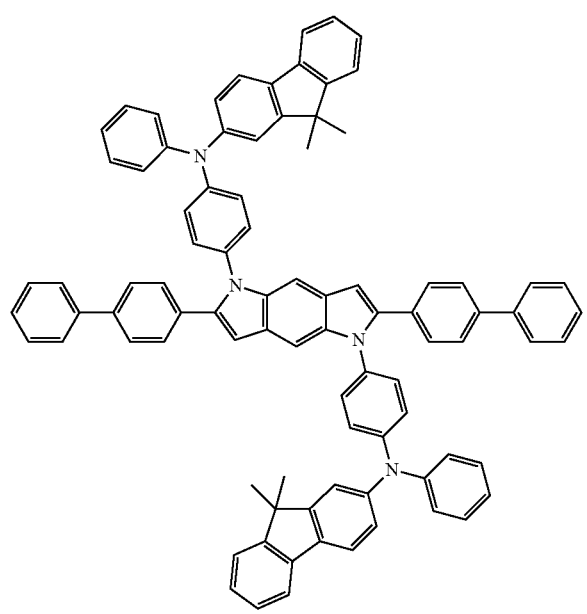
181
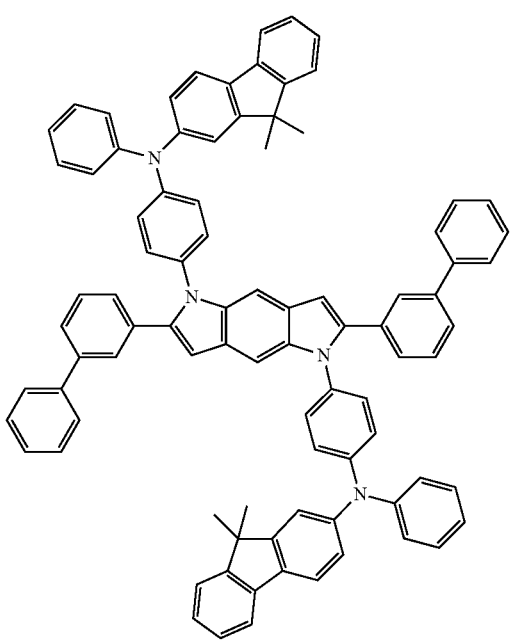

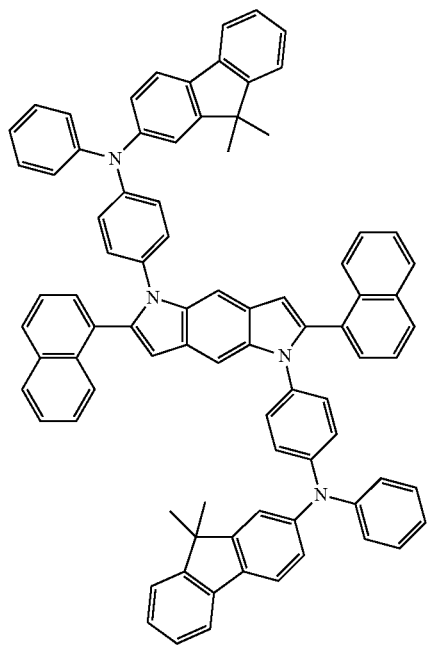

182

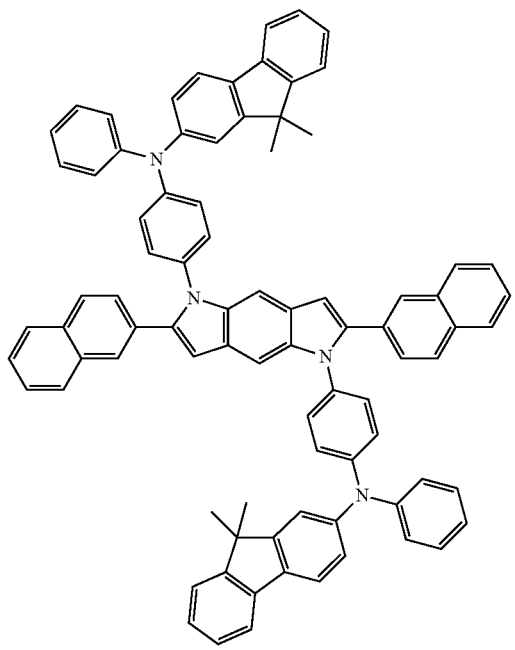

183

Hereinafter, a method of preparing a heterocyclic compound according to an embodiment of the present invention will be described in detail with reference to Reaction Scheme 1 below. However, Reaction Scheme 1 is for illustrative purposes only and is not intended to limit the scope of the present invention.

Reaction Scheme 1

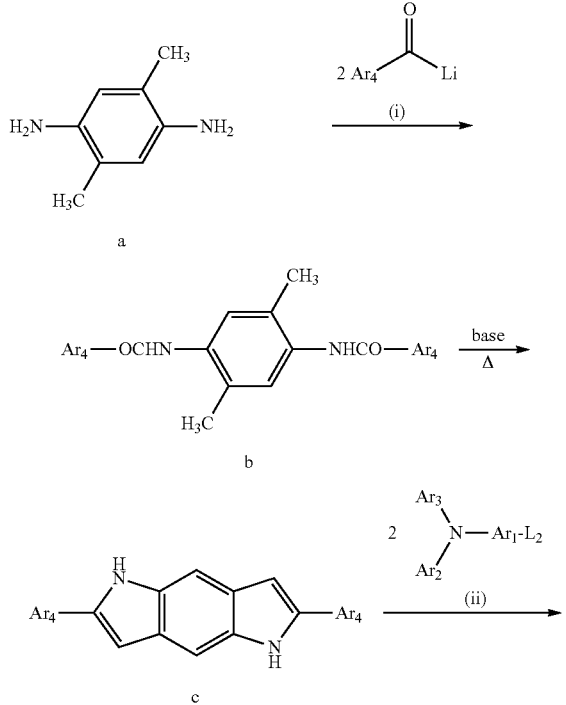

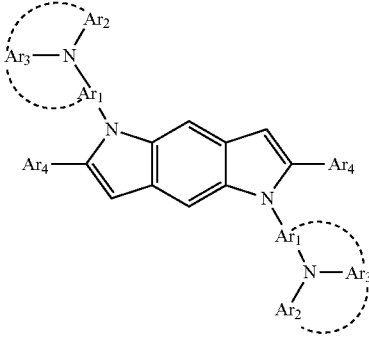

Formula I

First, 5-dimethyl-1,4-phenylenediamine (a) and a compound (I) were reacted to prepare an intermediate (b). $L_1$ of the compound (I) was a leaving group, for example a chloro group, a bromo group or an anhydride. Then, the cyclization reaction of the prepared intermediate (b) was performed at a high temperature under a high pressure in the presence of a base to prepare an intermediate (c). A compound (II) was reacted with the compound (c) in the presence of an appropriate catalyst to prepare a compound represented by Formula I. $L_2$ of the compound (II) was a leaving group, for example a chloro group, a bromo group or an anhydride. In compound (II), $Ar_1$ and $Ar_3$ or $Ar_2$ and $Ar_3$ may be connected to each other to form a ring.

An organic light emitting device according to an embodiment of the present invention includes: a first electrode; a second electrode; and at least one organic layer interposed between the first electrode and the second electrode, wherein the organic layer may include the heterocyclic compound represented by Formula I as described above.

The organic light emitting device may have a variety of structures. The organic layer including the heterocyclic compound of Formula I may be a hole injection layer, a hole transport layer or a single layer simultaneously having hole injecting and transporting functions, and preferably a hole injection layer.

The organic light emitting device may have a bottom emission type structure as shown in FIG. 1. FIG. 1 shows a structure of an organic light emitting device according to an embodiment of the present invention. Referring to FIG. 1, the organic light emitting device according to the current embodiment of the present invention has an anode, a hole injection layer (HIL), a hole transport layer (HTL), an emission layer (EML), an electron transport layer (ETL), an electron injection layer (EIL) and a cathode. However, the present invention is not limited thereto, and the organic light emitting device may have various other structures such as top emission type structures. If required, a single intermediate layers or double intermediate layers can be formed between the anode and the cathode.

The compound of Formula I can be efficiently used as a hole-related material, particularly a material used to form a hole injection layer due to its excellent hole injecting and transporting properties, and also used as host materials for blue, green and red fluorescent and phosphorescent devices. An organic light emitting device including the compound of Formula I has high efficiency, low driving voltage, high brightness and long lifetime.

Hereinafter, a method of manufacturing an organic light emitting device according to an embodiment of the present invention will be described with reference to the organic light emitting device illustrated in FIG. 1.

First, a first electrode is formed by depositing or sputtering a high work-function material on a substrate. The first electrode can be an anode. The substrate, which can be any substrate that is used in conventional organic light emitting devices, may be a glass substrate or a transparent plastic substrate that has excellent mechanical strength, thermal stability, transparency, and surface smoothness, and that can be easily treated and is waterproof. The first electrode can be formed of ITO, IZO, $SnO_2$, ZnO, or any transparent material which has high conductivity.

Then, a HIL can be formed on the first electrode by vacuum deposition, spin coating, casting, Langmuir Blodgett (LB) deposition, or the like.

The heterocyclic compound of Formula I can be used as a material that is used to form the HIL. However, any known material that is used to form a HIL can also be used. Examples of such material are 1,3,5-tricarbazolylbenzene, 4,4'-biscarbazolylbiphenyl, polyvinyl carbazole, m-biscarbazolylphenyl, 4,4'-biscarbazolyl-2,2'-dimethylbiphenyl, 4,4',4"-tri(N-carbazolyl)triphenylamine, 1,3,5-tri(2-carbazolylphenyl)benzene, 1,3,5-tris(2-carbazolyl-5-methoxyphenyl)benzene, bis(4-carbazolylphenyl)silane, N,N'-bis(3-methylphenyl)-N,N'-diphenyl-[1,1-biphenyl]-4,4'diamine (TPD), N,N'-di(naphthalene-1-yl)-N,N'-diphenyl benzydine (α-NPD), N,N'-diphenyl-N,N'-bis(1-naphthyl)-(1,1'-biphenyl)-4,4'-diamine CAPS), poly(9,9-dioctylfluorene-co-N-(4-butylphenyl)diphenylamine) (TFB) and poly(9,9-dioctylfluorene-co-bis-N,N-phenyl-1,4-phenylenediamine (PFB), but are not limited thereto.

The HIL can be formed using various known methods such as vacuum deposition, spin coating, casting and LB deposition.

When the HIL is formed by vacuum deposition, vacuum deposition conditions may vary according to the compound that is used to form the HIL, and the desired structure and thermal properties of the HIL to be formed. In general, however, the vacuum deposition may be performed at a deposition temperature of 50-500° C., a pressure of $10^{-8}$-$10^{-3}$ torr, a deposition speed of 0.01-100 Å/sec, and to a layer thickness of 10 Å-5 μm.

When the HIL is formed by spin coating, coating conditions may vary according to a compound that is used to form the HIL, and the desired structure and thermal properties of the HIL to be formed. In general, however, the coating speed may be in the range of about 2000 to 5000 rpm, and a temperature for a heat treatment process, which is performed to remove a solvent after coating, may be in the range of about 80 to 200° C.

A HTL is then formed on the HIL. The HTL can also be formed using a known method such as vacuum deposition, spin coating, casting, and LB deposition. When the HTL is formed by vacuum deposition or spin coating, the conditions for deposition and coating are similar to those for the formation of the HIL, although conditions for the deposition and coating may vary according to the material that is used to form the HTL.

The heterocyclic compound of Formula I can be used as a material that is used to form the HTL. However, any known material that is used to form a HTL can also be used. Examples of such material are carbazole derivatives such as N-phenylcarbazole and polyvinylcarbazole; and conventional amine derivatives including a fused aromatic ring such as N,N'-bis(3-methylphenyl)-N,N'-diphenyl-[1,1-b]phenyl-4,4'-diamine (TPD) and N,N'-di(naphthalene-1-yl)-N,N'-diphenyl benzydine (α-NPD).

An EML having red (R), green (G) and blue (B) regions can be formed on the HTL. Any material selected from known host materials and known dopant materials can be used as a material for forming the EML. Alternatively or with the know host materials, the heterocyclic compound of Formula I can be used as a host material for blue, green and red fluorescent and phosphorescent devices, and any known material can also be used.

For example, DCM1, DCM2, Eu(thenoyltrifluoroacetone)$_3$ (Eu(TTA)3), and butyl-6-(1,1,7,7,-tetramethyljulolidyl-9-enyl)-4H-pyran (DCJTB) can be used to form a red region of the EML. Alternatively, a dopant such DCJTB can be deposited with Alq3, Alq3 and rubrene can be co-deposited and a dopant can be deposited thereon, or dopants such as BTPIr or RD 61 can be deposited with 4,4'-N—N'-dicarbazole-biphenyl (CBP) to form a red region of the EML, but the present invention is not limited to the above-described examples.

For example, Coumarin 6, C545T, quinacridone and Ir(ppy)$_3$ can be used to form a green region of the EML. Alternatively, a dopant such Ir(ppy)$_3$ can be deposited with CBP, or a dopant such as a coumarin-based material can be deposited with Alq3 as a host to form a green region of the EML, but the present invention is not limited to the above-described examples. Examples of the coumarin-based material may include C314S, C343S, C7, C7S, C6, C6S, C314T and C545T.

For example, oxadiazole dimer dyes (Bis-DAPOXP), spiro compounds (Spiro-DPVBi, Spiro-6P), triarylamine compounds, bis(styryl) amine (DPVBi, DSA), Compound (A), Flrpic, CzTT, anthracene, TPB, PPCP, DST, TPA, OXD-4, BBOT, AZM-Zn, and BH-013x(Idemitsu Corporation) which is an aromatic hydrocarbon compound containing a naphthalene moiety can be used to form a blue region of the EML. Alternatively, a dopant such IDE 105 (Idemitsu Corporation) can be deposited with IDE 140 (Idemitsu Corporation) to form a blue region of the EML. However, the present invention is not limited to the above-described examples.

The thickness of the EML may be in the range of 200 to 500 Å, and preferably 300 to 400 Å. The thicknesses of the R, G and B regions of the EML layer may be identical to or different from each other. When the thickness of the EML is less than 200 Å, lifetime of the device may be decreased. On the other hand, when the thickness of the EML is greater than 500 Å, driving voltage of the device may be increased.

The EML may be formed using a known method such as vacuum deposition, spin coating, casting, or LB deposition. When the EML is formed by vacuum deposition or spin coating, the conditions for deposition and coating are similar to those for the formation of the HIL, although conditions for the deposition and coating may vary according to the material that is used to form the EML.

A hole blocking layer (HBL) (not shown) can optionally be formed on the EML by vacuum deposition or spin coating of a material that is used to form the HBL. The material should have a capability of transporting electrons and an ionization potential higher than EML materials, and thus examples of the material may include bis(2-methyl-8-quinolato)-(p-phenylphenolato)-aluminum (Balq), bathocuproine (BCP), and tris(N-aryl benzimidazole) (TPBI), but are not limited thereto.

The thickness of the HBL may be in the range of 30 to 60 Å, and preferably 40 to 50 Å. When the thickness of the HBL is less than 30 Å, a sufficient hole blocking capability may not be obtained. On the other hand, when the thickness of the HBL is greater than 50 Å, the driving voltage of the device may be increased.

The HBL can be formed using a known method such as vacuum deposition, spin coating, casting, LB deposition, or the like. When the HBL is formed by vacuum deposition and spin coating, conditions for deposition and coating are similar to those for formation of the HIL, although conditions for deposition and coating may vary according to the material that is used to form the HBL.

An ETL can be optionally formed on the EML or the HBL. The ETL may be formed by vacuum deposition or spin coating of a material that is used to form an ETL. The material may be Alq3, but is not limited thereto.

The thickness of the ETL may be in the range of 100 to 400 Å, and preferably, 250 to 350 Å. When the thickness of the ETL is less than 100 Å, sufficient charge balance cannot be maintained since electrons are transported too fast. On the other hand, when the thickness of the ETL is greater than 400 Å, the driving voltage of the device may be increased.

The ETL can be formed using a known method such as vacuum deposition, spin coating, casting, LB deposition, or the like. When the ETL is formed by vacuum deposition and spin coating, conditions for deposition and coating are similar to those for formation of the HIL, although conditions for deposition and coating may vary according to the material that is used to form the ETL.

An EIL may be formed by vacuum deposition or spin coating on the ETL, HBL or ETL. The material that is used to form the EIL may be $BaF_2$, LiF, NaCl, CsF, $Li_2O$, BaO, Liq, or the like, but is not limited thereto.

The thickness of the EIL may be in the range of 2 to 10 Å, preferably, 2 to 5 Å, and more preferably 2 to 4 Å. When the thickness of the EIL is less than 2 Å, sufficient electron injecting capability may not be obtained. On the other hand, when the thickness of the EIL is greater than 10 Å, the driving voltage of the device may be increased.

The EIL can be formed using a known method such as vacuum deposition, spin coating, casting, LB deposition, or the like. When the EIL is formed by vacuum deposition and spin coating, conditions for deposition and coating are similar to those for formation of the HIL, although conditions for deposition and coating may vary according to the material that is used to form the EIL.

Finally, a second electrode is formed on the EIL by deposition, thereby completing the manufacture of the organic light emitting device.

The material that is used to form the second electrode can be a transparent metal oxide with excellent conductivity such as ITO, IZO, $SnO_2$, and ZnO. Alternatively, Li, Mg, Al, Al—Li, Ca, Mg—In, Mg—Ag, and Ca—Al can be used to form a thin film of the second electrode, and thus the second electrode can be a reflective electrode, a semitransparent electrode or a transparent electrode in various forms. The material used to form the second electrode is not limited to the above-described examples.

The first electrode or the second electrode can be an anode or a cathode.

Hereinafter, the present invention will be described more specifically with reference to the following Examples including Synthesis Examples of a heterocyclic compound represented by Formula I and Preparation Examples of an organic light emitting device. However, the Examples are not intended to limit the scope of the present invention.

EXAMPLES

Synthesis Example 1

Preparation of Compound 1

Compound 1 was synthesized via Reaction Scheme 2 below.

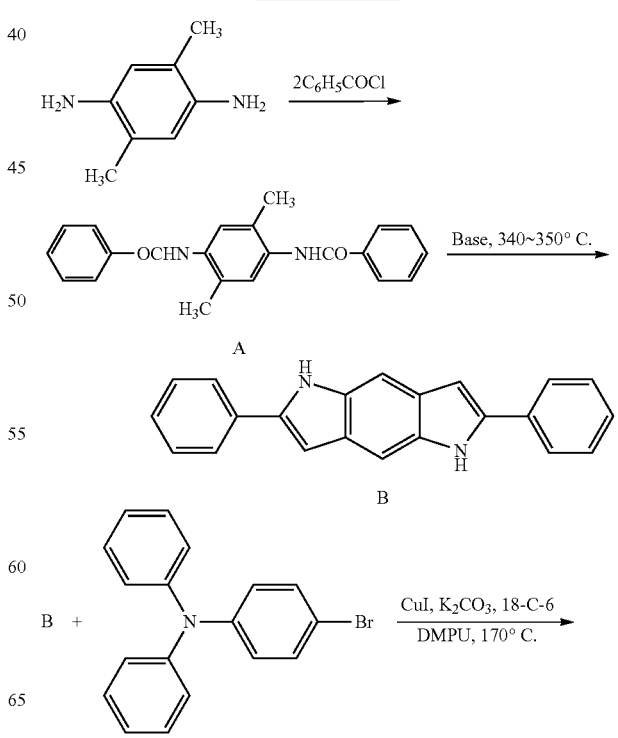

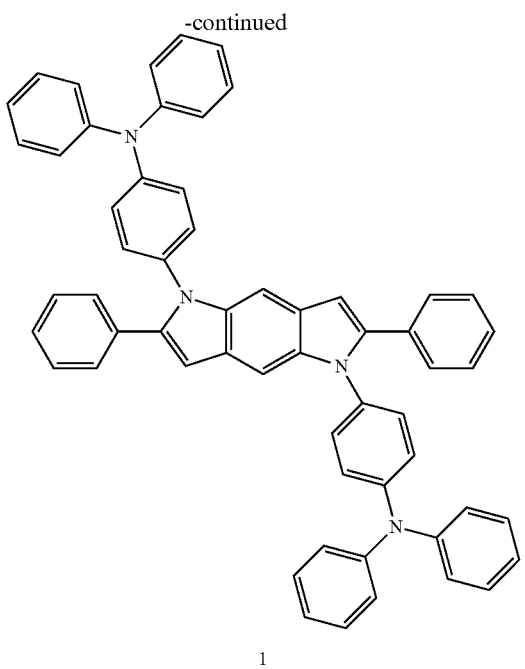

1

(1) Synthesis of Intermediate A 10 g (73.4 mmol) of 2,5-dimethyl-1,4-phenylenediamine was dissolved in 50 ml of dichloromethane, and 25 nit of triethylamine was added thereto. The mixture was cooled in an ice bath and 17 ml (0.147 mol) of benzoyl chloride was dropped thereto. Then, the resultant was stirred at 30° C. for 1 hour. After the solvent was removed from the reaction solution, the resultant was recrystallized in dimethylformamide (DMF). An obtained crystal was filtered while washing with acetone to obtain 23.4 g of white solid Intermediate A (Yield: 93%).

$^1$H NMR (CDCl$_3$, 400 MHz) δ (ppm) 8.15 (s, 2H), 7.95-7.41 (m, 10H), 7.29 (s, 2H) 2.28 (s, 6H); $^{13}$C NMR (CDCl$_3$, 100 MHz) δ (ppm) 165.2, 134.4, 133.5, 131.9, 128.6, 127.5, 126.3, 121.2, 13.8.

(2) Synthesis of Intermediate B

A mixture prepared by sufficiently pulverizing and stirring 4.5 g (12 mmol) of Intermediate A and 13.5 g (120 mmol) of potassium t-butoxide was added to an autoclave and reacted at 340-350° C. at 5 MPa for 2 hours. When the reaction was completed, the resultant was cooled to room temperature. The resultant in the form of tar was pulverized, neutralized, filtered while washing using distilled water and dried. The obtained crude product was purified in a soxhlet device using acetone for 2 days to obtain 0.94 g of white solid Intermediate B (Yield: 21%).

$^1$H NMR (DMSO-d6, 400 MHz) δ (ppm) 11.0, (s, 2H), 7.86 (d, 4H), 7.44 (t, 6H), 7.27 (t, 2H), 6.89 (s, 2H); $^{13}$C NMR (DMSO-d$_6$, 100 MHz) δ (ppm) 137.9, 134.6, 132.6, 128.7, 127.0, 126.9, 124.7, 99.3, 97.8.

(3) Synthesis of Compound 1

3.08 g (10 mmol) of Intermediate B and 9.73 g (30 mmol) of 4-bromotriphenylamine were added to 50 ml of 1,3-dimethyl-3,4,5,6-tetrahydro-(1H)-pyrimidinone (DMPU). 0.761 g (4 mmol) of CuI, 11.057 g (80 mmol) of potassium carbonate (K$_2$CO$_3$) and 0.1 g (4 mmol) of 18-Crown-6 were added thereto. The mixture was stirred at 170° C. for 20 hours and cooled to room temperature. The solvent in the resultant solution was removed by distillation under reduced pressure, and the residue was dissolved by adding 100 in dichloromethane and washed several times with water. The resultant organic layer was dried using MgSO$_4$ and dried under reduced pressure to obtain a crude product. The crude product was separated and purified using a silica gel column chromatography to obtain 3.74 g of solid Compound I (Yield: 47%).

$^1$H NMR (CD$_2$Cl$_2$, 400 MHz) δ (ppm) 7.91 (d, 4H), 7.45 (s, 2H), 7.38-7.08 (m, 38H); $^{13}$C NMR (CD$_2$Cl$_2$, 100 MHz) δ (ppm) 129.7, 129.3, 129.0, 128.6, 127.2, 126.4, 125.2, 124.5, 124.1, 123.5, 123.1, 122.2, 103.2, 100.4, 99.3, 98.3.

Synthesis Example 2

Preparation of Compound 73

Compound 73 was synthesized via Reaction Scheme 3 below.

Reaction Scheme 3

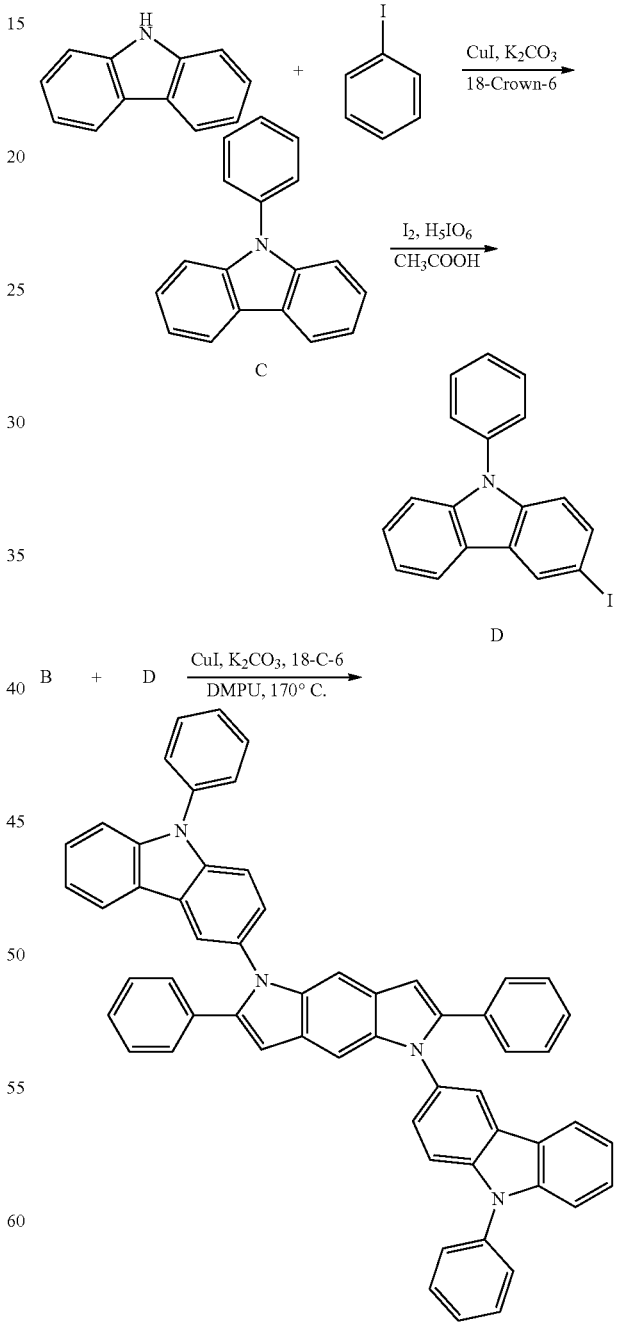

73

(1) Synthesis of Intermediate C 16.7 g (100 mmol) of carbazole, 26.5 g (130 mmol) of iodobenzene, 1.9 g (10 mmol) of CuI, 138 g (1 mol) of potassium carbonate ($K_2CO_3$), and 530 mg (2 mmol) of 18-crown-6 were dissolved in 500 ml of 1,3-dimethyl-3,4,5,6-tetrahydro-(1H)-pyrimidinone (DMPU), and the mixture was heat-treated at 170° C. for 8 hours. After the reaction was completed, the resultant was cooled to room temperature and a solid material was filtered. A small amount of ammonia water was added to the filtrate solution, and the filtrate was washed three times with 300 ml diethyl ether. The resultant organic layer was dried using $MgSO_4$, and dried under reduced pressure to obtain a crude product. The crude product was separated and purified using a silica gel column chromatography to obtain 22 g of white solid Intermediate C (Yield: 90%).

$^1$H NMR ($CDCl_3$, 400 MHz) δ (ppm) 8.12 (d, 2H), 7.58-7.53 (m, 4H), 7.46-7.42 (m, 1H), 7.38 (d, 4H), 7.30-7.26 (m, 2H); $^{13}$C NMR ($CDCl_3$, 100 MHz) δ (ppm) 141.0, 137.9, 130.0, 127.5, 127.3, 126.0, 123.5, 120.4, 120.0, 109.9.

(2) Synthesis of Intermediate D 2.433 g (10 mmol) of Intermediate C was added to 100 mL of 80% acetic acid. 1.357 g (5.35 mmol) of solid 12 and 0.333 g (1.46 mmol) of solid o-$H5IO_6$ were added thereto, and the mixture was stirred in a nitrogen atmosphere at 80° C. for 2 hours.

After the reaction was completed, the resultant was subject to extraction three times with 50 ml of diethyl ether. The organic layer was dried using $MgSO_4$, and a crude product obtained by evaporating the solvent was separated and purified using a silica gel column chromatography to obtain 3.23 g of white solid Intermediate D (Yield: 87%).

$^1$H NMR ($CDCl_3$, 300 MHz) δ (ppm) 8.43 (d, 1H), 8.05 (d, 1H), 7.62 (dd, 1H), 7.61-7.75 (m, 2H), 7.51-7.43 (m, 3H), 7.41-7.35 (m, 2H), 7.27 (dd, 1H), 7.14 (d, 1H)

(3) Synthesis of Compound 73

3.08 g (10 mmol) of Intermediate B and 11.1 g (30 mmol) of Intermediate D were added to 50 ml of DMPU, and 0.761 g (4 mmol) of CuI, 11.057 g (80 mmol) of potassium carbonate ($K_2CO_3$) and 0.1 g (4 mmol) of 18-Crown-6 were added thereto. Then, the mixture was stirred at 170° C. for 20 hours and cooled to room temperature, and the solvent was removed by distillation under reduced pressure. The resultant was dissolved using 100 ml dichloromethane and washed several times with water. The resultant organic layer was dried using $MgSO_4$, and dried under reduced pressure to obtain a crude product. The crude product was separated and purified using a silica gel column chromatography to obtain 3.32 g of light yellow solid Compound 73 (Yield: 42%).

$^1$H NMR ($CD_2Cl_2$, 400 MHz)δ (ppm) 8.22 (d, 2H), 7.70 (d, 4H), 7.68-6.81 (m, 32H); $^{13}$C NMR ($CD_2Cl_2$, 100 MHz)δ (ppm) 130.4, 129.6, 128.9, 128.7, 128.5, 128.3, 128.0, 127.2, 127.0, 126.8, 126.2, 125.1, 124.6, 124.2, 123.8, 121.8, 121.2, 120.5, 120.1, 110.4, 110.1, 103.2, 99.5, 98.5, 98.2

Example 1

Preparation of Organic Light Emitting Device

A Corning 15 Ω/$cm^2$ (1200 Å) ITO glass substrate was cut into pieces of 50 mm×50 mm×0.7 mm in size, then the pieces were cleaned by sonification in isopropyl alcohol and deionized water for 5 minutes each, and then the pieces were exposed to ultraviolet rays and UV ozone cleaned for 30 minutes. The glass substrates were installed in a vacuum deposition device.

Compound I was vacuum deposited to a thickness of 600 Å on the substrate to form a HIL. Then, 4,4'-bis[N-(1-naphthyl)-N-phenylaminobiphenyl (NPB) as a hole transporting compound was vacuum deposited to a thickness of 300 Å on the HIL to form a HTL.

IDE215 (Idemitsu Corporation) as a known blue fluorescent host and IDE 118 (Idemitsu Corporation) as a known blue fluorescent dopant were deposited at the same time in a weight ratio of 98:2 on the HTL to form an EML with a thickness of 200 Å.

Then, $Alq_3$ was deposited on the EML to a thickness of 300 Å to form an ETL. LiF as a halogenated alkali metal was deposited on the ETL to a thickness of 10 Å to form an EIL, and Al was vacuum deposited on the EIL to a thickness of 3000 Å (negative electrode) to form a LiF/Al electrode to complete the manufacture of an organic light emitting device.

At a current density of 100 mA/$cm^2$, the driving voltage of the organic light emitting device was 6.95 V, the brightness was 7,781 cd/$m^2$, the color coordinates were (0.144, 0.241), and the light emitting efficiency was 7.78 cd/A.

Example 2

Preparation of Organic Light Emitting Device

An organic light emitting device was manufactured in the same manner as in Example 1 except that Compound 73 was used instead of Compound I in the formation of the HIL.

At a current density of 100 mA/$cm^2$, the driving voltage of the organic light emitting device was 7.82 V, the brightness was 6,932 cd/$m^2$, the color coordinates were (0.143, 0.242), and the light emitting efficiency was 6.93 cd/A.

Comparative Example 1

Preparation of Organic Light Emitting Device

An organic light emitting device was manufactured in the same manner as in Example 1 except that 4,4',4''-tris[2-naphthyl(phenyl)aminotriphenylamine (2-TNATA) was used instead of Compound 1 in the formation of the HIL.

At a current density of 100 mA/$cm^2$, the driving voltage of the organic light emitting device was 7.757 V, the brightness was 6,219 cd/$m^2$, the color coordinates were (0.145, 0.243), and the light emitting efficiency was 6.22 cd/A.

Characteristics of the organic light emitting devices according to Examples 1 and 2 and Comparative Example 1 are shown in Table 1.

TABLE 1

| Example | Driving voltage (V) | Current density (mA/$cm^2$) | Brightness (cd/$m^2$) | Light emitting efficiency (cd/A) | Color coordinates (x, y) |
|---|---|---|---|---|---|
| Example 1 | 6.95 | 100 | 7,781 | 7.78 | 0.144, 0.243 |
| Example 2 | 7.28 | 100 | 6,932 | 6.93 | 0.143, 0.242 |
| Comparative Example 1 | 7.75 | 100 | 6,219 | 6.22 | 0.143, 0.243 |

As a result of comparing compounds represented by Formula I according to an embodiment of the present invention with 2-TNATA which is a known material, the compounds of the present invention had excellent current-voltage-luminance (1-V-L) properties equal to or higher than 2-TNATA. The organic light emitting devices prepared according to Examples 1 and 2 had improved characteristics such as high efficiency, low driving voltage and high brightness. In addition, the organic light emitting devices of Examples 1 and 2 had longer lifetime compared to that of Comparative Example 1.

When the compound represented by Formula I according to an embodiment of the present invention is used as a material for forming a hole injection layer (HIL) of an organic light emitting device, the organic light emitting device can have low driving voltage, high efficiency, high brightness and long lifetime based on its excellent hole injecting and transporting capability.

As described above, the heterocyclic compound according to an embodiment of the present invention has excellent electrical properties and high charge transport capability, and thus can be efficiently used as a material for forming at least one of a hole injection layer, a hole transport layer and an emission layer suitable for fluorescent and phosphorescent devices realizing all colors including red, green, blue and white. Therefore, an organic light emitting device having high efficiency, low driving voltage, high brightness and long lifetime can be manufactured.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A heterocyclic compound represented by Formula I:

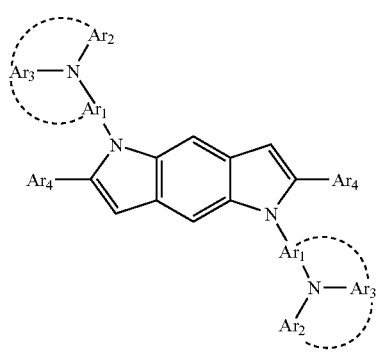

(I)

wherein $Ar_1$ is a bivalent linking group and is a C6-C16 substituted or unsubstituted arylene or heteroarylene group;

$Ar_2$ and $Ar_3$ are each independently selected from the group consisting of a C6-C20 substituted or unsubstituted aryl group, a C4-C20 substituted or unsubstituted heteroaryl group and a C6-C20 substituted or unsubstituted fused polycyclic group;

$Ar_4$ is selected from the group consisting of a C6-C20 substituted or unsubstituted aryl group, a C6-C20 substituted or unsubstituted aryloxy group, a C4-C20 substituted or unsubstituted heteroaryl group and a C6-C20 substituted or unsubstituted fused polycyclic group; and optionally, $Ar_1$ and $Ar_3$ or $Ar_2$ and $Ar_3$ are connected to each other to form a ring.

2. The heterocyclic compound of claim 1, wherein $Ar_2$ and $Ar_3$ are each independently selected from the group consisting of a phenyl group, a tolyl group, a fluorophenyl group, a biphenyl group, a (N,N'-diphenyl)aminophenyl group, a naphthyl group, a phenylcarbazolyl group and a dimethylfluorenyl group.

3. The heterocyclic compound of claim 1, wherein $Ar_4$ is selected from the group consisting of a phenyl group, a tolyl group, a cyanophenyl group, a fluorophenyl group, a biphenyl group, a naphthyl group and a naphthylphenyl group.

4. The heterocyclic compound of claim 1, wherein $Ar_1$ is a phenylene group or a biphenylene group.

5. The heterocyclic compound of claim 1, wherein $Ar_1$ and $Ar_3$ or $Ar_2$ and $Ar_3$ are connected to each other to form a carbazolyl group.

6. The heterocyclic compound of claim 1, wherein the compound represented by Formula I is selected from the group consisting of the compounds represented by the formulae below:

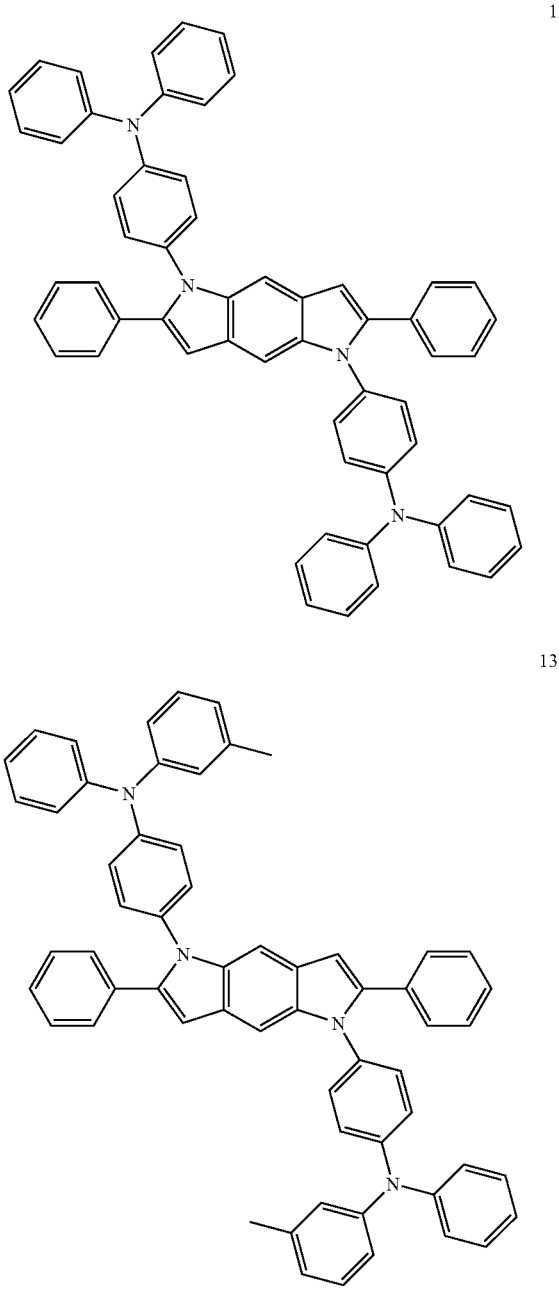

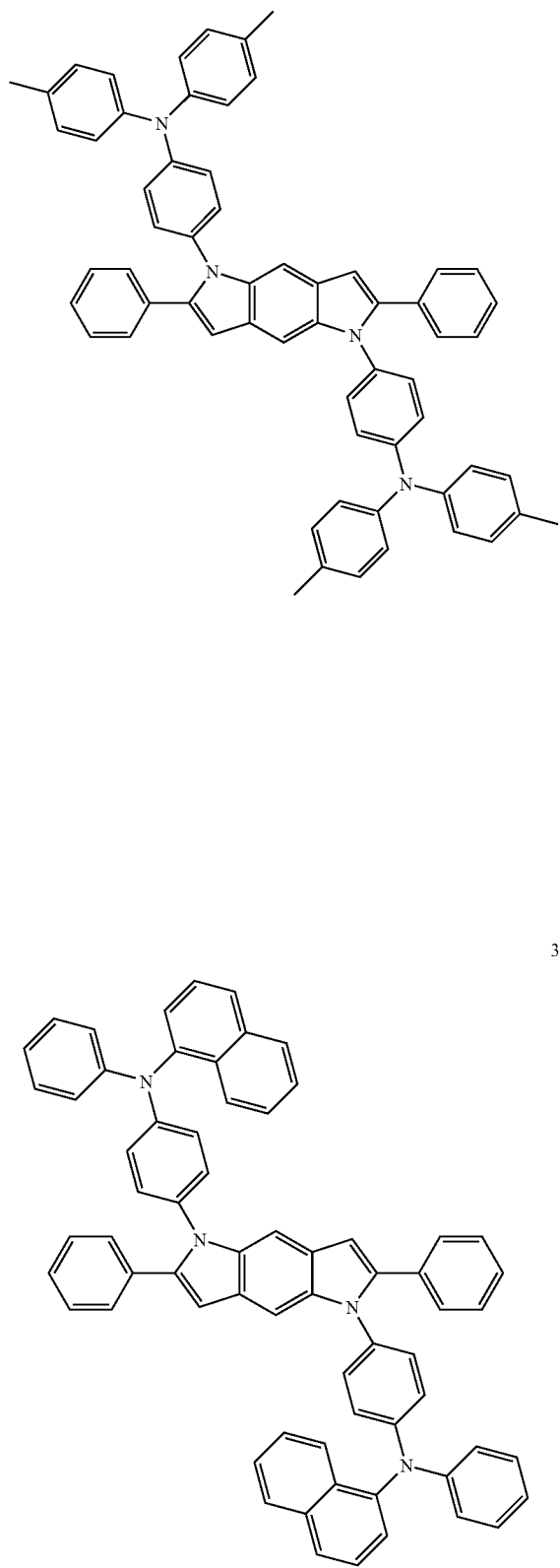
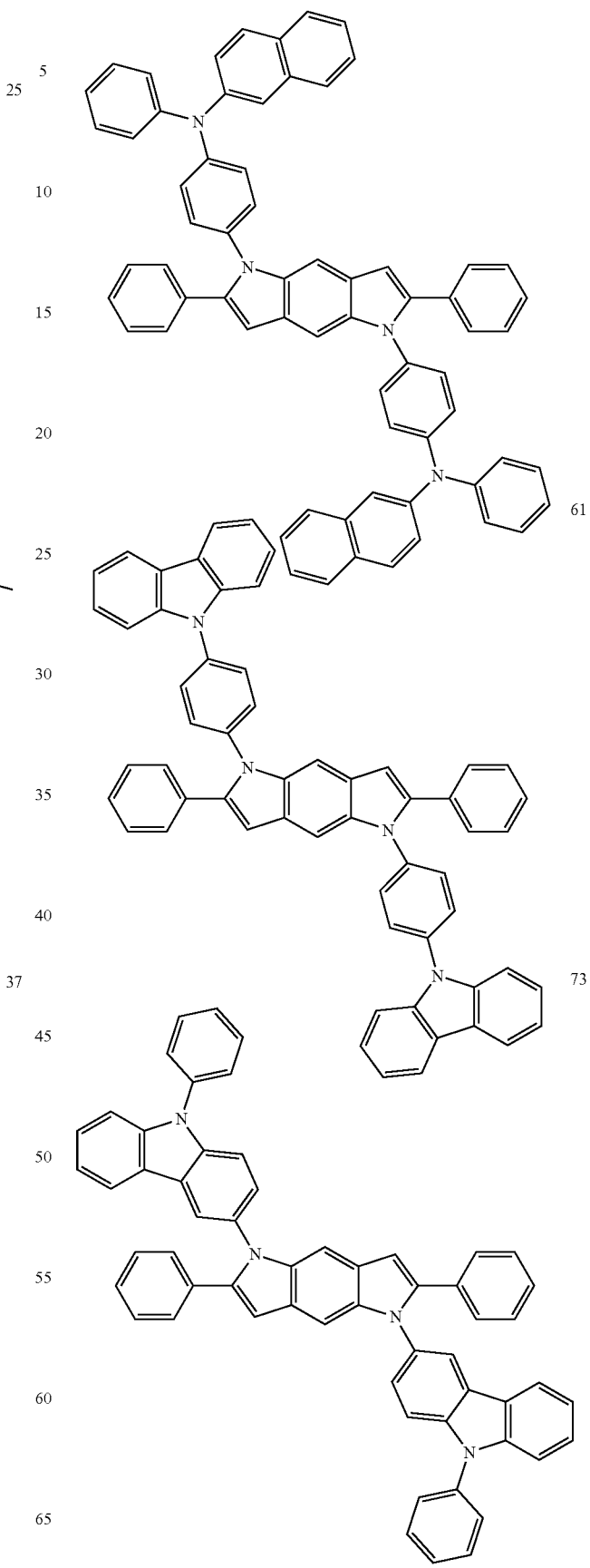

117
-continued
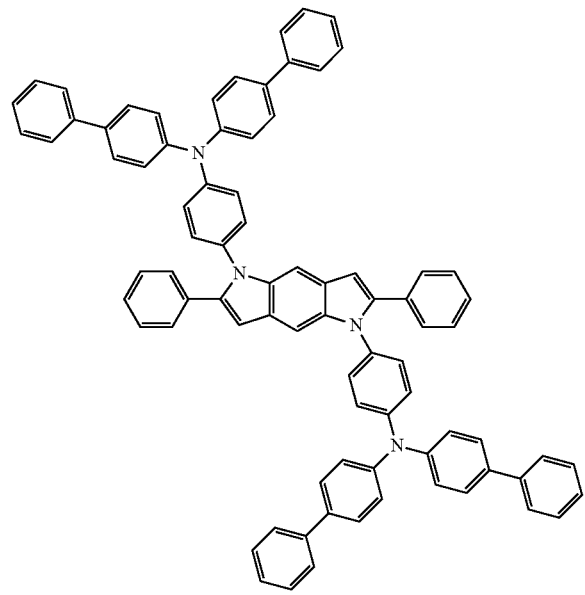
85
118
-continued
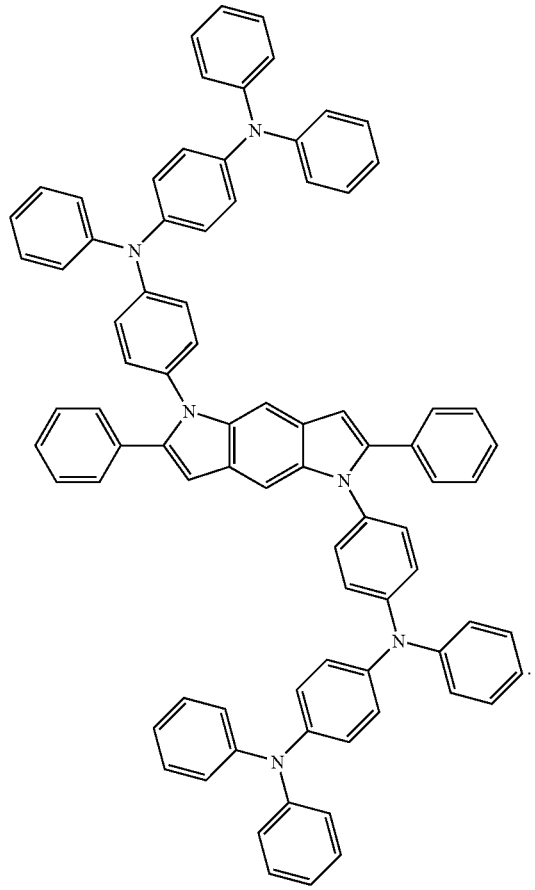
112
7. The heterocyclic compound of claim 1, wherein the compound represented by Formula I is selected from the group consisting of the compounds represented by Formulae 1 through 183:
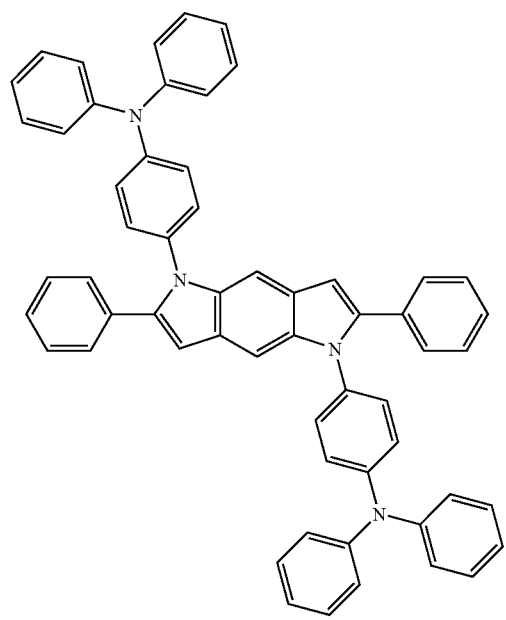
1
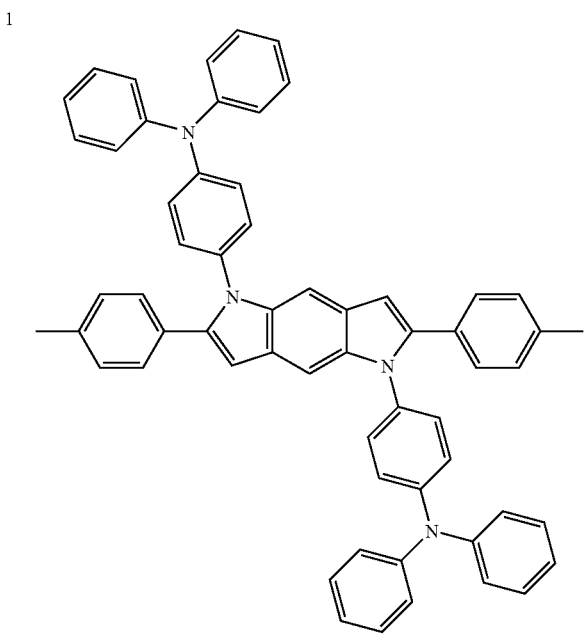
2

-continued
3
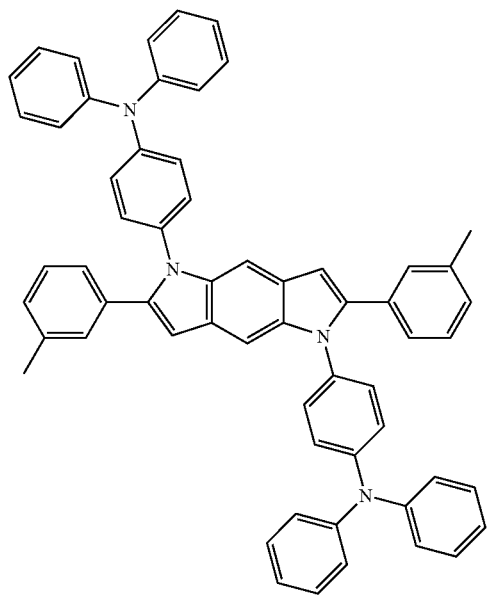
4
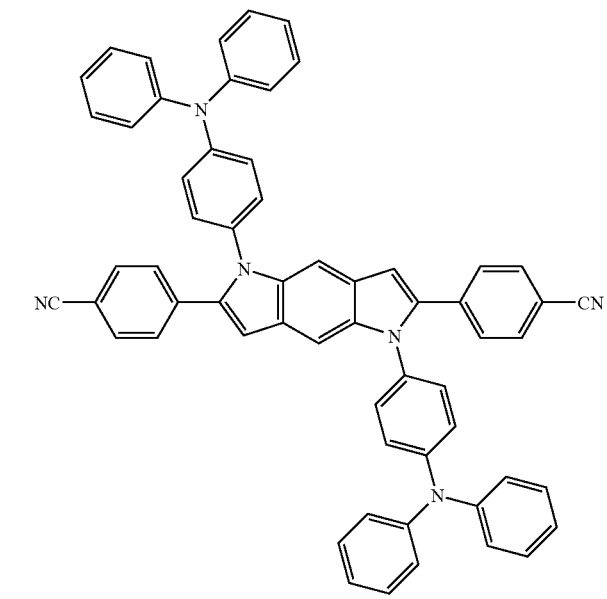
5
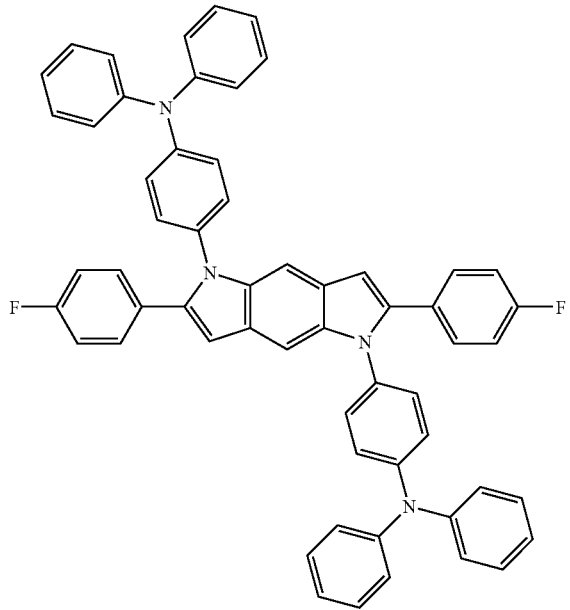
6
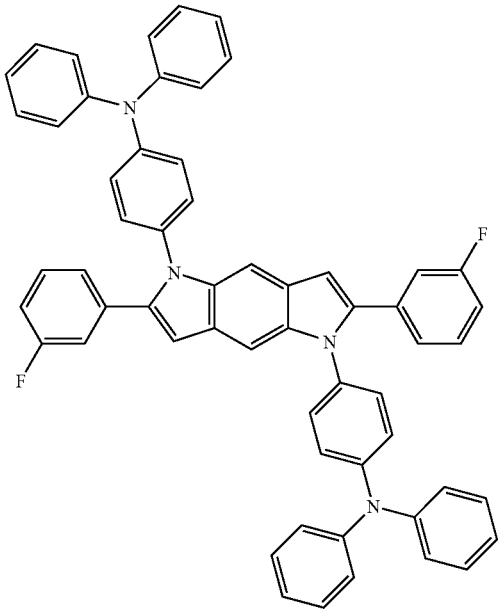
7
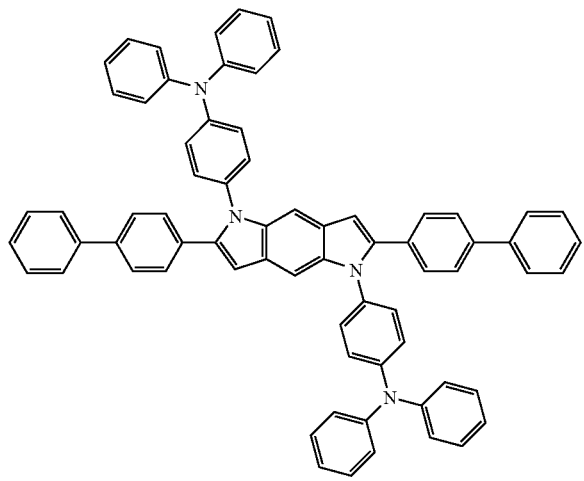
8
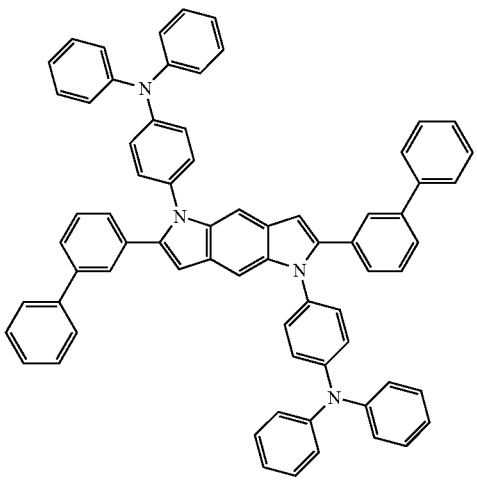

9
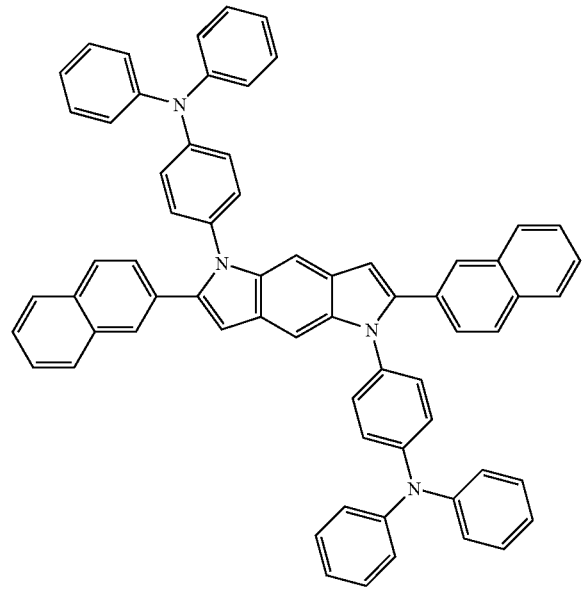
10
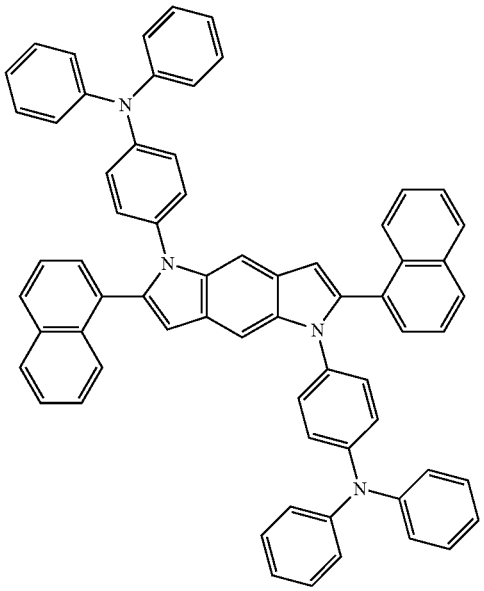
11
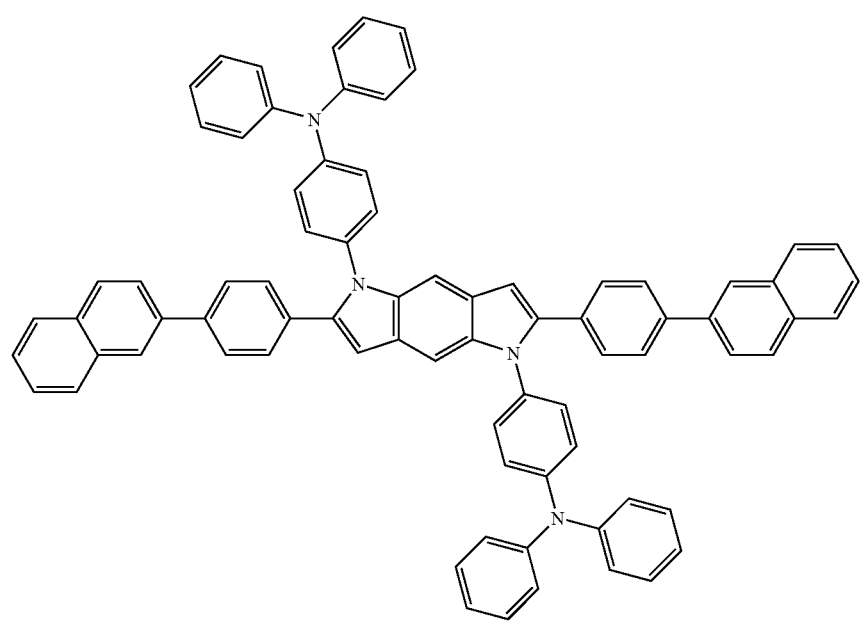

12
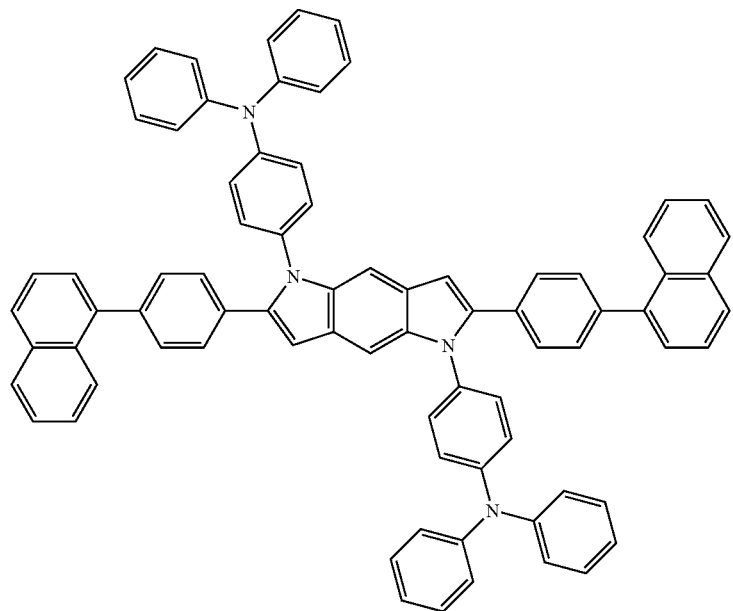
13
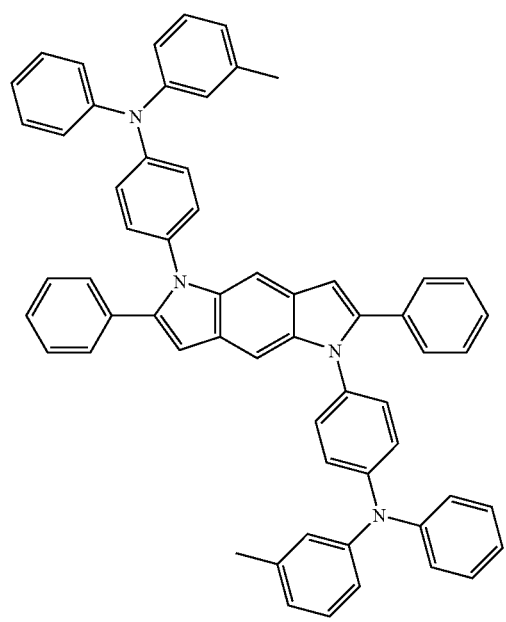
14
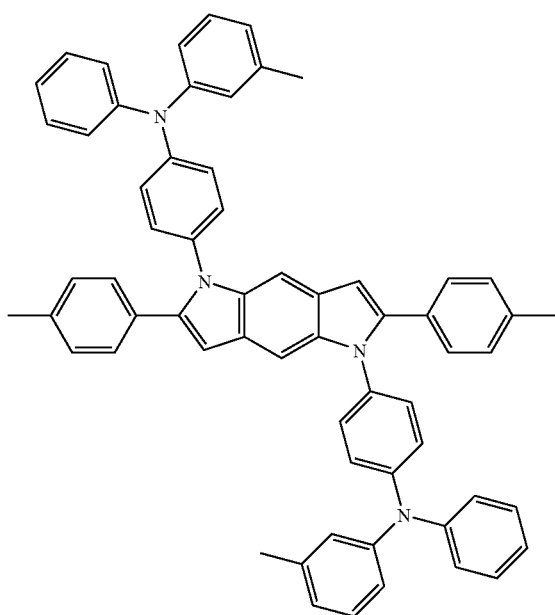

-continued
15
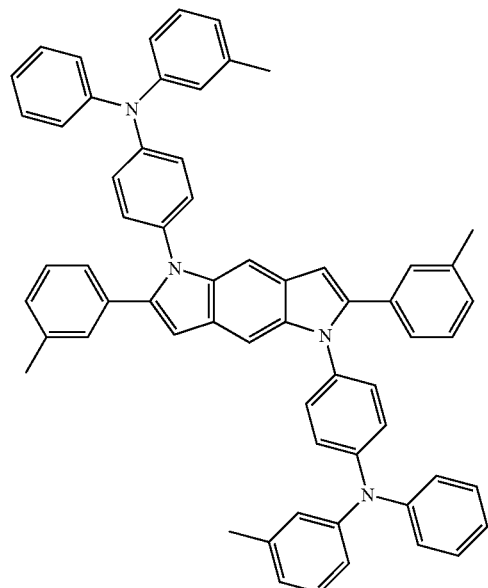
16
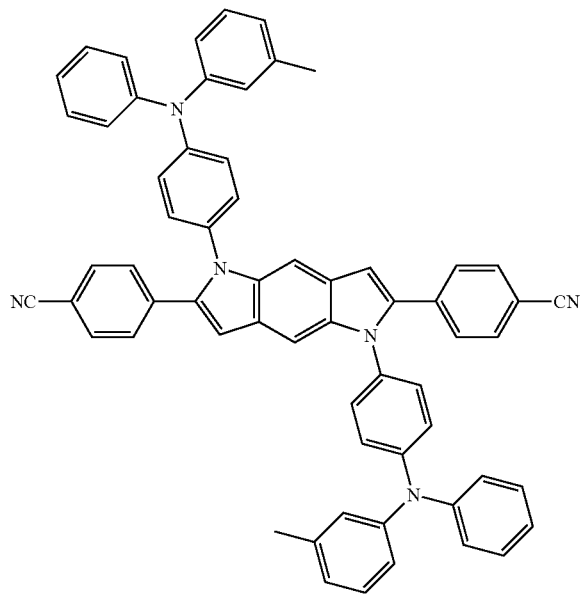
17
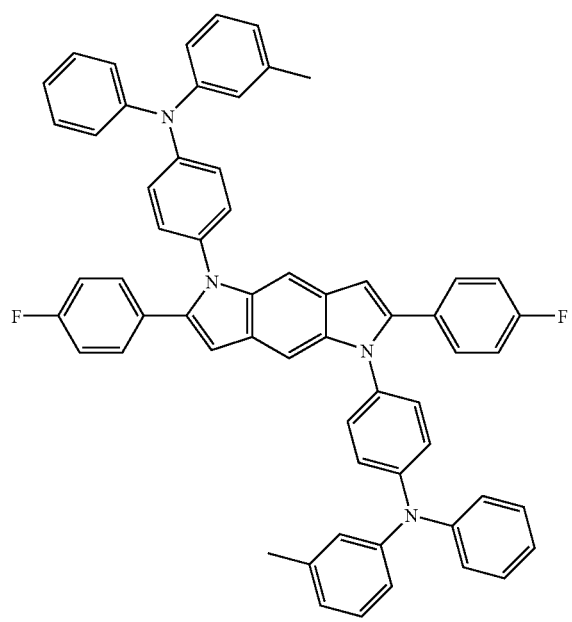
18
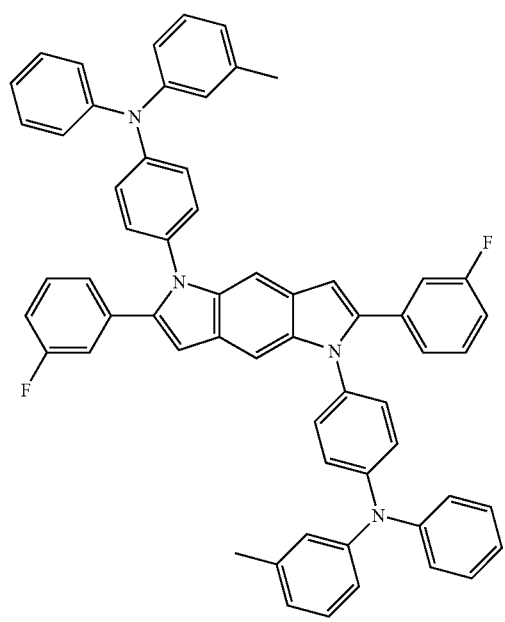

127
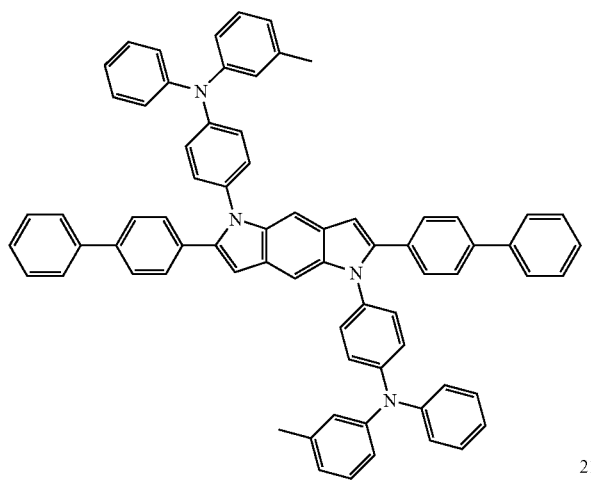
128
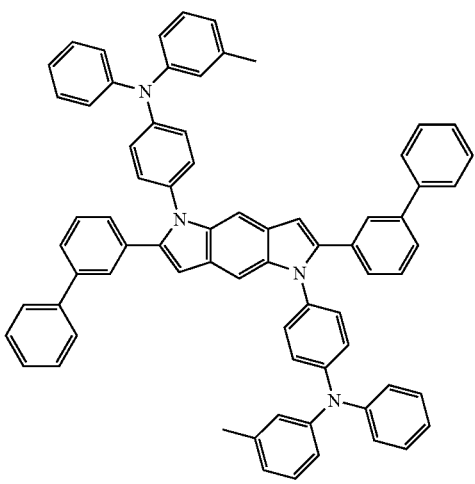
20
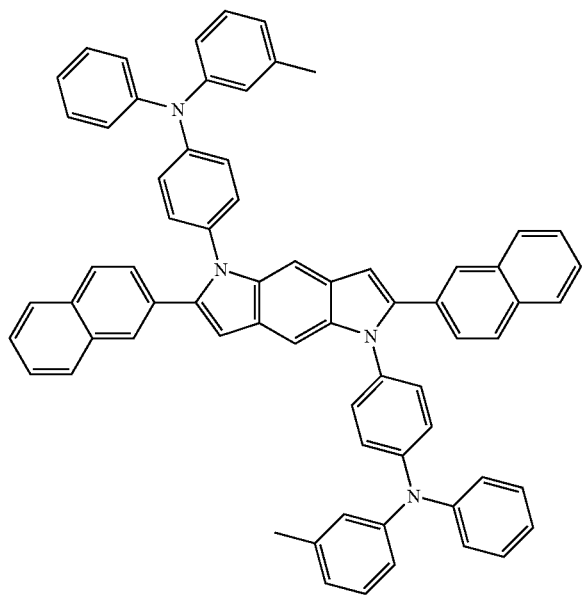
21
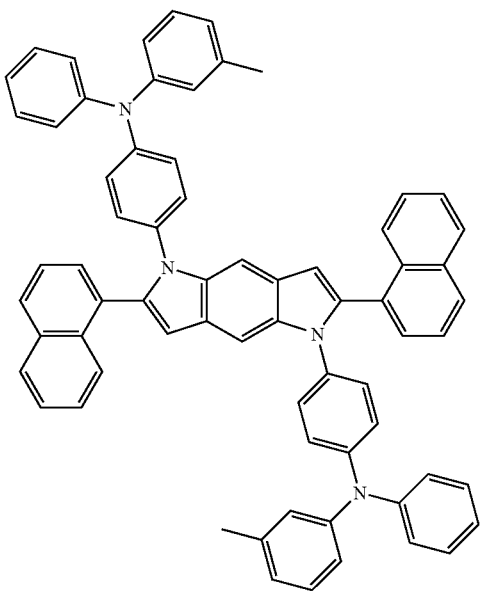
22
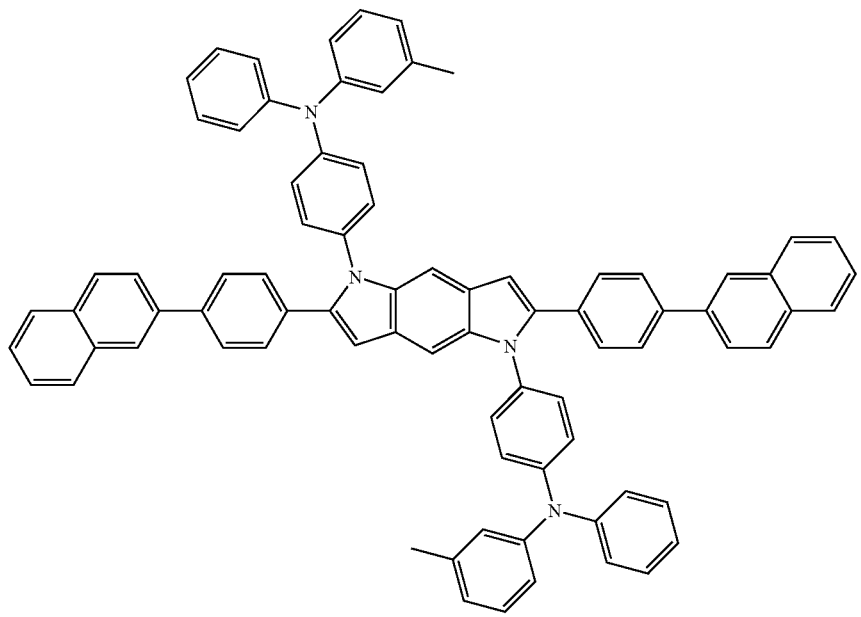
23

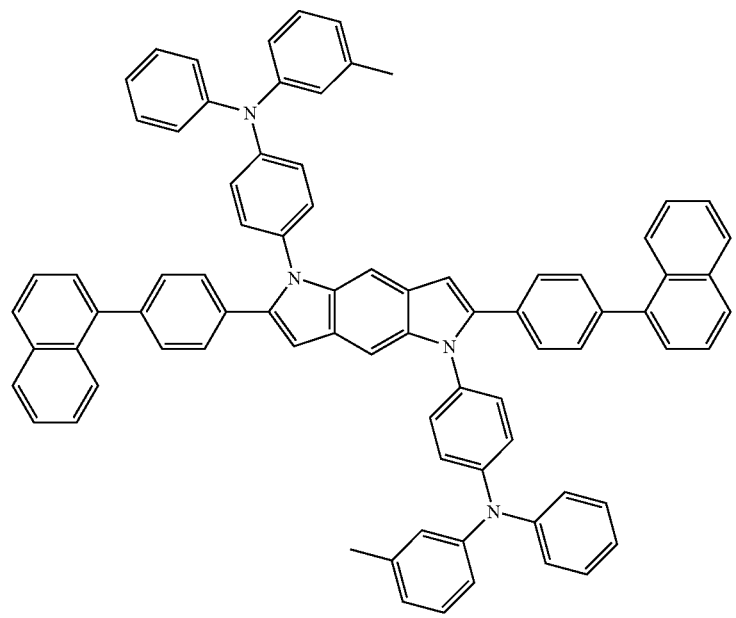
24
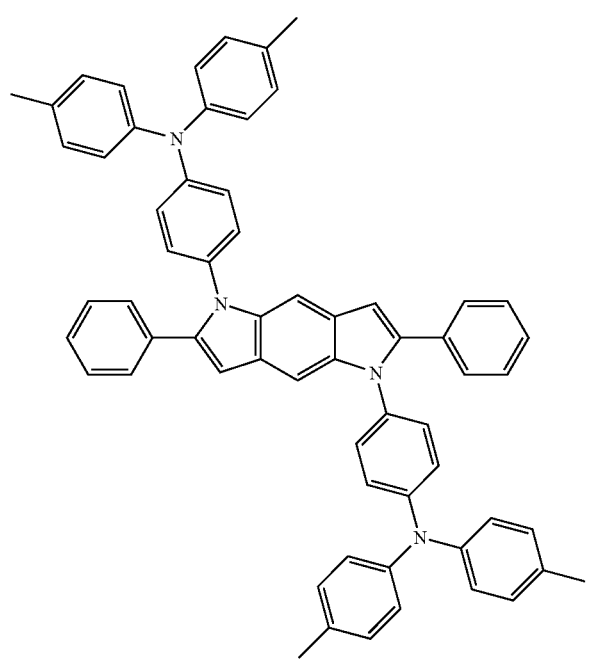
25
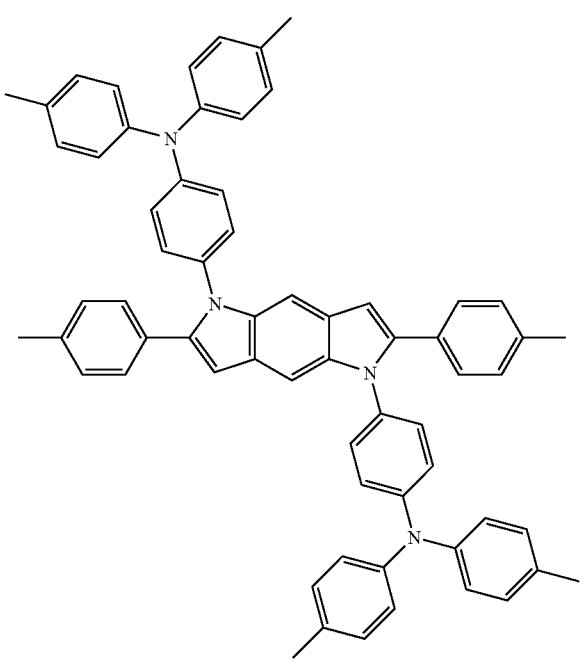
26

27
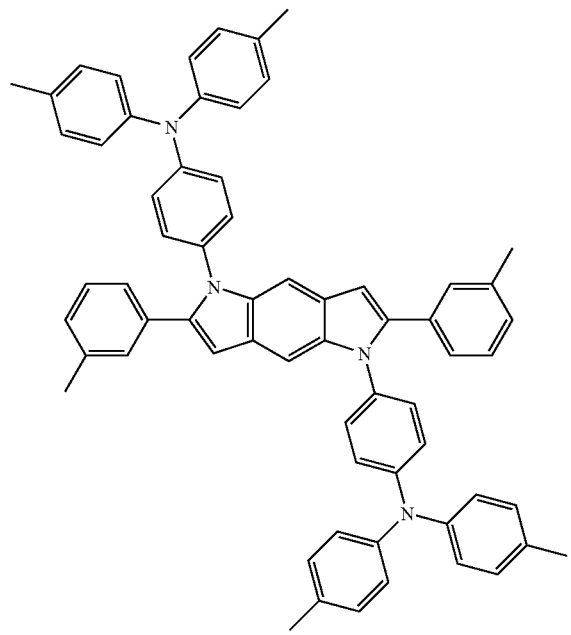
28
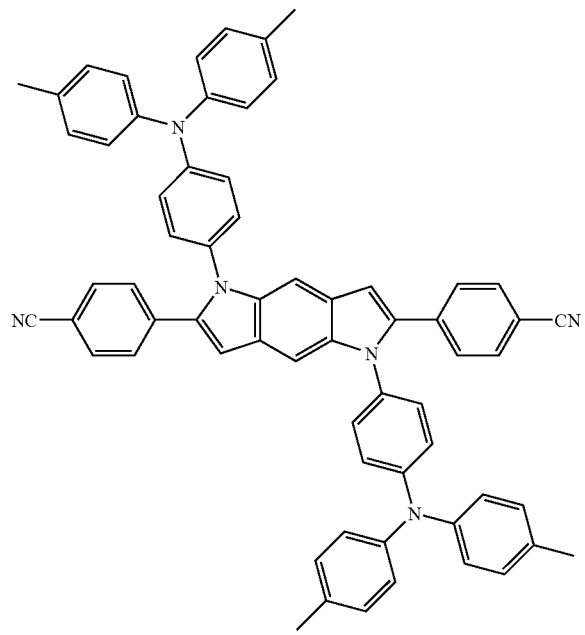
29
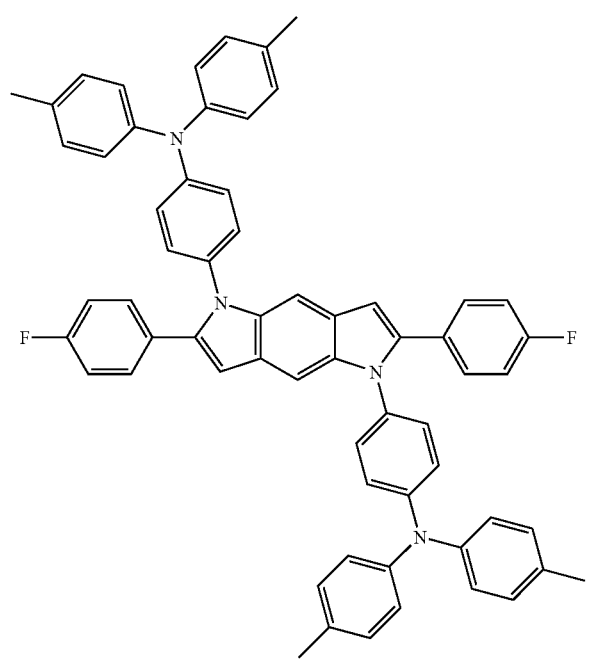
30
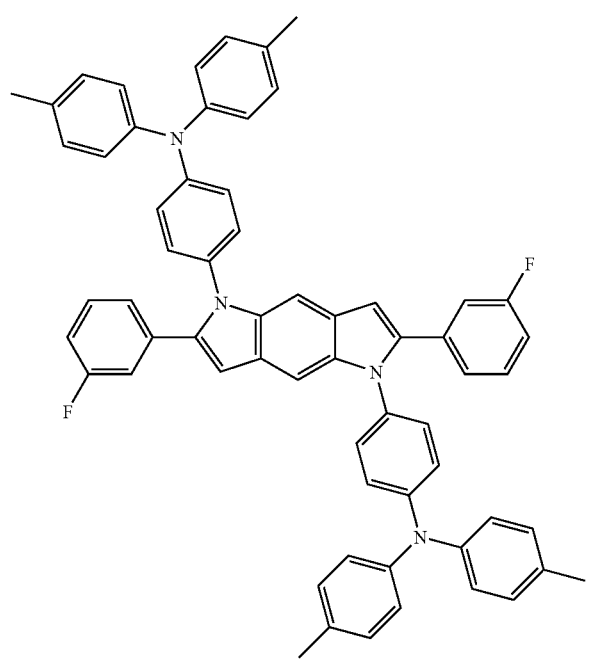

133
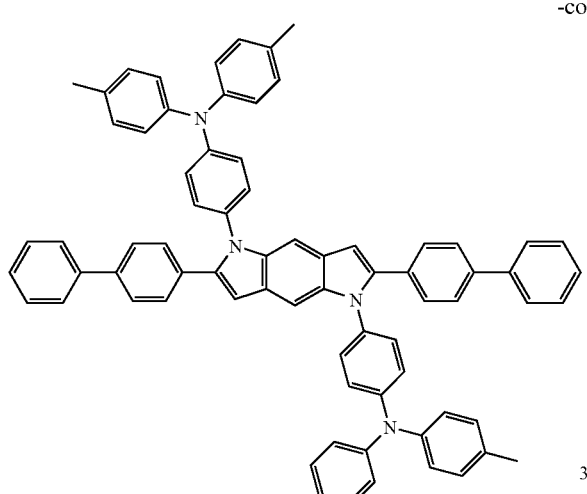
134
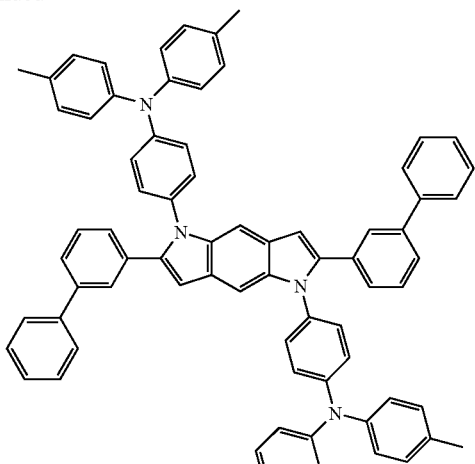
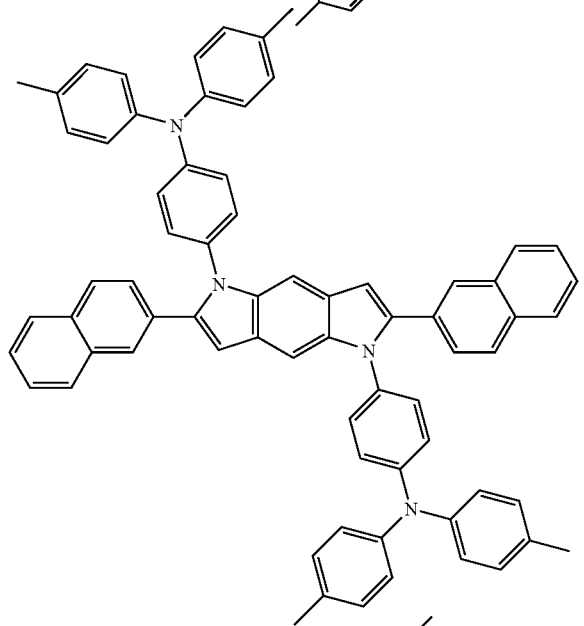
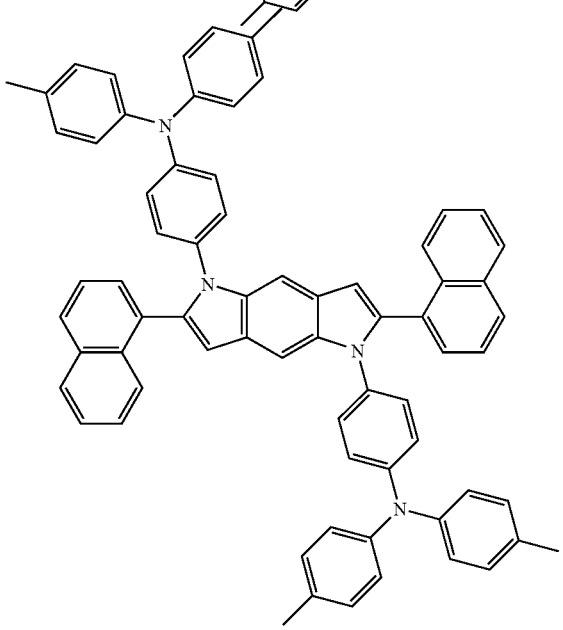
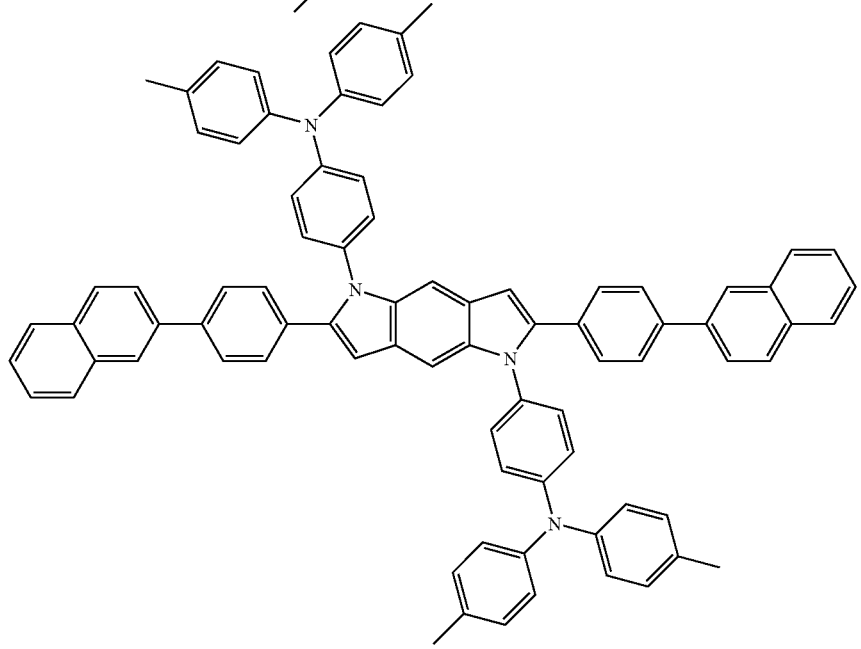

-continued
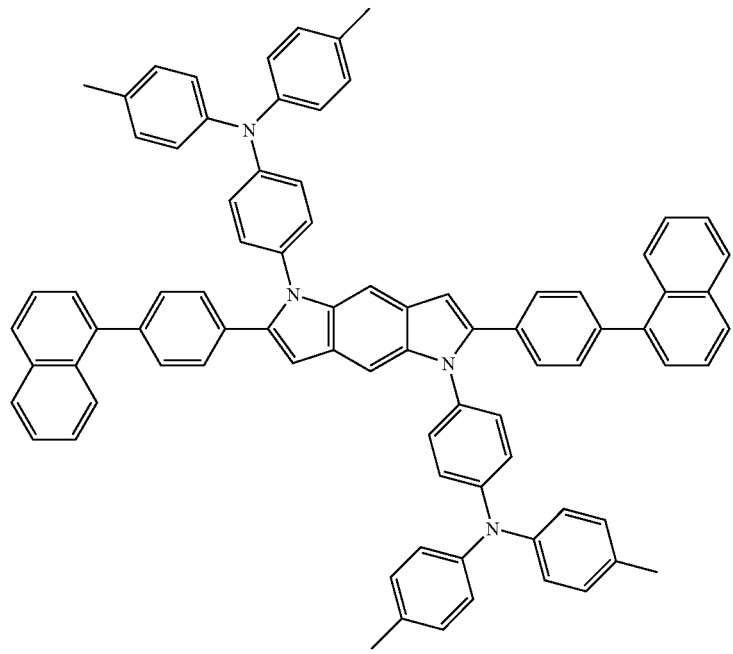
36
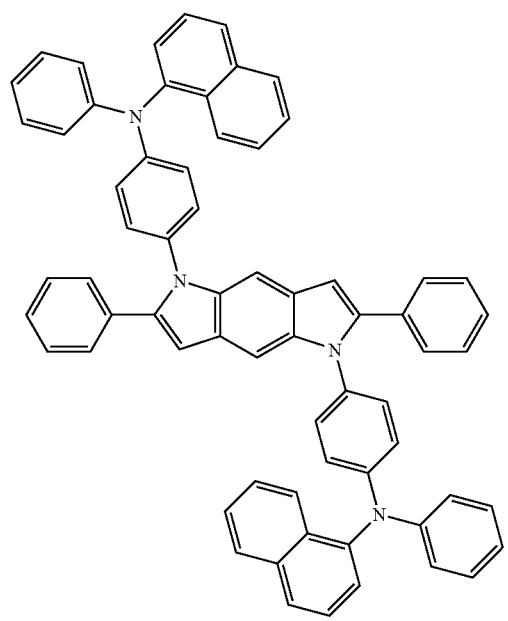
37
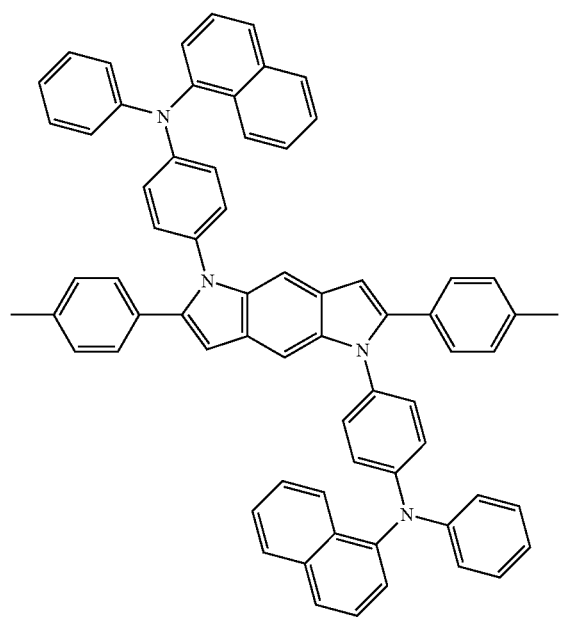
38

-continued
39
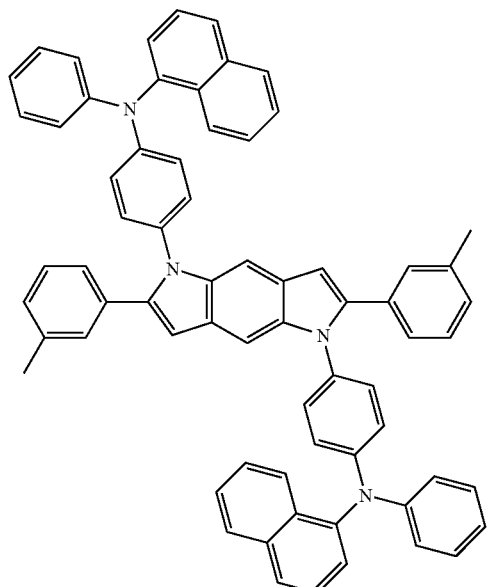
40
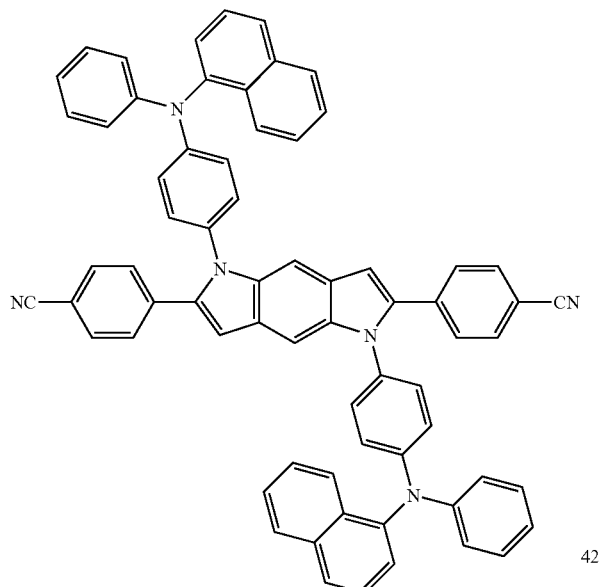
41
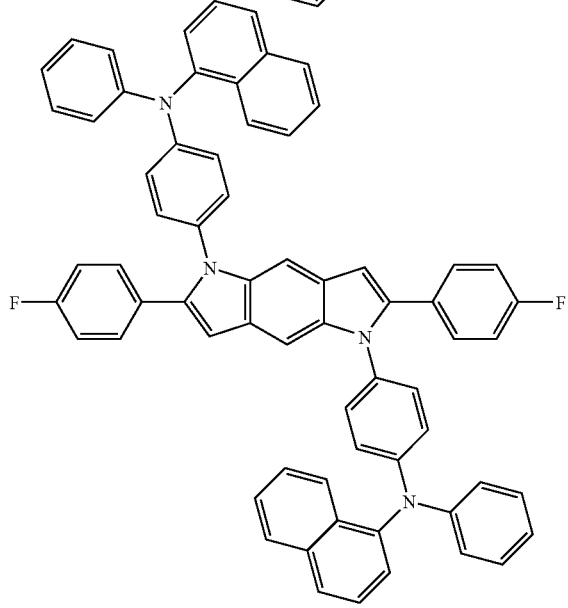
42
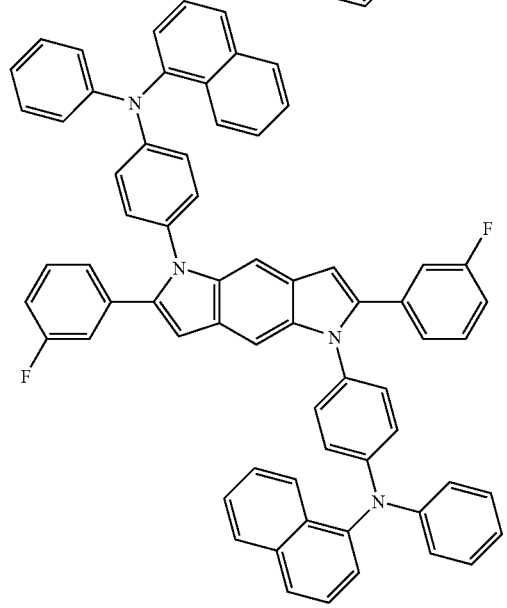
43
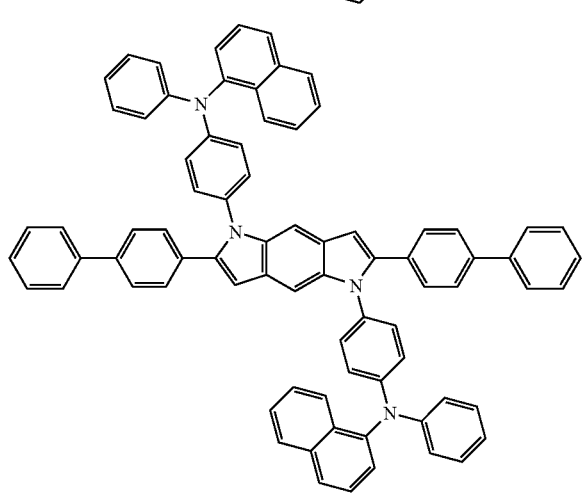
44
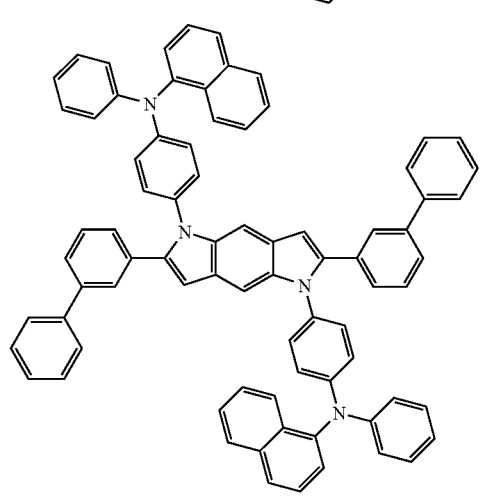

-continued
45
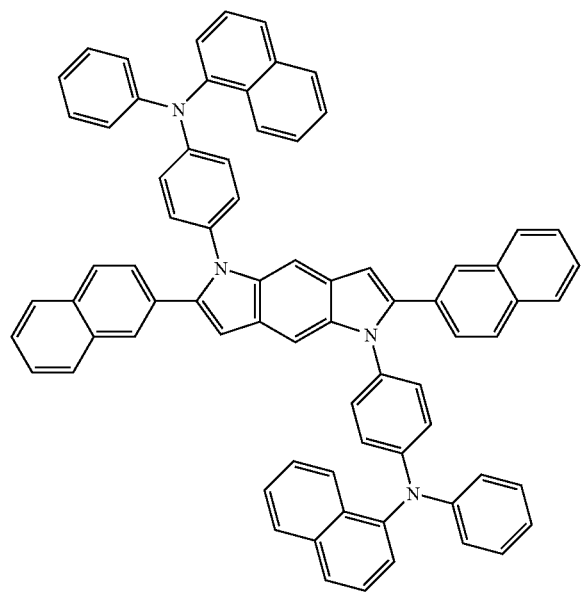
46
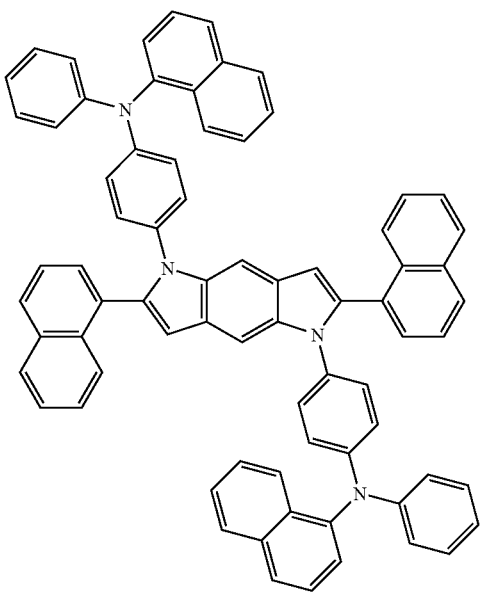
47
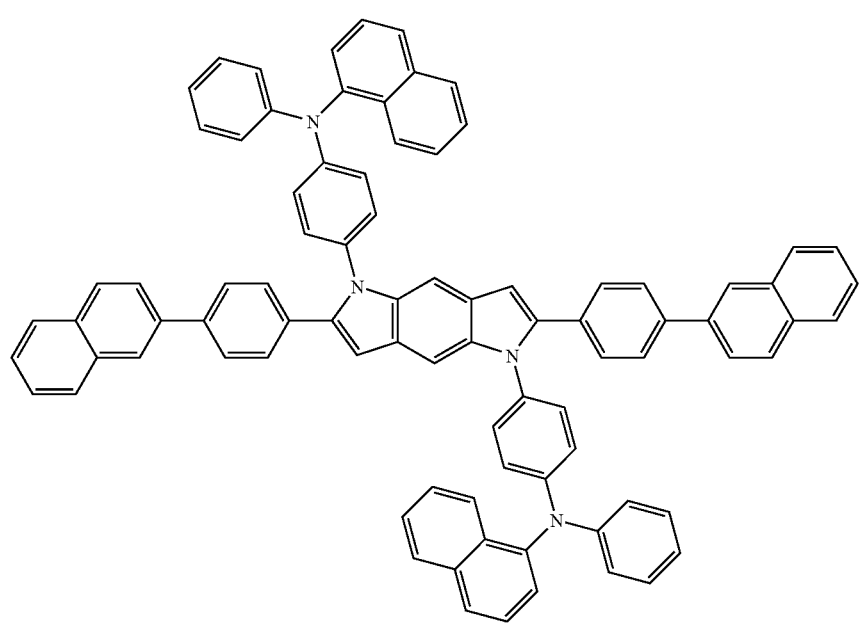

-continued
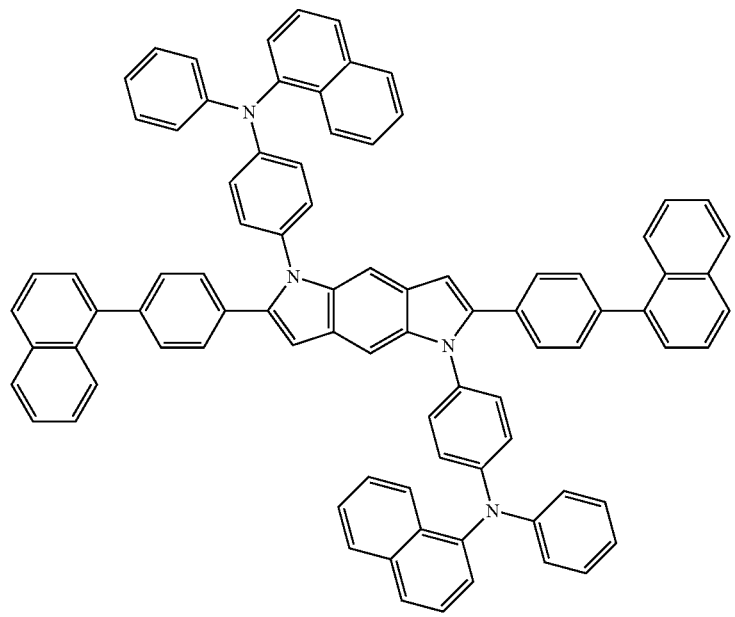
48
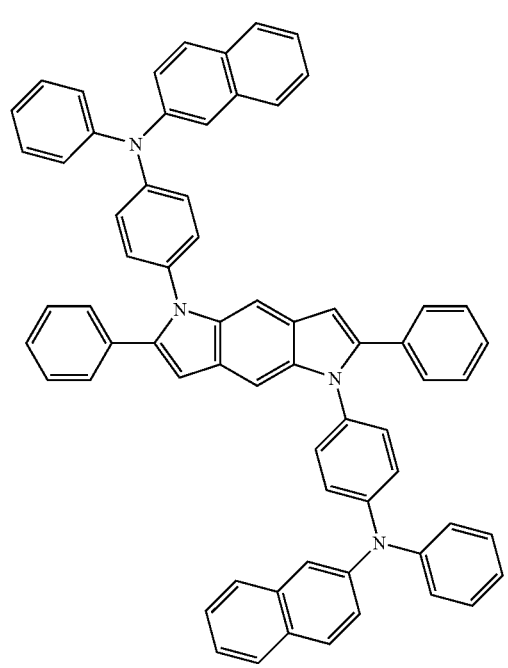
49
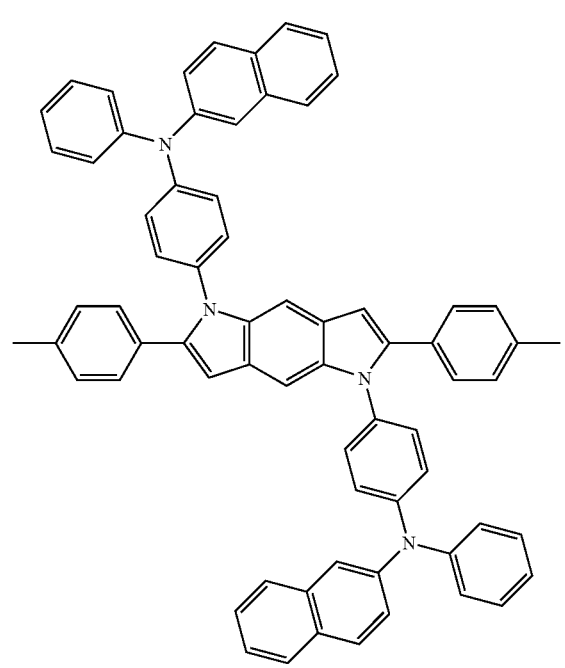
50

51
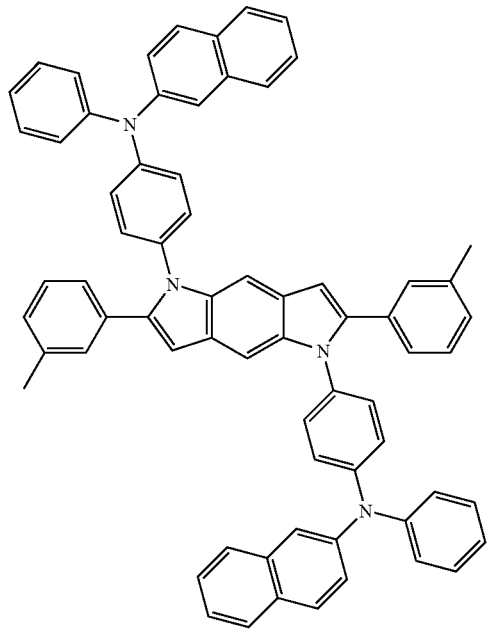
52
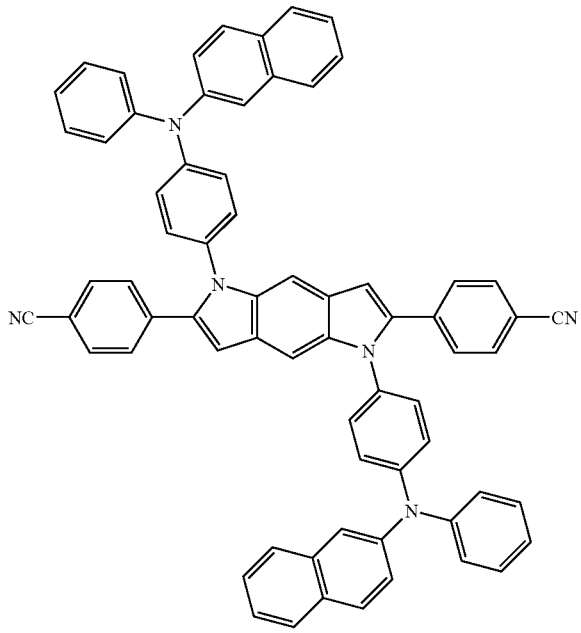
53
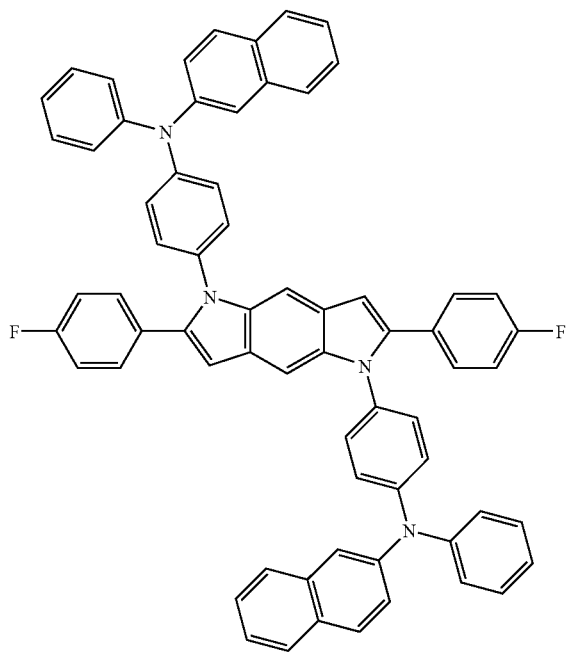
54
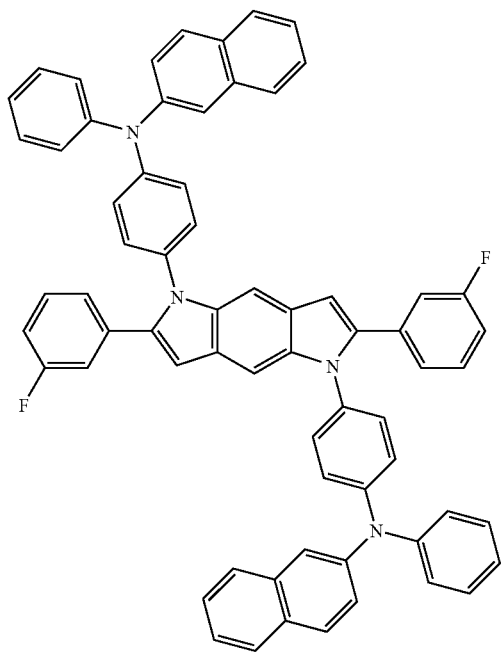

55
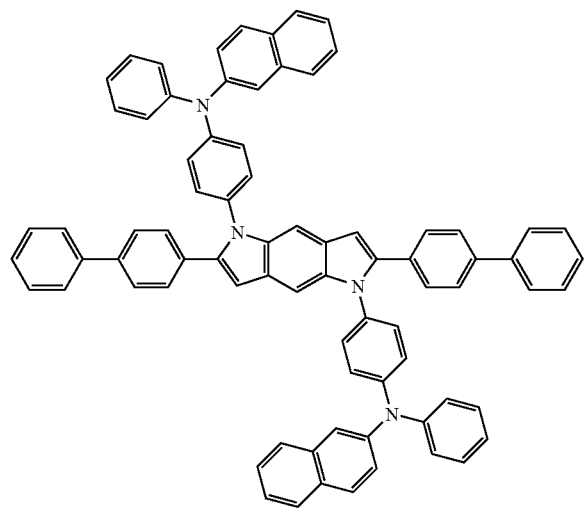
56
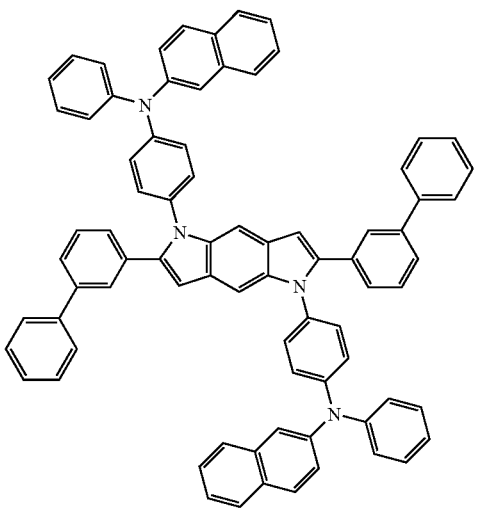
57
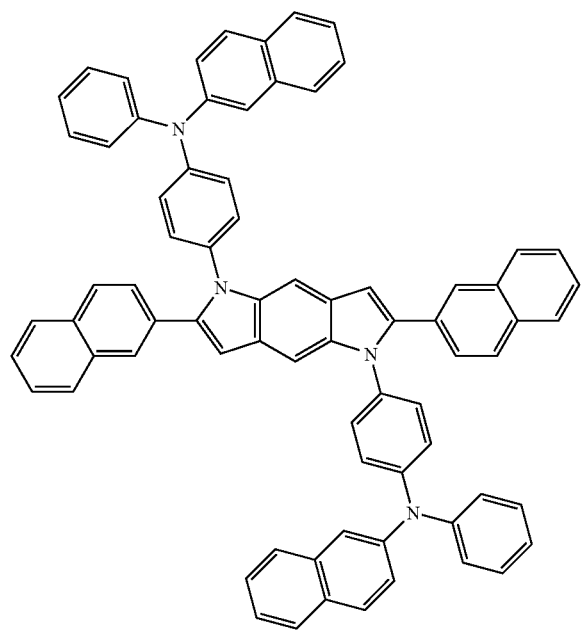
58
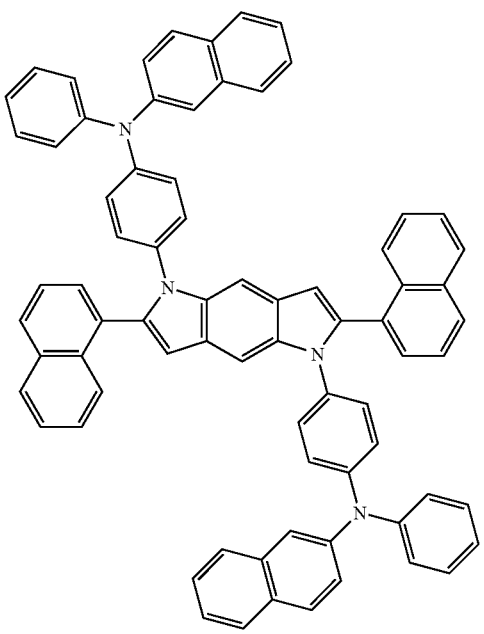

-continued
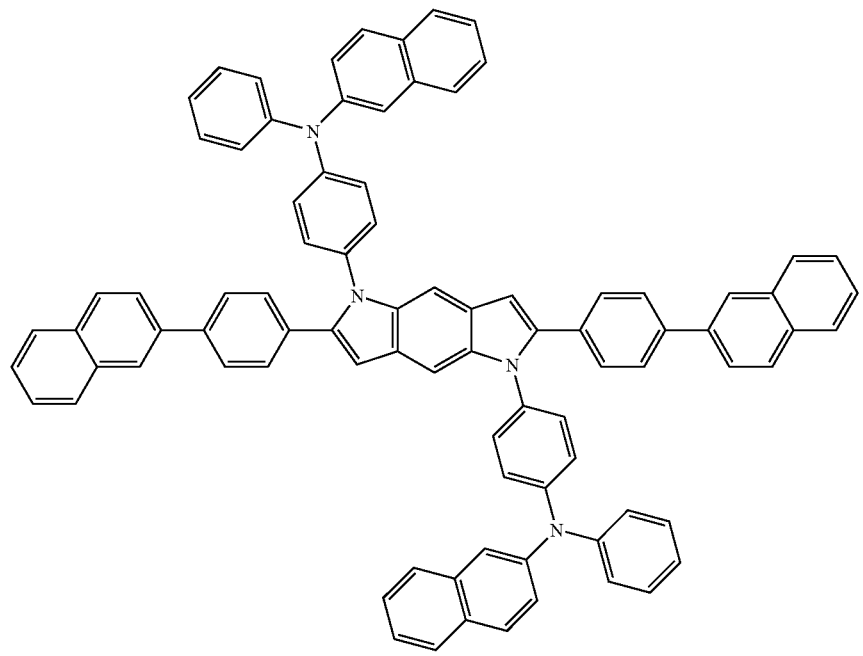
59
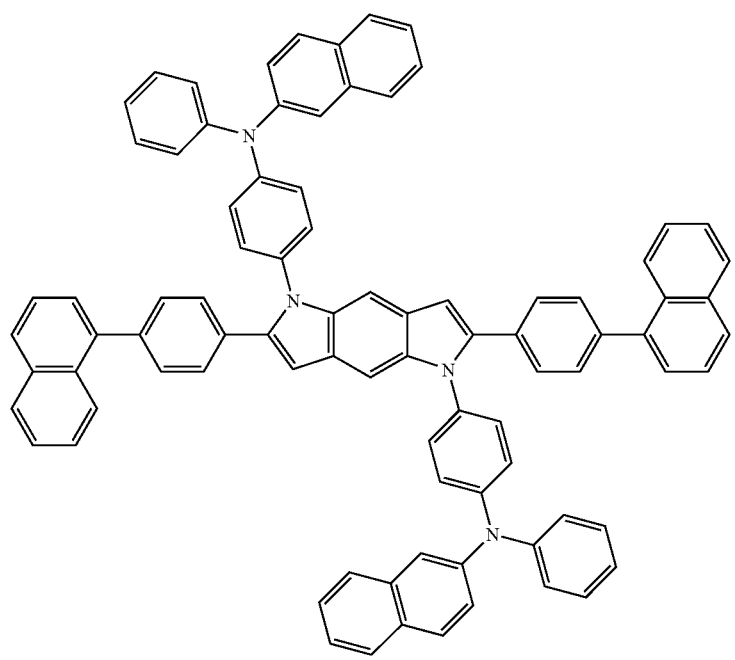
60

-continued
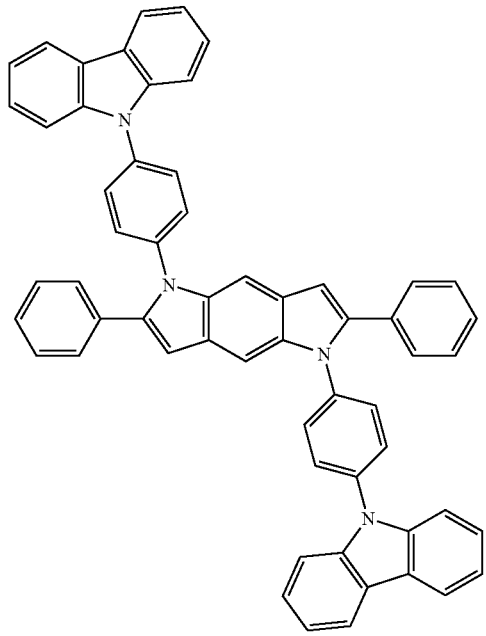
61
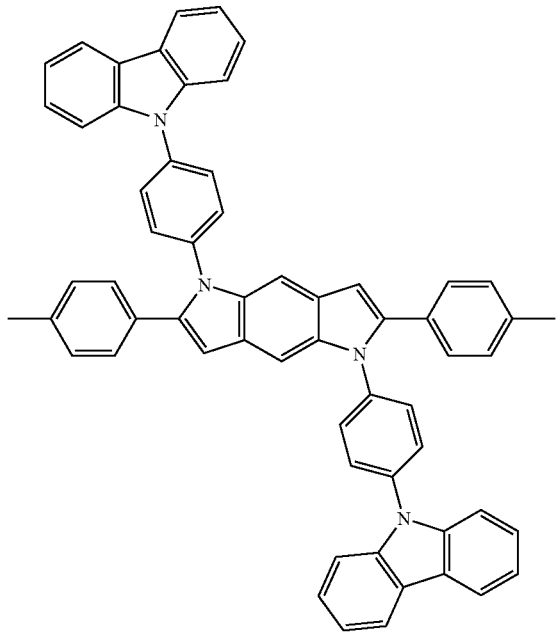
62
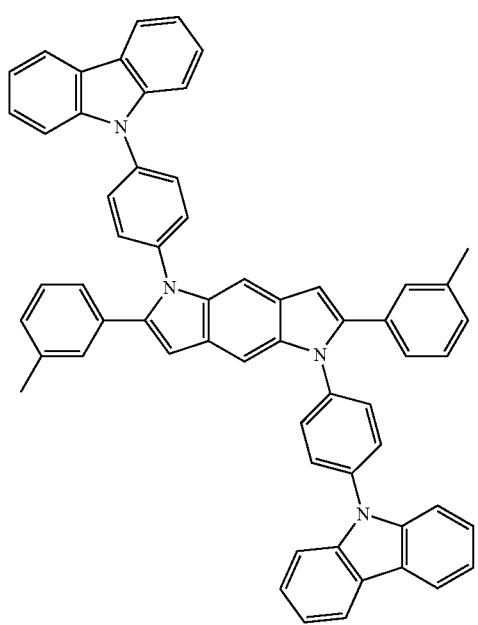
63
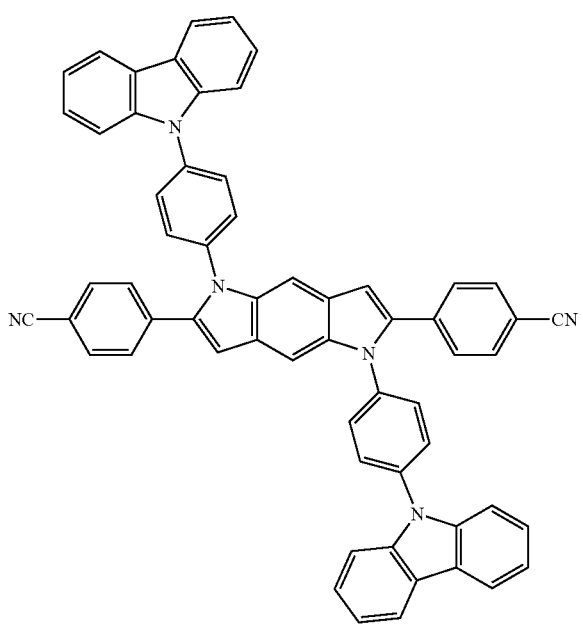
64

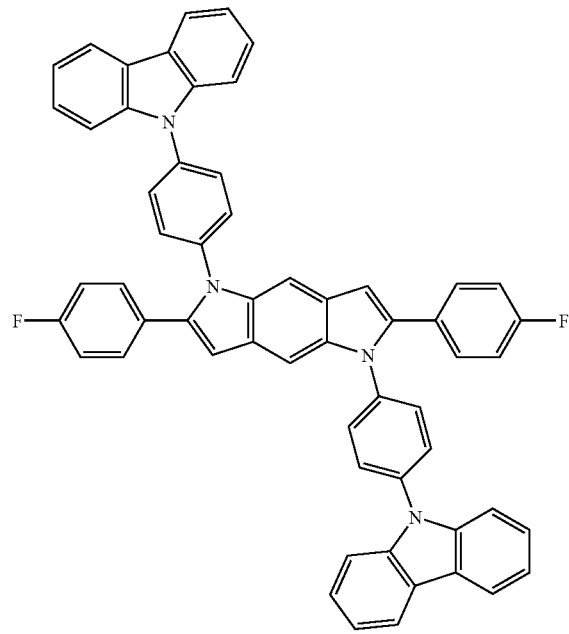
65
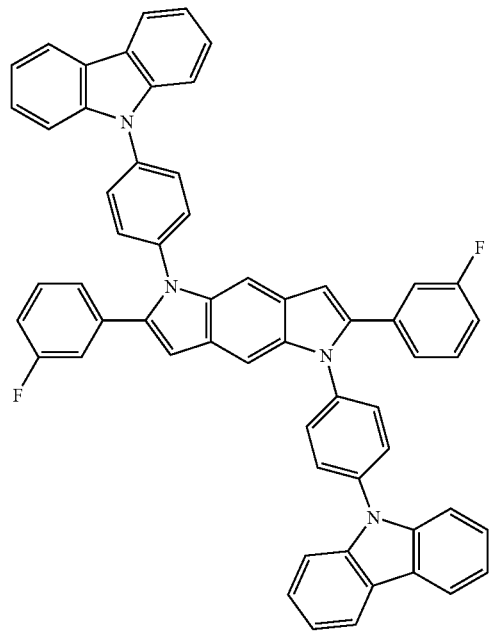
66
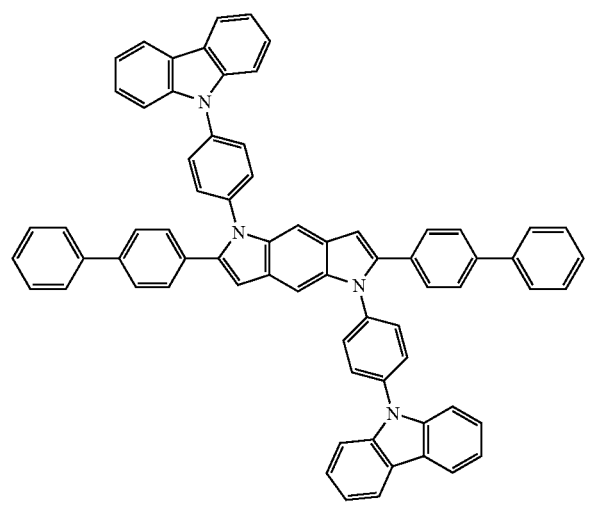
67
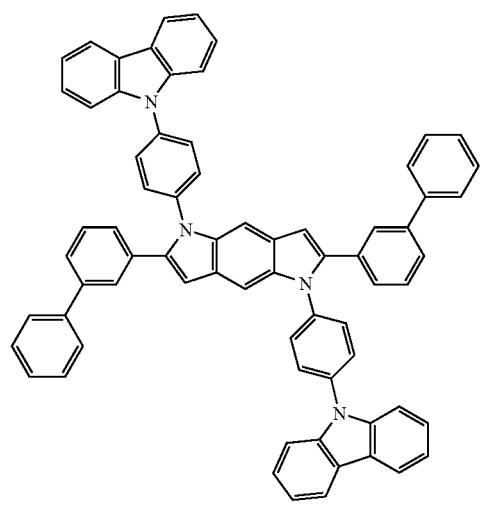
68

-continued
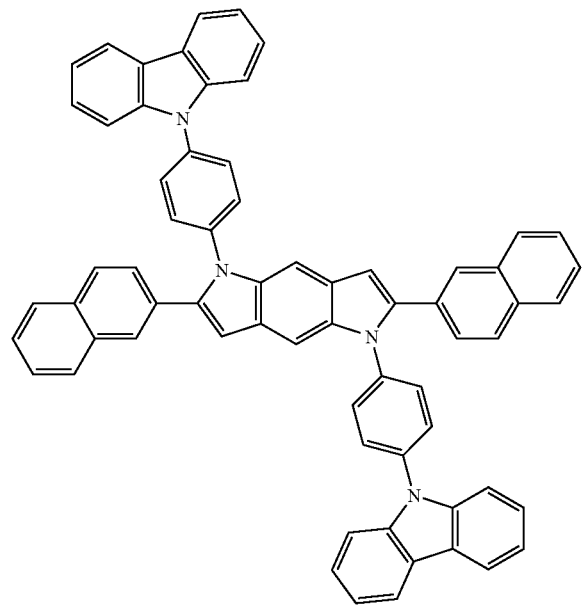
69
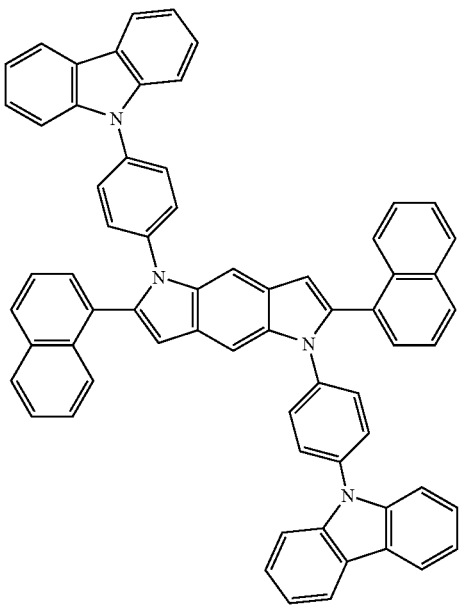
70
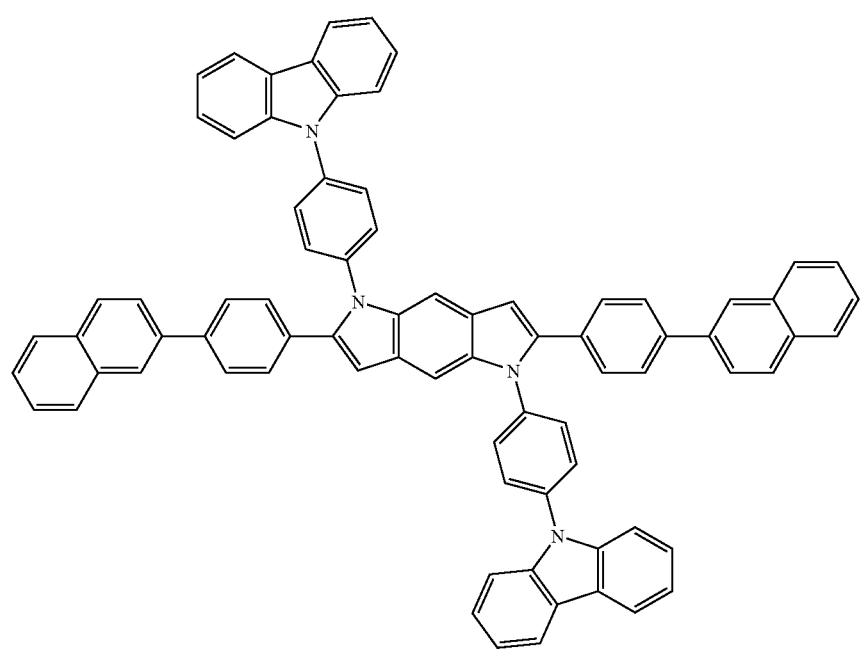
71

-continued
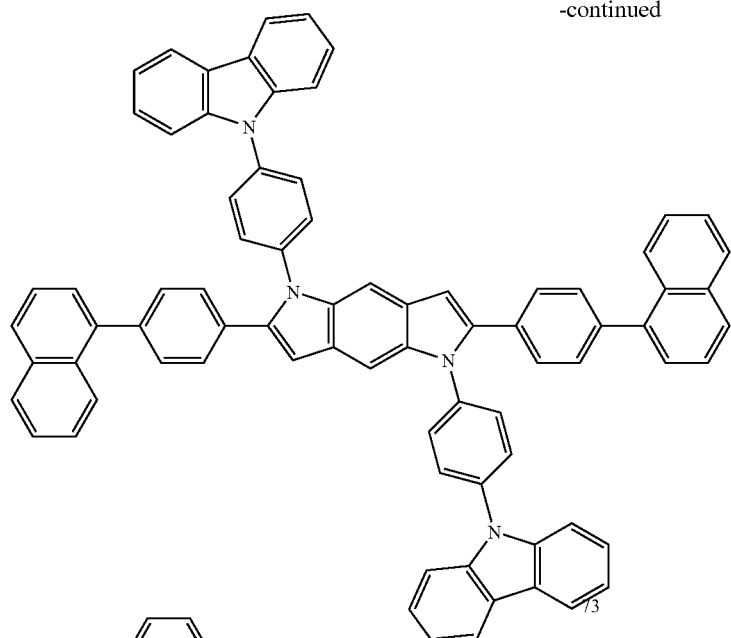
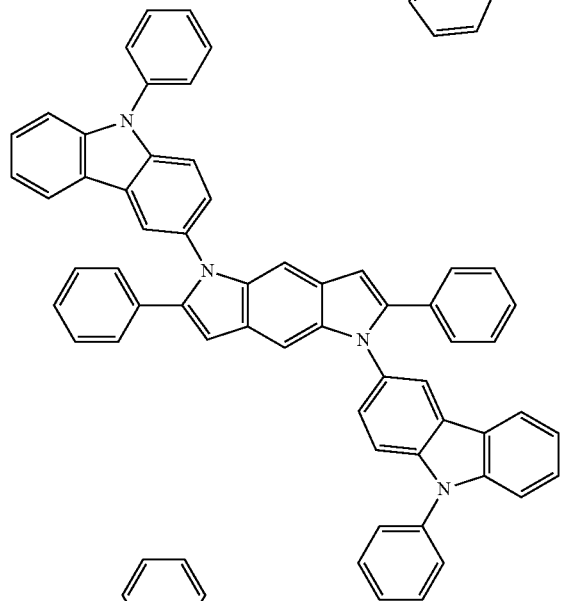
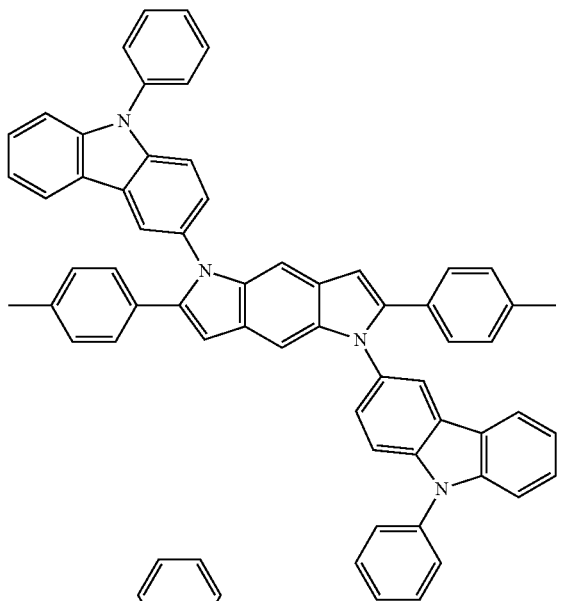
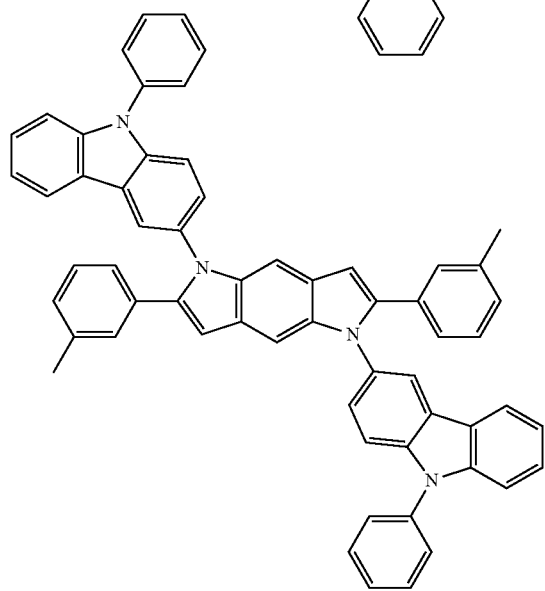
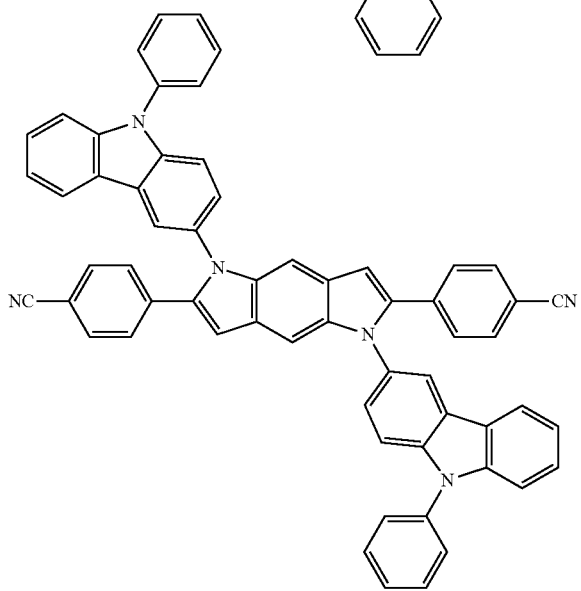

-continued
77
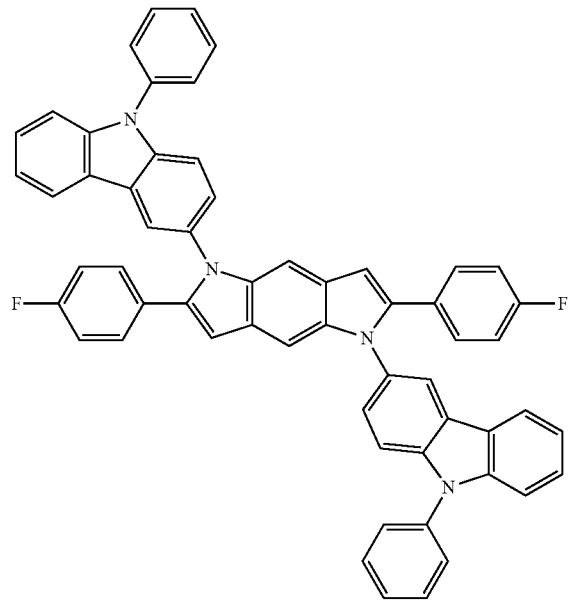
78
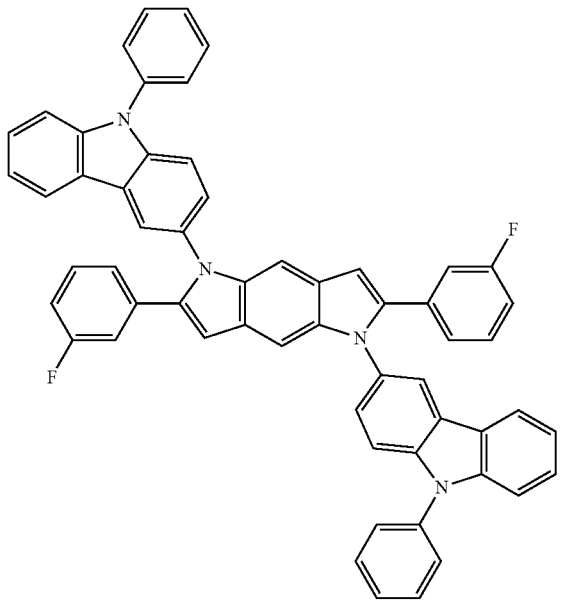
79
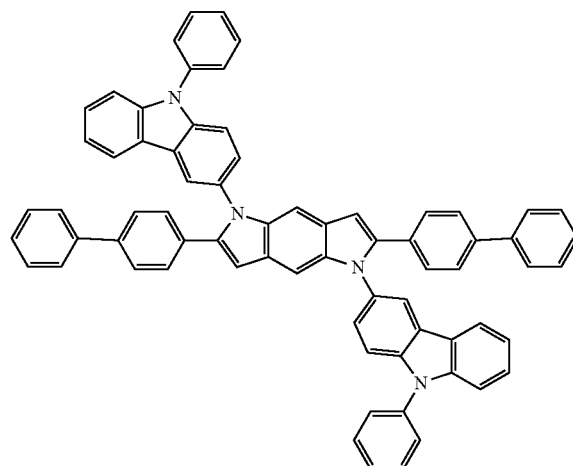
80
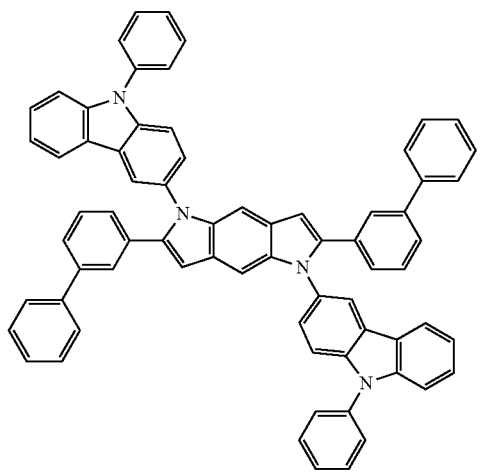
81
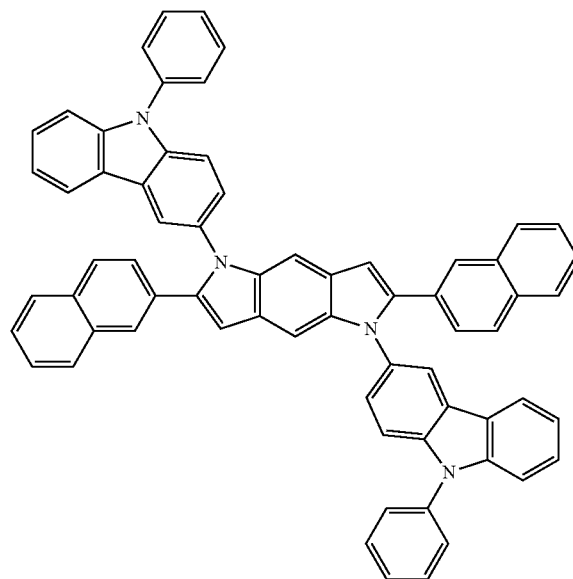
82
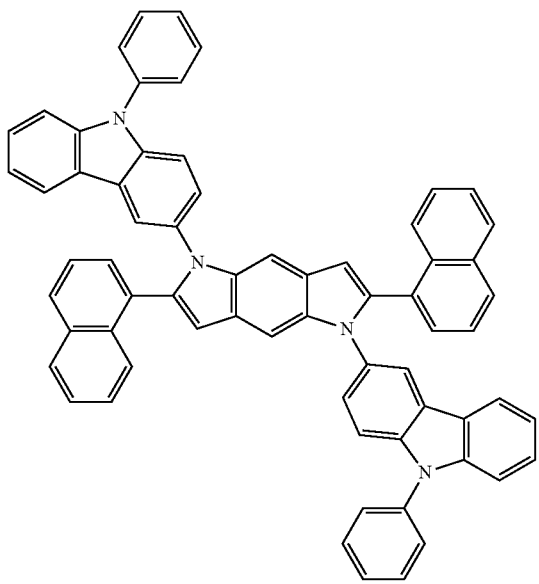

-continued
83
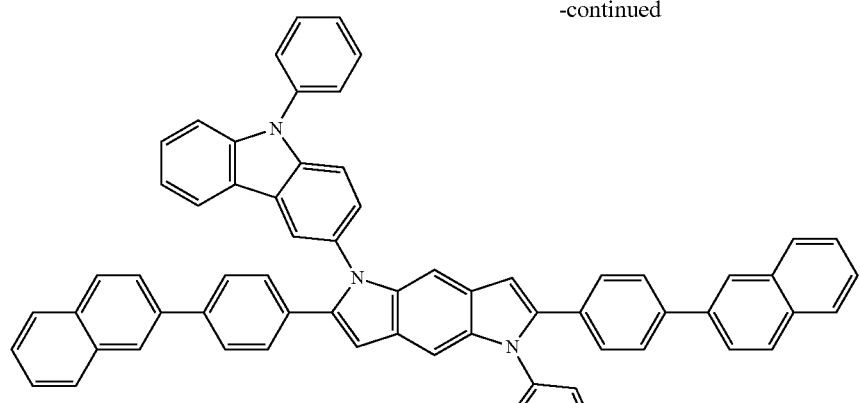
84
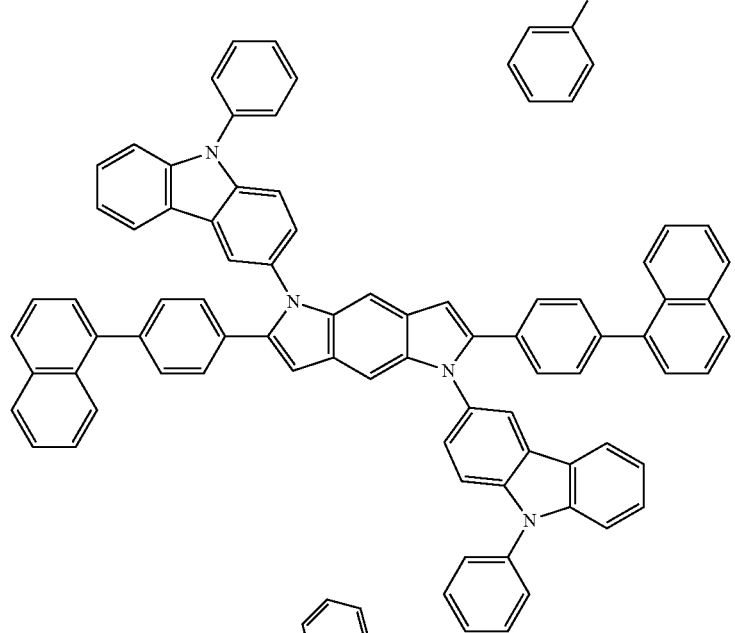
85
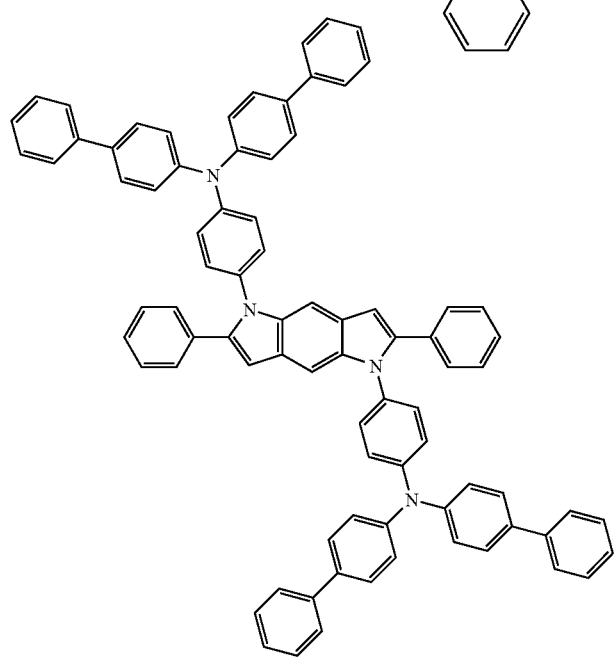

-continued
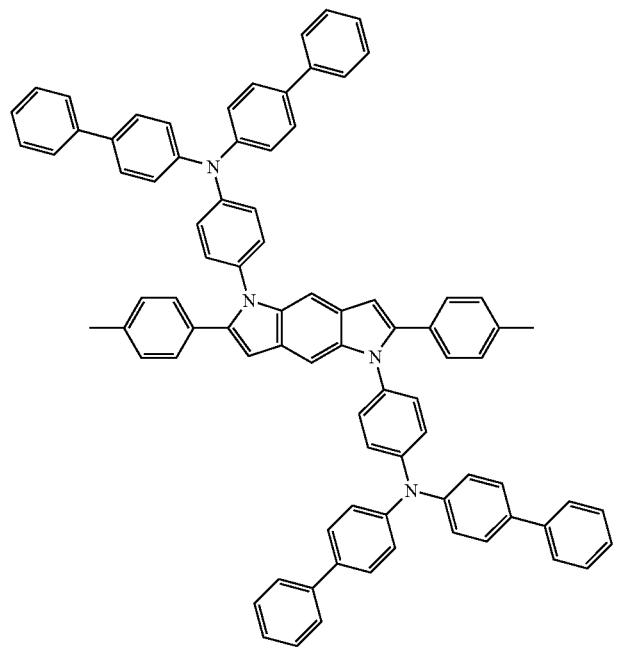
86
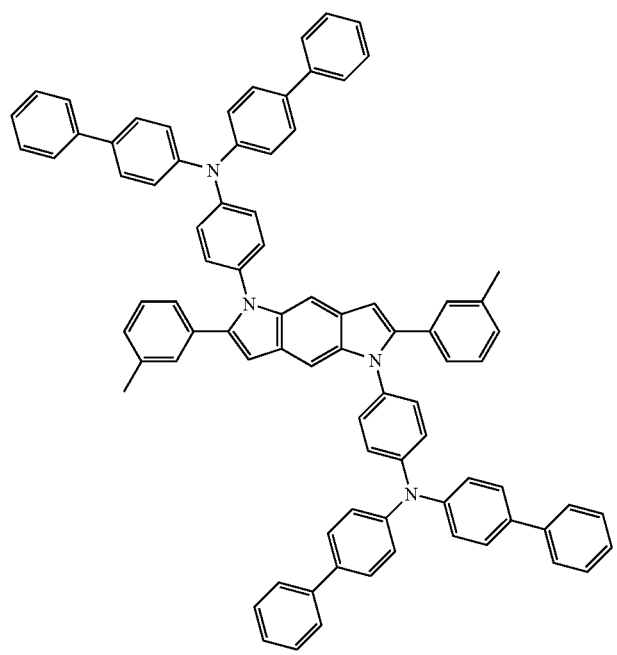
87

-continued
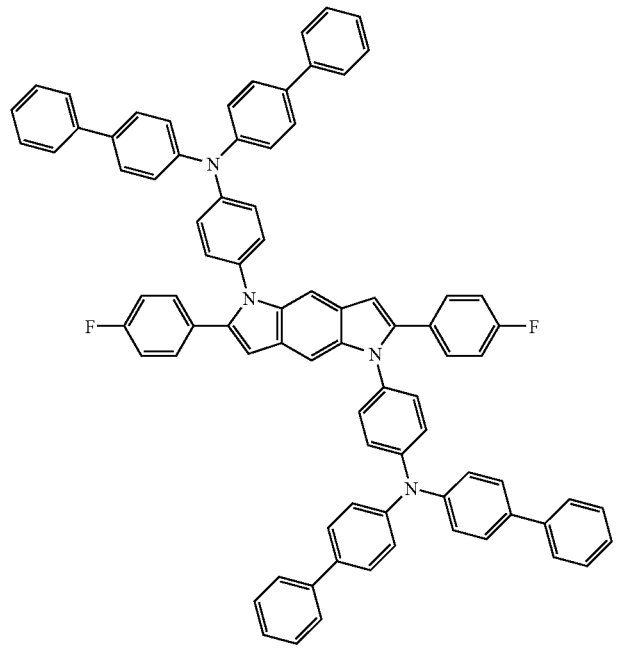
88
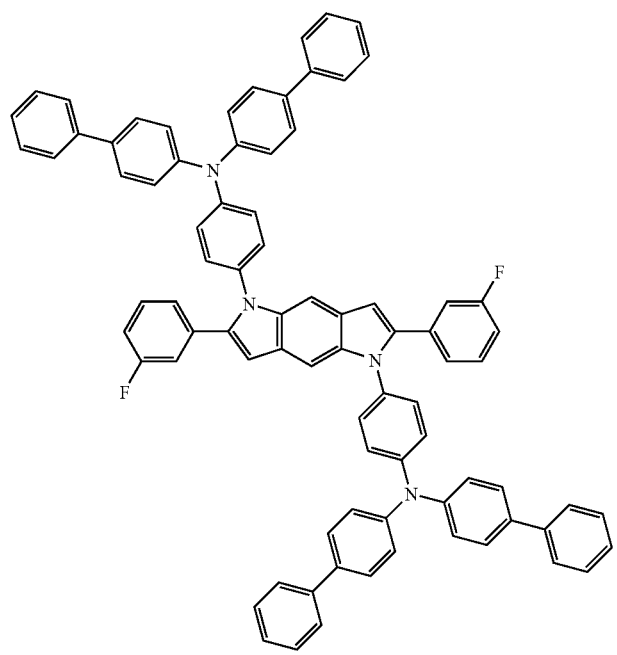
89

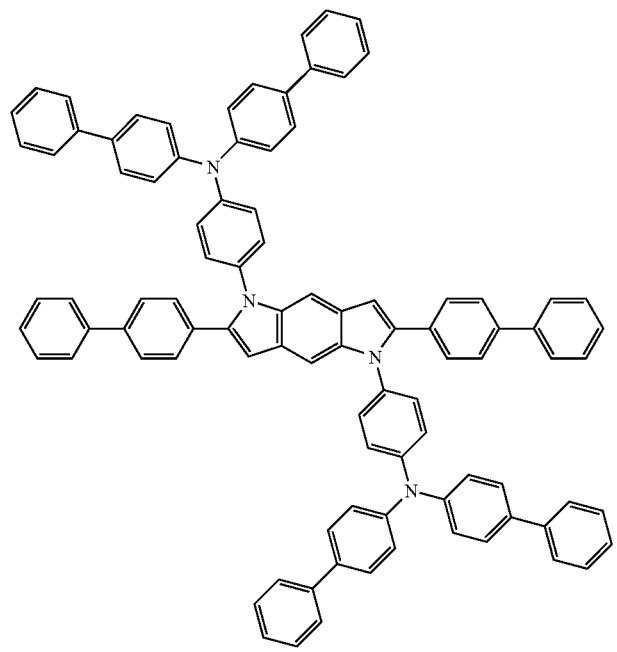
90
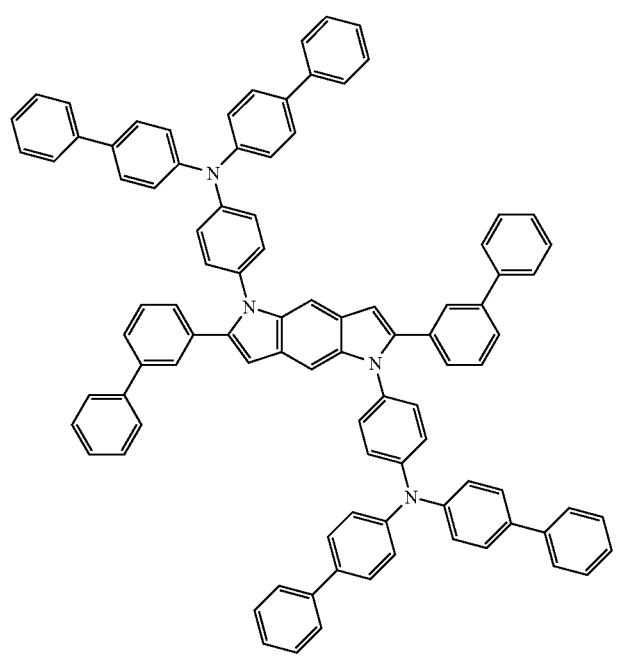
91

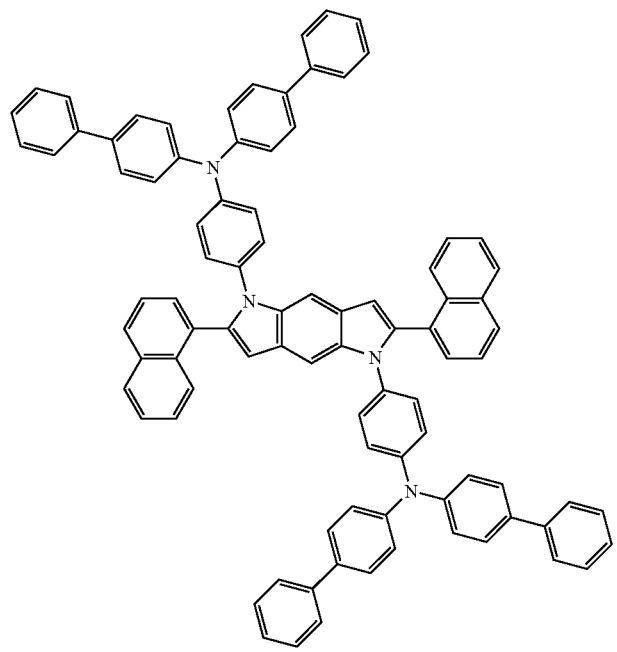
92
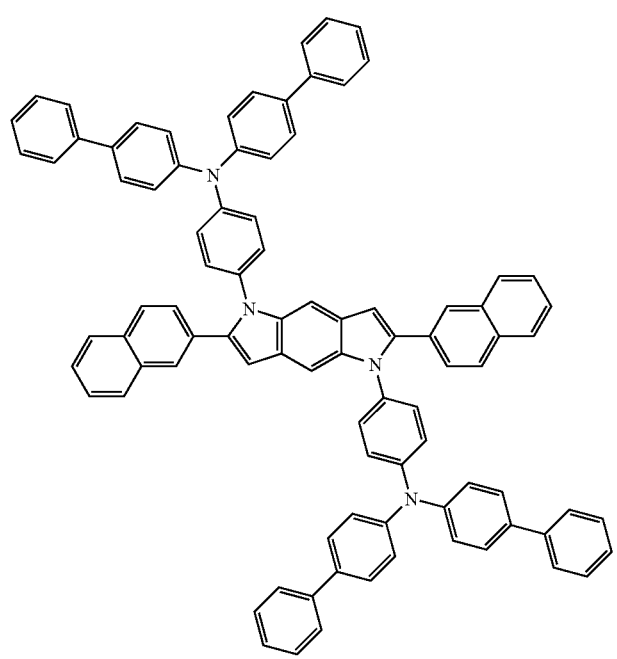
93

94
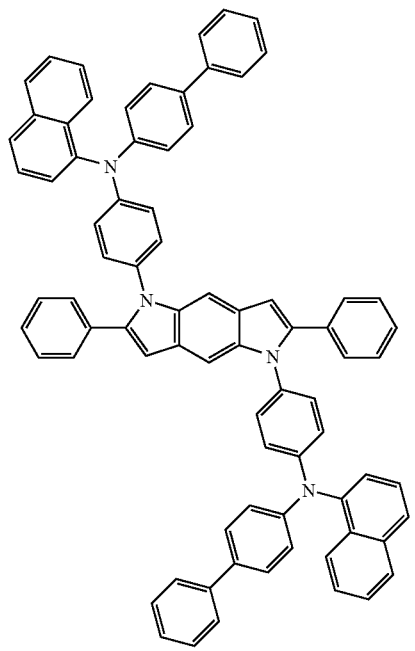
95
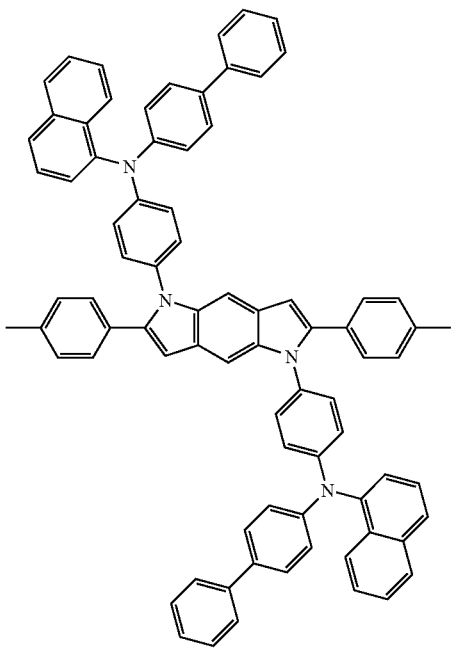
96
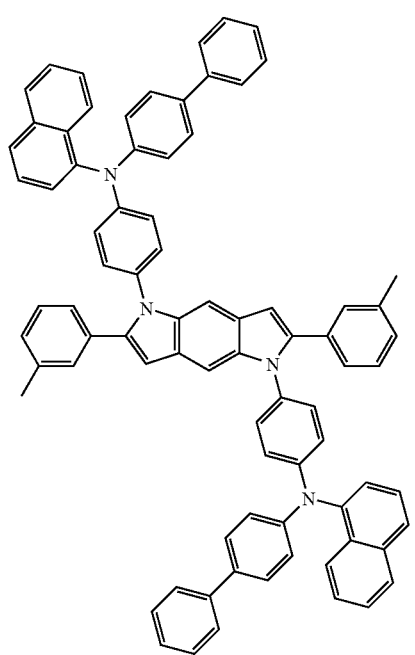
97
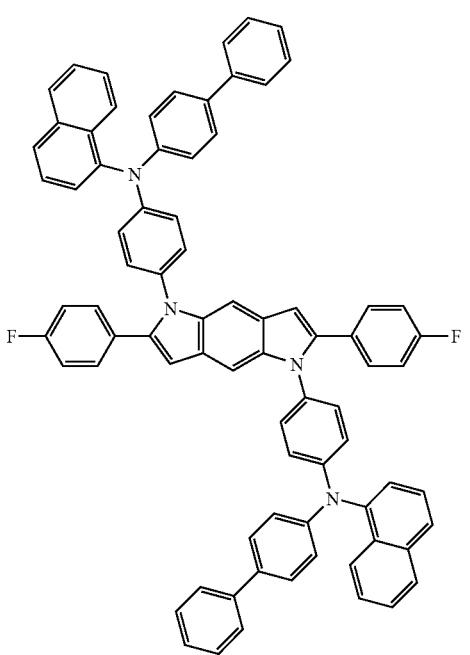

98
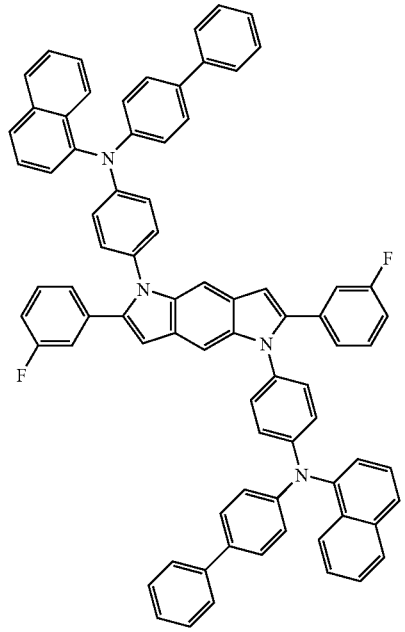
99
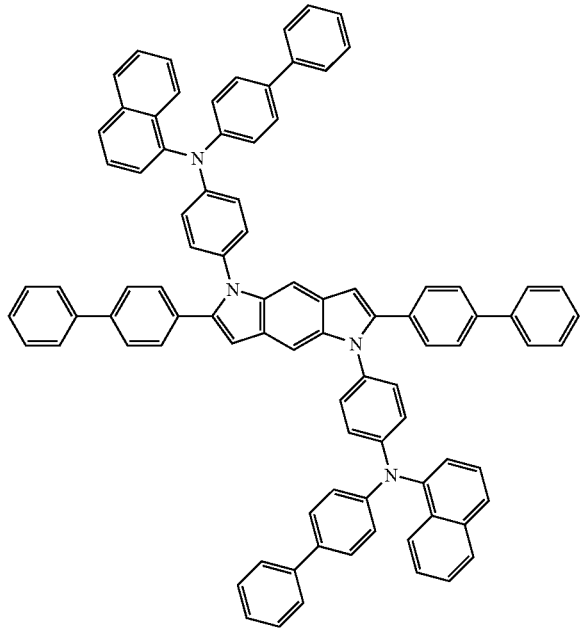
100
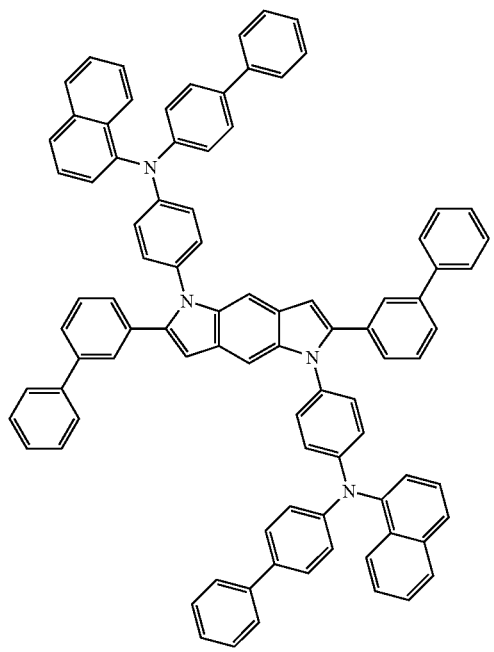
101
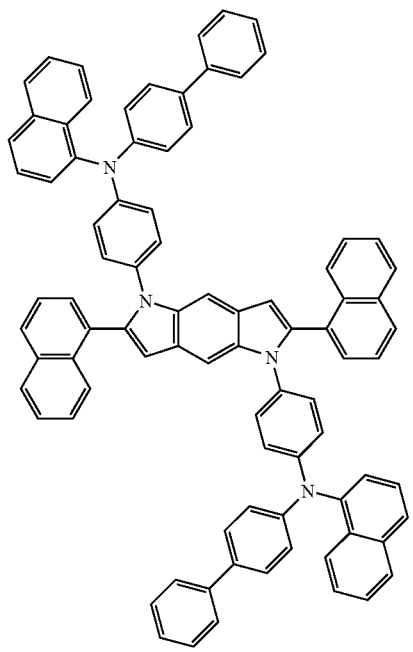

-continued
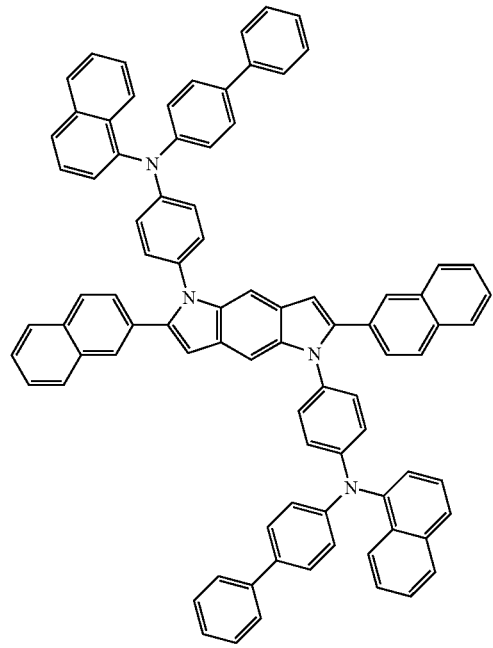
102
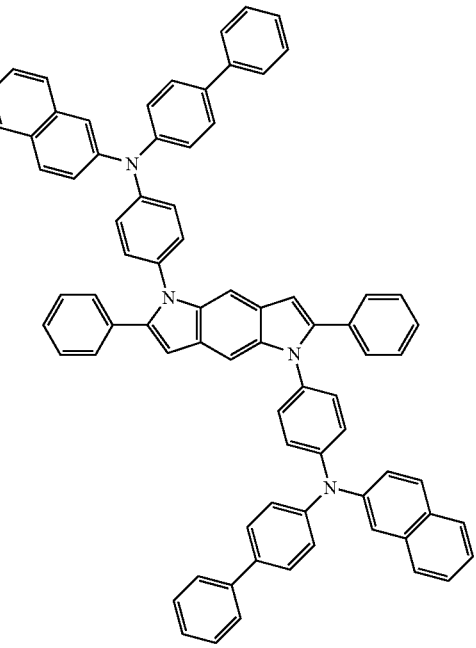
103
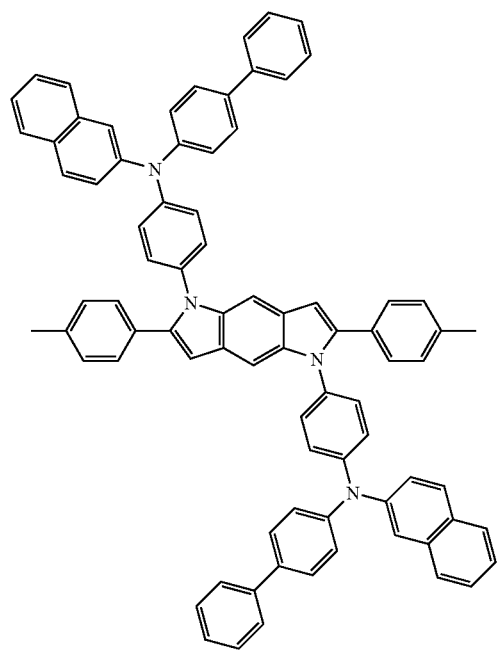
104
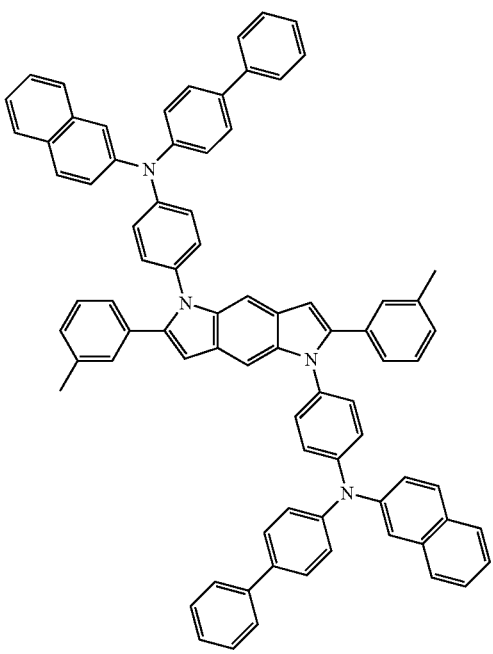
105

-continued
106
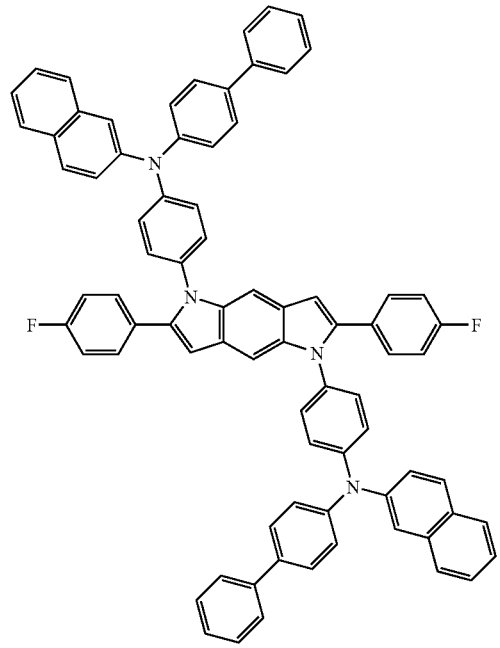
107
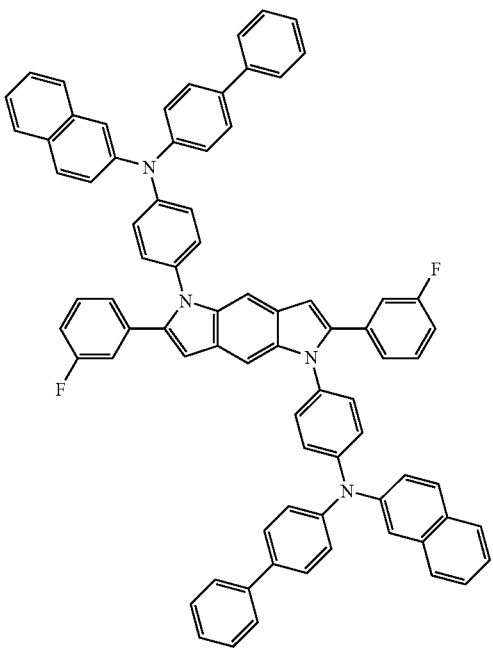
108
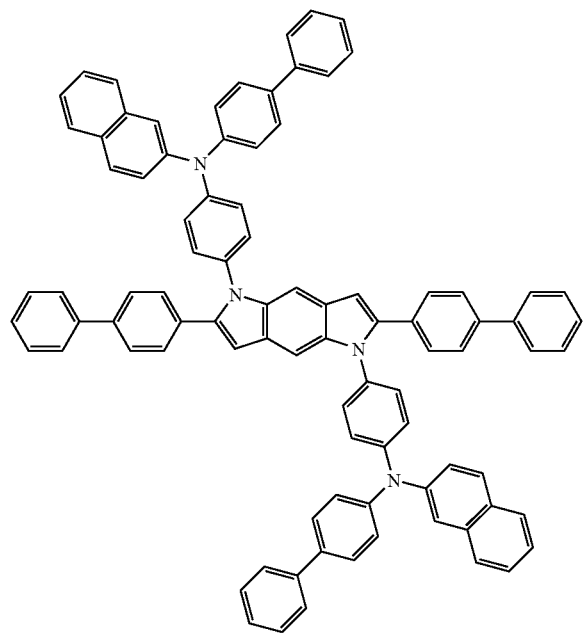
109
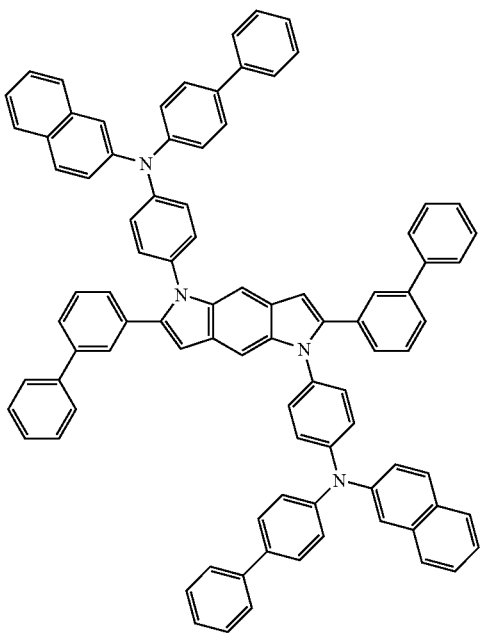

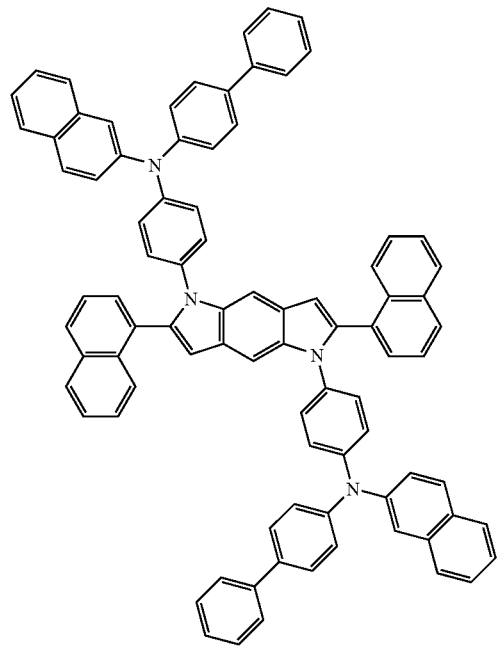
110
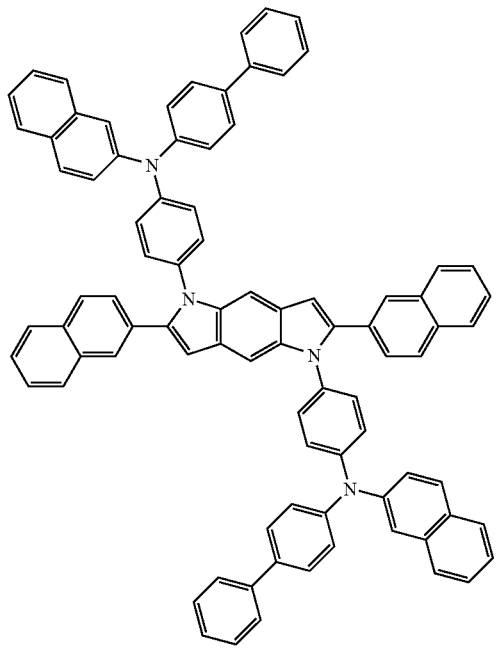
111
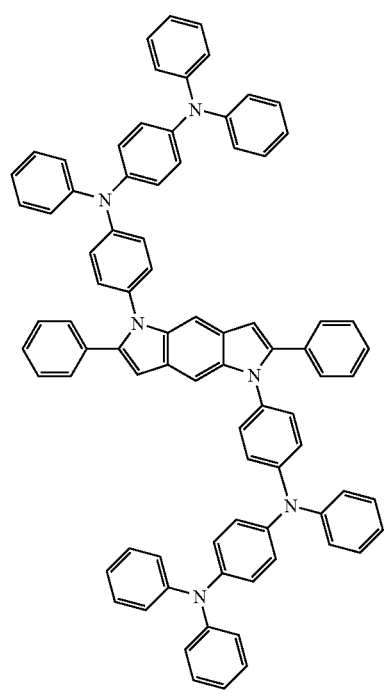
112
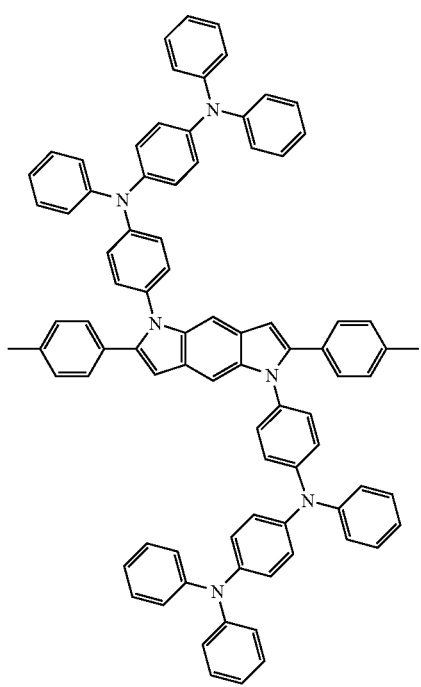
113

-continued
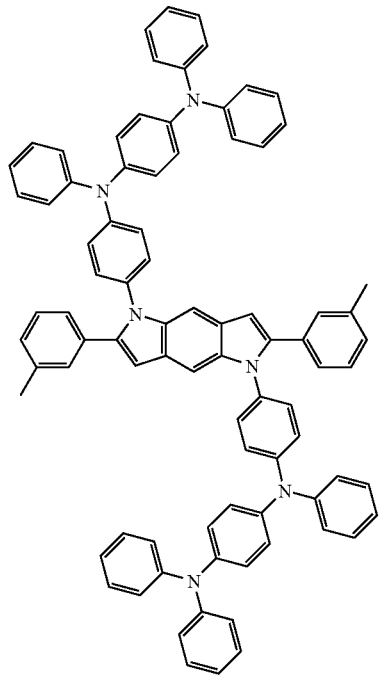
114
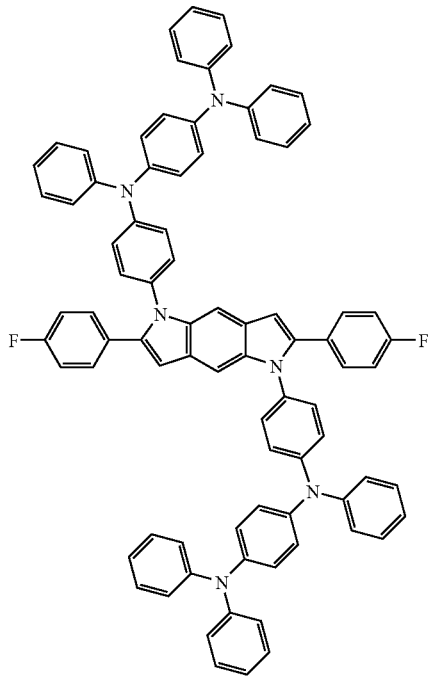
115
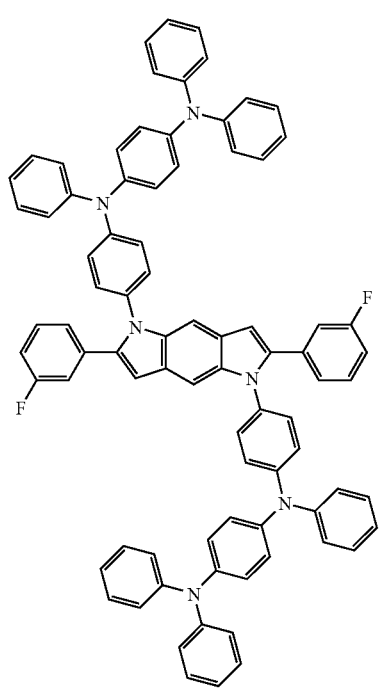
116
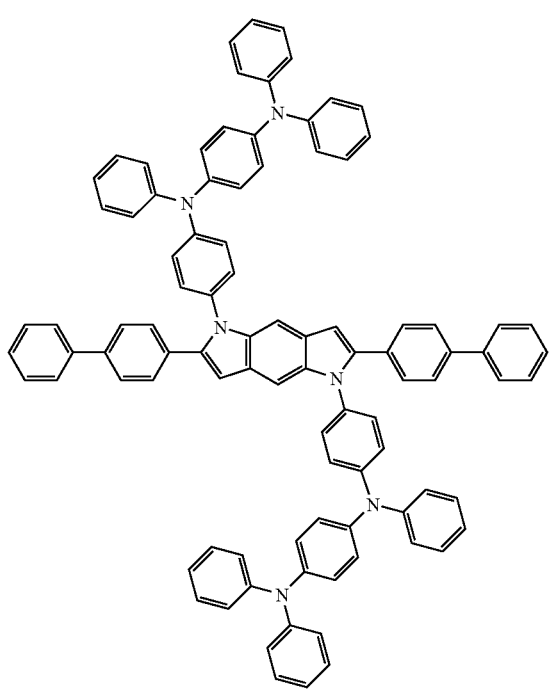
117

118
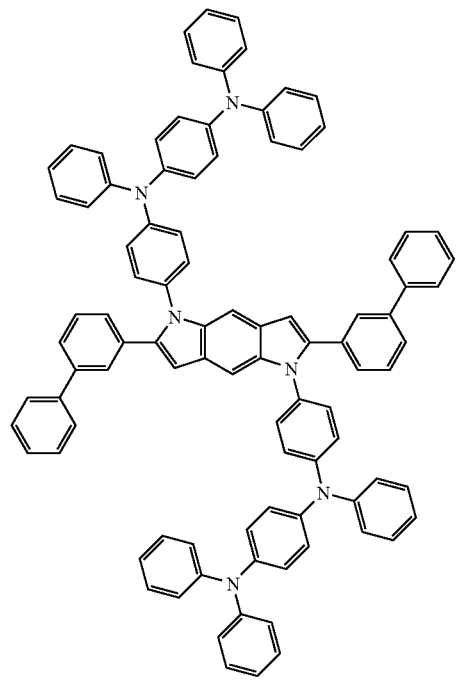
119
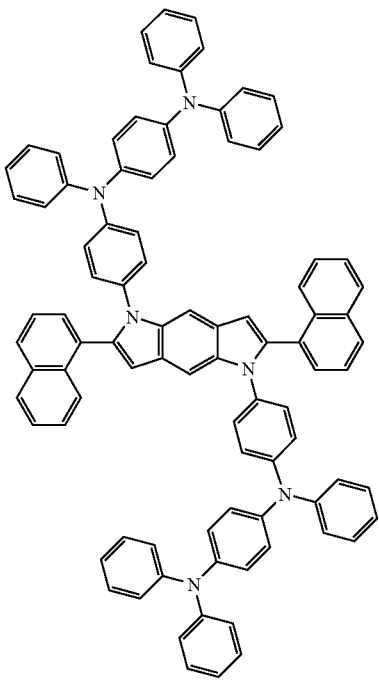
120
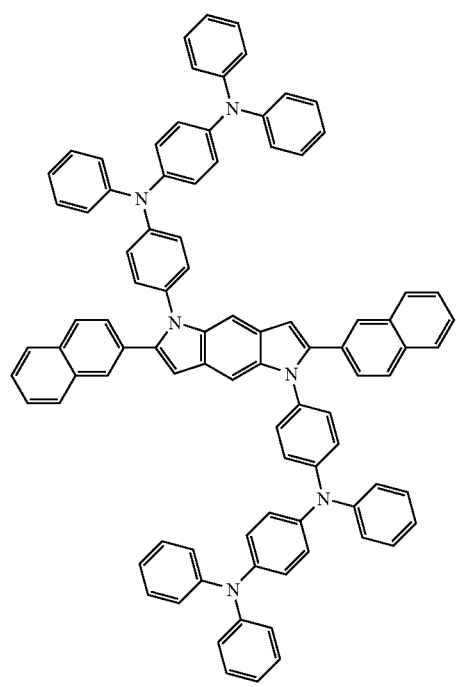
121
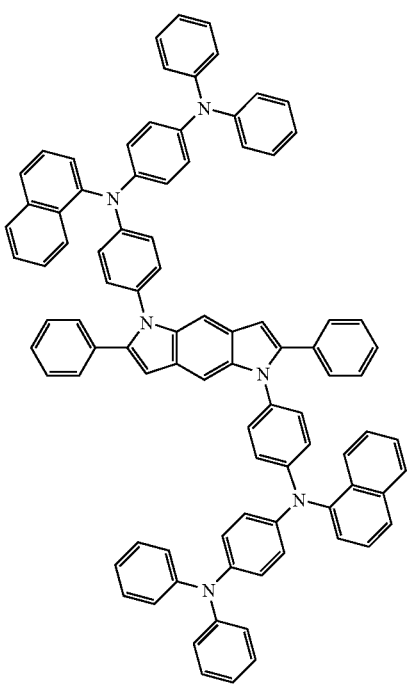

122
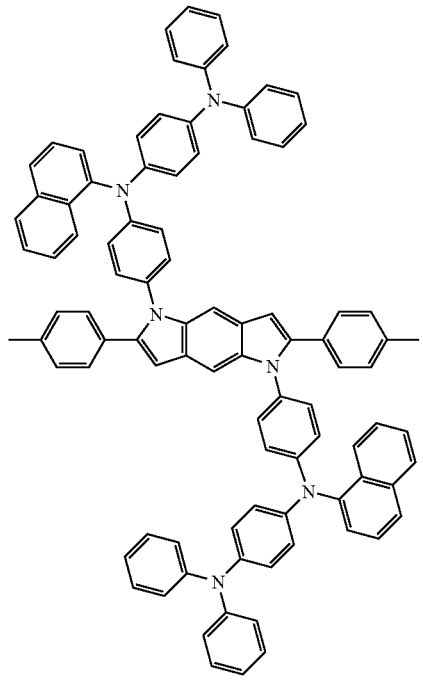
123
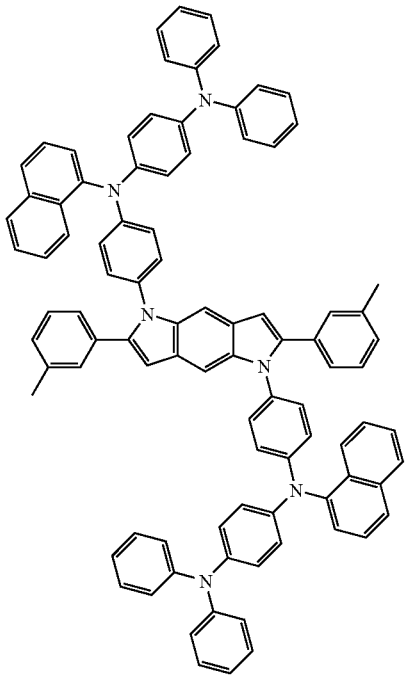
124
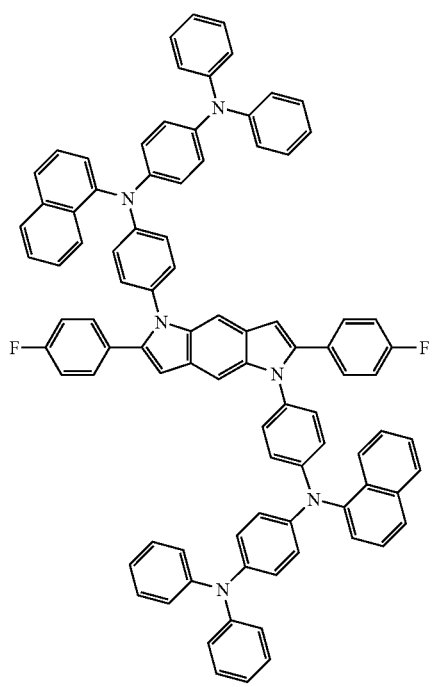
125
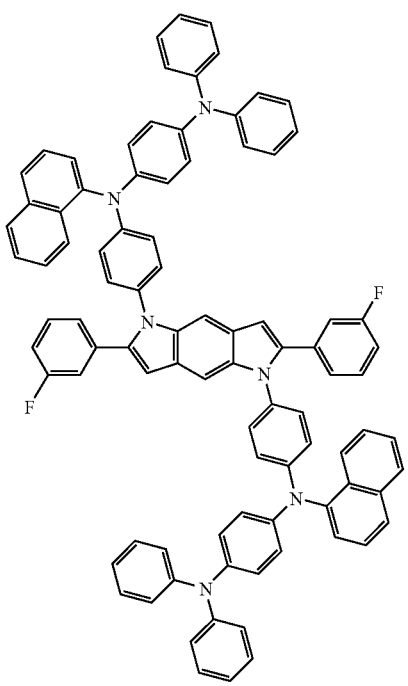

-continued
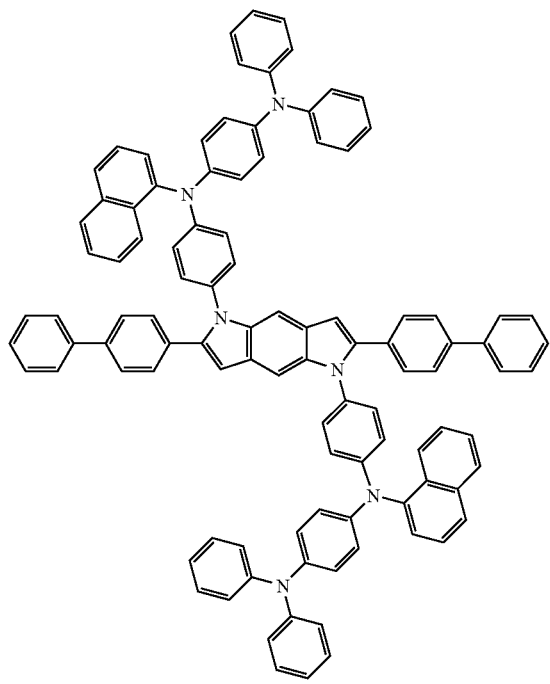
126
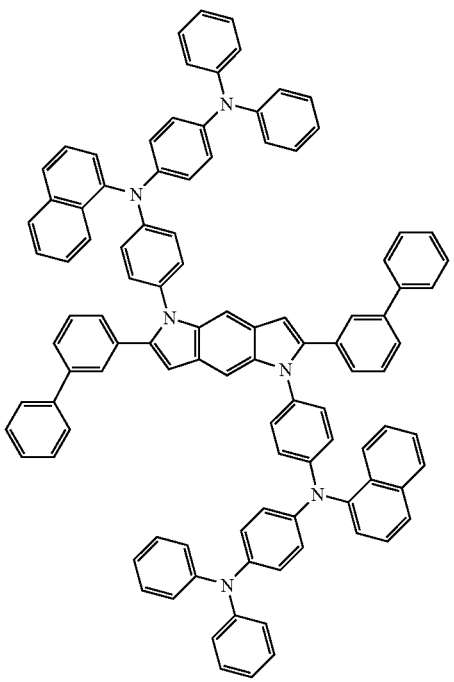
127
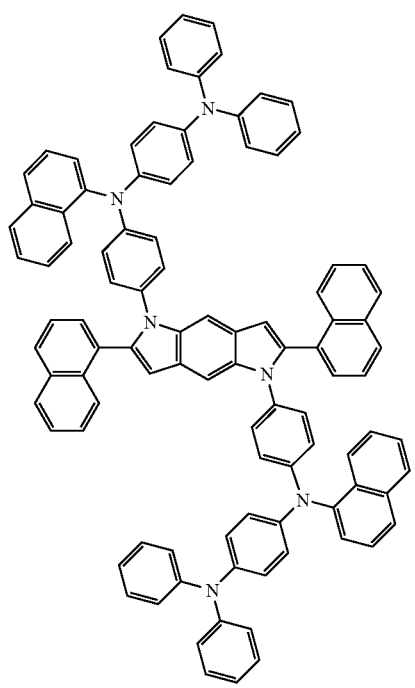
128
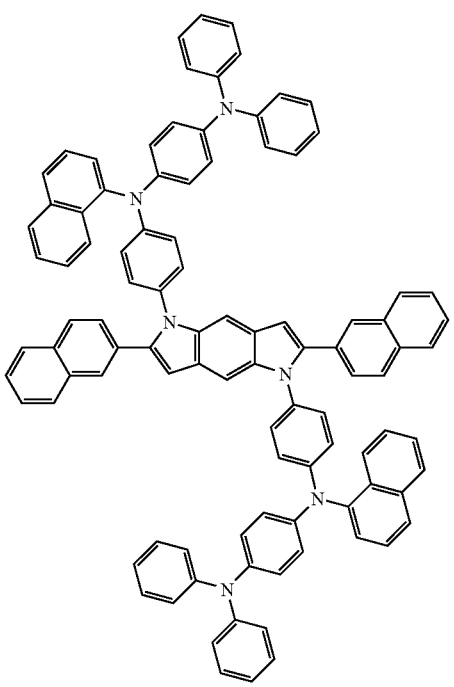
129

-continued
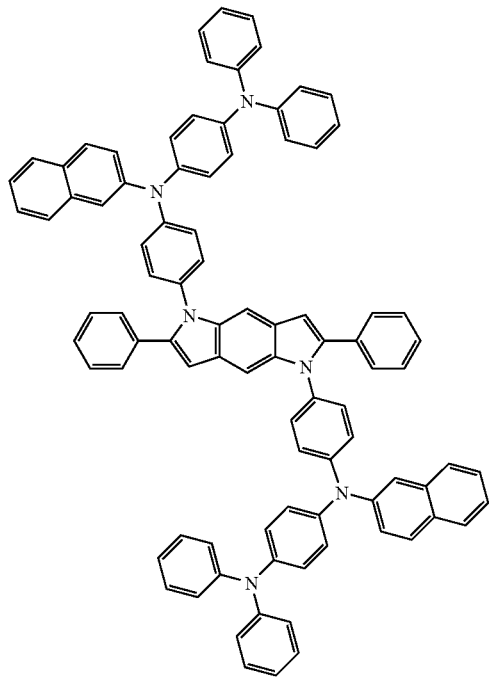
130
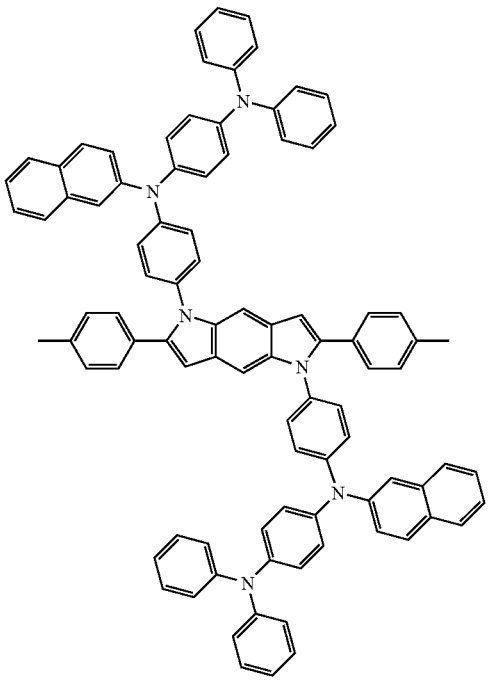
131
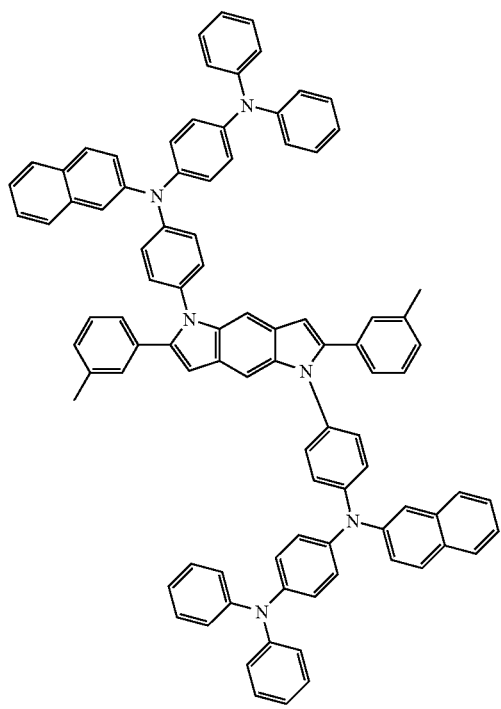
132
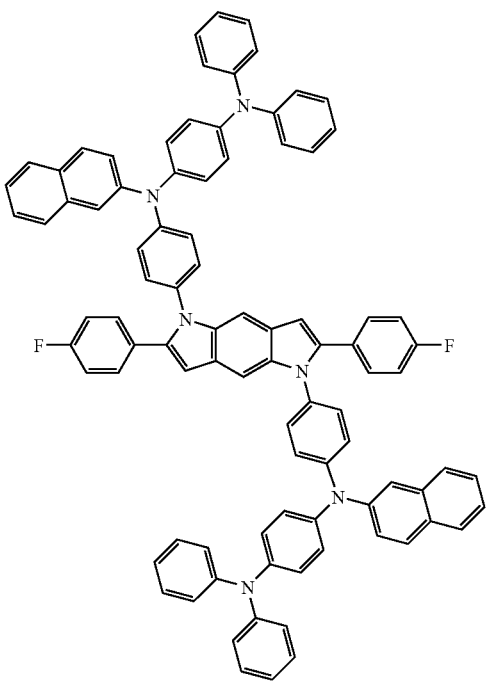
133

134
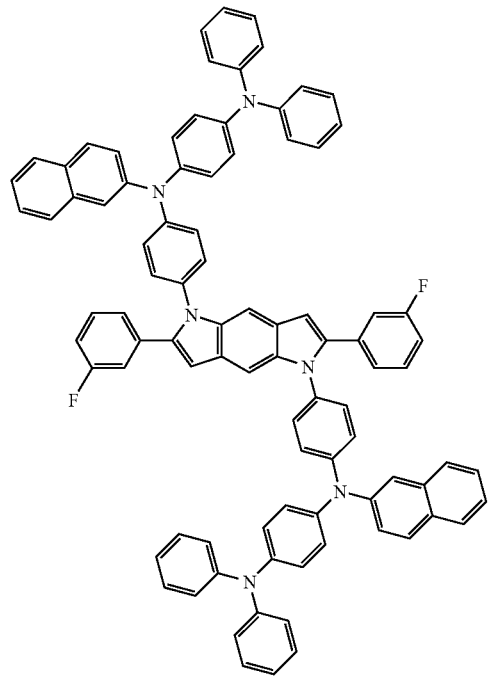
135
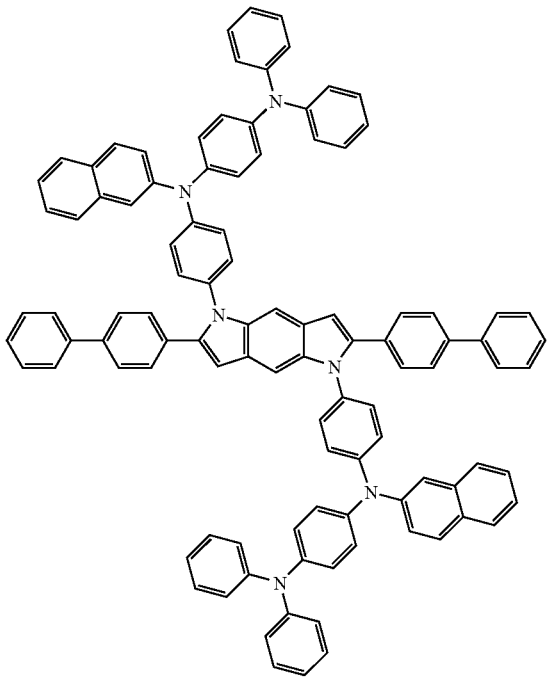
136
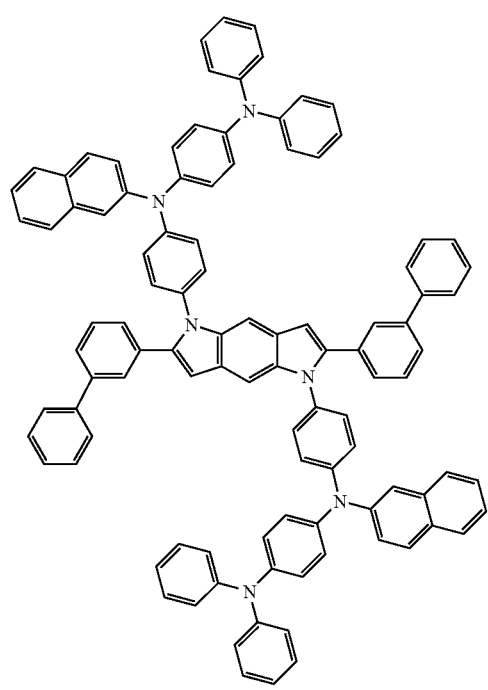
137
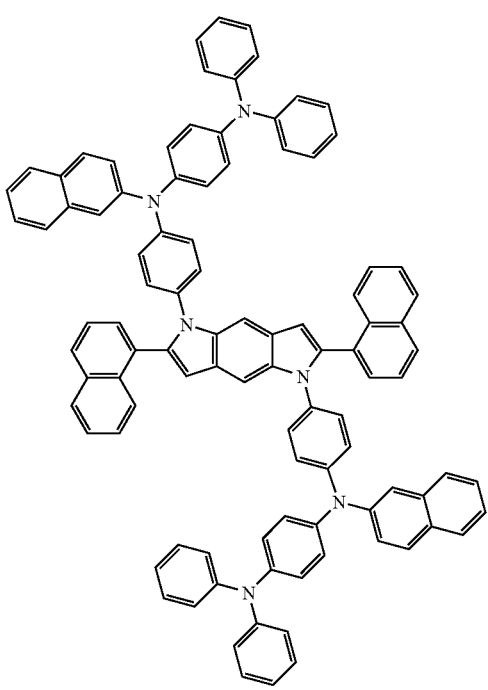

138
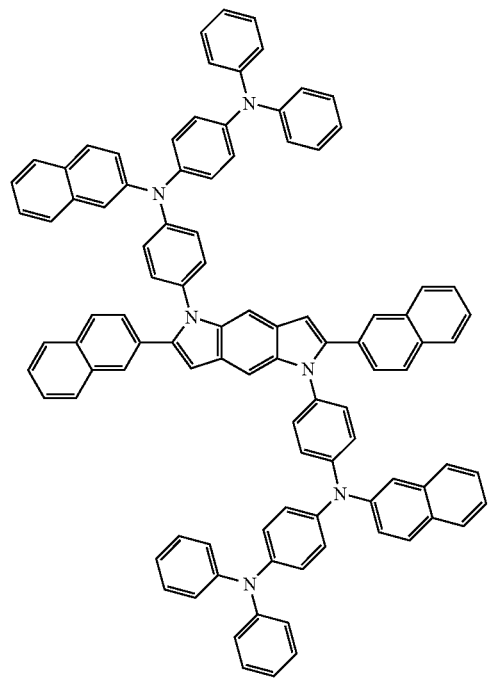
139
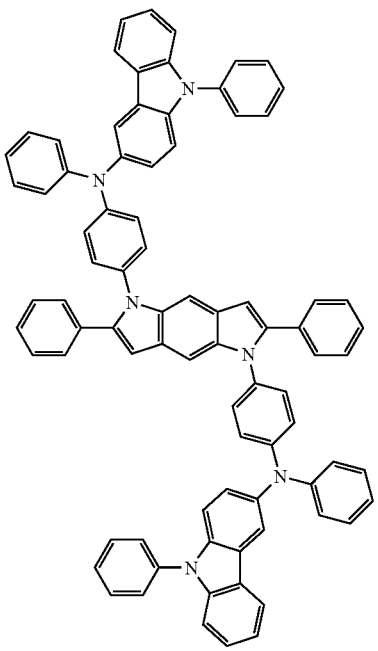
140
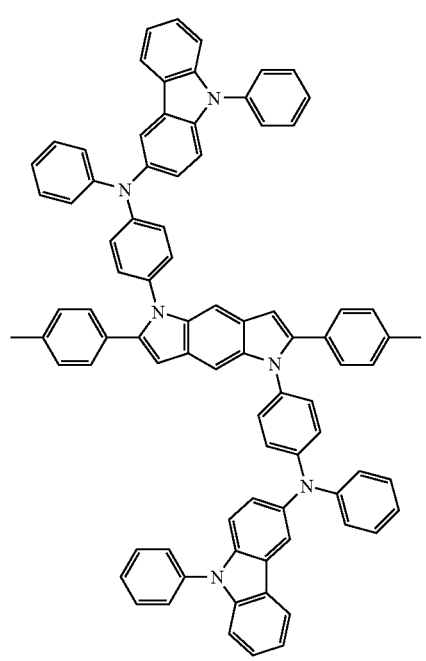
141
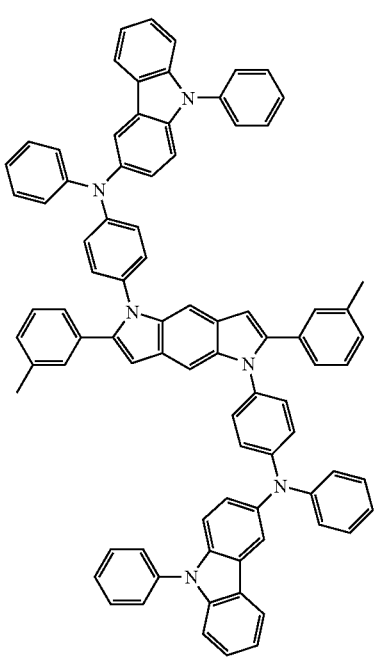

142
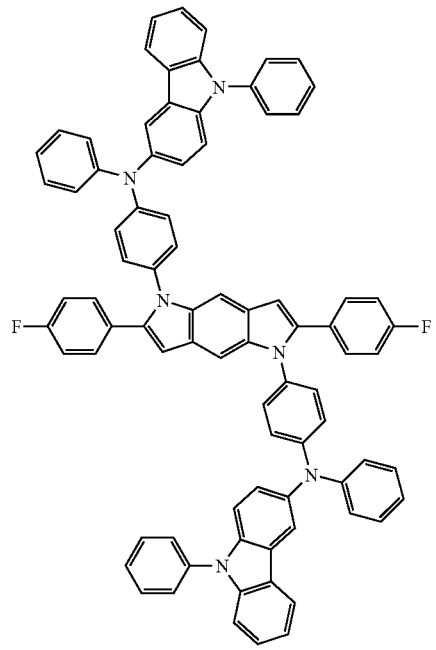
143
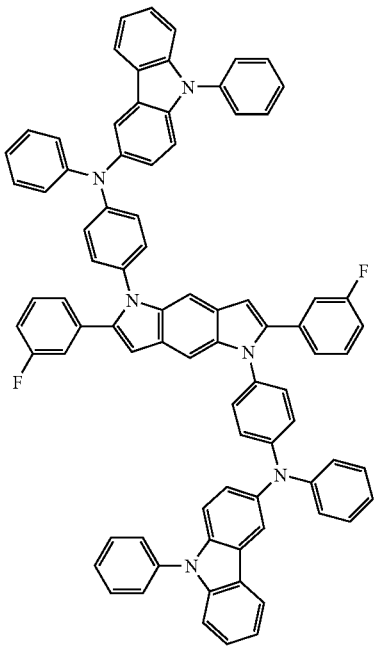
144
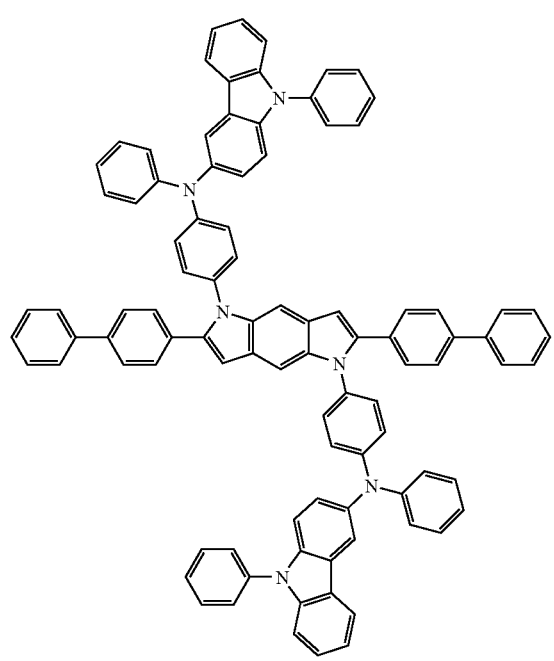
145
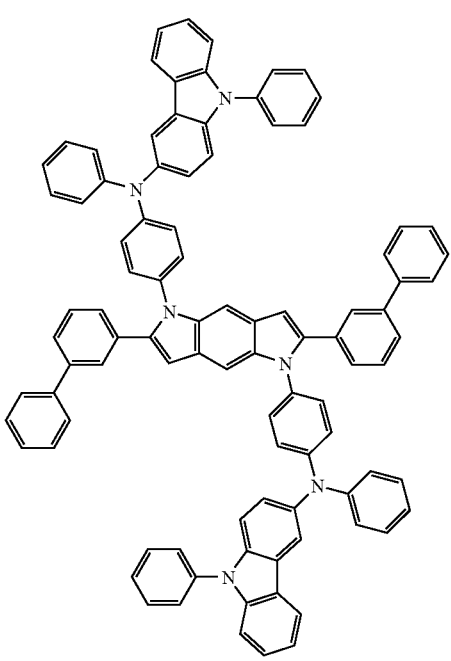

146
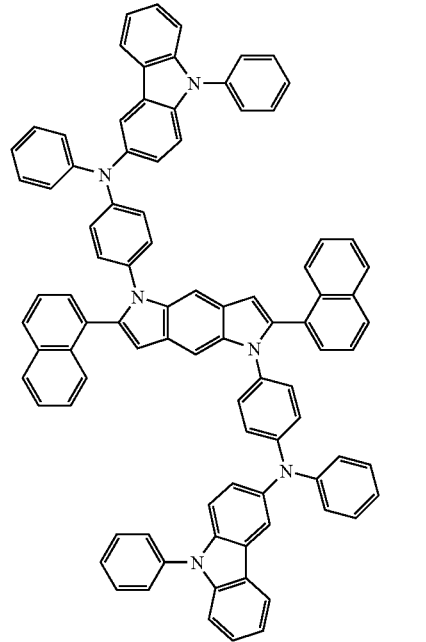
147
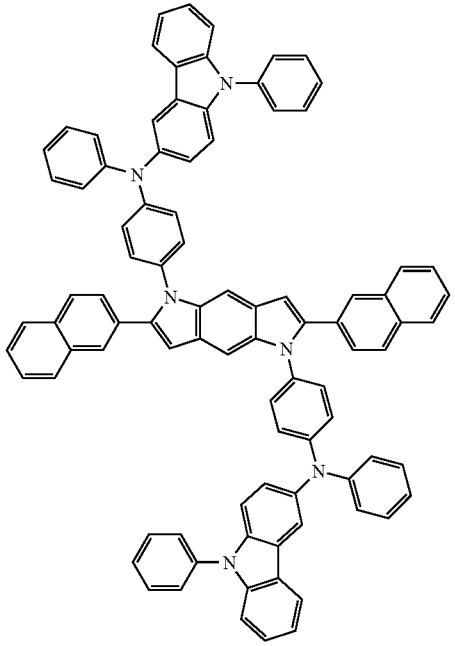
148
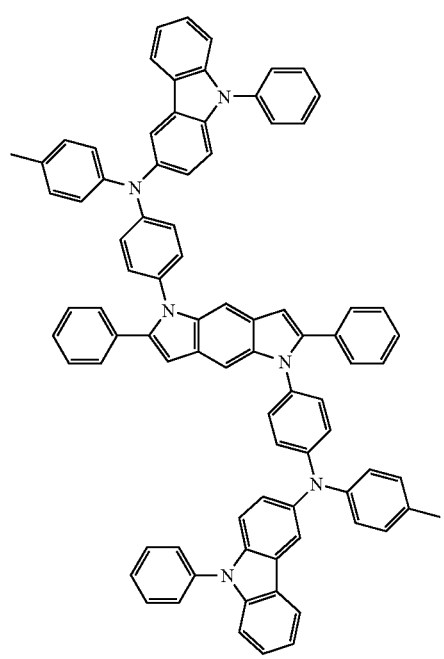
149
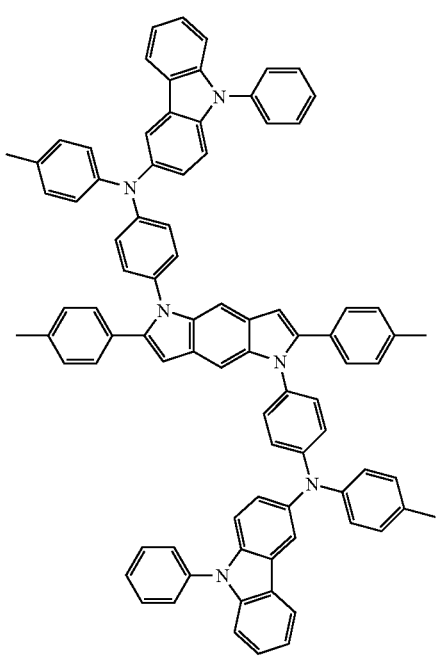

-continued
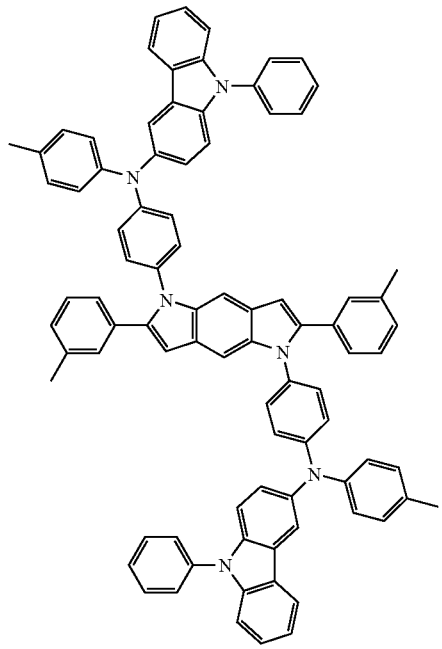
150
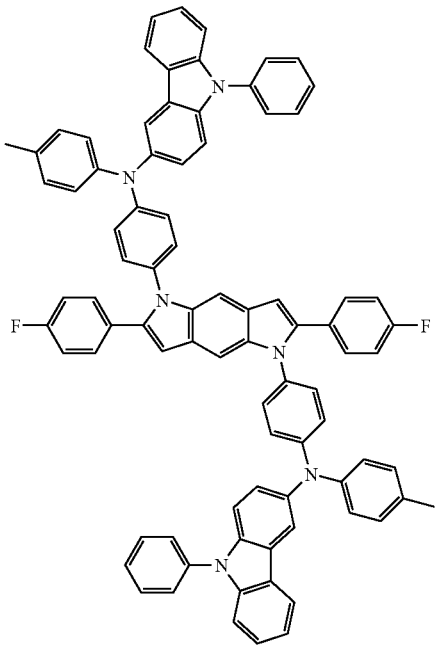
151
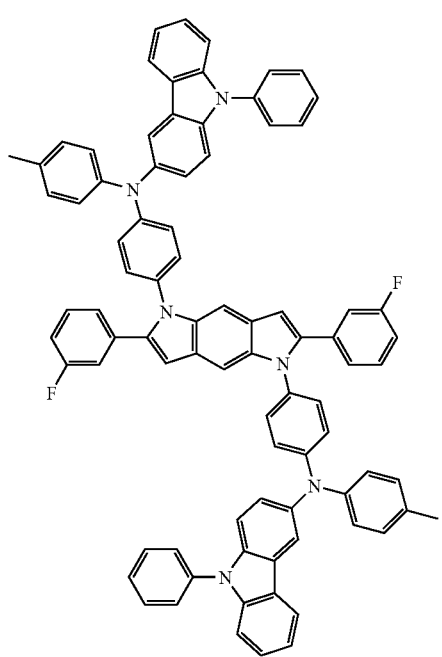
152
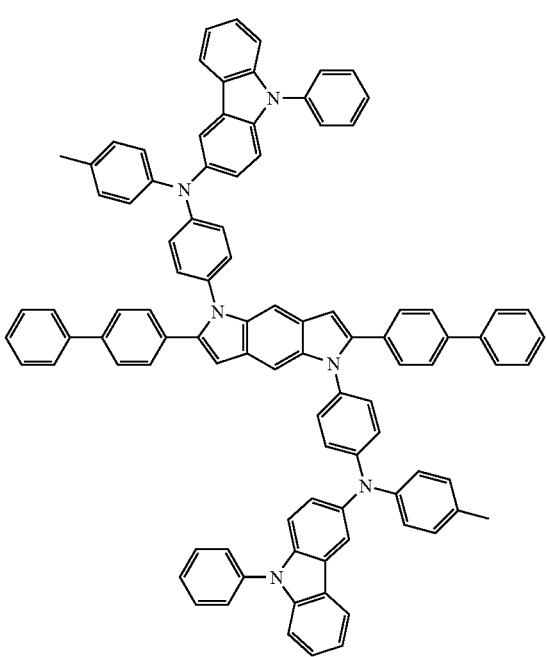
153

154
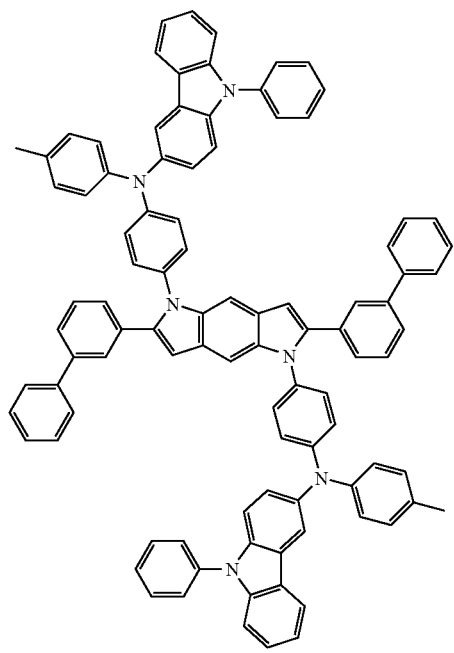
155
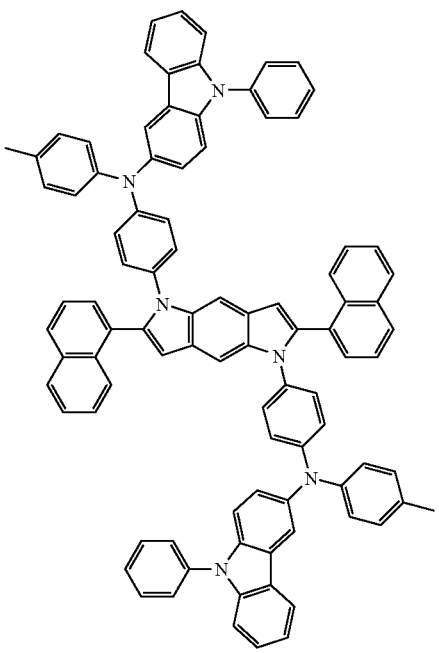
156
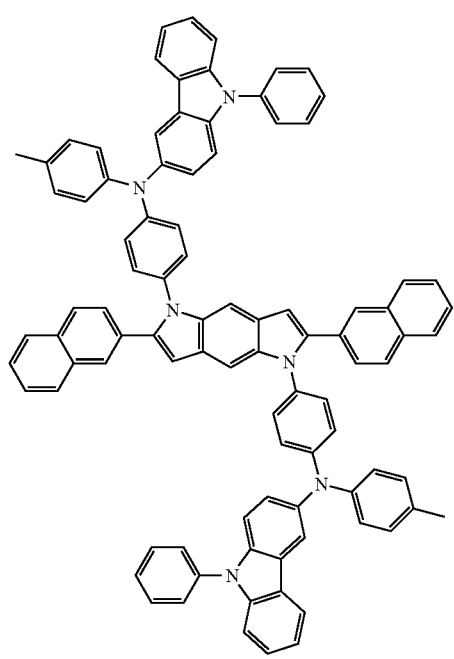
157
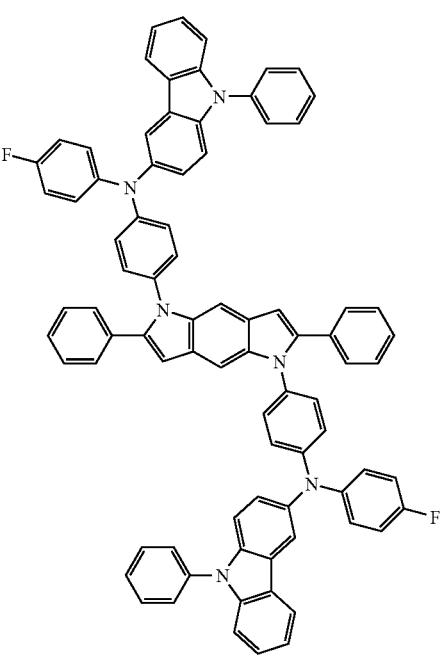

158
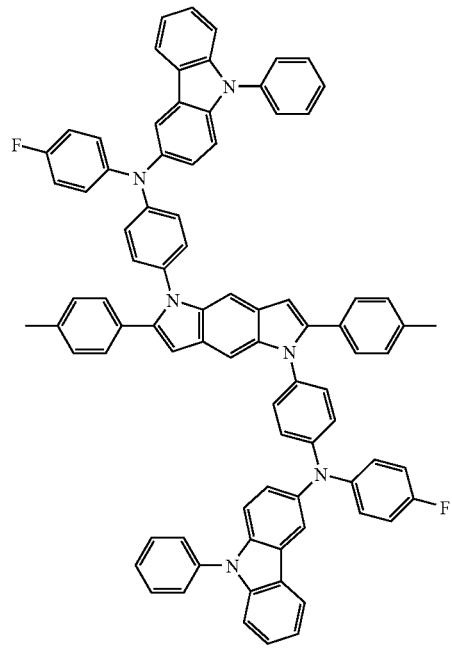
159
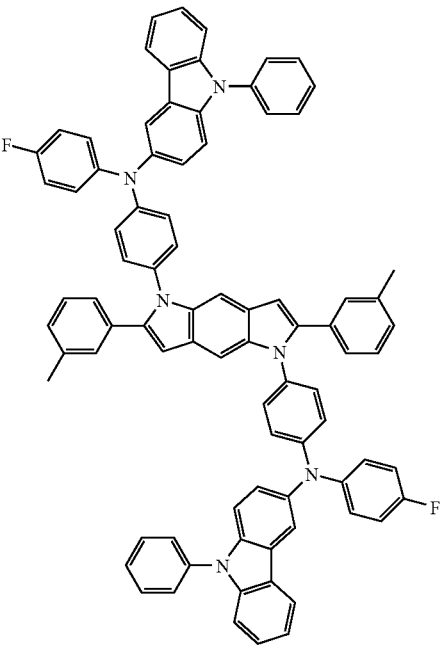
160
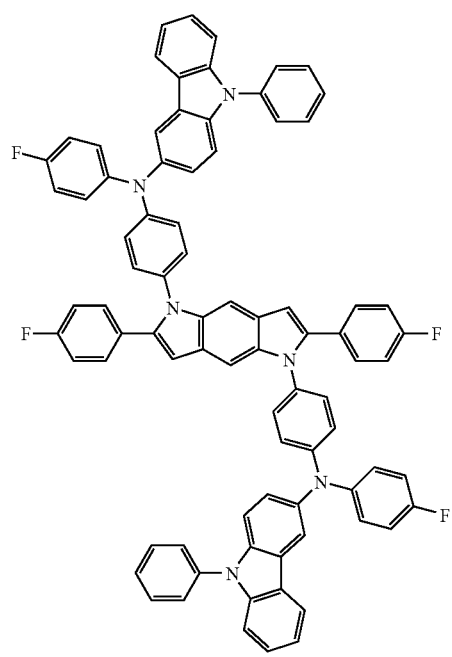
161
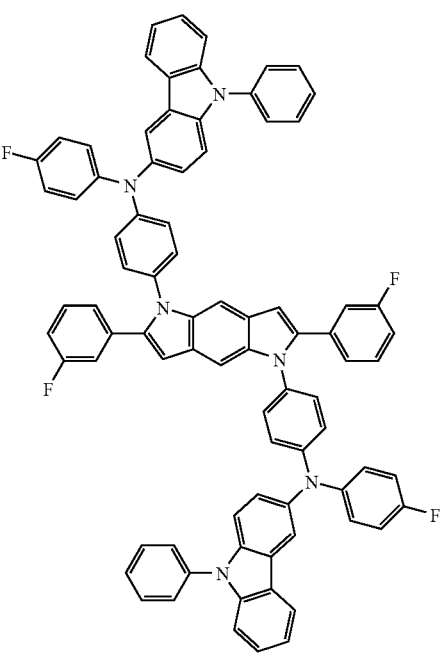

162
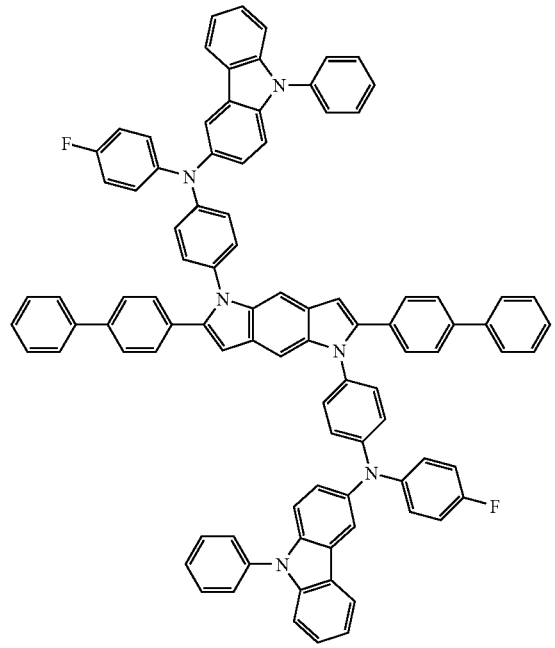
163
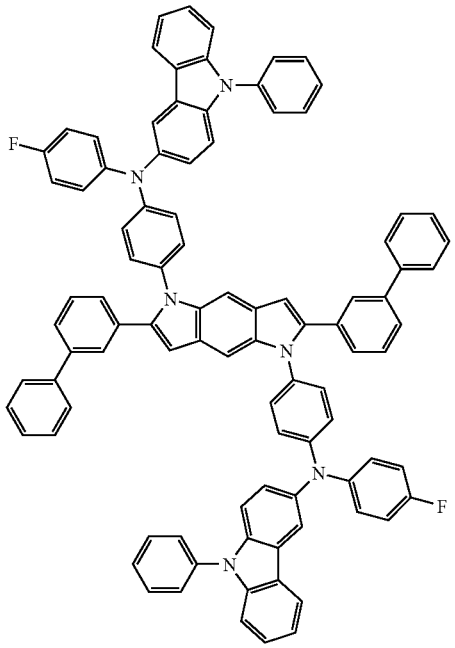
164
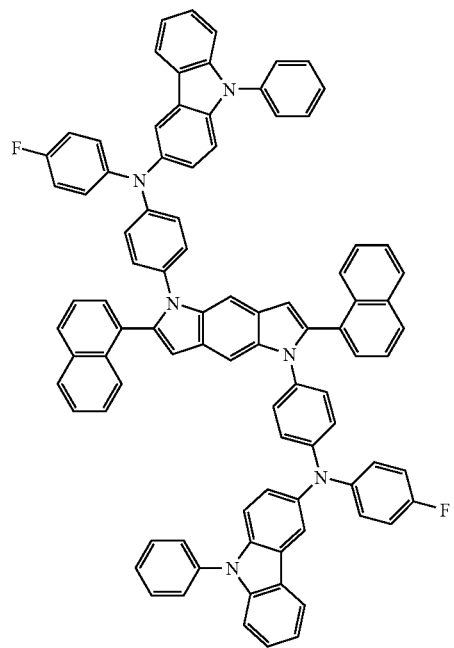
165
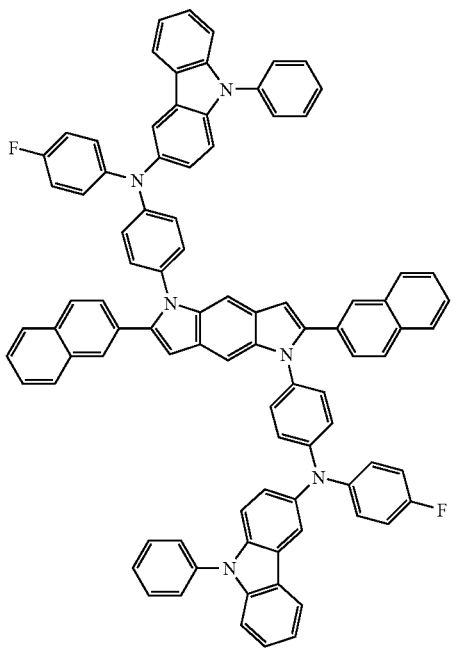

166
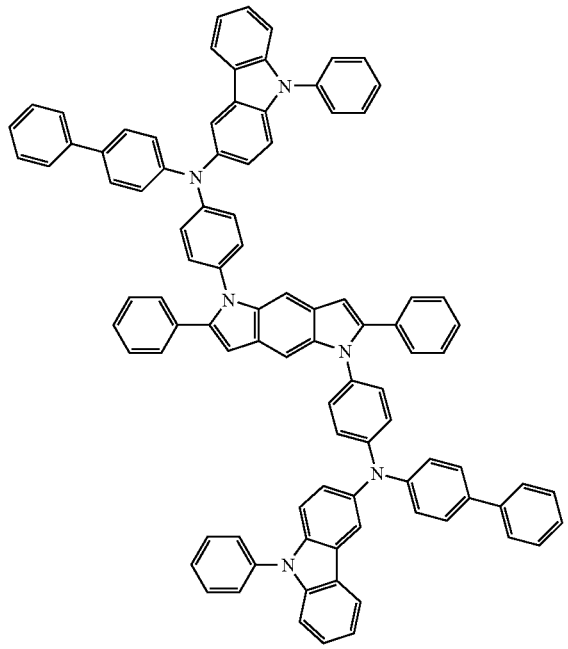
167
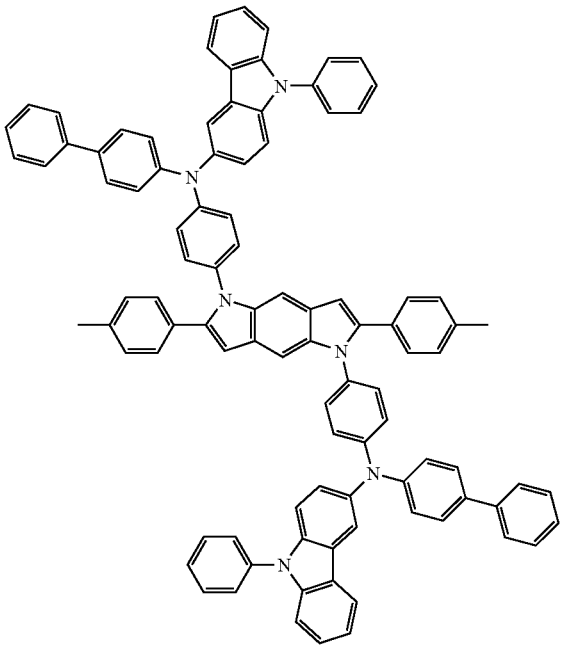
168
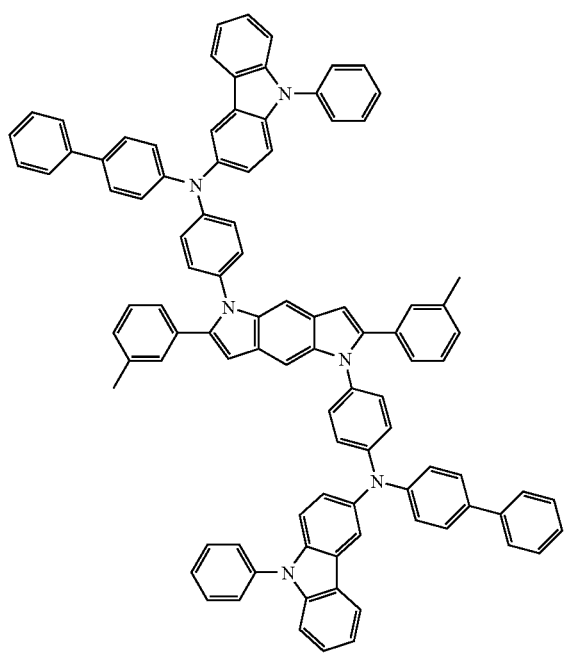
169
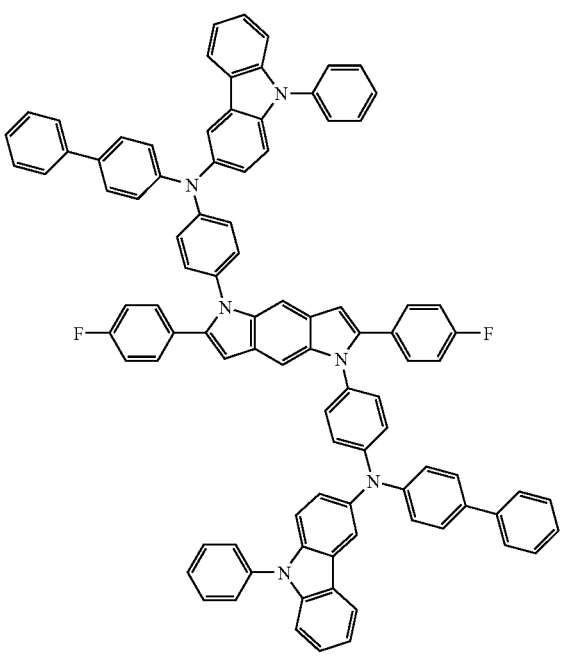

-continued
170
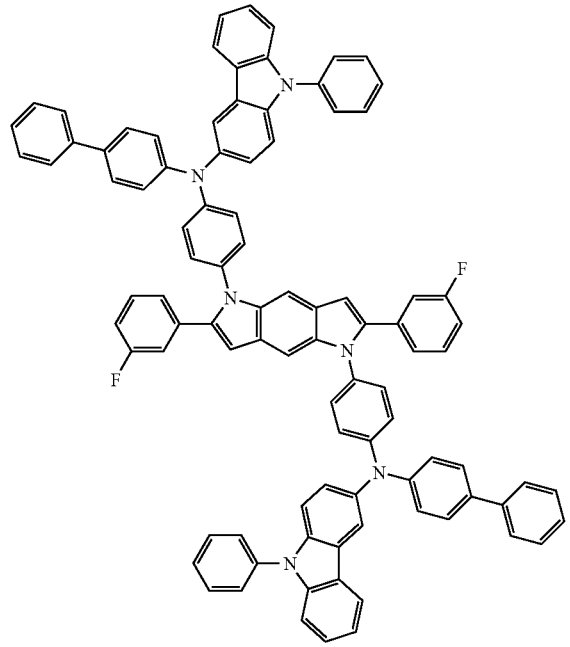
171
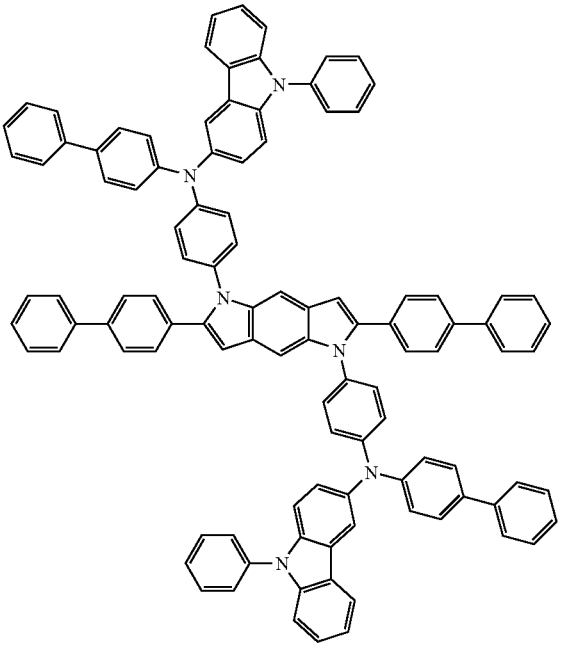
172
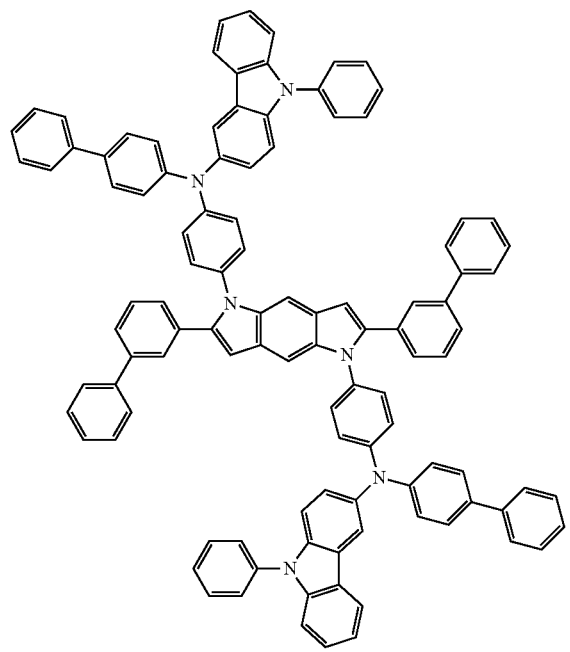
173
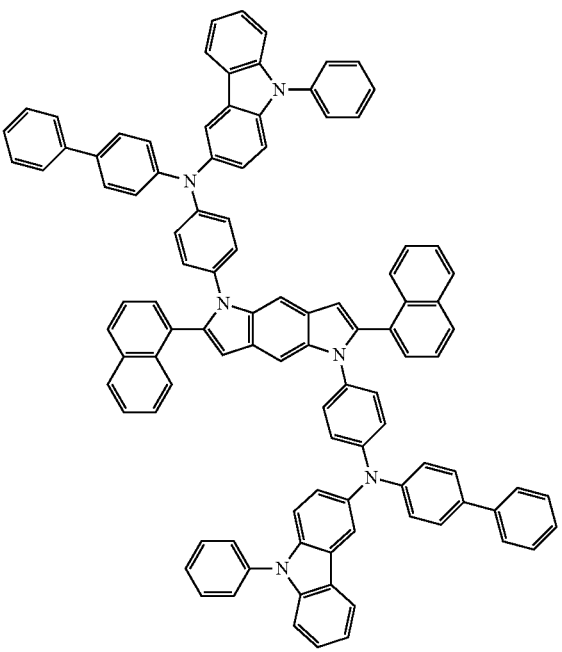

174
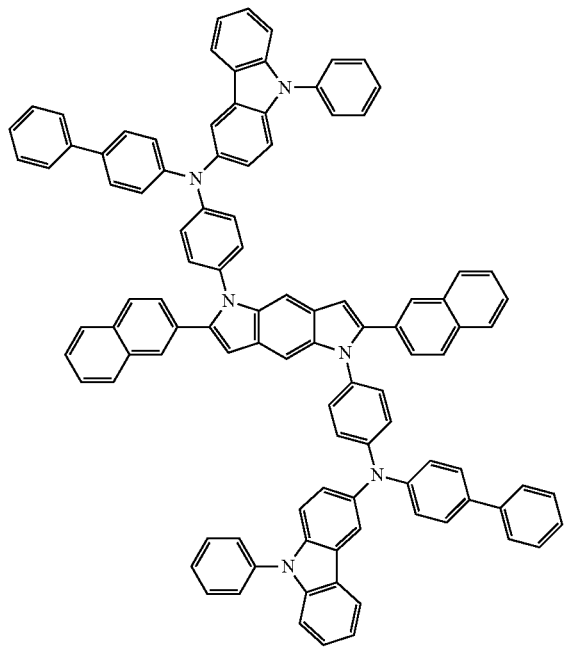
175
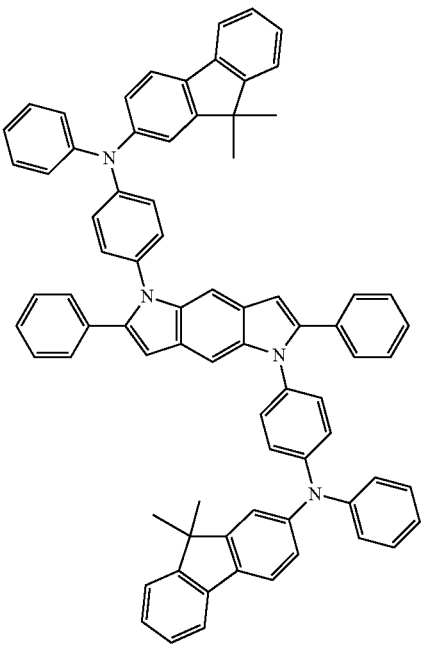
176
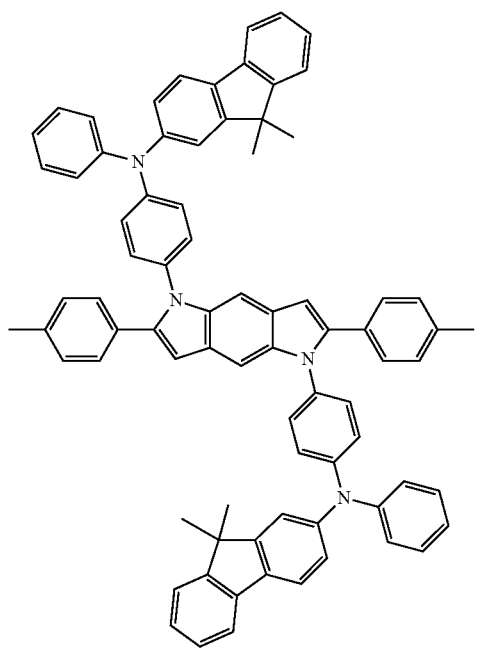
177
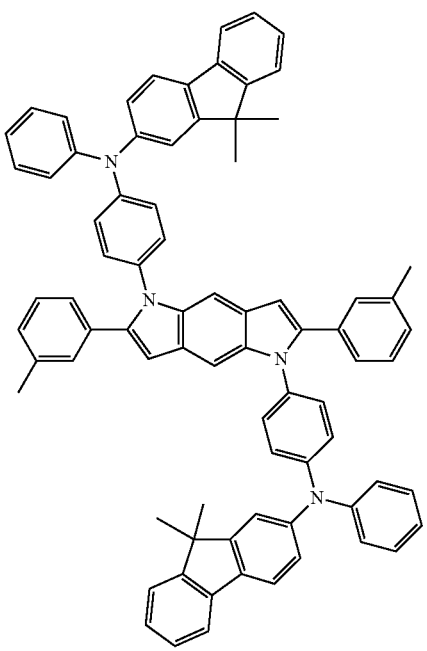

178
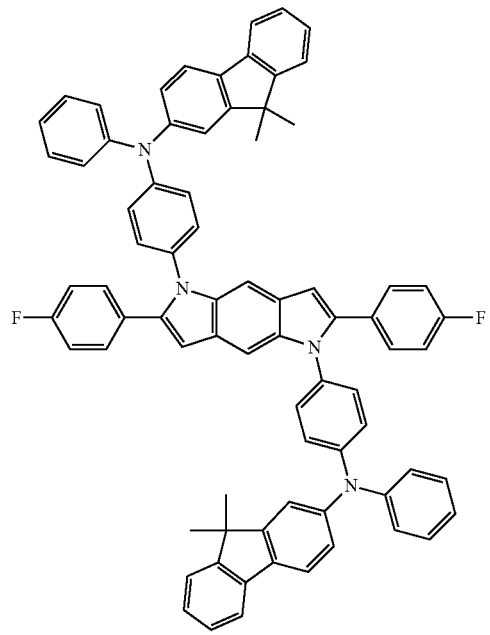
179
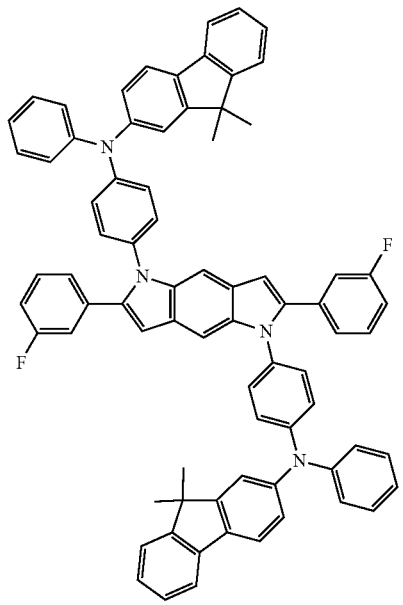
180
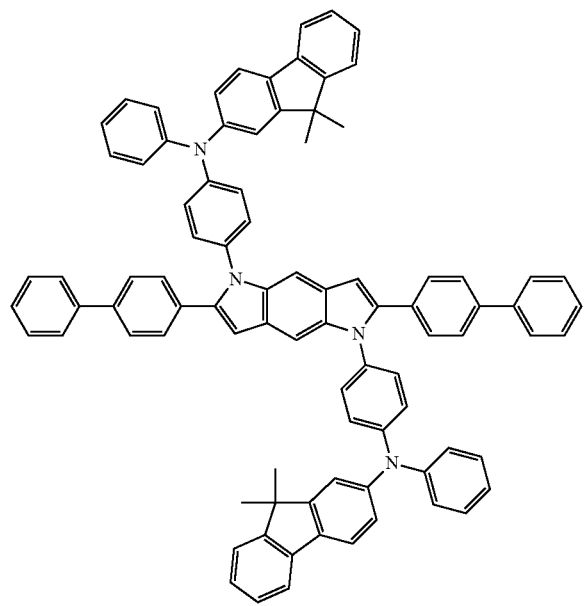
181
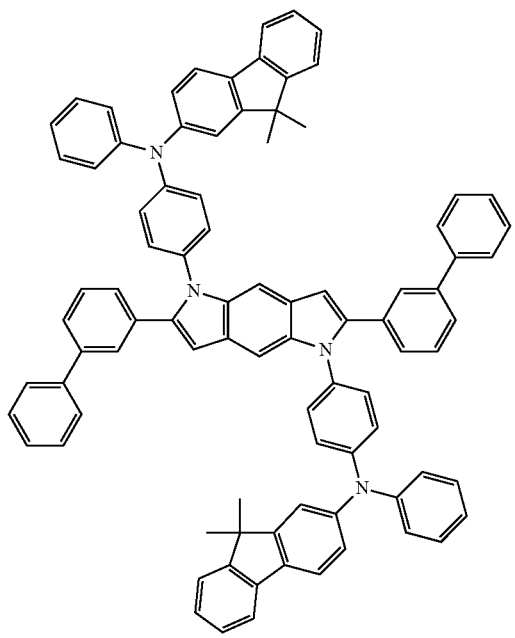

-continued

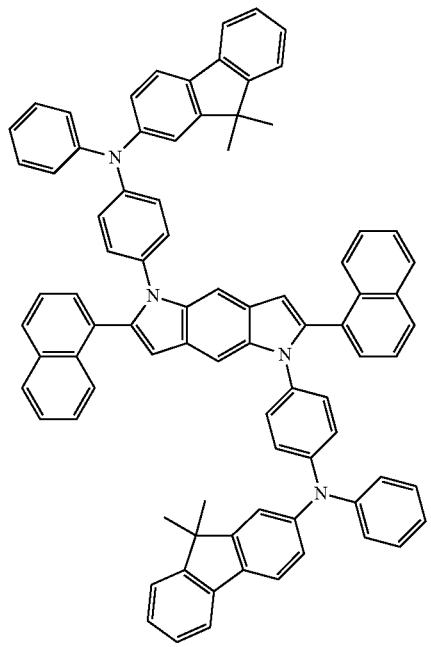
182

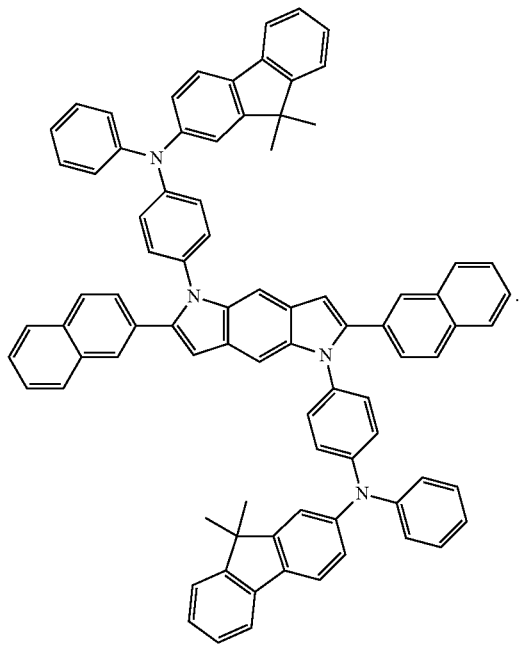
183

8. An organic light emitting device comprising a first electrode, a second electrode, and an organic layer interposed between the first electrode and the second electrode, the organic layer comprising at least one layer comprised of the heterocyclic compound of claim 1, said at least one layer being at least one selected from the group consisting of a hole injection layer, a hole transport layer and an emission layer.

9. An organic light emitting device, comprising:
a first electrode;
a second electrode; and
an organic layer interposed between the first electrode and the second electrode, the organic layer comprising a heterocyclic compound. represented by Formula I:

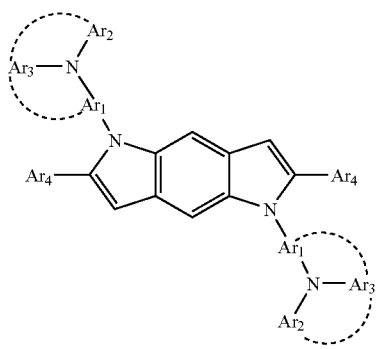
(I)

wherein $Ar_1$ is a bivalent linking group and is a C6-C16 substituted or unsubstituted arylene or heteroarylene group;
$Ar_2$ and $Ar_3$ are each independently selected from the group consisting of a C6-C20 substituted or unsubstituted aryl group, a C4-C20 substituted or unsubstituted heteroaryl group and a C6-C20 substituted or unsubstituted fused polycyclic group;

$Ar_4$ is selected from the group consisting of a C6-C20 substituted or unsubstituted aryl group, a C6-C20 substituted or unsubstituted aryloxy group, a C4-C20 substituted or unsubstituted heteroaryl group and a C6-C20 substituted or unsubstituted fused polycyclic group; and
$Ar_1$ and $Ar_3$ or $Ar_2$ and $Ar_3$ are optionally connected to each other to form a ring.

10. The organic light emitting device of claim 9, wherein the organic layer is a hole injection layer or a hole transport layer.

11. The organic light emitting device of claim 9, wherein the organic layer is a single layer having hole injecting and transporting functions.

12. The organic light emitting device of claim 9, wherein the organic layer is an emission layer.

13. The organic light emitting device of claim 9, wherein the heterocyclic compound represented by Formula I is used as a fluorescent or phosphorescent host in an emission layer.

14. The organic light emitting device of claim 9, wherein $Ar_2$ and $Ar_3$ are each independently selected from the group consisting of a phenyl group, a tolyl group, a fluorophenyl group, a biphenyl group, a (N,N'-diphenyl)aminophenyl group, a naphthyl group, a phenylcarbazolyl group and a dimethylfluorenyl group.

15. The organic light emitting device of claim 9, wherein $Ar_4$ is selected from the group consisting of a phenyl group, a tolyl group, a cyanophenyl group, a fluorophenyl group, a biphenyl group, a naphthyl group and a naphthylphenyl group.

16. The organic light emitting device of claim 9, wherein $Ar_1$ is a phenylene group or a biphenylene group.

17. The organic light emitting device of claim 9, wherein $Ar_1$ and $Ar_3$ or $Ar_2$ and $Ar_3$ are connected to each other to form a carbazolyl group.

18. A method of preparing a heterocyclic compound represented by Formula I, comprising:

performing a cyclization reaction of the compound (b) represented by

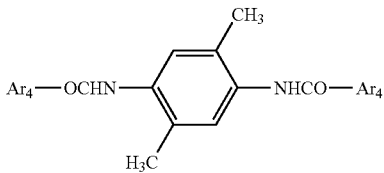

to prepare a compound (c) represented by

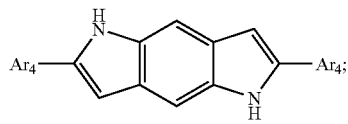

and
reacting the compound (c) and

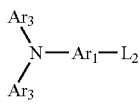

to prepare the heterocyclic compound represented by Formula I:

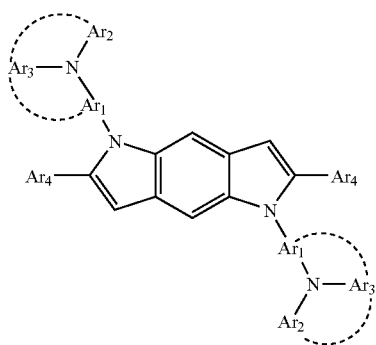

(I)

wherein $L_1$ and $L_2$ are leaving group;

$Ar_1$ is a bivalent linking group and is a C6-C16 substituted or unsubstituted arylene or heteroarylene group;

$Ar_2$ and $Ar_3$ are each independently selected from the group consisting of a C6-C20 substituted or unsubstituted aryl group, a C4-C20 substituted or unsubstituted heteroaryl group and a C6-C20 substituted or unsubstituted fused polycyclic group;

$Ar_4$ is selected from the group consisting of a C6-C20 substituted or unsubstituted aryl group, a C6-C20 substituted or unsubstituted aryloxy group, a C4-C20 substituted or unsubstituted heteroaryl group and a C6-C20 substituted or unsubstituted fused polycyclic group; and $Ar_1$ and $Ar_3$ or $Ar_2$ and $Ar_3$ are optionally connected to each other to form a ring.

19. The method of claim 18, wherein the compound (b) is prepared by reacting 5-dimethyl-1,4-phenylenediamine and

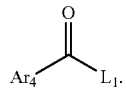

20. The method of claim 18, wherein $Ar_2$ and $Ar_3$ are each independently selected from the group consisting of a phenyl group, a tolyl group, a fluorophenyl group, a biphenyl group, a (N,N'-diphenyl)aminophenyl group, a naphthyl group, a phenylcarbazolyl group and a dimethylfluorenyl group;

$Ar_4$ is selected from the group consisting of a phenyl group, a tolyl group, a cyanophenyl group, a fluorophenyl group, a biphenyl group, a naphthyl group and a naphthylphenyl group; and $Ar_1$ is a phenylene group or a biphenylene group.

* * * * *